United States Patent
Geissmann et al.

(10) Patent No.: US 11,337,965 B2
(45) Date of Patent: May 24, 2022

(54) KINASE MUTATION-ASSOCIATED NEURODEGENERATIVE DISORDERS

(71) Applicant: MEMORIAL SLOAN KETTERING CANCER CENTER, New York, NY (US)

(72) Inventors: Frederic Geissmann, New York, NY (US); Elvira Mass, New York, NY (US); Rocio Vicario, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 97 days.

(21) Appl. No.: 16/640,146

(22) PCT Filed: Aug. 24, 2018

(86) PCT No.: PCT/US2018/047964
§ 371 (c)(1),
(2) Date: Feb. 19, 2020

(87) PCT Pub. No.: WO2019/040877
PCT Pub. Date: Feb. 28, 2019

(65) Prior Publication Data
US 2021/0315868 A1    Oct. 14, 2021

Related U.S. Application Data

(60) Provisional application No. 62/550,536, filed on Aug. 25, 2017.

(51) Int. Cl.
*A61K 31/437* (2006.01)
*A61P 25/28* (2006.01)
*A61K 45/06* (2006.01)

(52) U.S. Cl.
CPC ............ *A61K 31/437* (2013.01); *A61K 45/06* (2013.01); *A61P 25/28* (2018.01)

(58) Field of Classification Search
CPC .................................................. A61K 31/437
See application file for complete search history.

(56) References Cited

U.S. PATENT DOCUMENTS

| | | | |
|---|---|---|---|
| 2010/0183600 A1* | 7/2010 | Lapierre | A61P 43/00 424/133.1 |
| 2015/0030588 A1 | 1/2015 | Jessen et al. | |
| 2015/0354012 A1 | 12/2015 | Joy et al. | |
| 2016/0009663 A1 | 1/2016 | Qian et al. | |
| 2017/0321281 A1 | 11/2017 | Iavarone et al. | |

OTHER PUBLICATIONS

Ajami et al., "Infiltrating monocytes trigger EAE progression, but do not contribute to the resident microglia pool," Nat. Neurosci., vol. 14, No. 9, pp. 1142-1149 (2011).
Ajami et al., "Local self-renewal can sustain CNS microglia maintenance and function throughout adult life," Nat. Neurosci., vol. 10, No. 12, pp. 1538-1543 (2007).
Allen et al., "Cell-specific gene expression in Langerhans cell histiocytosis lesions reveals a distinct profile compared with epidermal Langerhans cells," J. Immunol., vol. 184, No. 8, pp. 4557-4567 (2010).
Arnaud et al., "Systemic perturbation of cytokine and chemokine networks in Erdheim-Chester disease: a single-center series of 37 patients," Blood, vol. 117, No. 10, pp. 2783-2790 (2011).
Badalian-Very et al., "Recurrent BRAF mutations in Langerhans cell histiocytosis," Blood, vol. 116, No. 11, pp. 1919-1923 (2010).
Bain et al., "Constant replenishment from circulating monocytes maintains the macrophage pool in the intestine of adult mice," Nat. Immunol., vol. 15, No. 10, pp. 929-937 (2014).
Banaei-Bouchareb et al., "Insulin cell mass is altered in Csf1op/Csf1op macrophage-deficient mice," J. Leuk. Bio., vol. 76, No. 2, pp. 359-367 (2004).
Bartunek et al., "GATA-1 and c-myb crosstalk during red blood cell differentiation through GATA-1 binding sites in the c-myb promoter," Oncogene, vol. 22, No. 13, pp. 1927-1935 (2003).
Berres et al., "BRAF-V600 expression in precursor versus differentiated dendritic cells defines clinically distinct LCH risk groups," J. Exp. Med., vol. 211, No. 4, pp. 669-683 (2014).
Bertrand et al., "Characterization of purified intraembryonic hematopoietic stem cells as a tool to define their site of origin," PNAS, USA., vol. 1202, No. 1, pp. 134-139 (2005).
Bertrand et al., "Three pathways to mature macrophages in the early mouse yolk sac," Blood, vol. 106, No. 9, pp. 3004-3011 (2005).
Bhatia et al., "Epidemiologic study of Langerhans cell histiocytosis in children," J. Pediatr., vol. 130, No. 5, pp. 774-784 (1997).
Brooks et al., "Tests to assess motor phenotype in mice: a user's guide," Ntl. Rev. Neurosci., vol. 10, No. 7, pp. 519-529 (2009).
Carter et al., "Characterization of progressive motor deficits in mice transgenic for the human Huntington's disease mutation," J. Neurosci., vol. 19, No. 8, pp. 3248-3257 (1999).
Chakravarty et al., "Smallmolecule MAPK inhibitors restore radioiodine incorporation in mouse thyroid cancers with conditional BRAF activation," J. Clin. Invest., vol. 121, No. 12, pp. 4700-4711 (2011).
Charles et al., "Major response to vemurafenib in patient with severe cutaneous Langerhans cell histiocytosis harboring BRAF V600E mutation," J. Am. Acad. Dermatol., vol. 71, No. 3, pp. 97-99 (2014).
Chen et al., "Runx1 is required for the endothelial to haematopoietic cell transition but not thereafter," Nature, vol. 457, No. 7231, pp. 887-891 (2009).

(Continued)

*Primary Examiner* — Paul V Ward
(74) *Attorney, Agent, or Firm* — Foley & Lardner LLP

(57) ABSTRACT

The present technology relates to methods for treating, preventing, and/or ameliorating kinase mutation-associated neurodegenerative diseases, including BRAFV600E-associated neurodegenerative diseases, in a subject in need thereof. In particular aspects, the present technology relates to the use of BRAF, MEK, and/or CSF-IR inhibitors to treat, prevent, and/or ameliorate kinase mutation-associated neurodegenerative diseases, including BRAFV600E-associated neurodegenerative diseases.

12 Claims, 77 Drawing Sheets

(56) References Cited

OTHER PUBLICATIONS

Chorro et al., "Langerhans cell (LC) proliferation mediates neonatal development, homeostasis, and inflammation-associated expansion of the epidermal LC network," J. Exp. Med., vol. 206, No. 13, pp. 3089-3100 (2009).
Chung et al., "Hematopoietic stem cell origin of BRAFV600E mutations in hairy cell leukemia," Sci. Transl. Med., vol. 6, No. 238, 25 pages (2014).
Constandinou et al., "Modeling liver fibrosis in rodents," Meth. Mol. Med., vol. 117, pp. 237-250 (2005).
Croker et al., "SOCS3 is a critical physiological negative regulator of G-CSF signaling and emergency granulopoiesis," Immunity, vol. 20, No. 2, pp. 153-165 (2004).
Davalos et al., "ATP mediates rapid microglial response to local brain injury in vivo.," Nat. Neuro., vol. 8, No. 6, pp. 752-758 (2005).
De Boer et al., "Transgenic mice with hematopoietic and lymphoid specific expression of Cre," Eur. J. Immunol., vol. 33, No. 2, pp. 314-325 (2003).
DeFalco et al., "Yolk-sac-derived macrophages regulate fetal testis vascularization and morphogenesis," PNAS, vol. 111, No. 23, pp. E2384-E2393 (2014).
Diamond et al., "Detection of an NRAS mutation in Erdheim-Chester disease," Blood, vol. 122, No. 6, pp. 1089-1091 (2013).
Diamond et al., "Diverse and Targetable Kinase Alterations Drive Histiocytic Neoplasms," Cancer Discov., 22 pages (2015).
Diamond et al., "Diverse and Targetable Kinase Alterations Drive Histiocytic Neoplasms," Cancer Discov., vol. 6, No. 2, pp. 154-165 (2016).
Donadieu et al., "French LCHSG. Endocrine involvement in pediatric-onset Langerhans' cell histiocytosis: a population based study," J. Pediatr., vol. 144, No. 3, pp. 344-350 (2004).
Donadieu et al., "Medical management of langerhans cell histiocytosis from diagnosis to treatment," Expert Opin. on Pharma., vol. 13, No. 9, pp. 1309-1322 (2012).
Egeler et al., "Differential in situ cytokine profiles of Langerhans-like cells and T cells in Langerhans cell histiocytosis: abundant expression of cytokines relevant to disease and treatment," Blood, vol. 94, No. 12, pp. 4195-4201 (1999).
Emile et al., "Recurrent RAS and PIK3CA mutations in Erdheim-Chester disease," Blood, vol. 124, No. 19, pp. 3016-2019 (2014).
Erny et al., "Host microbiota constantly control maturation and function of microglia in the CNS," Nat. Neurosci., vol. 18, No. 7, pp. 965-977 (2015).
Evans et al., "High-resolution intravital imaging reveals that blood-derived macrophages but not resident microglia facilitate secondary axonal dieback in traumatic spinal cord injury," Exp. Neurol., vol. 254, pp. 109-120 (2014).
Fantin et al., "Tissue macrophages act as cellular chaperones for vascular anastomosis downstream of VEGF-mediated endothelial tip cell induction," Blood, vol. 116, No. 5, pp. 829-840 (2010).
Fickert et al., "A new xenobiotic-induced mouse model of sclerosing cholangitis and biliary fibrosis," Am. J. Pathol., vol. 171, No. 2, pp. 525-536 (2007).
Fickert et al., "Lithocholic acid feeding induces segmental bile duct obstruction and destructive cholangitis in mice," Am. J. Pathol., vol. 168, No. 2, pp. 410-422 (2006).
Gibney et al., "Paradoxical oncogenesis—the long-term effects of BRAF inhibition in melanoma," Nat. Rev. Clin. Oncol., vol. 10, No. 7, 20 pages (2013).
Goke et al., "Genome-wide kinase-chromatin interactions reveal the regulatory network of ERK signaling in human embryonic stem cells," Molec. Cell, vol. 50, No. 6, pp. 844-855 (2013).
Gomez Perdiguero et al., "Myb-Independent Macrophages: A Family of Cells That Develops with Their Tissue of Residence and Is Involved in Its Homeostasis," Cold Spring Harbor Symp. Quant. Bio., vol. XXVIII, pp. 91-100 (2013).
Gomez Perdiguero et al., "The development and maintenance of resident macrophages," Nat. Immun., vol. 17, No. 1, pp. 2-8 (2015).
Gomez Perdiguero et al., "Tissue-resident macrophages originate from yolk-sac-derived erythro-myeloid progenitors," Nature, vol. 518, No. 7540*, pp. 547-551 (2015).
Gomez-Nicola et al., "Regulation of microglial proliferation during chronic neurodegeneration," J. Neuro., vol. 33, No. 6, pp. 2481-2493 (2013).
Gordon et al., "Macrophages define dermal lymphatic vessel calibre during development by regulating lymphatic endothelial cell proliferation," Development, vol. 137, No. 22, pp. 3899-3910 (2010).
Gosselin et al., "Environment drives selection and function of enhancers controlling tissue-specific macrophage identities," Cell, vol. 159, No. 6, pp. 1327-1340 (2014).
Grois et al., "Central nervous system disease associated with Langerhans' cell histiocytosis," Am. J. Pediatr. Hematol. Oncol., vol. 15, No. 2, pp. 245-254 (1993).
Grois et al., "Central nervous system disease in Langerhans cell histiocytosis," Br. J. Cancer Suppl., vol. 23, pp. S24-S28 (1994).
Haroche et al. "Dramatic efficacy of vemurafenib in both multisystemic and refractory Erdheim-Chester disease and Langerhans cell histiocytosis harboring the BRAF V600E mutation." Blood, vol. 121, No. 9, pp. 1495-1500 (2013).
Haroche et al., "High prevalence of BRAF V600E mutations in Erdheim-Chester disease but not in other non-Langerhans cell histiocytoses," Blood, vol. 120, No. 13, pp. 2700-2703 (2012).
Haroche et al., "Reproducible and sustained efficacy of targeted therapy with vemurafenib in patients with BRAF(V600E)-mutated Erdheim-Chester disease," J. Clin. Oncol., vol. 33, No. 5, pp. 411-418 (2015).
Haroche et al., "Vemurafenib as first line therapy in BRAF-mutated Langerhans cell histiocytosis," J. Am. Acad. Dermatol., vol. 73, No. 1, pp. e29-e30 (2015).
Hashimoto et al., "Tissue-resident macrophages self-maintain locally throughout adult life with minimal contribution from circulating monocytes," Immunity, vol. 38, No. 4, pp. 792-804 (2013).
Hatemi et al., "Adult Langerhans cell histiocytosis and sclerosing cholangitis: a case report and review of the literature," Hepatol. Int., vol. 4, No. 3, pp. 653-658 (2010).
Heritier et al., "BRAF Mutation Correlates With High-Risk Langerhans CellHistiocytosis and Increased Resistance to First-Line Therapy," J. Clin. Oncolo., vol. 34, No. 25, pp. 3023-2030 (2016).
Hoeffel et al., "C-Myb() erythro-myeloid progenitor-derived fetal monocytes give rise to adult tissue-resident macrophages," Immunity, vol. 42, No. 4, pp. 665-678 (2015).
Hyman et al., "Prospective blinded study of BRAFV600E mutation detection in cell-free DNA of patients with systemic histiocytic disorders," Cancer Disc., vol. 5, No. 1, pp. 64-71 (2015).
Hyman et al., "Vemurafenib in Multiple Nonmelanoma Cancers with BRAF V600 Mutations," NEJM, vol. 373, No. 8, pp. 726-736 (2015).
Ingman et al., "Macrophages promote collagen fibrillogenesis around terminal end buds of the developing mammary gland. Developmental dynamics : an official publication of the American Association of Anatomists," vol. 235, No. 12, pp. 3222-3229 (2006).
International Search Report and Written Opinion, PCT/US2018/047964, Memorial Sloan Kettering Cancer Center (dated Oct. 30, 2018).
Jenkins et al., "Local macrophage proliferation, rather than recruitment from the blood, is a signature of TH2 inflammation," Science, vol. 332, No. 6035, pp. 1284-1288 (2011).
Kierdorf et al., "Development and function of tissue resident macrophages in mice," Semin. Immunol., vol. 27, No. 6, pp. 369-378 (2015).
Kierdorf et al., "Microglia emerge from erythromyeloid precursors via Pu.1- and Irf8-dependent pathways," Nat. Neurosci., vol. 16, No. 3, pp. 273-280 (2013).
Kieusseian et al., "Immature hematopoietic stem cells undergo maturation in the fetal liver," Development, vol. 139, No. 19, pp. 3521-3530 (2012).
Kubota et al., "M-CSF inhibition selectively targets pathological angiogenesis and lymphangiogenesis.," J. Exp. Med., vol. 206, No. 5, pp. 1089-1102 (2009).

(56) References Cited

OTHER PUBLICATIONS

Kupffer, "Ueber Sternzellen der Leber," Arch Fur Mikrosk Anat., vol. 12, pp. 353-358 (1876).
Lachenal et al., "Neurological manifestations and neuroradiological presentation of Erdheim-Chester disease: report of 6 cases and systematic review of the literature," J. Neurol., vol. 253, No. 10, pp. 1267-1277 (2006).
Lai et al., "Erk is essential for growth, differentiation, integrin expression, and cell function in human osteoblastic cells.," J. Biolog. Chem., vol. 276, No. 17, pp. 14443-14450 (2001).
Langerhans, "Ueber die Nerven der menschlichen Haut," Arch Fur Pathol Anat Physiol Fur Klin Med., vol. 44, No. 2-3, pp. 325-327 (1868).
Larkin et al., "Combined vemurafenib and cobimetinib in BRAFmutated melanoma," NEJM, vol. 371, No. 20, pp. 1867-1876 (2014).
Lavin et al., "Tissue-resident macrophage enhancer landscapes are shaped by the local microenvironment," Cell, vol. 159, No. 6, pp. 1312-1326 (2014).
Levine et al., "Data-Driven Phenotypic Dissection of AML Reveals Progenitor-like Cells that Correlate with Prognosis," Cell, vol. 162, No. 1, pp. 184-197 (2015).
Li et al., "Phosphatidylserine receptor is required for clearance of apoptotic cells.," Science, vol. 302, No. 5650, pp. 1560-1563 (2003).
Lito et al., "Relief of profound feedback inhibition of mitogenic signaling by RAF inhibitors attenuates their activity in BRAFV600E melanomas," Cancer Cell, vol. 22, No. 5, pp. 668-682 (2012).
Mass et al., "A somatic mutation in erythro-myeloid progenitors causes neurodegenerative disease," Nature, vol. 549, No. 7672, pp. 389-393 (Sep. 21, 2017).
Mass et al., "Specification of tissue-resident macrophages during organogenesis," Science, vol. 353, No. 76304, 32 pages (2016).
McGrath et al., "Distinct Sources of Hematopoietic Progenitors Emerge before HSCs and Provide Functional Blood Cells in the Mammalian Embryo," Cell Reports, vol. 11, No. 12, pp. 1892-1904 (2015).
Menalled et al., "Early motor dysfunction and striosomal distribution of huntingtin microaggregates in Huntington's disease knock-in mice," J. Neurosci., vol. 22, No. 18, pp. 8266-8276 (2002).
Metzger et al., "Conditional site-specific recombination in mammalian cells using a ligand-dependent chimeric Cre recombinase," PNAS, vol. 92, No. 15, pp. 6991-6995 (1995).
Mittheisz et al., "Central nervous system-related permanent consequences in patients with Langerhans cell histiocytosis," Pediatr. Blood Cancer, vol. 48, No. 1, pp. 50-56 (2007).
Munoz-Espin et al., "Programmed cell senescence during mammalian embryonic development," Cell, vol. 155, No. 5, pp. 1104-1118 (2013).
Nimmerjahn et al., "Resting microglial cells are highly dynamic surveillants of brain parenchyma in vivo," Science, vol. 308, No. 5726, pp. 1314-1318 (2005).
Nishibu et al., "Behavioral responses of epidermal Langerhans cells in situ to local pathological stimuli," J Invest. Dermatol., vol. 126, No. 4, pp. 787-796 (2006).
Palis et al., "Development of erythroid and myeloid progenitors in the yolk sac and embryo proper of the mouse.," Development, vol. 126, No. 22, pp. 5073-5084 (1999).
Paolicelli et al., "Synaptic pruning by microglia is necessary for normal brain development," Science, vol. 333, No. 6048, pp. 1456-1458 (2011).
Pettirossi et al., "BRAF inhibitors reverse the unique molecular signature and phenotype of hairy cell leukemia and exert potent antileukemic activity," Blood, vol. 125, No. 8, pp. 1207-1216 (2015).
Poulikakos et al., "RAF inhibitors transactivate RAF dimers and ERK signalling in cells with wild-type BRAF," Nature, vol. 464, No. 7287, pp. 427-430 (2010).
Prabowo et al., "BRAF V600E mutation is associated with mTOR signaling activation in glioneuronal tumors," Brain Pathology, vol. 24, Iss. 1, pp. 52-66 (Aug. 13, 2013).
Pritchard et al., "Mouse models for BRAF-induced cancers," Biochem. Soc. Trans., vol. 35, Pt. 5, pp. 1329-1333 (2007).
Qian et al., "CCL2 recruits inflammatory monocytes to facilitate breast-tumour metastasis," Nature, vol. 475, No. 7355, pp. 222-225 (2011).
Ransohoff, "A polarizing question: do M1 and M2 microglia exist?," Nat. Neurosci., vol. 19, No. 8, pp. 987-991 (2016).
Rochet et al., "Vemurafenib for melanoma metastases to the brain," NEJM, vol. 365, No. 25, pp. 2439-2441 (2011).
Rouco et al., "Neurological manifestations in Erdheim-Chester disease: Two case reports," Neurologia, vol. 31, No. 6, pp. 426-428 (2016).
Rymo et al., "A Two-Way Communication between Microglial Cells and Angiogenic Sprouts Regulates Angiogenesis in Aortic Ring Cultures," PloS one, vol. 6, No. 1, 12 pages (2011).
Satoh et al., "B-RAF Mutant Alleles Associated with Langerhans Cell Histiocytosis, a Granulomatous Pediatric Disease," PloS one ,vol. 7, No. 4, 9 pages (2012).
Satoh et al., "B-RAF mutant alleles associated with Langerhans cell histiocytosis, a granulomatous pediatric disease," PLoS One, vol. 7, Iss. 4, pp. 1-9 (Apr. 10, 2010).
Schaefer et al., "Control of cognition and adaptive behavior by the GLP/G9a epigenetic suppressor complex," Neuron, vol. 64, No. 5, pp. 678-691 (2009).
Schmued et al., "Fluoro-Jade: a novel fluorochrome for the sensitive and reliable histochemical localization of neuronal degeneration," Brain Res., vol. 751, No. 1, pp. 37-46 (1997).
Schulz et al., "A lineage of myeloid cells independent of Myb and hematopoietic stem cells," Science, vol. 336, No. 6077, pp. 86-90 (2012).
Sevcikova et al., "Impact of anakinra treatment on cytokine and lymphocytes/ monocytes profile of an Erdheim-Chester patient," Klin. Onkol., vol. 27, No. 4, pp. 276-282 (2014).
Stamatiades et al., "Immune Monitoring of Trans-endothelial Transport by Kidney-Resident Macrophages," Cell, vol. 166, No. 4, pp. 991-1003 (2016).
Sumner et al., "Initiation of adult myelopoiesis can occur in the absence of c-Myb whereas subsequent development is strictly dependent on the transcription factor," Oncogene, vol. 19, No. 30, pp. 3335-3342 (2000).
Terpstra et al., "Scavenger receptors on liver Kupffer cells mediate the in vivo uptake of oxidatively damaged red blood cells in mice," Blood, vol. 95, No. 6, pp. 2157-2163 (2000).
Tiacci et al., "BRAF mutations in hairy-cell leukemia," NEJM, vol. 264, No. 24, pp. 2305-2315 (2011).
Tsai et al., "Discovery of a selective inhibitor of oncogenic B-Raf kinase with potent antimelanoma activity," PNAS, vol. 105, No. 8, pp. 3041-3046 (2008).
Tzoulis et al., "Excellent response of intramedullary Erdheim-Chester disease to vemurafenib: a case report," BMC Res. Notes, vol. 8, No. 171, 5 pages (2015).
Vanden Borre et al., "Combined BRAF(V600E)- and SRC-inhibition induces apoptosis, evokes an immune response and reduces tumor growth in an immunocompetent orthotopic mouse model of anaplastic thyroid cancer," Oncotarget, vol. 5, No. 12, pp. 3996-4010 (2014).
Wnorowski et al., "Pattern and course of neurodegeneration in Langerhans cell histiocytosis," J. of Pedatr., vol. 153, No. 1, pp. 127-132 (2008).
Wright et al., "Neurological manifestations of Erdheim-Chester disease," J. Neurol. Neurosurg. Psychiatry, vol. 66, No. 1, pp. 72-75 (1999).
Wynn et al., "Macrophage biology in development, homeostasis and disease," Nature, vol. 496, No. 7446, pp. 445-455 (2013).
Yamamoto et al., "Continuous ERK activation downregulates antiproliferative genes throughout G1 phase to allow cell-cycle progression," Current Biolo., vol. 16, No. 12, pp. 1171-1182 (2006).
Yamasaki et al., "Differential roles of microglia and monocytes in the inflamed central nervous system," J. of Exper. Med., vol. 2011, No. 8, pp. 1533-1549 (2014).
Yona et al., "Fate mapping reveals origins and dynamics of monocytes and tissue macrophages under homeostasis," Immunity, vol. 38, No. 1, pp. 79-91 (2013).

(56) References Cited

OTHER PUBLICATIONS

Yoshida et al., "Phosphatidylserinedependent engulfment by macrophages of nuclei from erythroid precursor cells," Nature, vol. 437, No. 7059, pp. 754-458 (2005).
Zhang et al., "MAPK signal pathways in the regulation of cell proliferation in mammalian cells," Cell Res., vol. 12, No. 1, pp. 9-18 (2002).
Haroche Julien et al: "Histiocytoses: emerging neoplasia behind inflammation", The Lancet Oncology, Elsevier, Amsterdam, NL, vol. 18, No. 2, Feb. 2, 2017 (Feb. 2, 2017).

* cited by examiner

|  | Cre-; BRAF^WT | Cre-; BRAF^V600E | Cre+; BRAF^WT | Cre+; BRAF^V600E |
|---|---|---|---|---|
| E10.5 | 10 | 11 | 10 | 8 |
| E11.5 | 11 | 10 | 15 | 21 |
| E12.5 | 22 | 18 | 18 | 15 |
| E13.5 | 5 | 4 | 3 | 2 |
| E14.5 | 5 | 6 | 7 | 0 |

FIG. 9A
FIG. 9B
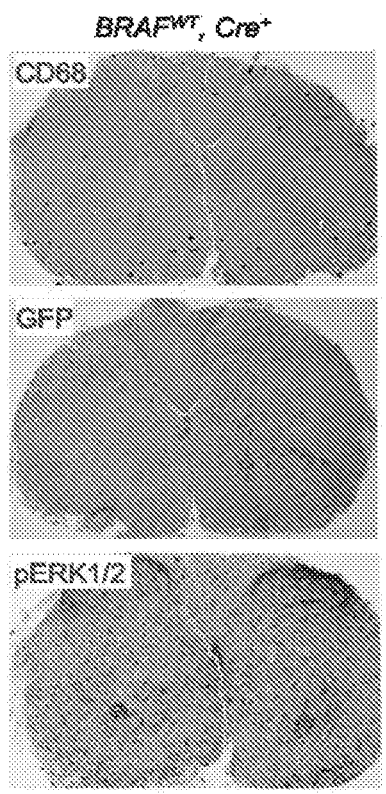
BRAF^WT, Cre+
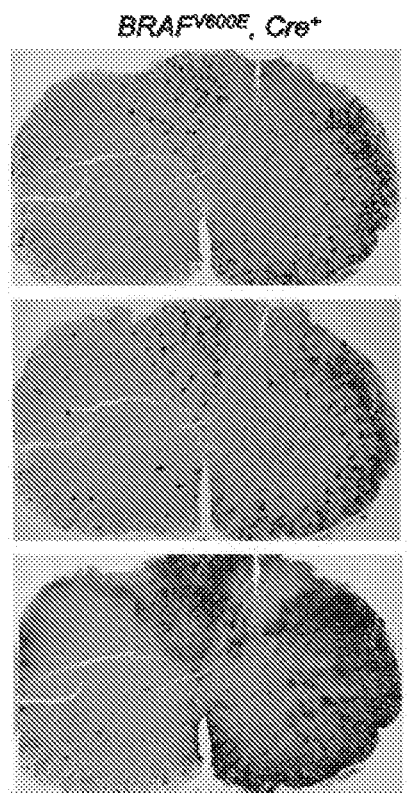
BRAF^V600E, Cre+

|       | Cre⁻; BRAF^WT | Cre⁻; BRAF^VE | Cre⁺; BRAF^WT | Cre⁺; BRAF^VE |
|-------|---------------|---------------|---------------|---------------|
| E10.5 | 10 | 11 | 10 | 8  |
| E11.5 | 11 | 10 | 15 | 21 |
| E12.5 | 22 | 18 | 18 | 15 |
| E13.5 | 5  | 4  | 3  | 2  |
| E14.5 | 5  | 6  | 7  | 0  |

FIG. 20G

| diet | mouse # | \multicolumn{9}{c|}{months} |
|---|---|---|---|---|---|---|---|---|---|---|
| | | 1 | 2 | 3 | 4 | 5 | 6 | 7 | 8 | 9 |
| Ctrl | 1 | 0 | 0 | 0 | 0 | 0 | 1 | 2 | 3 | Ā |
| | 2 | 0 | 0 | 0 | 0 | 1 | 2 | 2 | 2 | 2 |
| | 3 | 0 | 0 | 0 | 1 | Ā | | | | |
| | 4 | 0 | 0 | 0 | 0 | 0 | 2 | 2 | 2 | Ā |
| | 5 | 0 | 0 | 0 | 0 | 1 | 2 | Ā | | |
| | 6 | 0 | 0 | 0 | 1 | 2 | 3 | Ā | | |
| | 7 | 0 | 0 | 0 | 0 | 1 | 2 | 2 | Ā | |
| | 8 | 0 | 0 | 0 | 0 | 1 | 2 | 2 | 2 | 2 |
| | 9 | 0 | 0 | 0 | 1 | 1 | 1 | 1 | 1 | 2 |
| | 10 | 0 | 0 | 0 | 1 | 1 | 1 | 1 | 2 | 2 |
| | 11 | 0 | 0 | 0 | 0 | 0 | 1 | 2 | 2 | 2 |
| | 12 | 0 | 0 | 0 | 0 | 1 | 2 | 2 | Ā | |
| | 13 | 0 | 0 | 0 | 1 | 1 | 1 | 2 | Ā | |
| PLX 1m | 1 | 0 | 0 | 0 | 0 | 0 | 2 | 2 | Ā | |
| | 2 | 0 | 0 | 0 | 0 | 0 | 1 | 1 | 2 | 2 |
| | 3 | 0 | 0 | 0 | 0 | 0 | 0 | 1 | 1 | 2 |
| | 4 | 0 | 0 | 0 | 0 | 0 | 1 | 1 | 2 | 2 |
| | 5 | 0 | 0 | 0 | 0 | 0 | 1 | 2 | 2 | 4 |
| | 6 | 0 | 0 | 0 | 0 | 0 | 1 | 2 | Ā | |
| | 7 | 0 | 0 | 0 | 0 | 0 | 0 | 0 | 0 | 0 |
| | 8 | 0 | 0 | 0 | 0 | 0 | 1 | 1 | 1 | 2 |
| PLX 3m | 1 | 0 | 0 | 0 | 0 | 0 | 1 | Ā | | |
| | 2 | 0 | 0 | 0 | 0 | 0 | 0 | 0 | 0 | 0 |
| | 3 | 0 | 0 | 0 | 0 | 0 | 1 | 1 | 1 | 2 |
| | 4 | 0 | 0 | 0 | 0 | 1 | 2 | 2 | 2 | 2 |
| | 5 | 0 | 0 | 0 | 0 | 1 | 2 | 2 | 2 | 4 |
| | 6 | 0 | 0 | 0 | 0 | 1 | 1 | 1 | 1 | 1 |

FIG. 25A

| patient | BRAF status | Neurologic presentation | Macrophage morphology | Morphologic features of reactive infiltrate | Neuronal loss | Demyelination | Astrogliosis |
|---|---|---|---|---|---|---|---|
| ECD#1 | V600E | Insidious onset of dysarthria and difficulty with balance | Amoeboid | Intermixture of small lymphocytes. No granulocytes. | + | + | + with RF formation |
| ECD#2 | V600E | Mild dysmetria, decreased left facial sensation, myelopathic gait with several upper motor neuron signs | Amoeboid | Intermixture of small lymphocytes. No granulocytes. | + | - | + |
| ECD#3 | V600E | Multiple endocrinopathies, severe visual impairment, ataxia, and cognitive impairment | Amoeboid | Intermixture of small lymphocytes. No granulocytes. | n/a | n/a | n/a |

FIG. 27A

| | Brain Region | Population | mutant count | wt count | total counts | Allele Freq (%) |
|---|---|---|---|---|---|---|
| BRAF(V600E) by ddPCR | Frontal | NeuN | 0 / 0 / 0 | 4726 / 4987 / 2388 | 4726 / 4987 / 2388 | 0 / 0 / 0 |
| | | DN | 0 / 0 / 0 | 3665 / 5824 / 2681 | 3665 / 5824 / 2681 | 0 / 0 / 0 |
| | | Pu.1 | 3 / 0 / 1 | 8053 / 5791 / 1766 | 8056 / 5791 / 1767 | 0.04 / 0 / 0.06 |
| | | Whole Tissue | 0 / 0 | 8855 / 2493 | 8855 / 2493 | 0 / 0 |
| | Temporal | NeuN | 0 / 0 | 3976 / 3359 | 3976 / 3359 | 0 / 0 |
| | | DN | 0 / 0 | 3349 / 4590 | 3349 / 4590 | 0 / 0 |
| | | Pu.1 | 0 / 0 | 6810 / 2455 | 6810 / 2455 | 0 / 0 |
| | | Whole Tissue | 0 | 2958 | 2958 | 0 |
| | Cerebellum | NeuN | 0 / 3 | 6220 / 6518 | 6220 / 6521 | 0 / 0.05 |
| | | DN | 0 / 0 | 9042 / 3909 | 9042 / 3909 | 0 / 0 |
| | | Whole Tissue | 30 | 12476 | 12506 | 0.24 |
| | Hippocampus | NeuN | 1 | 4909 / 3156 | 4909 / 3157 | 0 / 0.03 |
| | | DN | 0 | 3367 | 3367 | 0 / 0 |
| | | Whole Tissue | 29 | 3159 | 3188 | 0.91 |
| | Pons | NeuN | 0 | 1712 | 1712 | 0 |
| | | DN | 5 | 1967 | 1972 | 0.25 |
| | | Whole Tissue | 9 | 1658 | 1667 | 0.54 |
| | Midbrain | NeuN | 0 | 642 | 642 | 0.00 |
| | | DN | 0 | 4259 | 4259 | 0.00 |
| | | Whole Tissue | 1 | 2980 | 2981 | 0.03 |
| | Medulla oblongata | NeuN | 0 | 349 | 349 | 0.00 |
| | | DN | 0 | 2410 | 2410 | 0.00 |
| | | Pu.1 | 1 | 829 | 830 | 0.12 |
| | | Whole Tissue | 0 | 1115 | 1115 | 0.00 |
| | Amygdala | NeuN | 0 | 5551 | 5551 | 0 |
| | | DN | 0 | 5738 | 5738 | 0 |
| | | Whole Tissue | 2 | 4505 | 4507 | 0.04 |
| | Blood | Myeloid | 0 / 1 / 0 | 41 / 1995 / 5674 | 41 / 1996 / 5674 | 0 / 0.05 / 0 |
| | | Lymphoid | 0 / 0 / 2 | 43 / 2393 / 5750 | 43 / 2393 / 5752 | 0 / 0 / 0.03 |

FIG. 27B

| | Brain Region | Population | mutant count | wt count | total counts | Allele Freq (%) |
|---|---|---|---|---|---|---|
| Heme-PACT BRAFV600E: (Missense_c.1799T>A) | Frontal | NeuN | 0 | 446 | 446 | 0.00 |
| | | DN | 0 | 459 | 459 | 0.00 |
| | | Pu.1 | 0 | 473 | 473 | 0.00 |
| | | Whole Tissue | 0 | 416 | 416 | 0.00 |
| | Temporal | NeuN | 0 | 371 | 371 | 0.00 |
| | | DN | 0 | 459 | 459 | 0.00 |
| | | Pu.1 | 0 | 445 | 445 | 0.00 |
| | | Whole Tissue | 0 | 533 | 533 | 0.00 |
| | Cerebellum | NeuN | 2 | 614 | 616 | 0.32 |
| | | DN | 0 | 562 | 562 | 0.00 |
| | | | | | | |
| | | Whole Tissue | 2 | 311 | 313 | 0.64 |
| | Hippocampus | NeuN | 0 | 406 | 406 | 0.00 |
| | | DN | 2 | 437 | 439 | 0.46 |
| | | | | | | |
| | | Whole Tissue | 3 | 510 | 513 | 0.58 |
| | Blood | Myeloid | 1 | 511 | 512 | 0.20 |
| | | Lymphoid | 0 | 408 | 408 | 0.00 |

SHARED AND LOCAL MUTATIONS

Unique PU1 mutations
N: 54, AF. 1% - 9% except for 2 mutations (*) common to hippocampus and cerebellum.

Unique NeuN mutations
N:35, AF 1% - 20%

KINASE MUTATION-ASSOCIATED NEURODEGENERATIVE DISORDERS

CROSS-REFERENCE TO RELATED APPLICATIONS

This application is a National Stage Application of PCT/US2018/047964, filed Aug. 24, 2018, which claims the benefit of and priority to U.S. Provisional Patent Application No. 62/550,536, filed Aug. 25, 2017, the entire contents of which are incorporated herein by reference.

STATEMENT OF RIGHTS UNDER FEDERALLY-SPONSORED RESEARCH

This invention was made with government support under grant number CA008748 awarded by the National Institutes of Health. The government has certain rights in the invention.

TECHNICAL FIELD

The present disclosure relates to a method for treatment of neurodegenerative disorders.

BACKGROUND

The pathophysiology of neurodegenerative diseases is poorly understood and therapeutic options are few. Neurodegenerative diseases are hallmarked by progressive neuronal dysfunction and loss, and chronic glial activation. Whether microglial activation, which is viewed in general as a secondary process, is harmful or protective in neurodegeneration remains unclear.

BRAF is a serine/threonine-protein kinase that is part of the RAS/MAPK/ERK signaling pathway, which affects cell senescence or proliferation, differentiation, and secretion, depending on the cell type. The BRAF$^{V600E}$ point mutation results in constitutive ERK activation, and is present in numerous tumors including melanomas, thyroid, colon and liver carcinoma, and hairy cell leukemia (HCL), as well as in clonal macrophage disorders known as histiocytoses. Histiocytoses display considerable heterogeneity in terms of prognostic and clinical presentation, and are characterized by the occurrence of neurodegenerative syndromes. Microglia belong to the lineage of tissue macrophages that develop during organogenesis from yolk-sac erythro-myeloid progenitors (EMPs) distinct from haematopoietic stem cells. However, the cellular consequences of BRAF$^{V600E}$ expression in microglia and the role of BRAF inhibitors for treating neurodegenerative disease have not been investigated.

SUMMARY

The technology of the present disclosure is based on the observation that the conditional expression of a BRAF$^{V600E}$ allele in a small number of erythro-myeloid progenitors (EMPs) does not grossly affect embryonic development, but results in the accumulation of BRAF$^{V600E}$ macrophage clones in various tissues and causes neurodegeneration.

By developing novel genetically and phenotypically accurate murine models of disease, it is possible to comprehensively explore the effects of BRAF$^{V600E}$ expression in tissue macrophages and other myeloid cells. The animal model described herein overcomes a limitation of previous murine models where constitutive expression of Cre resulted in a very high frequency of cells expressing BRAF$^{V600E}$ within hematopoietic cells of different lineages, which may not accurately model the behavior of a limited number of BRAF$^{V600E}$ progenitors of a particular hematopoietic lineage in competition with wild type progenitors in patients.

In one aspect, the present disclosure provides a method for treating or preventing BRAF$^{V600E}$-associated neurodegenerative disease in a subject in need thereof, comprising administering to the subject a therapeutically effective amount of a BRAF, MEK, and/or CSF-1R inhibitor or a pharmaceutically acceptable salt thereof. In some embodiments, at least a portion of the resident macrophages in the central nervous system of the subject are BRAF$^{V600E+}$.

In one aspect, the present disclosure provides a method for treating or preventing BRAF$^{V600E}$-associated neurodegenerative disease comprising: (a) isolating resident macrophages from a neuronal environment of the subject; (b) determining whether the resident macrophages express BRAF$^{V600E+}$; and (c) administering to the subject a therapeutically effective amount of a BRAF, MEK, and/or CSF-1R inhibitor, or a pharmaceutically acceptable salt thereof, when the isolated resident macrophages express BRAF$^{V600E+}$.

In some embodiments of the methods disclosed herein, the neurodegenerative disease is characterized by one or more of impaired cognitive functions, dementia, ataxia, dysarthria, reduced motor coordination and synchrony as compared to a normal control subject, paralysis, microglia accumulation, astrogliosis, microglia phagocytosis, demyelination, neuronal loss in the central nervous system, synaptic loss in the central nervous system, and amyloid precursor protein (APP) deposits in the brain.

In some embodiments of the methods disclosed herein, the BRAF inhibitor is selected from the group consisting of vemurafenib, dabrafenib, encorafenib, PLX7904, PLX8394, GDC-0879, LGX818, and PLX4720, the MEK inhibitor is selected from the group consisting of AZD8330, refametinib, E6201, MEK162 (binimetinib), PD0325901, pimasertib, R04987655, selumetinib, TAK-733, GDC-0623, WX-544, cobimetinib, and trametinib, and the CSF-1R inhibitor is selected from the group consisting of GW2580, BLZ945, pexidartinib (PLX3397), ARRY-382, PLX7486, and JNJ-40346527. In some embodiments, the BRAF inhibitor is vemurafenib. In some embodiments, the BRAF inhibitor is PLX4720.

In some embodiments of the methods disclosed herein, the route of administration of the BRAF, MEK, or CSF-1R inhibitor is parenteral, intradermal, intramuscular, intraperitoneal, intravenous, subcutaneous, intranasal, epidural, oral, sublingual, intranasal, intracerebral, intrathecal, intravaginal, transdermal, rectal, by inhalation, or topical.

In some embodiments of the methods disclosed herein, treatment of the neurodegenerative disease comprises one or more of improving cognitive functions, reducing dementia, reducing ataxia, reducing dysarthria, increasing motor coordination and synchrony, relieving paralysis, reducing microglia accumulation, reducing astrogliosis, reducing microglia phagocytosis, reducing demyelination, reducing neuronal loss, reducing synaptic loss, or reducing amyloid precursor protein (APP) expression in the brain as compared to an untreated control.

In one aspect, the present disclosure provides a method for treating or preventing neurodegenerative disease in a subject in need thereof, comprising administering to the subject a therapeutically effective amount of a PI 3-kinase inhibitor or a pharmaceutically acceptable salt thereof, wherein at least a portion of the resident macrophages in the central nervous system of the subject comprise one or more PI 3-kinase mutations. In some embodiments, at least a portion of the resident macrophages in the central nervous system of the subject are $PIK3CA^{H1047R+}$. In some embodiments, the PI 3-kinase inhibitor is selected from the group consisting of idelalisib, BKM120, GDC-0980, PF-04691502, XL147, IPI-145, BYL719, SF1126, BAY80-6946, GSK2126458, NVP-BEZ235, GDC-0941, PX-866, XL765, and ZSTK474.

In some embodiments of the methods disclosed herein, the route of administration of the PI 3-kinase inhibitor is parenteral, intradermal, intramuscular, intraperitoneal, intravenous, subcutaneous, intranasal, epidural, oral, sublingual, intranasal, intracerebral, intrathecal, intravaginal, transdermal, rectal, by inhalation, or topical.

In another aspect, the present disclosure relates to non-human animals, for example rodents, that conditionally express a mutant BRAF allele that confers a pathological phenotype on the non-human animal expressing the allele. In one embodiment, the pathological phenotype is histiocytosis.

In one embodiment, the non-human animal of the disclosure is characterized by expression of $BRAF^{V600E}$ in erythromyeloid progenitors.

In another aspect, the non-human animals comprise a mutant BRAF allele flanked upstream and downstream with site-specific recombinase recognition sites (SRRSs), and the non-human animal comprises a recombinase that recognizes the SRRSs, wherein the recombinase is inducible.

In a another aspect, the present disclosure relates to a genetically modified mouse that comprises a nucleic acid construct comprising a mutant exon encoding a $BRAF^{V600E}$ mutation, wherein the mutant is flanked upstream and downstream by SRRSs and the mouse comprises an inducible recombinase gene encoding a recombinase. In one embodiment, the SRRSs are recognized by the inducible Cre recombinase.

In one aspect, the present disclosure relates to a genetically modified mouse comprising the genotype $Csf1r^{iCre}$; $BRAF^{V600E}$; $Rosa26^{LSL-YFP}$.

In another aspect, the present disclosure relates to a method for recapitulating development of neurodegeneration in clonal histiocytic disorders comprising: (a) providing a transgenic mouse whose genome comprises a $BRAF^{V600E}$ transgene and a $Rosa26^{LSL-YFP}$ transgene, the transgenes operably linked to a tamoxifen-inducible regulatory sequence for expression of $BRAF^{V600E}$ and YFP in erythromyeloid progenitors (EMPs) of said mouse, and $Csf1r^{MeriCreMer}$; (b) contacting said mouse in utero with 4-hydroxy-tamoxifen (OH-TAM) wherein expression of $BRAF^{V600E}$ and $Rosa26^{LSL-YFP}$ is induced in EMPs of said mouse. The mouse (embryo) is exposed to OH-TAM at E8.5.

BRIEF DESCRIPTION OF THE DRAWINGS

(FIG. 3A) is a graphic showing the breeding scheme. (FIG. 3B) Embryonic lethality of $Csf1r^{iCre+}$; $BRAF^{V600E}$; $Rosa26^{LSL-YFP}$ mice, black bars represent the % of mice born from the cross depicted in (FIG. 3A) according to their genotype (n=39). (FIG. 3C) Brightlight (upper panel) and epifluorescence microscopy (lower panel) of $Csf1r^{iCre+}$; $BRAF^{WT}$; $Rosa26^{LSL-YFP}$ and $Csf1r^{iCre+}$; $BRAF^{V600E}$; $Rosa26^{LSL-YFP}$ embryos showing hemorrhagic foci in the liver (arrow) and accumulation of YFP+ cells in fetal liver. Cross (†) indicates dead embryo. (FIG. 3D) $Csf1r^{iCre+}$; $BRAF^{V600E}$; $Rosa26^{LSL-YFP}$ mice are associated with 100% lethality beyond E14.5.

(FIG. 5A) Breeding scheme. (FIG. 5B) % of mice born from the cross depicted in (FIG. 5A) according to their genotype (n=201). (FIGS. 5C and 5D) Flow cytometric analysis and IF analysis of livers of 4-week old mice. YFP+ cells are F4/80hi CD11blo (gated on CD45+ cells). (FIG. 5E) Histologic analysis of the brain. Clusters of YFP+ cells in the cerebellum and brainstem. YFP+ cells also stain for CD68 (and Iba1, not shown).

(FIG. 6A) Test of limb-clasping reflexes of 6-8-month old mice. When lifted by the tail $BRAF^{WT}$ mice behave normally, extending their hind limbs. In contrast, $BRAF^{V600E}$ mice bend their legs towards their trunk. (FIG. 6B) Cumulative incidence rate of behavioral abnormalities. (FIG. 6C) Footprint assay assessing locomotion defects. Front paws were painted with red ink, hind paws with blue ink. $BRAF^{V600E}$ mice lose coordination; front/hind legs do not overlap, and later mice are paralyzed (far right panel). (FIG. 6D) Measurement of footprint assay. Numbers below graphs correspond to the measurements performed as displayed in (FIG. 6C).

(FIG. 7A) Iba1+ microglia accumulate in the white matter. (FIG. 7B) Flow cytometry analysis of F4/80+ macrophages from the spinal cord. Littermates are color-coded.

(FIG. 8A) Luxol fast blue stain shows demyelination and leukocyte infiltration in the white matter of the spinal cord. (FIG. 8B) Flow cytometry analysis shows that CD3+ cells accumulate in the spinal cord in Cre+ $BRAF^{V600E}$ mice.

FIGS. 9A and 9B show histological analysis of the spinal cord from 6-month old $BRAF^{V600E}$ and control mice. Immunostaining was performed with CD68, GFP, and pERK antibodies.

(FIG. 11A) Flow cytometry analysis of total and YFP+ Kupffer cells. Littermates are color-coded. (FIG. 11B) Histological analysis shows accumulation of YFP+ Kupffer cells (stained with a cross-reactive GFP antibody). (FIG. 11C) Serum analysis of liver enzymes.

(FIGS. 13A and 13B) Breeding scheme for experimental mice and genotype distribution (n=342). (FIGS. 13C and 13D) YFP expression on BM LSK, blood leukocytes and microglia from 1-month-old mice, representative of n=5 per group. (FIG. 13E) Proportion of YFP$^+$F4/80$^+$ cells in tissues from 1-month-old mice. Circles represent individual mice. Unpaired two-tailed t-test. (FIG. 13F) A>T transversion encoding BRAF$^{V600E}$ in YFP$^+$ Kupffer cells at the Braf locus. Red and blue bars indicate forward and reverse strands. (FIG. 13G) Ki67 and cleaved Caspase 3 (Casp3) expression in YFP$^+$ microglia from 1-month-old brains. n=5 per group. Unpaired two-tailed t-test. (FIG. 13H) GSEA of differentially expressed genes in YFP$^+$ microglia from BRAF$^{VE}$ (n=3) and littermates (n=2) mice. q-value <0.01. (FIG. 13I) Heatmap representation of selected genes from (FIG. 13H), values are displayed as z-score. See also FIG. 17.

(FIG. 14A) Footprint assays. Front and hind paws are painted with red and blue ink, respectively, n=20 mice per group. (FIG. 14B) Limb-clasping reflexes in 6-8-month old mice. n=10 per group. (FIG. 14C) Cumulative incidence of behavioral abnormalities in BRAF$^{VE}$ mice and controls. Log-rank (Mantel-Cox) test. (FIG. 14D) Overlap distance, and stride length of mice on control or PLX4270 diet from 1 month or 3 months of age. Average values±s.d. for each group, 2 way ANOVA, *p<0.05, p<0.01, *p<0.001. (FIG. 14E) Disease progression in mice from (d), average score excluding mice euthanized for paralysis (†). (FIG. 14F) Cumulative incidence of behavioral abnormalities in mice from (d). Log-rank (Mantel-Cox) test (FIG. 14G) Scheme depicting microglia (Iba1) and neuronal (NeuN) densities in brain regions from BRAF$^{VE}$ and BRAF$^{WT}$ (n=4 per group). (FIG. 14H) Iba1 staining and quantitative analysis of microglial accumulation (Iba1+), phagocytosis (Iba1+/Lamp2+), astrogliosis (GFAP+308), relative synapse density (determined by Synaptophysin and Homer1), neuronal loss (NeuN) and amyloid precursor protein (APP) in brainstem from 5-9 month-old BRAF$^{VE}$ mice on control diet (n=4), BRAF$^{VE}$ mice on PLX diet (n=4-6), and BRAF$^{WT}$ (n=4). One-way ANOVA. See also FIGS. 20 and 22.

(FIG. 15A) CD68, YFP and pERK staining in spinal cord from 7-month old mice. Scale bars=500 µm, 10 µm for insets. n=4 per group. (FIG. 15B) pERK$^+$ microglia in brainstem. Circles represent individual mice. One-way ANOVA. (FIG. 15C) ERK phosphorylation in spinal cords and brains from 6-9 month-old mice. Top: representative western blot, bottom: pERK/ERK ratio, n=5 per group. One-way ANOVA. (FIG. 15D) pERK expression in YFP$^+$ microglia from BRAF$^{VE}$ mice. n=5 per group. Scale bars=5 µm. (FIG. 15E) Numbers of microglia from 5-9 month-old mice Circles represent individual mice. One-way ANOVA. (FIG. 15F) Heatmap representation of cell frequency among CD45$^+$ in the brain littermates. n=3 per group. (FIG. 15G) Ki67$^+$ and cleaved Caspase 3$^+$ (Casp3) expression in YFP$^+$ microglia from 5-9 month-old BRAF$^{VE}$ mice. n=6 per group. Unpaired two-tailed t-test. See also FIG. 23.

(FIG. 16A) GSEA of differentially expressed genes in YFP$^+$ microglia from 6-7 month-old littermates. q-value <0.05. EMT: epithelial-mesenchymal transition. (FIG. 16B) Heatmap representation of selected DEG, values are displayed as z-score. (FIG. 16C) Validation of gene expression in YFP$^+$ microglia. n=5 per group. FMO: fluorescence minus one. (FIG. 16D) Il1b expression in spinal cords from 6-7 month-old mice. n=3 per group. Scale bars=10 µm. (FIG. 16E) Bioplex analysis of Il1b and Il17a in spinal cords from 6-9 month-old mice. Circles represent individual mice. Unpaired two-tailed t-test. (FIG. 16F) Collagen IV and collagen VI expression in spinal cord from (FIG. 16D). n=3 per group. Scale bars=10 µm. (FIG. 16G) CD163, pERK and BRAF$^{V600E}$ expression in Erdheim-Chester disease (ECD) brain tissue. Scale bar upper panels: 40 µm, lower panels: 5µm. (FIG. 16H) Quantification of pERK microglia in control (n=6) and ECD (n=3) brains. Mann-Whitney test. (FIG. 16I) Heatmap representation of selected genes from RNA-seq analysis of brain tissue from 5 control brains and 2 histiocytoses patients (Juvenile Xanthogranuloma (JXG) and Langerhans Cell Histiocytosis (LCH)), values are displayed as z-score. q-value <0.01. See also FIG. 25.

(FIG. 17A) % of mice born from the cross depicted in FIG. 13a according to their genotype (n=42), but no injection of hydroxy-tamoxifen (4-OHT) to test for adverse effects of 4-OHT administration. (FIG. 17B) Flow cytometry analysis of YFP expression on blood leukocytes. Representative for n=8 per genotype. (FIG. 17C) Flow cytometry analysis of YFP$^+$ cells in the liver. YFP$^+$ cells, present only in Csf1r$^{MeriCreMer+}$ (Cre$^+$) mice (upper panels), fall into the F4/80$^+$CD11b$^+$ Kupffer cell gate (lower panels). Representative for n=8 per genotype. (FIG. 17D) YFP expression by immunofluorescence in the liver of BRAF$^{VE}$ mice and BRAF$^{WT}$ YFP$^+$ cells are F4/80$^+$ Kupffer cells. Representative of n=6 mice per genotype. Scale bars=200 µm (5 µm for insets). (FIG. 17E) Total tissue-resident macrophages cell numbers per gram (FIG. 17G) of tissue were analyzed by flow cytometry in BRAF$^{VE}$ mice (n=4) and BRAF$^{WT}$ (n=6). Circles represent individual mice. Unpaired two-tailed t-test. (FIG. 17F) In situ analysis of phospho-Histone H3 (pHis3) staining in YFP$^+$ cells from brains of BRAF$^{VE}$ and BRAF$^{WT}$ Circles represent individual mice (n=3). Unpaired two-tailed t-test. (FIG. 17G) RNA-seq analysis, heatmap representation of MAPK target genes in YFP$^+$ microglia from BRAF$^{VE}$ (n=3) and BRAF$^{WT}$ (n=2) mice, values are displayed as z-score. (FIG. 17H) Histological analysis of liver, lung, kidney and spleen in BRAF$^{VE}$ mice and BRAF$^{WT}$. Representative of n=4 mice per genotype. Scale bars=100 µm (10 µm for insets).

(FIG. 18A) Breeding scheme. (FIG. 18B) Embryonic lethality of Csf1r$^{iCre+}$; BRAF$^{LSL-V600E}$; Rosa26L$^{SL-YFP}$ mice, black bars represent the % of mice born from the cross depicted in (FIG. 18A) according to their genotype (n=39). (FIG. 18C) Brightlight (upper panel) and epifluorescence microscopy (lower panel) of Csf1r$^{iCre+}$ BRAF$^{VE}$ and Csf1r$^{iCre+}$; BRAF$^{WT}$ embryos showing haemorrhagic foci in the liver (arrow) and accumulation of YFP$^+$ cells in fetal liver. † indicates dead embryo. Pictures are representative of n=3 per genotype. (FIG. 18D) Mouse embryos found alive during different developmental stages. Csf1r$^{iCre+}$; BRAF$^{LSL-V600E}$; Rosa26$^{LSL-YFP}$ mice are associated with 100% lethality beyond E14.5. (FIG. 18E) Liver weight in E12.5 embryos. Circles represent individual mice. n=8 for WT; Cre$^-$, n=14 for VE; Cre$^-$, n=16 for VE; Cre$^-$, n=12 for VE; Cre$^+$. One-way ANOVA. (FIG. 18F) Flow cytometry analysis of Lin$^-$Kit$^+$ blast, erythroid cell (Ter119) and hematopoietic stem cell numbers (LSK CD150$^+$CD48$^-$ and CD150$^-$CD48$^-$) in the E12.5 fetal liver and of E12.5 tissue-resident macrophages in the limbs, head and liver. Circles represent individual mice. n=4 for BRAF$^{WT}$ and n=6 for BRAF$^{VE}$. Unpaired two-tailed t-test.

(FIG. 19A) Kaplan-Meier survival curve of BRAF$^{VE}$ (n=16) and BRAF$^{WT}$ (n=66) controls. Log-rank (Mantel-Cox) test. (FIG. 19B) Representative photographs of lung and spleen from BRAF$^{VE}$ mice at time of death with representative BRAF$^{WT}$ control organs. (FIGS. 19C and 19D) Hematoxylin and eosin (HE) stain of lung tissue from BRAF$^{VE}$ and littermate controls. (FIG. 19E) CD68 immunohistochemistry (IHC) of BRAF$^{VE}$ lung tissue. (FIG. 19F) HE stain of liver tissue from BRAF$^{VE}$ and littermate controls with magnified view of granuloma in the BRAF$^{VE}$ liver. (FIG. 19G) HE stain of bone marrow (BM) from BRAF$^{VE}$ and littermate controls with CD68 IHC of BRAF$^{VE}$ mouse. All pictures for (FIGS. 19B-19GA) are representative of n=5 per genotype.

FIGS. 20A-20G. Longitudinal study and PLX treatment of the Csf1r$^{MeriCreMer}$; BRAF$^{V600E}$; Rosa26$^{LSL-YFP}$ mice. (FIGS. 20A and 20B) Latency to fall in the rotarod assay and footprint assay quantification for BRAF$^{VE}$ mice (n=7) and BRAF$^{WT}$ (n=8). (FIG. 20A) Rotarod assay at 1 to 4 months of age. Values are mean±s.d. (FIG. 20B) Rotarod and footprint assay at 4 months of age displaying single values. Mice that are score 1 are labeled in red. (FIG. 20C) Footprint assay quantification of BRAF$^{VE}$ mice at score 1 and littermate controls. Circles represent individual mice. n=10 for BRAF$^{WT}$ and n=11 for BRAF$^{VE}$. (FIG. 20D) Representative weight curve of BRAF$^{WT}$ and BRAF$^{VE}$ mice on control or PLX4720 diet. (FIG. 20E) PLX4720 concentration in serum (ng/ml), liver and brain (ng/g) of 7-9 month old BRAF$^{WT}$ (n=9) and BRAF$^{VE}$ mice placed on the diet at 1 (n=8) or at 3 months (n=3) of age. Circles represent individual mice. (FIG. 20F) Footprint assay quantification from BRAF$^{VE}$ mice on PLX4720 diet at 1 month (n=8) or at 3 months (n=6) and control (Ctrl) diet (n=13) and BRAF$^{WT}$ (n=32, black). Mice reaching paralysis were excluded from further analysis. See also (FIG. 20G) where † indicates when BRAF$^{VE}$ animals were euthanized. Values are mean±s.d. 2 way ANOVA comparing treated and not treated BRAF$^{VE}$ mice. *p<0.05, p<0.01, *p<0.001. (FIG. 20G) Disease progression for BRAF$^{VE}$ mice on control or PLX4720 diet. † indicates animal death due to paralysis.

(FIG. 21A) Histological analysis by hematoxylin and eosin (HE) and Luxol-fast-blue-PAS (LFB-PAS) and immunohistochemistry analysis of T-cells (CD3), B-cells (B220) and astrocyte activation (GFAP) in one-month old BRAF$^{VE}$ mice and BRAF$^{WT}$ Representative of n=5 per for BRAF$^{WT}$ and n=4 for BRAF$^{VE}$. (FIG. 21B) Immunohistochemistry analysis and quantification of Iba1$^+$ cell density, cortical neurons (NeuN) and expression of amyloid precursor protein (APP), a positive signal for neurodegeneration in one-month old BRAF$^{VE}$ mice and BRAF$^{WT}$. Representative of n=5 per for BRAF$^{WT}$ and n=4 for BRAF$^{VE}$ Circles represent individual mice. Scale bars=100 µm (10 µm for insets). Unpaired two-tailed t-test.

(FIG. 22A) Iba1 and GFAP immunohistochemistry of brain and spinal cord from 6-month-old BRAF$^{VE}$ and BRAF$^{WT}$. Anatomical regions of insets are indicated. Representative for n=5 BRAF$^{WT}$ and n=4 BRAF$^{VE}$. Scale bars=500 µm for spinal cords and 1 mm for brains (50 µm for insets). (FIG. 22B) Immunohistochemistry and immunofluorescence as used for quantification in FIG. 14H of brain stem for NeuN (neurons), APP (amyloid precursor protein) and GFAP (astrocytes), Iba1$^+$/Lamp2$^+$ cells (phagocytosis), Synaptophysin (Syn) and Homer1 (synapse density) and staining with Luxol-fast-blue (LFB)-PAS. Scale bars=100 µm (10 µm for insets). Iba1/Lamp2 scale bar=25 µm, Syn/Homer1 scale bar=10 µm. Representative for 6-9 month old BRAF$^{WT}$ (n=5), BRAF$^{VE}$ (n=4), and for BRAF$^{VE}$ on PLX diet (n=4-6). (FIG. 22C) LFB staining of spinal cord samples from (FIG. 22A). Scale bar=100 µm. (FIG. 22D) Immunohistochemistry of brain stem for B220 (B-cells) from BRAF$^{VE}$ on control and PLX diet. Representative for n=4 per genotype. Scale bars=10 µm (10 µm for insets).

(FIG. 23A) Representative pERK staining in Iba1$^+$ microglia as used for the quantification in FIG. 15B in brain stem of 5-9 month old BRAF$^{WT}$ and BRAF$^{VE}$ mice on control or PLX diet. Scale bar=50 µm. (FIG. 23B) Representative tSNE analysis of flow cytometry staining of CD45$^+$ cells from the brain of paralyzed BRAF$^{VE}$ mice and littermate controls. Arrow indicates expansion of F4/80$^+$ YFP$^+$ cells. Representative for n=3 per genotype. (FIG. 23C) FSC profile of YFP$^+$ and YFP$^-$ microglia from (FIG. 23B) from BRAF$^{VE}$ and BRAF$^{WT}$ mice indicates an increase of YFP$^+$ microglia cell size. Representative for n=3 per genotype. (FIG. 23D) Proportion of YFP$^+$F4/80$^+$ cells in indicated organs analyzed by flow cytometry. The proportion of YFP$^+$ among F4/80$^+$ cells from Cre$^+$BRAF$^{WT}$ on control diet was normalized and set to 1. Analysis was performed on 5-8 month-old BRAF$^{VE}$ mice (n=5-6) and BRAF$^{WT}$ mice (n=6) on control diet, and 7-9 month-old BRAF$^{VE}$ mice (n=6) and BRAF$^{WT}$ mice (n=4) on PLX diet. Circles represent values for individual mice. One-way ANOVA. *p<0.05, p<0.01, *p<0.001. (FIG. 23E) CD3 immunohistochemistry of brain and spinal cord from 6-month-old BRAF$^{VE}$ and BRAF$^{WT}$ Anatomical regions of insets are indicated. Representative for n=5 BRAF$^{WT}$ and n=4 BRAF$^{VE}$ Scale bars=500 µm for spinal cords and 1 mm for brains (50 µm for insets). (FIGS. 23F and 23G) Analysis of CD8$^+$, CD4$^+$ and Foxp3$^+$ T-cell numbers (FIG. 23F) and proliferation (FIG. 23G) in brain/spinal cord by flow cytometry in 5-8 month-old BRAF$^{VE}$ (n=4) and BRAF$^{WT}$ (n=6) on control diet, and 7-9 month-old BRAF$^{VE}$ (n=6) and BRAF$^{WT}$ (n=5) on PLX diet. Circles represent values for individual mice. One-way ANOVA.

(FIG. 24A) Proportion of YFP$^+$F4/80$^+$ cells in indicated organs from analyzed by flow cytometry. The proportion of YFP$^+$ among F4/80$^+$ cells from Cre$^+$ BRAF$^{WT}$ (n=6) was normalized and set to 1. Circles represent values for individual BRAF$^{VE}$ mice (n=7). Unpaired two-tailed t-test. (FIG. 24B) Analysis of liver Kupffer cells as in (FIG. 24A) was performed on 5-8 month-old BRAF$^{VE}$ (n=5) and BRAF$^{WT}$ (n=4) on control diet, and 7-9 month-old BRAF$^{VE}$ (n=6) and BRAF$^{WT}$ mice (n=4) on PLX diet. Circles represent values for individual mice. One-way ANOVA. *p<0.05, p<0.01, *p<0.001. (FIG. 24C)

Immunofluorescent analysis of pERK in F4/80+ Kupffer cells from 5-8 month-old BRAF$^{VE}$. Results are representative for n=3. (FIG. 24D) Serum analysis of BRAF$^{VE}$ mice (score 1, n=6) and their littermates controls (n=6). ALB: albumin, ALP: alkaline phosphatase, ALT: alanine aminotransferase, AST: aspartate aminotransferase. (FIG. 24E) Gross liver, lung, kidney and spleen structure (HE, Trichrome) of paralyzed BRAF$^{VE}$ and BRAF$^{WT}$. Representative of n=7 per genotype. Scale bars=200 μm (10 μm for insets). (FIG. 24F) Liver and spleen gross organs from paralyzed BRAF$^{VE}$ and BRAF$^{WT}$. Representative of n=5 per genotype.

FIGS. 25A-25C. Erdheim-Chester disease (ECD) patients. (FIG. 25A) Table summarizing observed pathological and molecular findings in brain tissue of three ECD patients with neurologic presentations. BRAF status was determined by immunohistochemical analysis and by sequencing. Neuronal loss and demyelination was determined by immunohistochemistry of neurofilament and myelin basic protein (MBP). RF: Rosenthal fiber. n/a: not applicable/no tissue available for further analysis. (FIG. 25B) Immunohistochemistry and immmunofluorescent analysis of ECD brain tissue for CD163, pERK and BRAF$^{V600E}$ (anti-BRAFVE1 antibody). Upper panel scale bar=200 μm. Lower panel scale bar=5 μm. (FIG. 25C) Immunohistochemistry analysis of ECD brain tissue for neurofilament and MBP shows areas of myelin deficits with preserved axons in the same region. Scale bar=200 μm.

(FIG. 26A) Nuclei extracted from ~350 mg of fresh frozen control brain tissue using a non-ionic detergent buffer containing DAPI and flow-sorted using anti-NeuN and anti-Pu.1. DN: double negative. (FIG. 26B) Top panel: Nuclei extraction and flow-sorting using anti-Pu.1 and anti-NeuN antibodies was performed in four different brain regions, two affected and two non-affected, obtained from a deceased patient with histiocytosis and neurodegenerative disease. Double negative (DN), NeuN+, and Pu.1+ populations were sorted for sequencing. Patient's blood was separated based on Lin+(lymphocytes) and Lin-HLA-DR+(myeloid cells, not shown). Bottom panel: FACS graph of nuclei isolated from 3 patients with Alzheimer's disease (AD), Parkinson's disease (PD), and Adult-Onset-Leukoencephalopathy with spheroids (ALSP). (FIG. 26C) Example of quality control of DNA obtained from AD patient. DNA is immediately isolated after nuclei sorting with QIAamp DNA Mini Kit (Qiagen). DNA quality is determined based on DNA Integrity Number (DIN) measured by Agilent 4200 TapeStation.

FIGS. 27A-27B. Analysis of BRAF$^{V600E}$ mutation in microglia, neuron, and glia nuclei from a 25-year old patient with neurodegeneration. (FIG. 27A) BRAF$^{V600E}$ allele frequency determined ddPCR in sorted nuclei from 8 brain areas from 1 patient with neurodegeneration, whole brain tissue and blood were processed for gDNA extractions using QIAamp DNA Mini Kit (Qiagen) and quality and quantity was determined with Agilent 4200 TapeStation. BRAF$^{V600E}$ allele frequency is determined by ddPCR in the same DNA samples before library preparation. Multiple numbers indicate independent determinations. Counts <5 are not reproducible and below sensitivity level. (FIG. 27B) BRAF$^{V600E}$ allele frequency determined by targeted deep sequencing (HEME-PACT, mean sequencing depth 409x) in sorted nuclei from four of the above brain areas, whole brain tissue, and blood. Approximately 200 ng of DNA were used for library preparation with KAPA HyperPrep Kit (Roche). Libraries are then captured with custom-designed biotinylated probes (NimbleGen) and sequenced with Illumina HiSeq 2500. Counts <4 (1%) are considered below sensitivity level.

(FIG. 31A) Cumulative incidence of behavioral abnormalities in PIK3CA$^{HR}$ mice and control. (FIG. 31B) Footprint assay example, which measures the overlap distance between hind and front paws.

DETAILED DESCRIPTION

Figure 1:
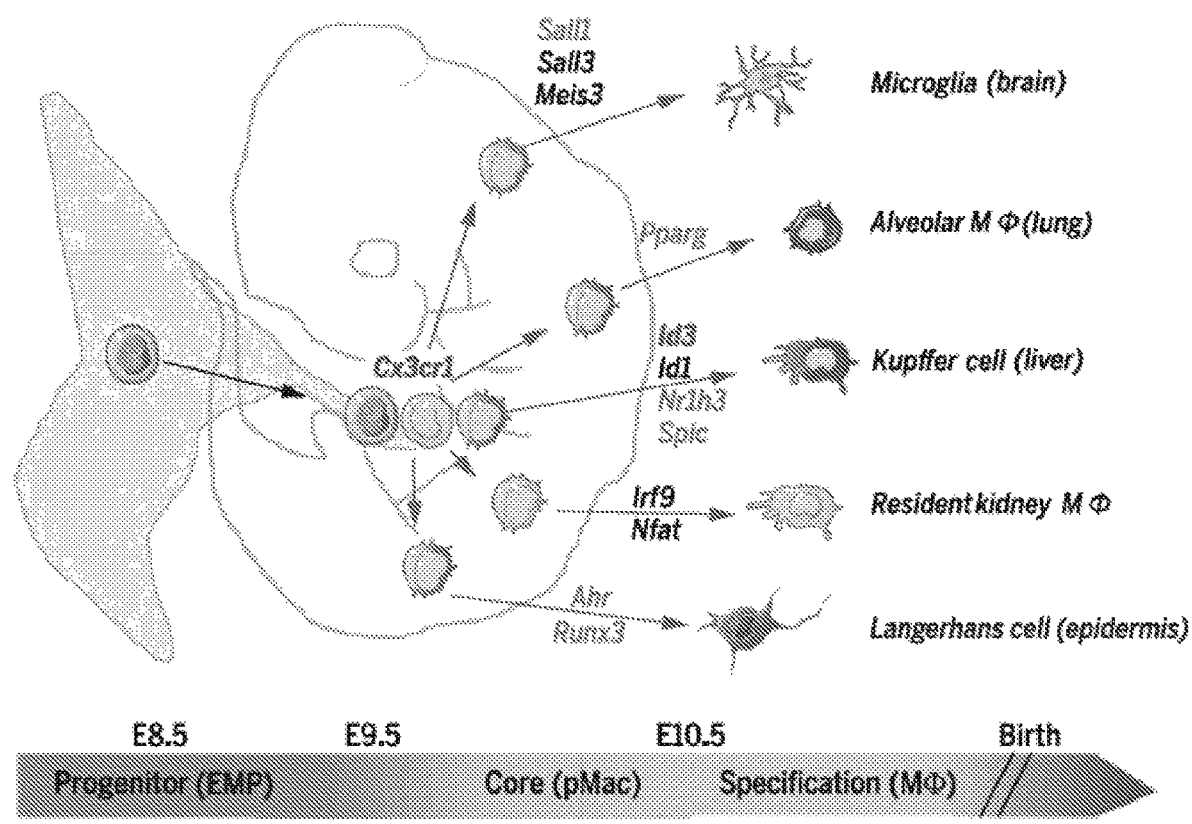
FIG. 1 is a schematic showing that the erythro-myeloid progenitors (EMP) from the yolk sac colonize the fetal liver and give rise to macrophage (MΦ) precursors that colonize the embryo from E9.5 in a Cx3cr1-dependent manner, to give rise to adult F4/80+ resident macrophages. MΦ specification, starting from E10.25, is initiated by the expression of tissue-specific transcriptional regulators.

All patents, published applications and other publications and references are hereby incorporated by reference in their entirety into the present disclosure.

It is to be appreciated that certain aspects, modes, embodiments, variations and features of the present technology are described below in various levels of detail in order to provide a substantial understanding of the present technology.

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a," "an," and "the" include plural referents unless the content clearly dictates otherwise. For example, reference to "a cell" includes a combination of two or more cells, and the like.

As used herein, the term "about" encompasses the range of experimental error that may occur in a measurement and will be clear to the skilled artisan.

The embryonic stages used herein relate to embryonic day (for example D1 is E1.0) of mouse development. This staging by "days" relate to in the female presence of a vaginal plug indicating that the mating occurred.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, the terms "subject," "individual," or "patient" can be an individual organism, a vertebrate, a mammal, or a human.

As used herein, a "therapeutically effective amount" of a compound refers to compound or agent levels in which the physiological effects of a disease or disorder are, at a minimum, ameliorated. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

"Treating," "treat," or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

The term "administer," "administering," or "administration" as used in this disclosure refers to either directly administering a therapeutic agent, such as, but not limited to, a BRAF, MEK, or CSF-1R inhibitor, or a combination of thereof, to a subject.

In certain embodiments, routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and will depend in-part upon the site of the medical condition. In most instances, administration results in the release of any agent described herein into the bloodstream. In specific embodiments, it may be desirable to administer locally to the area in need of treatment or blocking.

The term "neuronal environment" refers to "tissue" or cellular niche where the resident macrophages are found.

General

The technology of the present disclosure relates to the observation that conditional expression of a $BRAF^{V600E}$ allele in EMP clones in vivo does not grossly affect embryonic development, but results in the accumulation of $BRAF^{V600E}$ macrophage clones in various tissues, and is responsible for a neurodegenerative syndrome in adult mice that recapitulates for the first time one of the most poorly understood and adverse characteristics of human histiocytic neoplasms. Characterizing a yolk sac origin for Erdheim-Chester disease (ECD) and Langerhans Cell Histiocytosis (LCH) carries significant implications for the pathophysiology of these diseases, and in particular may illuminate the cause of neurodegenerative syndromes as well as liver/lung fibrosis in these disorders, which are only partially sensitive or even refractory to current therapy.

The involvement of somatic mutations that confer a proliferative, survival, or activation advantage (called "oncogenic" or "driver" mutations) in the clonal evolution of cancer is well known. Progress in sequencing technologies has revealed a high burden of somatic mutations, including driver mutations, in normal (non-tumoral) tissues and their association with neurodevelopmental disorders, neurodegeneration, and non-cancerous proliferative diseases. As an example, inherited mutations that activate the RAS/MAPK/ERK pathway are incompatible with life, or cause severe and early-onset tumoral, developmental, and neurodevelopmental disorders ("RASopathies") and are therefore rarely observed. However, somatic mosaicism for such mutations is frequently observed in "normal" tissues and results in distinct phenotypes that vary according to several factors related to the time at which mutations occur, including the cellular lineage(s) harboring the mutation, the size of the clone, defects in DNA repair, and the occurrence of secondary hits. For example, mosaicism for mutations activating the RAS pathway in the early embryo can cause RASopathies, while mosaicism restricted to melanocytes is responsible for limited melanocyte proliferation and activation and give rise to the common and giant nevi. Mosaicism for mutations activating the RAS pathway in macrophages causes histiocytic lesions, but causes leukemia in hematopoietic cells.

Tissue resident macrophages such as microglia in mice originate from erythro-myeloid precursors (EMP) after gastrulation. EMP-derived cells colonize the brain during embryogenesis to give rise to microglia that self-maintain in the adult brain due to their long life span and slow local proliferation. Therefore, resident macrophages, including microglia, develop and maintain independently from the hematopoietic stem cell (HSC) lineage that give rise to blood cells. A prediction from this model was that somatic mosaicism generated during development of microglia or later in life is stable over long periods of time as microglia self-maintain rather than turnover from blood derived progenitors. To test the hypothesis that somatic mutations that confer a proliferative/survival advantage and activate macrophages ("driver" mutations) may be pathogenic, $BRAF^{V600E}$ mutation the most frequent mutation that drives constitutive activation of the RAS-MEK-ERK pathway was expressed in a mosaic manner in EMPs in mouse embryos. It was observed that somatic mosaicism for the $BRAF^{V600E}$ in a limited number of embryonic EMP precursors does not have detectable effects on development but results in mosaicism of mutant macrophages well tolerated in all organs, except for the brain, where positive selection of microglia mutant clones is associated with the progressive development of the cardinal features of neurodegeneration: microgliosis, astrogliosis, synaptic loss, and neuronal death. Interestingly, as shown herein, treatment of adult mice with a $BRAF^{V600E}$ inhibitor (PLX) slows the course of the neurological disease and reduces its mortality.

The Cell Lineage of Origin of Histiocytoses.

Figure 2:
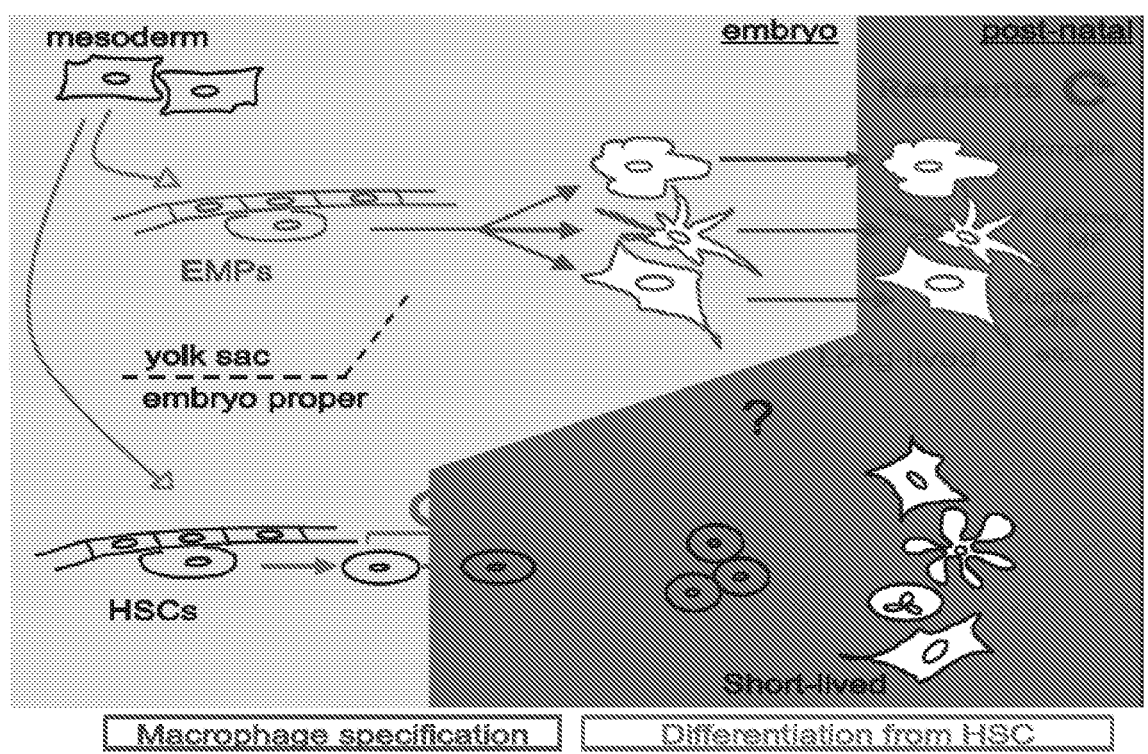
FIG. 2 is a schematic showing the developmental diversity of the myeloid system. EMPs emerge in the yolk sac at E8.5, migrate to the fetal liver, and give rise to fetal macrophages in vivo. Resident macrophages develop from EMPs in the absence of Myb and persist as residents in post-natal tissues. Within the embryo proper, the hemogenic endothelium of large arteries gives rise to Hematopoietic Stem Cells (HSCs) at ~E10.5. HSCs migrate to the fetal liver and to the bone marrow, where they persist, self-renew throughout life, and give rise to adult-type red blood cells, lymphoid cells and short-lived myeloid cells.

The previous "mononuclear phagocyte system" model, supported by bone marrow transplantation in irradiated hosts and in vitro studies over the past four decades, held that tissue macrophages originate and renew from hematopoietic stem cells (HSCs) via circulating progenitors such as blood monocytes. In contrast, recent studies have led to a major paradigm shift identifying that tissue-resident macrophages, including brain microglia, liver Kupffer cells, kidney macrophages, and Langerhans cells of the epidermis, persist in adult tissues with little contribution from bone marrow progenitors and monocytes. Instead, these cells develop during embryogenesis from yolk sac erythro-myeloid progenitors (EMP), cells distinct from HSCs (See FIGS. 1 and 2). In the model that follows from these findings, two distinct types of myeloid cells are considered: (i) tissue-resident macrophages, which contribute to cellular niches involved in tissue growth, morphogenesis, homeostasis and repair; and (ii) HSC-derived "passenger" leukocytes, including monocytes, which are recruited to inflamed or infected tissues to perform anti-microbial and immune-regulatory functions.

HSC Origin of Histiocytoses is Demonstrated in a Small Number of Cases.

In recent studies in human patients, the presence of a $BRAF^{V600E}$ mutation in CD34$^+$ bone marrow cells or blood monocytes was found in a small proportion of LCH patients. In murine models, previous attempts to analyze the role of $BRAF^{V600E}$ expression in hematopoietic cells in murine models have not succeeded in recapitulating many characteristic features of LCH and ECD. Interestingly, hematopoietic phenotypes differed greatly depending on the cell in which $BRAF^{V600E}$ was expressed. Constitutive expression of Cre recombinase to target the expression of $BRAF^{V600E}$ to HSC-derived progenitors in Vav$^{Cre}$; $BRAF^{V600E}$ mice or in all myeloid cells in Csf1r$^{Cre}$; $BRAF^{V600E}$ mice did not result in histiocytoses, but in a lethal and transplantable hematopoietic disorder in mouse embryos. Targeted expression of $BRAF^{V600E}$ in CD11c$^+$ cells that include dendritic cell precursors in the post-natal bone marrow also resulted in an aggressive leukemic-like disease with reduced lifespan and accumulation of circulating CD11c$^+$ cells in bone marrow, blood and peripheral organs. Interestingly, however, targeted expression of $BRAF^{V600E}$ in Langerin$^+$ cells resulted in the moderate accumulation of Langerin$^+$ dendritic cells in the lung and liver, an observation consistent with clinical features of LCH, although it does not recapitulate neurodegenerative disease or fibrotic disorders of the liver and lung, which represent key clinical problems in these diseases. As outlined below, Langerhans cells are part of the EMP-derived myeloid lineage, thus it is possible that both HSC-derived and EMP-derived resident macrophages could give rise to histiocytoses.

Tissue-Resident Macrophages Originate at Least in Part from EMPs from the Yolk Sac.

EMPs emerge from yolk sac hemogenic endothelium at embryonic day (E)8.25. They are distinguished from HSCs by the lack of lymphoid potential, both in vitro and in vivo, the lack of long term repopulating potential, and cell surface phenotype (Sca1$^-$ CD45$^{low}$ AA4.1$^+$, CD41$^+$, FcγRII/III$^+$). EMPs express Myb but, in contrast to HSCs, their commitment and differentiation into myeloid fate is unaltered in Myb-deficient embryos, although their erythroid potential is blocked. In vivo, EMPs are generated from Tie2$^+$ yolk sac ancestors from E7.5 to E10.5. They seed the fetal liver as early as E9.5. EMPs and EMP-derived Kit$^+$ cells can be detected until E14.5. EMPs are thus distinct from HSCs, which develop from the intra-embryonic hemogenic endothelium around embryonic day E10.5, require the transcription factor Myb to colonize the fetal liver and later the bone marrow, and give rise to specialized hematopoietic cells, including myeloid cells in postnatal mice. The present disclosure is based on several key observations (summarized below) that demonstrate that tissue-resident macrophages originate in large part from EMPs, and provide novel experimental tools and strategies for the study of histiocytoses. First, in two independent models of transplantation without irradiation the majority of F4/80$^{bright}$ macrophages are self-maintained and do not renew from bone marrow HSCs in most adult murine tissues, with the notable exception of the gut. These findings have been replicated by a number of investigators. Second, development of these resident F4/80$^{bright}$ macrophages is unaltered in Myb-deficient mice, lacking HSCs, thus providing the first genetic indication that resident macrophages develop from a progenitor distinct from HSCs. Third, F4/80$^{bright}$ macrophages in most adult mouse tissues were traced to progenitors that express Kit, CD45$^{low}$, AA4.1, and the Csf1-receptor (Csf1r) at E8.5, two days before HSCs are identified in the embryo, and developmental distinct from HSCs using Cre-mediated hydroxy-tamoxifen (OH-TAM) induced pulse-labeling in Csf1r$^{MeriCreMer}$ and Tie2$^{MeriCreMer}$ embryos. Altogether, it has been shown that EMPs colonize the fetal liver and give rise to pre-macrophages that colonize the embryo and differentiate into tissue macrophages. Thus, the majority of resident tissue macrophages that are present in mouse tissues originate from Kit$^+$, CD45$^{low}$, AA4.1$^+$, Csf1r$^+$ yolk sac early hematopoietic progenitors (defined as EMP) and can self-maintain in adults.

Resident Macrophages are a Diverse Family of Professional Phagocytes and "Accessory Cells" Involved in Tissue Remodeling.

Resident macrophages are sessile but continuously explore their immediate environment/niche using motile filopodia, recognize, and scavenge pathogens as well as unfit cells and cell debris, glycoproteins and lipids, and produce a large range of bioactive molecules and growth factors. In mammals, macrophages are found all over the body within each specialized tissue and their serous membranes. Long elongated dendritic filopodial processes frequently extend from their cell bodies and build up 3D network-like structures that provide for extensive contacts with specialized cells such as brain, liver, kidney, or epidermal cells, thereby allowing constant surveillance or scavenging of their tissue. Macrophages are involved in the clearance of apoptotic and senescent cells during organogenesis, in the brain, limbs and lung, in branching morphogenesis, and regulate blood and lymphatic vessel morphogenesis and maturation during fetal and postnatal development. They pursue this task in adults, contribute to the pruning of neuronal synapses, and scavenge and digest nuclei released daily by billions ($2\times10^{11}$ in humans) of maturing erythroblasts. Altogether, a considerable literature indicates that macrophages play a role as regulators of morphogenesis, homeostasis and tissue remodeling, inflammatory processes and tumor growth.

The distinction between monocytes and macrophages is relevant to disease pathogenesis and may be relevant to the pathophysiology of histiocytoses. Rossi and colleagues demonstrated that the two cell types have distinct expansion mechanisms and distinct functions in the brain during Experimental Auto-immune Encephalitis (EAE); infiltrating monocytes are recruited via extravasation from blood vessels and produce inflammatory mediators important for disease progression but do not persist after the resolution of inflammation, while in contrast activated resident microglia proliferate locally, persist, and return to quiescence following remission. In another elegant model, investigators showed that pleural resident macrophages adopt "anti-inflammatory" phenotypes in host carrying helminths while passenger monocytes exhibit pro-inflammatory responses. These studies underlie the notion that the two cell types, monocytes and macrophages, can exert distinct functions within the same environment and in response to the same challenge, suggesting that tissue cues or polarizing signals may not suffice to account for their functions. Of note, it might not be always accurate, however, to describe tissue macrophages as being anti-inflammatory as opposed to passenger monocytes being pro-inflammatory. For example, in a model of chronic neurodegeneration proliferating resident microglial cells were proposed to contribute to neuronal damage during the development of the disease.

Models to Study the Pathophysiology of Histiocytoses In Vivo.

The data discussed above suggested (1) that somatic BRAF$^{V600E}$ mutations in EMPs may be causative of histiocytoses, and (2) that BRAF$^{V600E}$ somatic mutations in HSCs and EMPs may have different consequences at the clinical, cellular, and molecular levels, and may thus contribute to the clinical heterogeneity of the disease and influence its prognosis and clinical course. As EMPs are not self-renewing and disappear in the late embryo the mutation would be detectable only in their progeny, the resident macrophages, and not in HSCs. Therefore, modeling BRAF$^{V600E}$ mutations in EMPs in mice is a strategy of choice to understanding its role in resident macrophage biology, should provide insight into the role of macrophages in promoting neurological dysfunction as well as lung and liver fibrosis, and may thus illuminate the pathophysiology of histiocytoses.

In one embodiment therefore, the technology of the present disclosure relates to a method for preventing or treating BRAF$^{V600E}$-associated neurodegeneration by administering to a subject in whom BRAF$^{V600E+}$ resident macrophages have been identified in the neuronal microenvironment of the subject a therapeutically effective amount of a BRAF, MEK, PI 3-kinase, Ras, and/or CSF-1R inhibitor. Suitable BRAF inhibitors include, but are not limited to, vemurafenib, dabrafenib, encorafenib, PLX7904, PLX8394, GDC-0879, LGX818, and PLX4720. Suitable MEK inhibitors include, but are not limited to, AZD8330, refametinib, E6201, MEK162 (binimetinib), PD0325901, pimasertib, R04987655, selumetinib, TAK-733, GDC-0623, WX-544, cobimetinib, and trametinib. Suitable PI 3-kinase inhibitors include, but are not limited to, idelalisib, BKM120, GDC-0980, PF-04691502, XL147, IPI-145, BYL719, SF1126, BAY80-6946, GSK2126458, NVP-BEZ235, GDC-0941, PX-866, XL765, and ZSTK474. Suitable Ras inhibitors include, but are not limited to, salirasib and TLN-4601. Suitable CSF-1R inhibitors include, but are not limited to, GW2580, BLZ945, pexidartinib (PLX3397), ARRY-382, PLX7486, and JNJ-40346527.

Therapeutic Methods

The following discussion is presented by way of example only, and is not intended to be limiting.

One aspect of the present technology includes methods of treating BRAF$^{V600E}$-associated neurodegenerative disease in a subject diagnosed as having, suspected as having, or at risk of having one or more BRAF$^{V600E}$ mutations comprising the administration of a BRAF, MEK, PI 3-kinase, Ras, and/or CSF-1R inhibitor. In some embodiments, the present technology includes methods of treating neurodegenerative disease in a subject in need thereof, wherein the neurodegenerative disease is characterized by cells expressing one or more BRAF$^{V600E}$ mutations. In some embodiments, the cells are resident macrophages in the central nervous system, or microglia. In some embodiments, the neurodegenerative disease is Alzheimer's disease, Parkinson's disease, Huntington's disease, amyotrophic lateral sclerosis (ALS), or multiple sclerosis. In some embodiments, treatment of a BRAF$^{V600E}$-associated neurodegenerative disease comprises relieving one or more symptoms selected from the group consisting of: impaired cognitive functions and dementia, ataxia, dysarthria, decreased motor coordination and synchrony, paralysis, microglia accumulation, astrogliosis, microglia phagocytosis, demyelination, neuronal loss, synaptic loss, and amyloid precursor protein (APP) expression.

One aspect of the present technology includes methods of treating phosphoinositide 3-kinases (PI 3-kinase)-associated neurodegenerative disease in a subject diagnosed as having, suspected as having, or at risk of having one or more mutations in one or more PI 3-kinases comprising the administration of a BRAF, MEK, PI 3-kinase, Ras, and/or CSF-1R inhibitor. In some embodiments, the present technology includes methods of treating neurodegenerative disease in a subject in need thereof, wherein the neurodegenerative disease is characterized by cells expressing one or more mutations in one or more PI 3-kinases. In some embodiments, the cells are resident macrophages in the central nervous system, or microglia. In some embodiments, the neurodegenerative disease is characterized by at least a portion of the resident macrophages in the central nervous system of the subject being PIK3CA$^{H1047R+}$. In some embodiments, the neurodegenerative disease is Alzheimer's disease, Parkinson's disease, Huntington's disease, or amyotrophic lateral sclerosis (ALS). In some embodiments, treatment of a PI 3-kinase-associated neurodegenerative disease comprises relieving one or more symptoms selected from the group consisting of: ataxia, decreased motor coordination and synchrony, paralysis, microglia accumulation, astrogliosis, microglia phagocytosis, demyelination, neuronal loss, synaptic loss, and amyloid precursor protein (APP) expression in the brain.

In therapeutic applications, compositions or medicaments comprising a BRAF inhibitor, MEK inhibitor, Ras inhibitor, PI 3-kinase inhibitor, CSF-1R inhibitor, or a combination thereof, as disclosed herein, are administered to a subject suspected of, or already suffering from a neurodegenerative disorder, in an amount sufficient to cure, or at least partially arrest, the symptoms of the disease, including its complications and intermediate pathological phenotypes in development of the disease. In some embodiments, the BRAF inhibitor is selected from the group consisting of vemurafenib, dabrafenib, encorafenib, PLX7904, PLX8394, GDC-0879, LGX818, and PLX4720. In some embodiments, the BRAF inhibitor is PLX4720. In some embodiments, the MEK inhibitor is selected from the group consisting of AZD8330, refametinib, E6201, MEK162 (binimetinib), PD0325901, pimasertib, R04987655, selumetinib, TAK-733, GDC-0623, WX-544, cobimetinib, and trametinib. In some embodiments, the Ras inhibitor is selected from the group consisting of salirasib and TLN-4601. In some embodiments, the PI 3-kinase inhibitor is selected from the group consisting of idelalisib, BKM120, GDC-0980, PF-04691502, XL147, IPI-145, BYL719, SF1126, BAY80-6946, GSK2126458, NVP-BEZ235, GDC-0941, PX-866, XL765, and ZSTK474. In some embodiments the CSF-1R inhibitor is selected from the group consisting of GW2580, BLZ945, pexidartinib (PLX3397), ARRY-382, PLX7486, and JNJ-40346527.

Modes of Administration and Effective Dosages

Any method known to those in the art for contacting a cell, organ, or tissue with a BRAF, MEK, PI 3-kinase, Ras, and/or CSF-1R inhibitor of the present technology, may be employed. In some embodiments, the BRAF inhibitor is selected from the group consisting of vemurafenib, dabrafenib, encorafenib, PLX7904, PLX8394, GDC-0879, LGX818, and PLX4720. In some embodiments, the BRAF inhibitor is PLX4720. In some embodiments, the MEK inhibitor is selected from the group consisting of AZD8330, refametinib, E6201, MEK162 (binimetinib), PD0325901, pimasertib, R04987655, selumetinib, TAK-733, GDC-0623, WX-544, cobimetinib, and trametinib. In some embodiments, the Ras inhibitor is selected from the group consisting of salirasib and TLN-4601. In some embodiments, the PI 3-kinase inhibitor is selected from the group consisting of idelalisib, BKM120, GDC-0980, PF-04691502, XL147, IPI-145, BYL719, SF1126, BAY80-6946, GSK2126458, NVP-BEZ235, GDC-0941, PX-866, XL765, and ZSTK474. In some embodiments the CSF-1R inhibitor is selected from the group consisting of GW2580, BLZ945, pexidartinib (PLX3397), ARRY-382, PLX7486, and JNJ-40346527. Suitable methods include in vitro, ex vivo, or in vivo methods. In vivo methods typically include the administration of BRAF, MEK, PI 3-kinase, Ras, and/or CSF-1R inhibitor, such as those described above, to a mammal, suitably a human. When used in vivo for therapy, the BRAF, MEK, PI 3-kinase, Ras, and/or CSF-1R inhibitor inhibitors are administered to the subject in effective amounts (i.e., amounts that have desired therapeutic effect). The dose and dosage regimen will depend upon the degree of the neurodegenerative disease in the subject, the characteristics of the particular BRAF, MEK, PI 3-kinase, Ras, and/or CSF-1R inhibitor used, e.g., its therapeutic index, the subject, and the subject's history.

The effective amount may be determined during preclinical trials and clinical trials by methods familiar to physicians and clinicians. An effective amount of a particular BRAF, MEK, PI 3-kinase, Ras, and/or CSF-1R inhibitor useful in the methods of the present technology may be administered to a mammal in need thereof by any of a number of well-known methods for administering pharmaceutical compounds. The BRAF, MEK, PI 3-kinase, Ras, and/or CSF-1R inhibitor may be administered systemically or locally.

Pharmaceutical compositions are typically formulated to be compatible with its intended route of administration. Examples of routes of administration include, but are not limited to orally, intranasally, parenterally (e.g., intravenously, intramuscularly, intraperitoneally, intradermally, or subcutaneously), systemically, transdermally, iontophoretically, intradermal, intraocularly, or topically.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the BRAF, MEK, PI 3-kinase, Ras, and/or CSF-1R inhibitor, sufficient for achieving a therapeutic or prophylactic effect, ranges from about 0.000001 mg per kilogram body weight per day to about 10,000 mg per kilogram body weight per day. In some embodiments, the dosage ranges are from about 0.0001 mg per kilogram body weight per day to about 100 mg per kilogram body weight per day. In some embodiments, the dosage ranges are from about 0.0001 mg per kilogram body weight per day to about 50 mg per kilogram body weight per day. For example dosages can be 1 mg/kg body weight, 10 mg/kg body weight, or 50 mg/kg body weight every day, every two days or every three days or within the range of 1-50 mg/kg every week, every two weeks, or every three weeks. In one embodiment, a single dosage of a BRAF, MEK, PI 3-kinase, Ras, and/or CSF-1R inhibitor ranges from 0.001-10,000 micrograms per kg body weight. In one embodiment, BRAF, MEK, PI 3-kinase, Ras, and/or CSF-1R inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Examples

The following examples are provided to further illustrate the methods of the present disclosure. These examples are illustrative only and are not intended to limit the scope of the disclosure in any way.

Materials and Methods

Targeting of $BRAF^{V600E}$ mutation to EMPs and MP-derived cells. EMPs appear in the yolk sac at embryonic day (E) 8.5 and express the Csf1 receptor (Csf1r). They colonize the fetal liver from E9.5 and give rise to macrophage precursors (pMacs) that distribute in embryonic tissues and differentiate into tissue-specific macrophage subsets such as microglia in the central nervous system. Therefore, to investigate the consequences of $BRAF^{V600E}$ expression in the EMP lineage, EMPs were genetically targeted by pulse labeling $Csf1r^{MeriCreMer}$; $BRAF^{LSL-V600E}$; $Rosa26^{LSL-YFP}$ E8.5 embryos with 4-hydroxytamoxifen (4-OHT, Sigma). Embryonic development was estimated considering the day of vaginal plug formation as 0.5 days post-coitum (dpc). Cre recombination in Csf1r$^{MeriCreMer}$; Rosa26$^{LSL-YFP}$; BRAF$^{LSL-V600E}$ embryos was induced by single injection of 37.5 mg per kg (body weight) of OH-TAM into pregnant females. Short-lived 4-OHT leads to transient nuclear translocation of the estrogen receptor-Cre recombinase fusion protein (MeriCreMer) in cells expressing the Csfr1$^{MeriCreMer}$ transgene and deletion of a floxed stop cassette (LSL) in the BRAF$^{LSL-V600E}$ and Rosa26L$^{SL-YFP}$ alleles. OH-TAM was supplemented with 18.75 mg per kg (body weight) progesterone (Sigma) to counteract the mixed oestrogen agonist effects of tamoxifen, which can result in fetal abortions.

Mice. Csf1r$^{MeriCreMer}$, Csf1r$^{iCre}$, CD11$^{Cre}$, Rosa26$^{YFP-LSL}$ mice and BRAF$^{LSL-V600E}$ mice kindly provided by C. Pritchard (Leicester, UK) were maintained under SPF conditions. Animal procedures were performed in adherence to our project licenses issued by the Institutional Review Board (IACUC 15-04-006 and 13-04-003) from MSKCC. Genotyping was performed according to protocols described previously for Csf1r$^{iCre}$ Csf1r$^{MeriCreMer}$, CD11$^{Cre}$ and BRAF$^{LSL-V600E}$ mice. Cre recombination in Csf1r$^{MeriCreMer}$; Rosa26$^{LSL-YFP}$; BRAF$^{LSL-V600E}$ embryos was induced by single injection at E8.5 of 37.5 mg per kg (body weight) of 4-hydroxytamoxifen (OH-TAM, Sigma) into pregnant females. OH-TAM was supplemented with 18.75 mg per kg (body weight) progesterone (Sigma) to counteract the mixed oestrogen agonist effects of tamoxifen, which can result in fetal abortions. Embryonic development was estimated considering the day of vaginal plug formation as 0.5 dpc. For BRAF inhibition, animals were placed on ad libitum PLX4720 diet at 1 or 3 months of age (PLX4720-containing chow 417 ppm, provided by Plexxikon Inc.). BRAF$^{WT}$ and BRAF$^{VE}$ male and female littermates were assigned randomly into the control or treated group. Scoring of mice was performed blinded and at least weekly by assessing hindlimb reflexes and other behavioral phenotypes such as axial rolling. The investigators were not blinded to allocation during experiments and outcome assessment.

Footprint analysis. Mice were given two trials to run down a runway before the experiment. Mouse forepaws and hindpaws were painted with red and blue ink, respectively. Mice were then allowed to run down a runway lined with white paper. At least four steps from the middle portion of each run were measured for (1) overlap between forepaw and hindpaw placement, (2) stride length, (3) front-base width (the distance between the right and left forelimb strides), and (4) hind-base width (the distance between the right and left hindlimb strides). Mean values were used for graphs and statistical analyses.

Rotarod assay. The assay was conducted using a ROTO-ROD series 8 (IITC Life Sciences) with accelerating speed (accelerated from 4 to 40 rpm over 120 s). The mice were trained on the accelerating rotarod with 3 training session per day for 3 days. On the day of the experiment, the mean latency to fall off the rotarod recorded in the 3 trials was used in the analysis.

Preparation of cell suspensions, flow cytometry and cell sorting. Pregnant females were killed by exposure to CO2. Embryos were removed from the uterus, washed in 4° C. phosphate-buffered saline (PBS, Invitrogen) and dissected under a Leica M80 microscope. For blood phenotyping of adult mice, mice were anaesthetized and blood was collected by cardiac puncture. Bone marrow was collected by flushing one leg with 5 ml RPMI (Invitrogen). For flow cytometry experiments, organs were incubated in PBS containing 1 mg/ml collagenase D (Roche), 100 U/ml DNase I (Sigma), 2.4 mg/ml of dispase (Invitrogen) and 3% FCS (Invitrogen) at 37° C. for 30 min prior to mechanical disruption. For embryonic tissue incubation time at 37° C. was reduced to 20 min. For cell sorting, tissues were digested for 30 min at RT in PBS containing 2 mg/ml of collagenase D (Roche), 200 U/ml DNase I (Sigma), 4.8 mg/ml of dispase (Invitrogen), 3% FCS (Invitrogen) and 1 uM of flavopiridol (Sigma) followed by mechanical disruption under a 100 um filter. Cell suspensions were centrifuged at 320 g for 7 min, resuspended in FACS buffer (PBS, 0.5% BSA and 2 mm EDTA) containing purified anti-CD16/32 (1:100 dilution) and 5% normal mouse, 5% normal rat and 5% normal rabbit serum and incubated for 15 min at 4° C. Samples were immunostained with antibodies mixes for 30 min at 4° C. For FMO (fluorescence minus one), brain cell suspensions from BRAF$^{WT}$ and BRAF$^{VE}$ mice were mixed prior to staining. The full list of antibodies used can be found in Supplementary Table 5. Cell sorting was performed using an Aria II BD cell sorter. Single live cells were gated on the basis of dead cell exclusion (DAPI), side (SSC-A) and forward scatter (FSC-A) gating, and doublet exclusion using forward scatter width (FSC-W) against FSC-A. Macrophage populations were identified after gating on CD45 based on expression of F4/80, CD11b and YFP. 200 cells for each sample were directly sorted into a 96 well plate (Biorad) in 4 ul of H2O containing 0.2% of triton-X (Sigma) and 0.8 U/ul of RNAse inhibitor (Clontech), and processed as indicated below.

For intracellular stainings, cell suspensions were purified by a Percoll (Sigma) gradient (70/37/30%), and cells were collected from the 70/37 interface. After washing twice with PBS, cells were stained with a viability dye (Ghost Dye Red 780, Tonbo Biosciences) according to the manufacturer's protocol. Cells were first stained with antibodies for surface markers (see Supplementary Table 5), then processed for intracellular stainings using the Foxp3/Transcription Factor Staining Buffer Set (Affymetrix eBioscience) according to the manufacturer's protocol. Cell numbers per organ or per gram of tissue were calculated as follows. For embryonic tissues, cell suspensions were prepared, stained, and acquired from whole organs, and the number of live cells per tissue was directly obtained from FCS files. In adult mice, organs were weighted, cell suspensions were prepared from 20 to 500 mg of tissue, and the number of cells per gram of tissue was determined using a cell counter (GUAVA easyCyte HT). For gating strategies used for different tissues, see Supplementary FIG. 2. Proportion of YFP$^+$F4/80$^+$ cells in tissues from BRAF$^{VE}$ and BRAF$^{WT}$ littermates were analyzed by calculating the proportion of YFP$^+$ among F4/80$^+$ cells. Values from BRAF$^{WT}$ littermates were then normalized and set to 1.

Generation and analysis of Kupffer cells and microglia RNA-seq in BRAF$^{VE}$ and BRAF$^{WT}$ littermate controls. Sorted cells underwent amplification (14 cycles) using the SMART-seq V4 (Clonetech) ultra low input RNA kit for sequencing. 10 ng of amplified cDNA was used to prepare Illumina hiseq libraries with the Kapa DNA library preparation chemistry (Kapa Biosystems) using 8 cycles of PCR. Samples were barcoded and run on a Hiseq 2500 1T in a 50 bp/50 bp Paired end run, using the TruSeq SBS Kit v3 (Illumina). An average of 54 million paired reads were generated per sample and the percent of mRNA bases was closed to 77% on average. FASTQ files were mapped to the Mouse genome mm10 using the Star aligner that maps reads gnomically and resolves reads across splice junctions. Several QC metrics were used for the RNA-seq library, including intronexon ratio, intragenic reads fraction, and GC bias. Exon and gene expression were quantified using Sailfish against the *Mus musculus* transcriptome GRCh38. After merging technical replicates, differential expression tests were performed using the DESEQ2 algorithm. Genes that had a FDR<0.01 were considered to be significantly different between genotypes and ranked significant genes by fold-change with a cutoff of 1. Gene set enrichment analysis on KEGG pathway, GO term, Reactome, and MSigDB gene set collection was done using the over-representation test with hypergeometric model to assess whether the number of selected genes associated with disease is larger than expected.

Generation and analysis of human brain RNA-seq. Snap frozen normal brain tissues were obtained from the MSKCC Medical Donation Program. RNA was extracted using the Qiagen all prep DNA/RNA mini kit (Cat #80204) according to the manufacturer's instructions. RNAs were submitted to ribogreen quantification and quality control on Agilent Bio-Analyzer. Average amount was 5.3 ug, Average RIN was 8.9. 500 ng of total RNA underwent polyA selection and Truseq library preparation according to instruction provided by Illumina (TruSeq™ RNA Sample Prep Kit v2), with 8 cycles of PCR. Samples were barcoded and run on a Hiseq 4000 in a 125 bp/125 bp Paired end run, using the TruSeq SBS Kit v3 (Illumina). An average of 75 million paired reads was generated per sample. At the most the ribosomal reads represented 7% and the percent of mRNA bases was closed to 45% on average. FASTQ files from control brains and previously sequenced Juvenile Xanthogranuloma (JXG) and Langerhans Cell Histiocytosis (LCH) brain samples (SJLCH13 and SJLCH14) were mapped to Human genome GRCh37 using Star aligner. Several QC metrics were used for the RNA-seq library, including intronexon ratio, intragenic reads fraction, and GC bias. Exon and gene expression were quantified using Salmon against *Homo sapiens* transcriptome GRCh37. Differential expression tests, statistical tests and pathway analysis was performed as described above for murine RNA-seq.

Immunofluorescence, imaging and analysis (mouse). Embryos were imaged using a Leica M80 or Zeiss Axio Zoom.V16. Tissues were fixed for 1-3 days in 4% formaldehyde (Sigma). After fixation, tissues for cryosections were incubated overnight in 30% sucrose and embedded in OCT compound (Sakura Finetek). Cryoblocks were cut at a thickness of 16 µm for liver and 50 µm for spinal cord and brain and then blocked with PBS containing 10% normal goat serum (Invitrogen); 1% BSA (w/v); 0.3% Triton X-100 for 1 hour at room temperature. Livers were incubated overnight, brains and spinal cord for 48 hours at 4° C. with rat anti-mouse F4/80 (1:300, cat no: MCA497GA, Biorad), rabbit anti-mouse Iba1 (1:300; cat no: 019-19741, Wako), chicken anti-GFP for YFP detection (1:500, cat no: A10262, Invitrogen), rabbit anti-pHis3 (1:100, cat no: sc-8656-R, Santa Cruz), goat anti-IL-1b (1:40, cat no: AF-401-SP, R&D), rabbit anti-pERK1/2 (1:100, cat no: #4370, Cell signaling), rabbit anti-Collagen IV (1:100, cat no: 2150-1470, Biorad), rabbit anti-Collagen VI (1:200, cat no: ab6588, Abcam), rabbit anti-cleaved Caspase3 (1:600, cat no: #9661, Cell Signaling), rat anti-Ki-67 (1:200, cat no: 14-5698-80, eBioscience). Secondary antibodies used were anti-rabbit Cy3 (1:500, Invitrogen), anti-chicken Alexa Fluor 488 (1:500, Invitrogen), anti-rat Alexa Fluor 647 (1:500, Invitrogen), anti-goat Alexa Fluor 568. Samples were then mounted with Fluoromount mounting medium with DAPI (eBiosciences) and visualized using a LSM880 Zeiss microscope with 20×/0.5 (dry) and 40×/1.4 (oil) performing a tile scan and Z-stack on whole tissue. Image analysis and cell quantification was performed using Imaris (Bitplane) software. For paraffin sections, 3 µm sections were prepared before staining with H&E, Trichrome, and luxol fast blue (LFB-PAS). Primary antibodies were rabbit anti-CD68 (5 µg/ml, Boster Biological Technology, cat. no: PA1518), rabbit anti-pERK1/2 (1 µg/ml, cat no: #4370, Cell signaling), chicken anti-GFP for YFP detection (1:5000, cat no: AB13970, Abcam), mouse anti-APP (1:3000, cat no: MAB348, Millipore), rabbit anti-Iba-1 (1:500, cat no: 019-19741, Wako), rabbit anti-GFAP (1:200, cat. no. Z0334, Dako), mouse anti-NeuN (1:200, cat. no. MAB377, Merck Millipore), rat anti-LAMP-2 (1:250, ab13524, Abcam, Cambridge, UK), mouse anti-pERK1/2 (1:200, sc-136521, Santa Cruz), rabbit anti-homer1 (1:200, cat. no. 160003, Synaptic Systems), mouse anti-synaptophysin (1:500, cat. no.101 011, Synaptic Systems). Primary antibodies were incubated overnight at 4° C. Secondary Alexa- or HRP-conjugated antibodies were added at 1:200 in antibody buffer for 2 hr at room temperature. For immunofluorescent stainings nuclei were counterstained with 4,6-diamidino-2-phenylindole (DAPI, cat. no. 236276, Boehringer). All slides were mounted in Vectashield (Vector Laboratories). Images were taken using a Zeiss Lab.A1 or BZ-9000 Biorevo microscope (Keyence) and analyzed using the BZ-II Analyzer (Keyence). For quantification of cell numbers, at least three parasagittal sections per mouse were analyzed. In cases, where the cell density was too high and single cells could not be quantified, the immunolabeled area size per brain section was calculated. To determine synapse density, imaging was performed using an Olympus Fluoview 1000 confocal laser scanning microscope using a 20×0.95 NA objective. Z-stacks with 0.05-µm steps in the z direction, 1,024×1,024 pixel resolution, were recorded and analyzed using Imaris software (Bitplane). Colocalization of the presynaptic marker synaptophysin with the postsynaptic marker Homer1 was quantified.

Immunofluorescence, imaging and analysis (human). Written informed consent was obtained from histiocytosis patients for DNA/RNA sequencing and immunohistochemical studies according to Helsinki convention, and this study received approval from the Institutional Review Board at MSKCC (IRB Protocol 06-107). For all ECD patients, ECD was diagnosed in light of published guidelines for the diagnosis and clinical management of ECD42. Biopsy material was retrieved from the pathology archives at Memorial Sloan Kettering Cancer Center. Immunohistochemistry of human ECD and control tissue (see Supplementary Table 6) was carried out on 3-4 µm thick paraffin sections, fixed with PFA. Immunohistochemical analysis was performed on paraffin sections with rabbit anti-Iba-1 (1:500, cat no: 019-19741, Wako) and mouse anti-pERK1/2 (1:200, sc-136521, Santa Cruz), or mouse anti-CD163 (0.06 ug/mL, cat #760-4437, Cell Marque), rabbit anti-pERK1/2 (1 µg/ml, cat no: #4370, Cell Signaling) and mouse anti-BRAF V600E (VE1) (1:800, cat no: #E19294, clone VE1, Spring). Secondary Alexa- or HRP-conjugated antibodies (Invitrogen) were added at 1:200. Images were taken with using a Zeiss Lab.A1, BondIII (Leica-Microsystems, Buffalo Groove, Ill.), BZ-9000 BIOREVO microscope (Keyence) and analyzed using the BZ-II Analyzer (Keyence), or with a LSM880 Zeiss microscope with 40×/1.4 (oil) performing a tile scan and Z-stack on whole tissue and manually analyzed using Imaris (Bitplane) software.

Western blot. Tissues were homogenized using a cell lysis kit (Biorad) and a Precellys homogenizer. Primary antibodies were added overnight at a dilution 1:1000 for rabbit anti-pERK1/2 (cat no: #4370, Cell Signaling) and rabbit anti-ERK1/2 (cat no: #9102, Cell Signaling), and 1:5000 mouse anti-beta actin (cat no: #ab6276, abcam). Secondary antibody anti-rabbit HRP (cat no: #7074, Cell Signaling) or anti-mouse AP (cat no: #AP-2000, Vector laboratories) was added for 1 hour at a dilution of 1:2000. Detection of HRP was performed using Pierce ECL Western Blotting substrate (cat no: #32106). Detection of AP vas performed using BCIP/NBT substratekit (cat no: #SK-5400, Vector laboratories). For quantification, a ratio was made of the total integrated optical density (IOD) of pERK bands to the IOD of bands of the corresponding total ERK protein using ImageJ.

Cytokine analysis in spinal cords. Proteins were extracted from 25 mg of tissue using Bio-Plex cell lysis kit. Cytokine concentrations were measured using Bio-Plex Pro Mouse Cytokine 23-plex Assay according to manufacturer's protocol.

Serum analysis. 70-75 uL of serum were analyzed for liver enzymes using Beckman Coulter AU680 Chemistry analyzer.

PLX4720 concentration measurement. Analysis of PLX4720 concentrations in brain, liver and serum was performed in collaboration with Plexxikon Inc. 25 µl serum and 20 mg of homogenized tissue were measured using a standard curve that was generated by adding known amounts of PLX4720 to an untreated serum or homogenized sample.

Statistical analysis and reproducibility. Data are shown as mean with individual values per mouse being represented as circles, unless stated otherwise. Statistical significance was analyzed with Graph Pad Prism by using Mann-Whitney tests, unpaired two-tailed t-tests, 1-way and 2-way ANOVA and Log-rank (Mantel-Cox) test as indicated in the figure legends.

The n value represents biological replicates. For RNA-seq statistical analysis R software was used (see Generation and analysis of Kupffer cells and microglia of RNA-seq in BRAFVE 548 and BRAFWT littermate controls and Generation and analysis of human brain RNA-seq). Significance was considered at p<0.05. Animals that were labeled moribund by veterinarian services had to be euthanized and were therefore excluded from further longitudinal analyses as indicated in the figure legends. Kaplan-Meier survival analysis was used to estimate overall survival and cumulative incidence rate. Experiments were repeated to ensure reproducibility of the observations. Equal variance was assumed for cell counting experiments. No statistical methods were used to predetermine sample size.

Figure 3A:
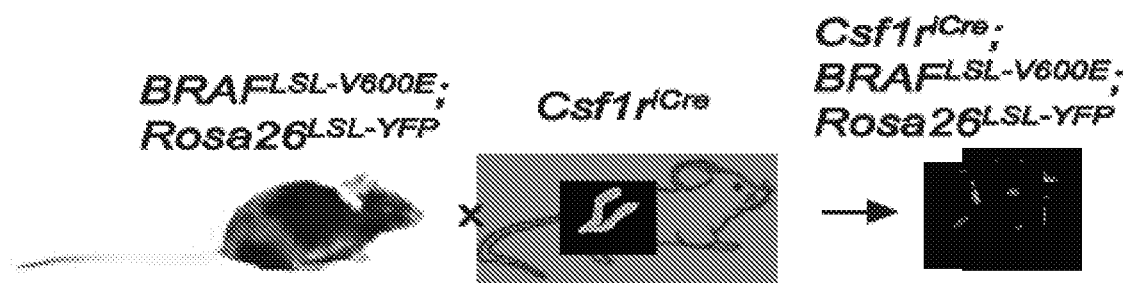
FIGS. 3A-3D show constitutive expression of $BRAF^{V600E}$ in Csf1r+ cells.
Figure 3B:
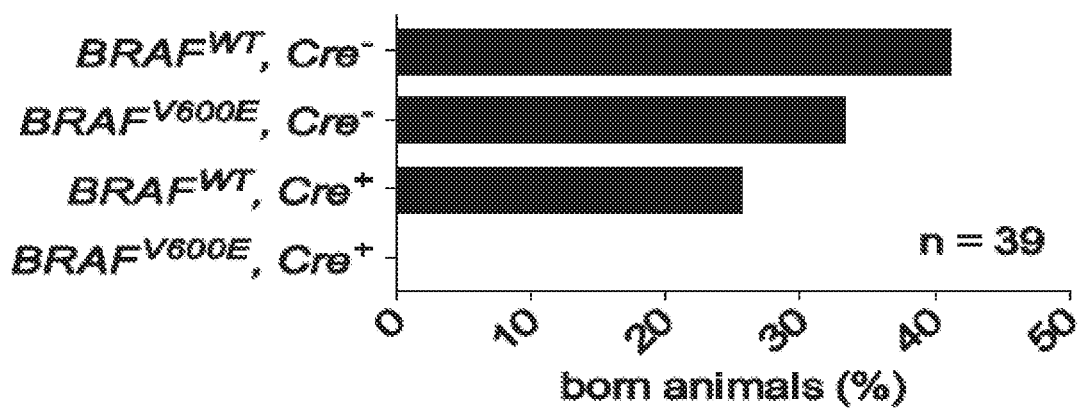
Figures 3C, 3D:
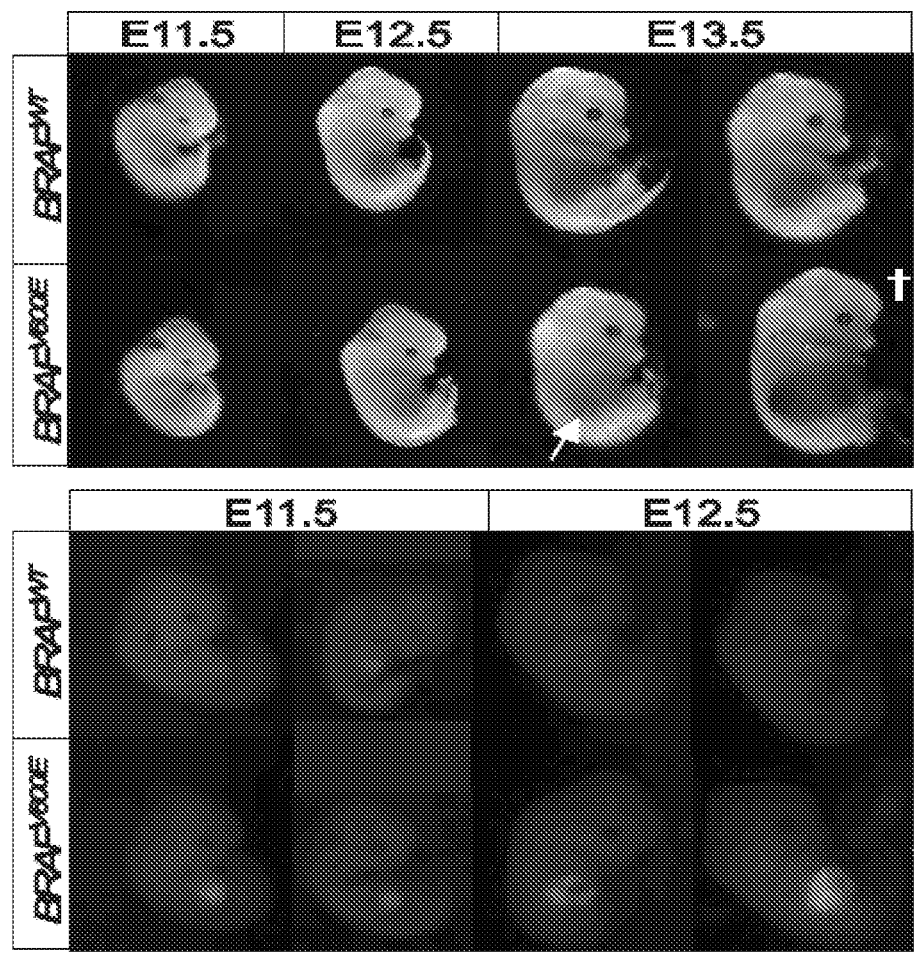

Example 1: Constitutive Expression of $BRAF^{V600E}$ in Csf1r-Expressing Cells Results in a Leukemic Phenotype $BRAF^{V600E}$ expression in hematopoietic progenitors in $Vav^{Cre}$; $BRAF^{V600E}$ mice results in a lethal and transplantable hematopoietic disorder characterized by splenomegaly, anemia, and thrombocytopenia. In an attempt to limit expression of the $BRAF^{V600E}$ mutation to myeloid cells and their progenitors (EMP and HSCs), a triple transgenic mouse model: $Csf1r^{iCre}$; $BRAF^{V600E}$; $Rosa26^{LSL-YFP}$ was established to target expression of $BRAF^{V600E}$ and a fluorescent YFP reporter to cells expressing Csf1r (FIG. 3). The $Rosa26^{LSL-YFP}$ transgene allows for facile identification of targeted cells in vivo and ex vivo. The resulting embryos develop normally until E11.5, but show increased fetal liver size, weight, and accumulation of YFP$^+$ lineage-negative cells in the fetal liver and haemorrhagic foci from E12.5 onwards (FIG. 3C, and not shown) and all $BRAF^{V600E}$ fetuses die between E13.5-E14.5 with a phenotype reminiscent of the $Vav^{Cre}$; $BRAF^{V600E}$ mice (30) (FIGS. 3B-3D).

In addition, expression of $BRAF^{V600E}$ in a large number of early hematopoietic precursors leads to a leukemic-like phenotype and an increase of early macrophages (not shown). This did not phenocopy histiocytoses, where a leukemic phenotype is rare. A limitation of this and previous murine models is that constitutive expression of Cre results in a very high frequency of cells expressing $BRAF^{V600E}$ within a target population, and this may not accurately model the behaviour of a limited number of $BRAF^{V600E}$ clonogenic progenitors. Therefore, an aim of the present technology is to target the $BRAF^{V600E}$ mutation to only a fraction of myeloid progenitors either EMPs or HSCs to investigate the contribution of the affected cell lineage to disease pathophysiology. To test this hypothesis, mouse models are utilized that will allow targeting of a small proportion of EMPs or HSCs, thereby obtaining mosaicism and more closely modelling a somatic mutation.

Example 2: Tamoxifen-Inducible Models to Target Resident Macrophages or HSCs

Figure 4:
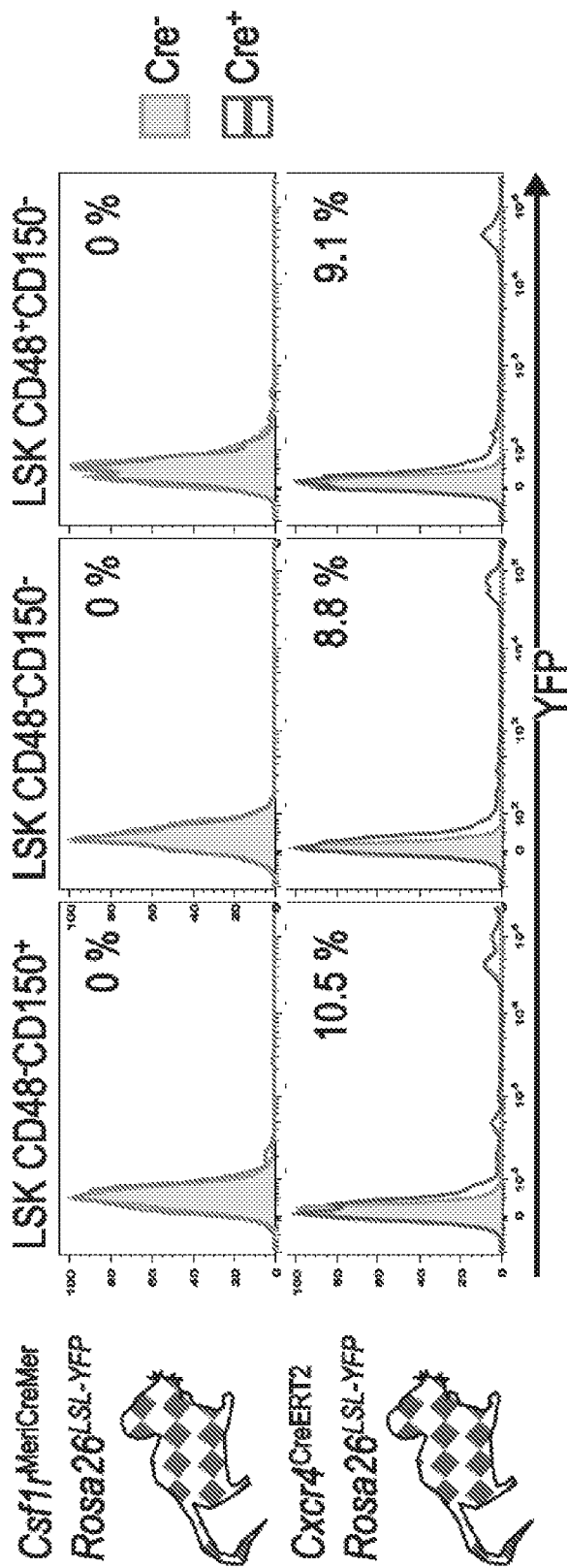
FIG. 4 shows Tamoxifen-inducible mouse models used to target EMP versus HSC. $Csf1r^{MeriCreMer}$; $Rosa26^{LSL-YFP}$ do not target HSCs in adult mice, while pulse-labeling of $Cxcr4^{CreERT2+}$; $Rosa26^{LSL-YFP}$ results in labeling of 10% HSCs. LSK: Lin-Sca1+Kit+.

To target $BRAF^{V600E}$ expression specifically to a small number of EMPs or HSCs, $BRAF^{V600E}$; $Rosa26^{LSL-YFP}$ and $Rosa26^{LSL-YFP}$ mice were crossed either to a tamoxifen-inducible $Csf1r^{MeriCreMer}$ model, thereby allowing selective targeting of EMPs when pulsed with OH-TAM at E8.5, at time when EMP start to express Csf1r, or to a $Cxcr4^{CreERT2}$ model allowing selective targeting of HSCs when pulsed with OH-TAM at E9.5 (FIG. 4). Pregnant females receive low doses of OH-TAM via i.p. injection, so that only a small proportion of EMPs express $BRAF^{V600E}$ and YFP. Analysis of 4-week-old $Csf1r^{MeriCreMer}$; $Rosa26^{LSL-YFP}$; $BRAF^{V600E}$ Cre$^+$ mice indicates that YFP expression is not detected in bone marrow HSC (Lineage negative, Sca1$^+$Kit$^+$ or LSK) as expected (FIG. 4), while ~10% of LSK cells were labelled in the bone marrow of $Cxcr4^{CreERT2}$; $Rosa26^{LSL-YFP}$ mice (FIG. 4).

Figure 5A:
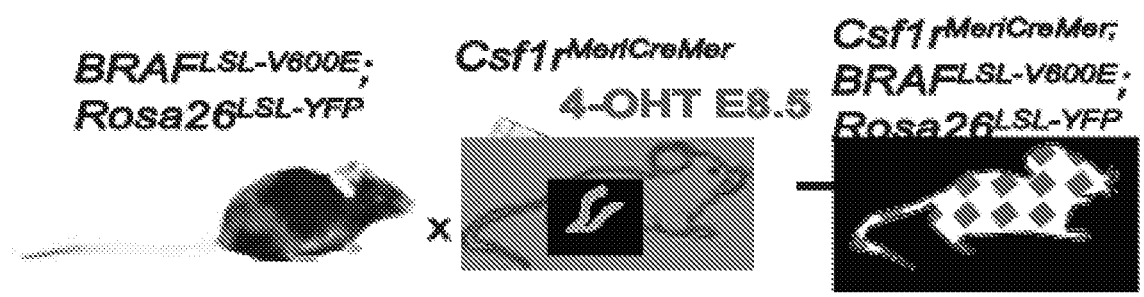
FIGS. 5A-5E show the results of experiments with a $Csf1r^{MeriCreMer}$; $BRAF^{V600E}$; $Rosa26^{LSL-YFP}$ inducible model.
Figure 5B:
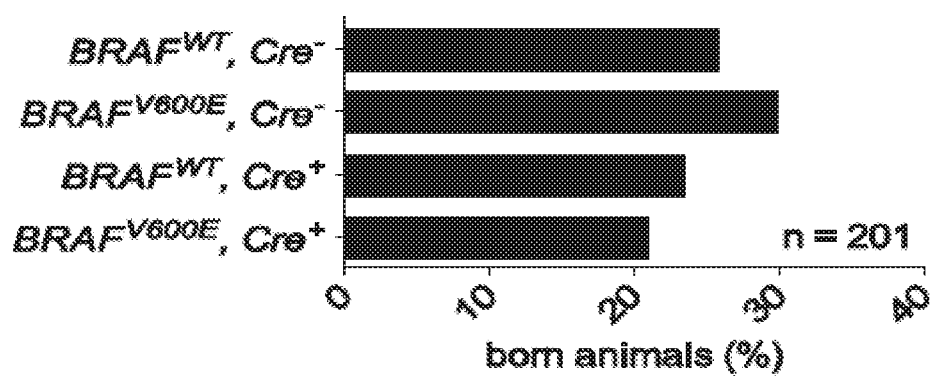
Figure 5C:
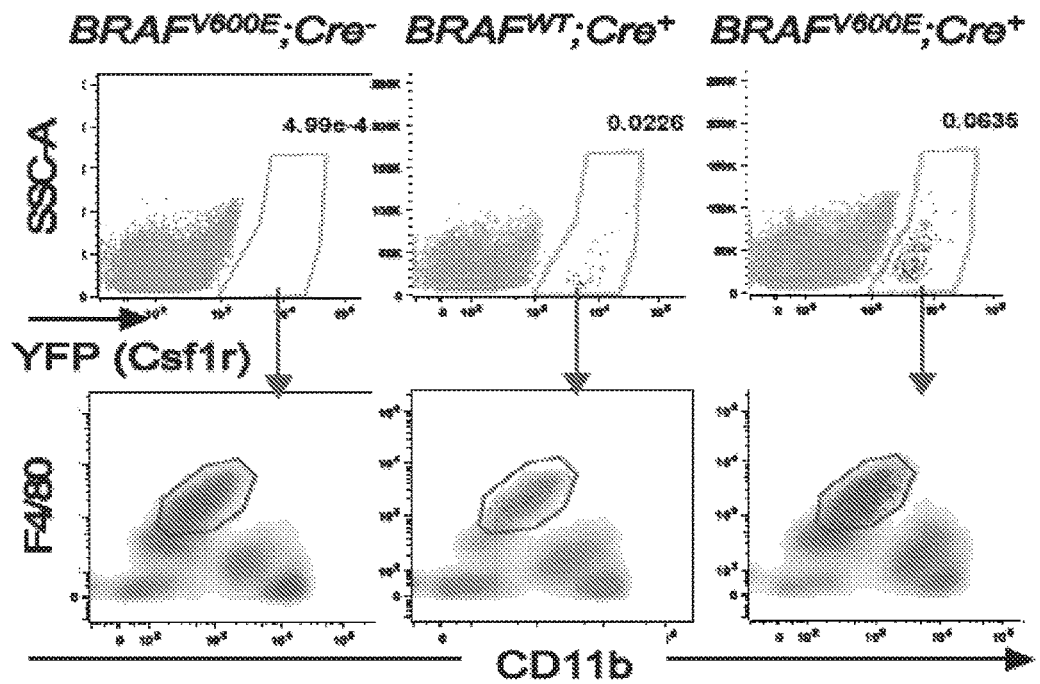
Figure 5D:
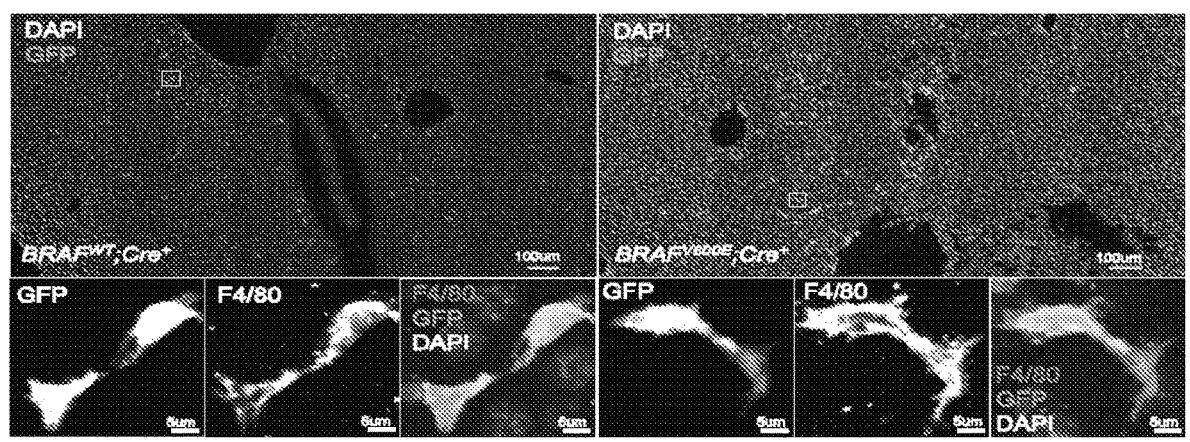
Figure 5E:
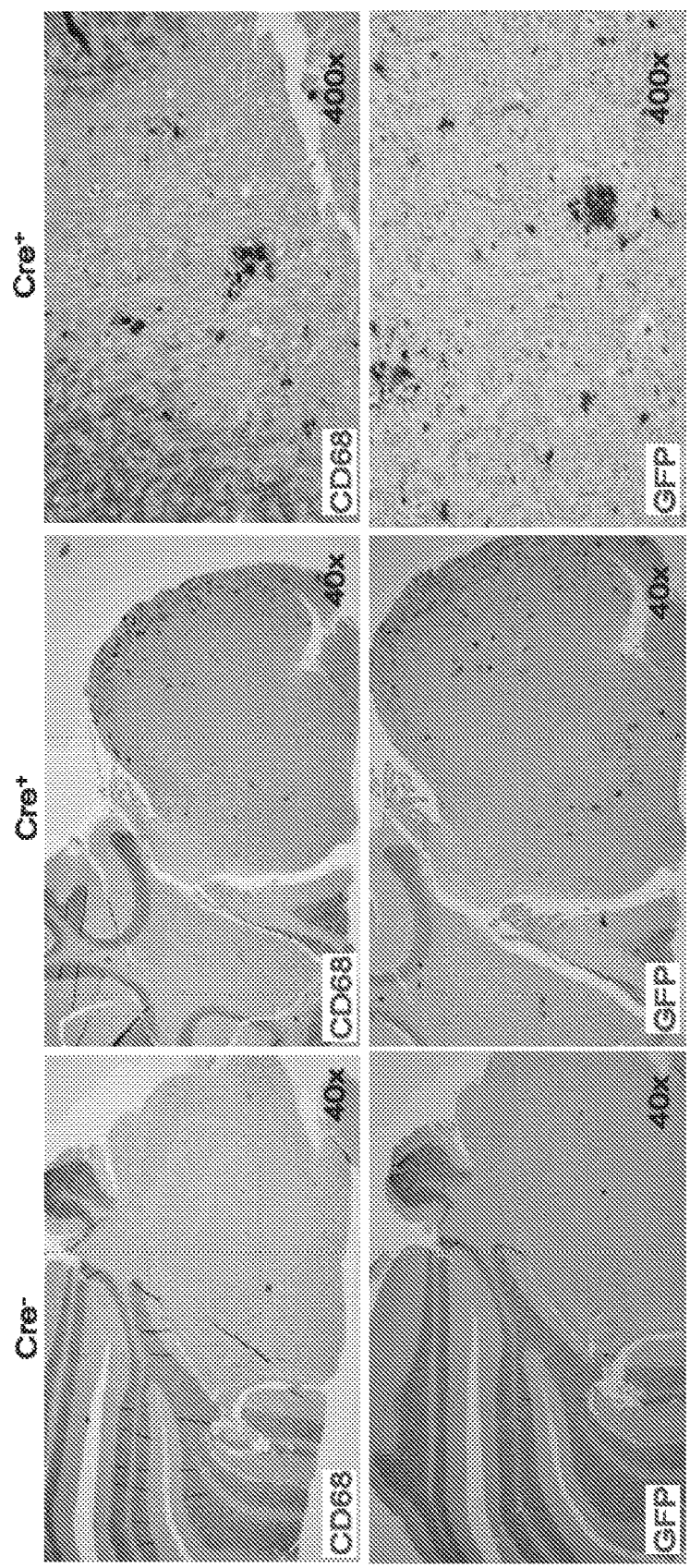

Example 3: The Tamoxifen-Inducible $Csf1r^{MeriCreMer}$; $BRAF^{V600E}$; $Rosa26^{"LSL-YFP}$ Mouse Model Targets Resident Macrophages Littermates born from $BRAF^{V600E}$; $Rosa26^{LSL-YFP}$ crossed to $Csf1r^{MeriCreMer}$ pulsed with OH-TAM at E8.5 are viable, and born at almost perfect Mendelian ratios (FIGS. 5A and 5B). At a young age (4 weeks old), Cre$^+$BRAF$^{V600E}$ animals did not display any gross phenotypic abnormality. YFP expression in $Csf1r^{MeriCreMer}$; $Rosa26^{LSL-YFP}$; $BRAF^{V600E}$ mice was restricted to small populations of F4/80$^+$ tissue macrophages (FIG. 5C) that form clones within the liver tissue (FIG. 5D) as well as the nervous system, mostly brain stem, cerebellum and spinal cord (FIG. 5E). YFP expression was not observed in hepatocytes or neurons.

Figure 6A:
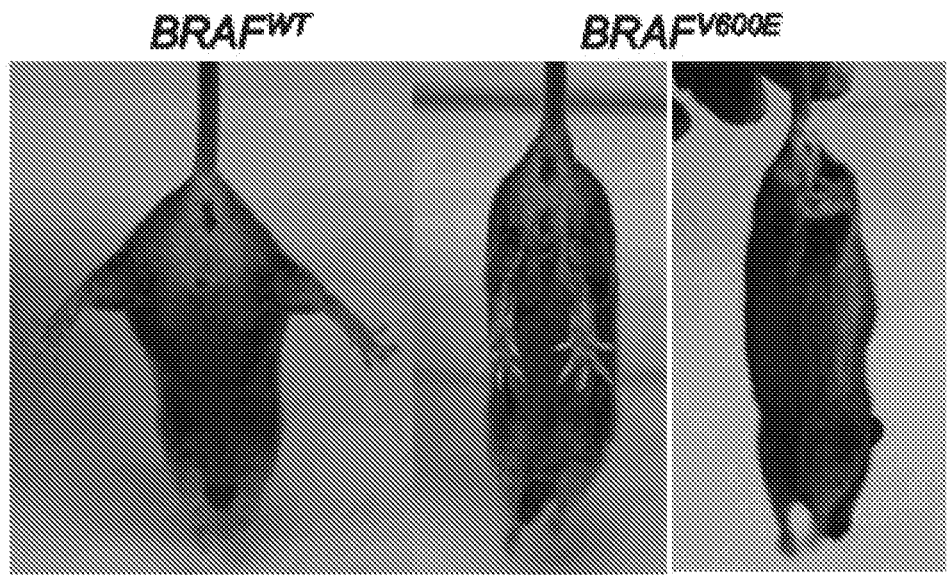
FIGS. 6A-6D show neurological disease in the $Csf1r^{MeriCreMer}$; $BRAF^{V600E}$; $Rosa26^{LSL-YFP}$ model.
Figure 6B:
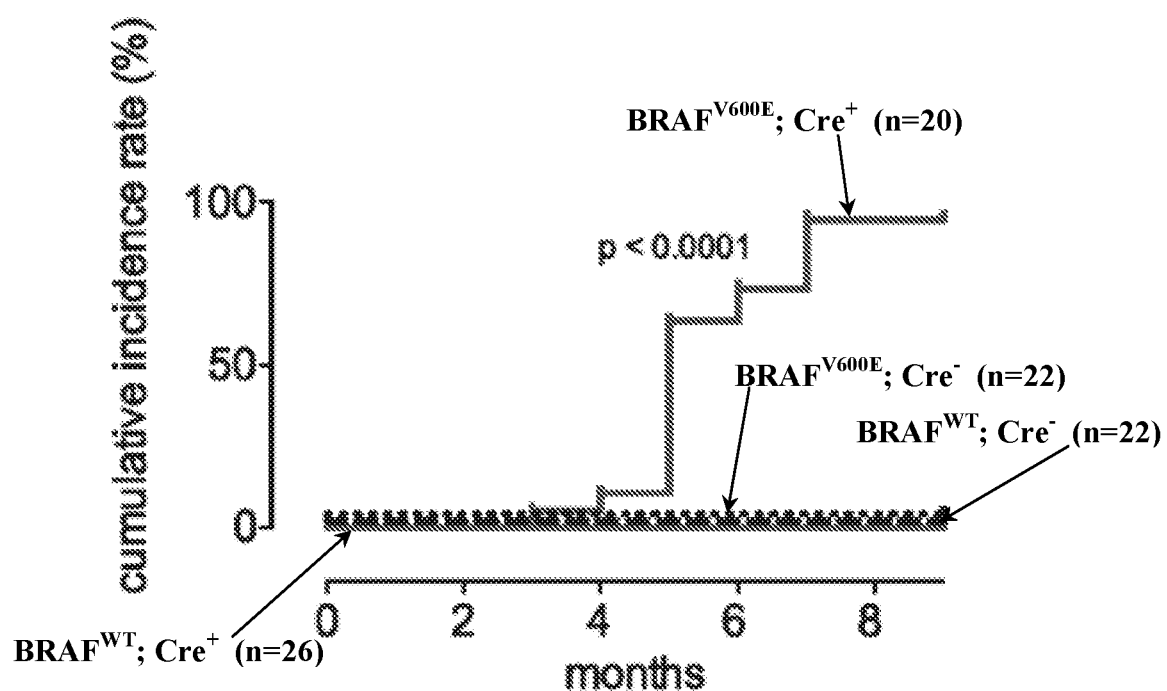
Figure 6C:
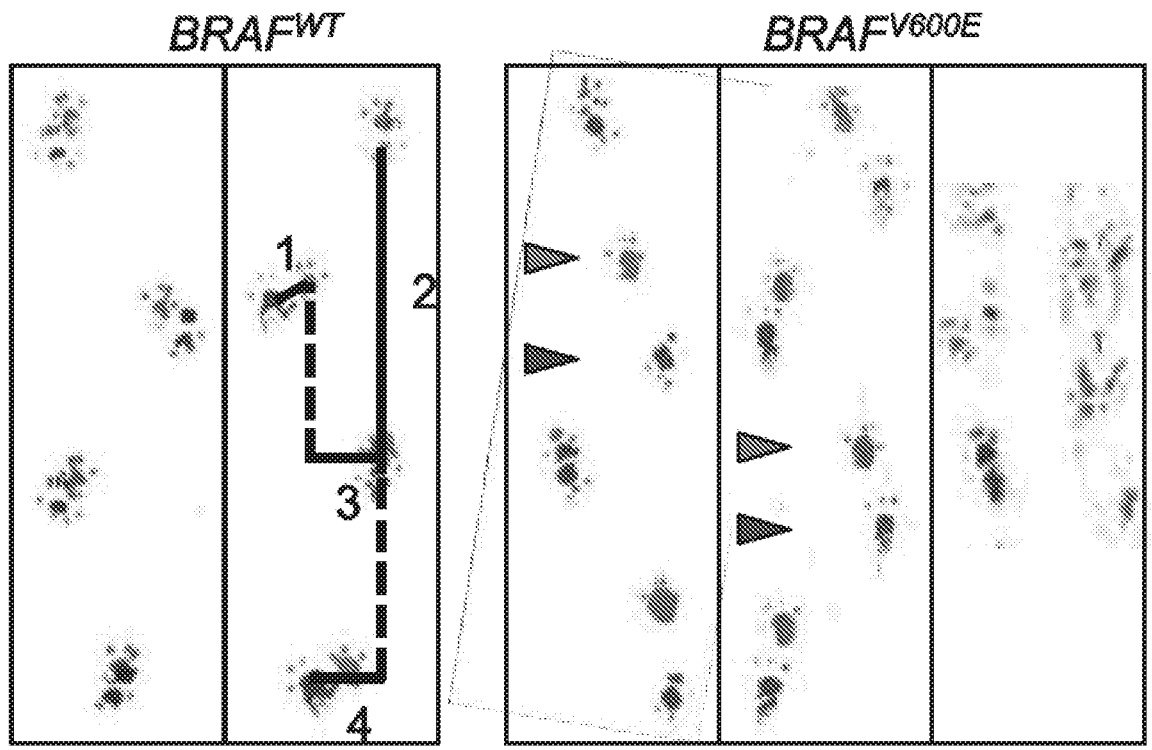
Figure 6D:
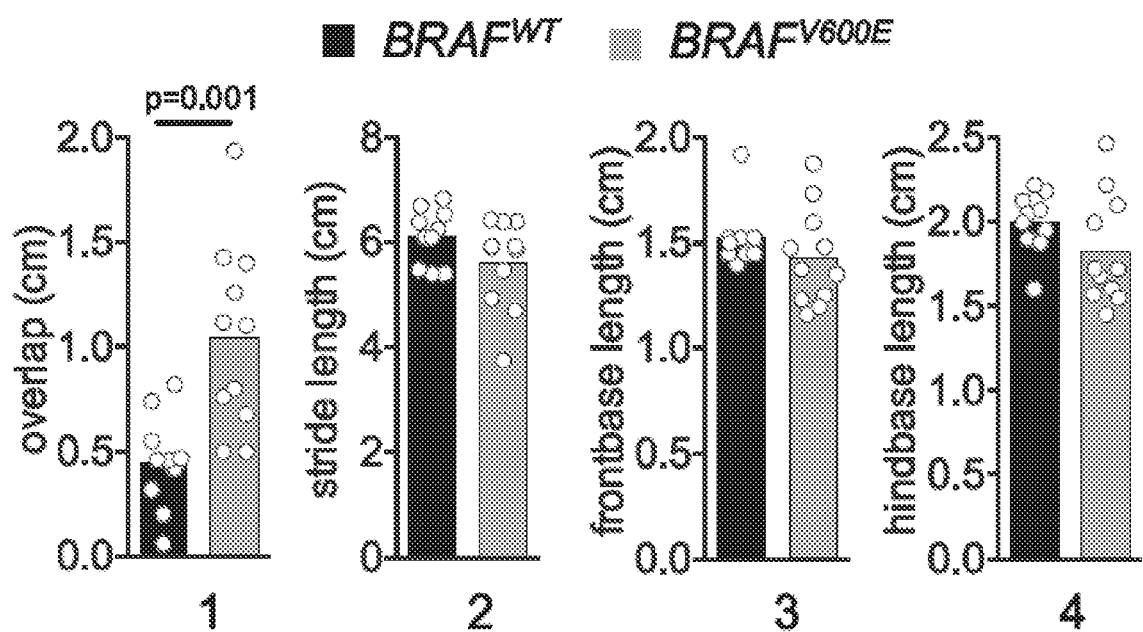

Example 4: $Csf1r^{MeriCreMer}$; $Rosa26^{LSL-YFP}$; $BRAF^{V600E}$ Mice Develop Clinical Features of Neurodegenerative Disease In a cohort of 5-9 month-old Cre+R$_{AFB}$ v600E (n=20) mice and littermates (FIG. 6), Cre$^+$BRAF$^{V600E}$ mice began to develop impaired limb-clasping reflexes and ataxia, which was not detected in control littermates (FIGS. 6A and 6C). The cumulative incidence of these phenotypes reached ~95% by 7 months of age, while $BRAF^{WT}$ littermates remained normal (FIG. 6B). Motor coordination and synchrony was assessed by footprint assay, measuring stride length, base width, and overlap between fore and hind paws (FIG. 6C). During the early stages of ataxia, the overlap of front and hind paws of Cre$^+$BRAF$^{V600E}$ animals was significantly increased, while the other coordination measurements remained similar to Cre$^+$BRAF$^{WT}$ littermates (FIG. 6D). Later, paralysis of the hind legs became apparent in the footprint assay, showing full loss of coordination (FIG. 6C). This observation is important, as the development of ataxia is a component of the clinical phenotype of histiocytosis patients that develop neurodegenerative disease. In patients with LCH, symptoms of neurodegenerative disease (ND-LCH) include cerebellar ataxia with dysarthria, dysdiadochokinesis, and associated with concentration deficits, psychomotor retardation, severe headaches, and psychosis, developing 3 to 15 years (median 6 years) after initial LCH diagnosis.

Figure 7A:
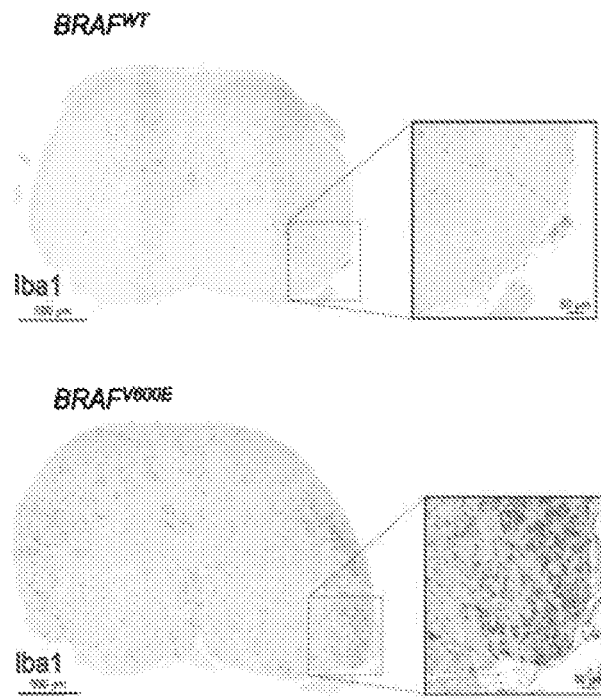
FIGS. 7A and 7B show histological analysis of the spinal cord in Cre+ $BRAF^{V600E}$ and littermate controls.
Figure 7B:
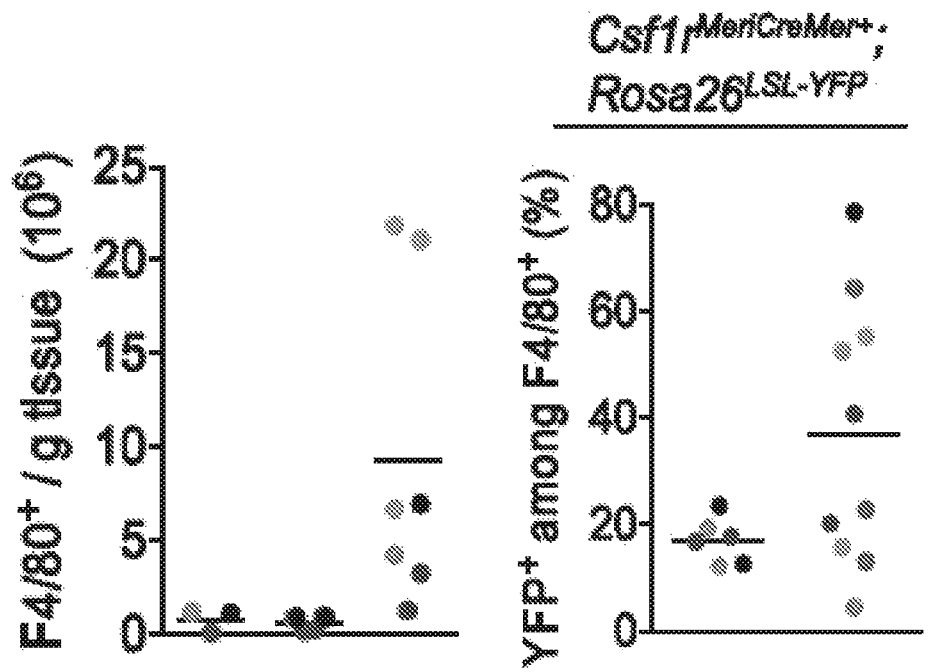
Figure 8A:
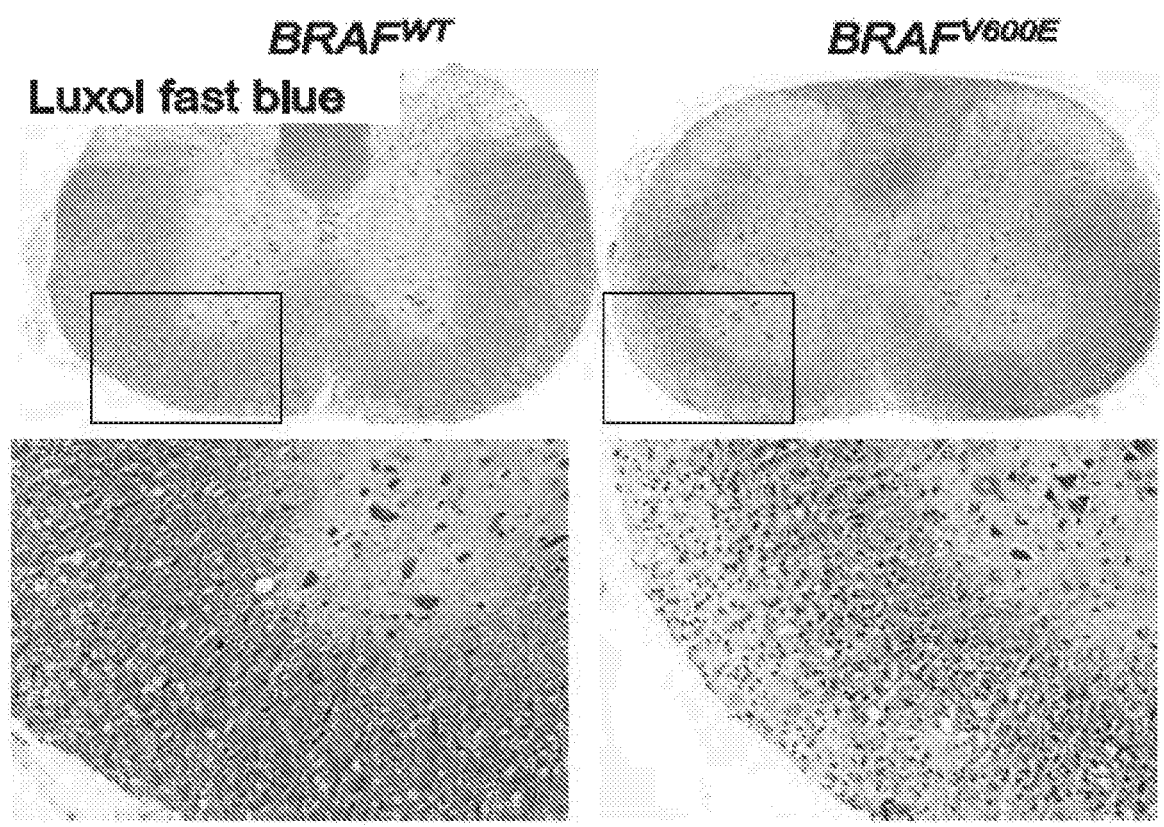
FIGS. 8A and 8B show demyelination of the spinal cord of Cre+ $BRAF^{V600E}$ mice compared to wild type mice.
Figure 8B:
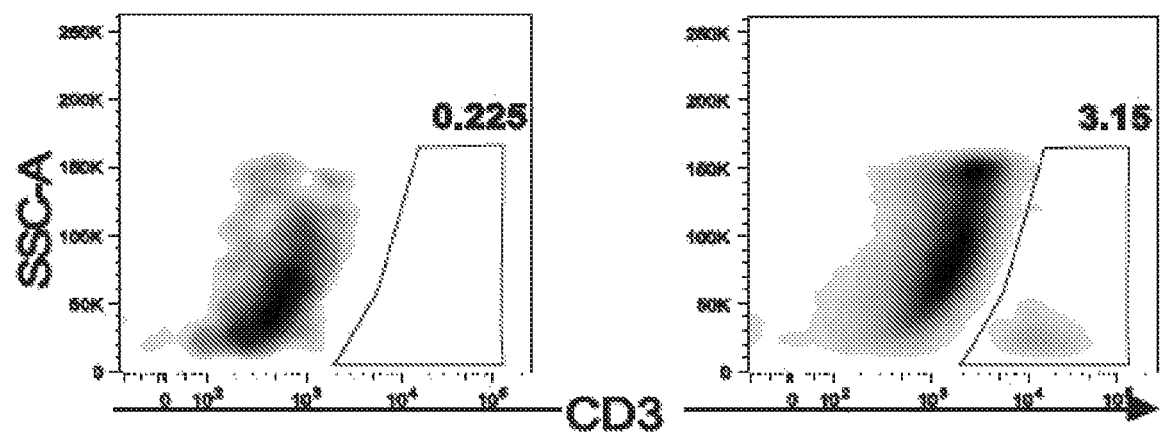

The pathophysiology of these neurological signs and symptoms are unknown, however, as biopsies are rarely performed in patients and when performed, pathological histiocytes are rarely identified. A preliminary histological analysis and flow cytometric analysis of the brain and spinal cord from Csf1r$^{MeriCreMer}$; BRAF$^{V600E}$, Rosa26$^{LSL-YFP}$ mice presenting with ataxia and littermates, indicated the presence of foci of increased numbers of YFP$^+$Iba1$^+$ microglia in the cerebellum and spinal cord in BRAF$^{V600E+}$ littermates (FIG. 7), suggesting active involvement of pathological BRAF$^{V600E}$ histiocytes in the process of neurodegeneration. At the time of analysis, mice with a neurological phenotype already presented with extended histological lesions, such as a massive demyelination in the white matter of the spinal cord (FIG. 8A) associated with an inflammatory infiltrate rich in CD3$^+$ T lymphocytes (FIG. 8B). These data are also reminiscent of MRI studies in patients, which show signal changes in cerebellar white matter. However, it is likely that the histological lesions started to develop long before clinical symptoms appeared. These preliminary results suggest that targeting BRAF$^{V600E}$ expression to a small number of EMPs gives rise to BRAF$^{V600E}$ tissue resident macrophages in adult mice that may be responsible for the most troubling clinical sequelae of LCH and ECD. This model may faithfully recapitulate the disease in a manner, which has not been accomplished by BRAF$^{V600E}$ expression in other hematopoietic cellular compartments. These results warrant a detailed analysis of the neurological disease that develops in Csf1r$^{MeriCreMer}$; BRAF$^{V600E}$; Rosa26$^{LSL-YFP}$ mice to elucidate the cellular and molecular mechanisms involved, justify investigations into other pathological consequences of BRAF$^{V600E}$ expression in macrophages in the liver, lung, and bones and determine whether these phenotypes can also result from mutated HSCs. These results also offer a unique opportunity to study the effects of therapeutic interventions and identify novel therapeutic targets.

Example 5: Determining the Molecular and Cellular Mechanisms that Underlie the Development of Brain Neurodegenerative Disease At the onset of clinical symptoms, the nervous system of Csf1r$^{MeriCreMer}$; BRAF$^{V600E}$; Rosa26$^{LSL-YFP}$ mice displays extensive damage. As outlined above, it is likely that the histological lesions in the nervous system started to develop long before clinical symptoms appeared. When limb-clasping reflexes and ataxia are detected by gross examination in 6 month old mice, histological evaluation of the spinal cord indicated extensive demyelination (FIG. 8A) and flow cytometry analysis indicated infiltration by CD3$^+$ cells (FIG. 8B). Immunostaining for phosphorylated ERK (pERK), a downstream effector of the Ras/Raf pathway showed extensive areas of strong pERK staining in Cre$^+$BRAF$^{V600E}$ microglia in comparison with littermates controls (FIG. 9). Clustering of YFP$^+$CD68$^+$ microglia in the cerebellum and spinal cord white matter was most prominent in the posterior columns and spinocerebellar tracts (FIG. 9, and data not shown), which are important for proprioception and fine touch of the hind limbs and lower trunk. Anatomical lesions involving these neurological tracts could explain the lack of coordination of the hind limbs with the forelimbs and may contribute to paralysis. However, the mice are paralyzed at this stage and the cellular damage is extensive, making it difficult to properly assess the course of the disease.

Example 6: Determining the Onset of Neurological Disease in the Csf1r$^{MeriCreMer}$; BRAF$^{V600E}$; Rosa26$^{LSL-YFP}$ Mice As stated above, the onset of neurological defects that would impact locomotion, muscular strength or memory at early stages of the disease remain unknown. To identify the onset of the disease the occurrence of diabetes insipidus (DI), which corresponds to pituitary involvement and is associated with neurodegeneration in patients such that ~95% of clinical neurodegenerative syndrome cases have DI is investigated. Serum and urine sodium osmolarity are tested for a cohort of mice (n=10 per genotype) between 4 and 8 weeks, and if DI is suspected (high plasma/low urine sodium concentration), mice are tested in metabolic cages. A set of fine motor tests that will provide a good read-out of neurological function are also performed on a cohort of age matched Csf1r$^{MeriCreMer}$; BRAF$^{V600E}$; Rosa26$^{LSL-YFP}$ mice and BRAF$^{WT}$ littermate controls (n=10 for each genotype) starting at the age of 4 weeks, and every two weeks initially until tests are positive. The rotarod assay is a sensitive assay that can detect subtle impairments in motor activity, and can be repeated over time in a cohort of animals, to monitor the onset and progression of neurological impairment or a motor coordination phenotype. The rotarod is a horizontally oriented cylinder that can rotate at a fixed or an accelerating speed. Normally, animals try to stay on the rotarod, and avoid falling to the ground. During the training period, each mouse is placed on the rotarod at a constant speed (24 rpm) for 60 seconds. Csf1r$^{MeriCreMer}$; BRAF$^{V600E}$; Rosa26$^{LSL-YFP}$ mice and BRAF$^{WT}$ littermate controls at the age of 4 weeks receive four trials per day for three consecutive days, by which time they reach a steady performance baseline level. After the training trials, mice receive two trials for 60 seconds at eight increasing speed levels: 4, 8, 15, 20, 24, 31, 33 and 44 rpm. The mean latency to fall off the rotarod is used in subsequent analysis. If a mouse stays on the rod until the end of the trial, a time of 60 sec is recorded. The same mice are analyzed over a time period of 6 months (or until paralysis) every 2 weeks. The cohort of mice tested with rotarod above is also longitudinally studied with the footprint assay. The footprint assay measures motor coordination and synchrony, and has been used to assess microglial inflammation in murine models, and it was found that 6-9 months old Csf1r$^{MeriCreMer}$; BRAF$^{V600E}$; Rosa26$^{LSL-YFP}$ mice presented with ataxia in this assay (see FIG. 6). To obtain footprints, the front and hind paws of the mice are coated with red and blue ink, respectively. The animals are then allowed to walk along a 50-cm-long, 20-cm-wide runway (with 15-cm-high walls). All mice will have 2-3 training runs before ink is applied. A fresh sheet of white paper is placed on the floor of the runway before each run. The footprint patterns are analyzed for four parameters (see also FIG. 6): (1) Stride length, (2) hind-base width, and (3) front-base width are measured as the average distance between left and right hind footprints and left and right front footprints, respectively. These values are determined by measuring the perpendicular distance of a given step to a line connecting its opposite preceding and proceeding steps. (4) Distance from left or right front footprint/hind footprint overlap is used to measure uniformity of step alternation. If the center of the front footprint falls on the center of the preceding hind footprint, a value is recorded as 0 cm. When the footprints do not overlap, the distance between the centers of the footprints is measured. For each step parameter, at least three values are measured and averaged, excluding footprints made at the beginning of the run where the animal was initiating movement. Locomotion and exploratory behavior are also assessed using an open field analysis in a new environment (clear plexiglas 40×40×30 cm open-field arena). This test can only be performed once in a cohort to avoid the confounding effects of habituation to the open field, and is initially performed on the cohort at the time of the first symptoms in the rotarod or footprint assays. Activity in the open-field is quantified by a computer-operated Photobeam activity system (AccuScan Instruments, Columbus, Ohio). Mice are recorded for the total distance moved (cm), number of vertical episodes (rearing), and distance moved in the center of the arena (cm). The distance moved in the center (cm) is divided by the total distance moved (cm) to obtain center/total distance ratio values. Data is collected at 5-10 min intervals over 20-60 min test sessions. All results are analyzed comparing Cre$^+$BRAF$^{V600E}$ and BRAF$^{WT}$ mice, for statistical analyses Student's t-test is performed and p-values of <0.05 are considered significant.

Results from this longitudinal approach characterize the onset of the motor coordination phenotype observed in the Csf1r$^{MeriCreMer}$; BRAF$^{V600E}$; Rosa26$^{LSL-YFP}$ mice. These results guide the animal imaging histological and molecular analysis described below. To assure an unbiased analysis of behavioral assays the researcher is blind to the genotype of the mice during testing and in case of the open field study, also later during analysis of the tapes.

Example 7: Analyzing Brain Histology and Neural Cell Populations in Csf1r$^{MeriCreMer}$; BRAF$^{V600E}$; Rosa26$^{LSL-YFP}$ Mice During Development and Through Progress of Neurodegeneration Microglia play important roles in the homeostasis of the brain and spinal cord, during development and in adults. They are involved in pruning synapses, modulating overactive neurons, promoting neuronal survival, organizing axonal projections and, in the adult, supporting synapse formation during learning. To uncover the consequences of BRAF$^{V600E}$ expression in microglia differentiation, proliferation, and activation during development and in post-natal animals, a detailed analysis of microglia proliferation and activation and its consequences on other neural cells populations is performed at different time points during development of Csf1r$^{MeriCreMer}$, BRAF$^{V600E}$; Rosa26$^{LSL-YFP}$ mice and BRAF littermate controls. Experiments are performed at E12.5, E14.5, E18.5, and after birth at postnatal week 1, week 2, at week 4 (before the onset of clinical symptoms), at the onset of symptoms, and in 5-6 month old mice. Embryos and brains are harvested for flow cytometry experiments or immediately fixed in a solution of 4% formaldehyde before processing for cryosections (for immunofluorescence) or paraffin sections (immunohistochemistry, IHC). Proliferation rate of BRAF$^{V600E}$ and BRAFWT microglia (F4/80$^+$CD11b$^+$CD45$^{lo}$ is quantitated in situ and by flow cytometry using phosphorylated histone H3 (pHis3) antibody. To analyze EMP-derived BRAF$^{V600E}$ and BRAF$^{WT}$ microglia and their impact on neurons, 30 μm thick cryosections will be co-stained for YFP, Iba1, and pERK and the neuronal antigen NeuN. Automatic quantification of cell morphometry on three-dimensional reconstruction with Imaris will assess dendrite length, number of segments, branch points and terminal points as well as volume. To study how BRAF$^{V600E}$ expressing microglia may affect neurogenesis/neuronal loss, staining for Fluoro-Jade, a fluorochrome commonly used to label degenerating neurons, will be performed. The number of astrocytes is typically elevated when destruction of neurons occurs, and this is assessed by IHC of GFAP, a classic marker for reactive gliosis. Expression of maturation and activation markers Csf1r, CD31, CD44, CD62L and MHC class II by microglia (F4/80$^+$)CD11b$^+$CD45$^{lo}$, and the presence and composition of an inflammatory infiltrate are determined by flow cytometry using a LSR Fortessa flow cytometer to identify T cells (CD3, CD4, CD8), B cells (CD19), eosinophils, monocytes and neutrophils (Ly6C, Ly6G, Siglec-F, CD11b). In all experiments, immunostainings and flow cytometry analyses are performed on at least 3 embryos/brains per genotype and 3 imaged sections per embryo/brain. p-values of <0.05 obtained using student's t-test are considered significant.

Results from this longitudinal approach, which follows BRAF$^{V600E}$ expressing microglia throughout development to adulthood characterizes the disease onset and provides a better molecular understanding for the pathophysiology of central nervous system LCH and neurological manifestations in ECD.

Figure 10:
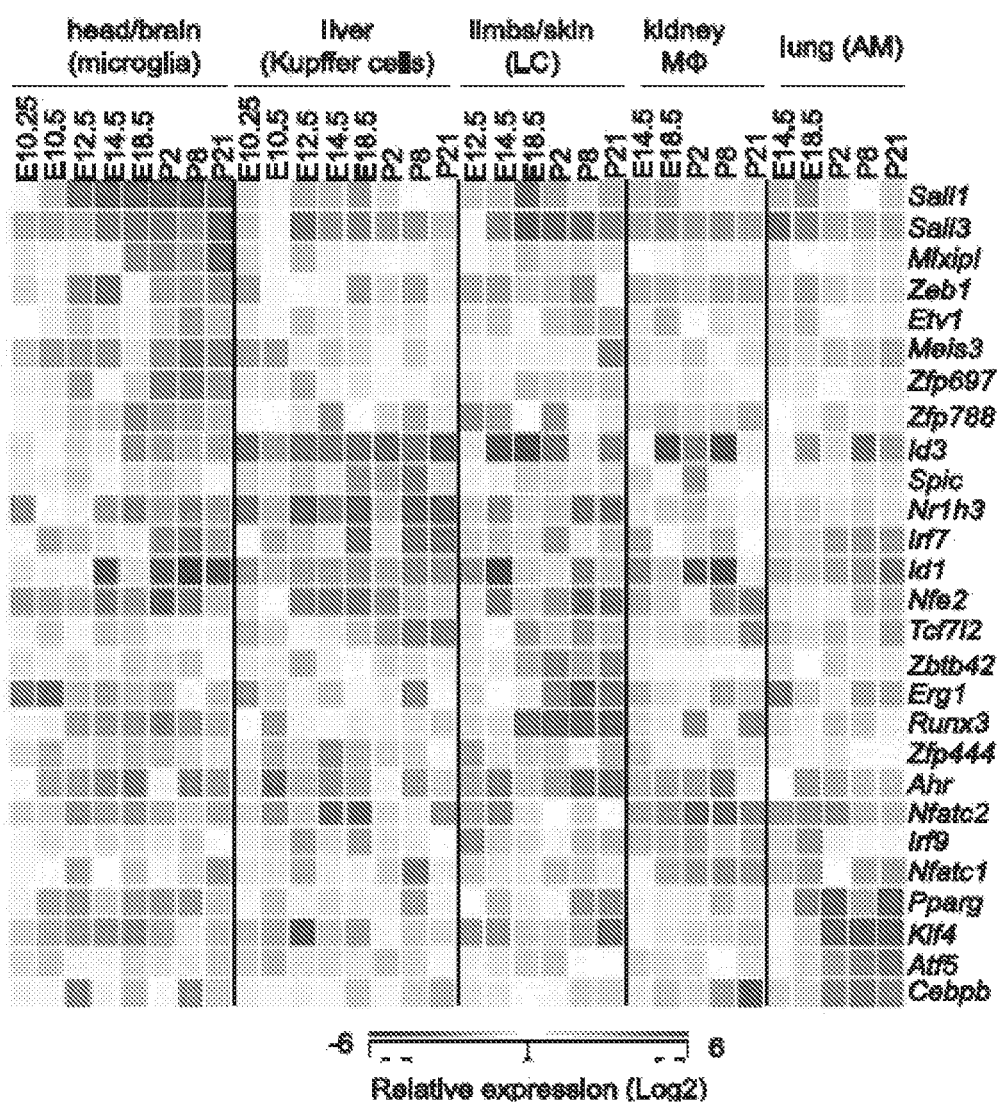
FIG. 10 shows transcription factors that are differentially expressed between macrophages from the brain, liver, skin, kidney, and lung during development and in postnatal mice.

Example 8: Characterize the Role of BRAF$^{V600E}$ Expression on the Transcriptional Profile of Microglia Raf-Mek-Erk signaling is involved in differentiation and cell identity, cell proliferation and activation via the control of gene transcription and chromatin accessibility. The transcriptional consequences of BRAF$^{V600E}$ expression in macrophages have not been investigated. The transcriptional profiles of EMP-derived WT macrophages were identified in murine tissues, during development and in adults, using RNAseq analysis (FIG. 10). A transcriptional analysis of YFP$^+$ and YFP$^-$ macrophages obtained from the brain (microglia) is performed and for comparison from the liver (Kupffer cells) of Csf1r$^{MeriCreMer}$; BRAF$^{V600E}$; Rosa26$^{LSL-YFP}$ and BRAF$^{WT}$ littermates, at 4 weeks, before the onset of disease, at the onset of disease and at 5 months, when the mice are sick. Comparison of YFP$^+$ cells from BRAF$^{V600E}$ mice and BRAF$^{WT}$ littermates will provide a first set of data, which will identify pathways and genes that characterize the presence of a BRAF$^{V600E}$ allele. Comparison between brain and liver macrophages, will inform the presence of tissue-specific BRAF signatures. Such tissue-specific BRAF-mutant macrophage signatures are likely to exist as the existence of tissue-specific transcriptional profiles of normal macrophages have been shown. Finally, comparison between the 3 time points should identify genes and pathways involved in macrophages as the disease progresses. For each time point, macrophages are FACS-sorted using an Aria II BD cell sorter from mouse tissues (liver, and brain) from 3 mice for each genotype. Gating of single live cells is performed using side (SSC-A) and forward scatter (FSC-A) gating, and doublet exclusion using forward scatter width (FSC-W) against FSC-A as well as dead cell exclusion with DAPI. Macrophages are identified after gating on CD45$^+$CD11b$^{low}$F4/80$^{high}$ cells in liver and CD45$^{low}$CD11b$^+$F4/80$^+$ in the brain. 200 cells for each sample are sorted directly into a 96-well plate in 4 µl of H$_2$O containing 0.2% of tritonX and 0.8 U/µl of RNAse inhibitor and processed for sequencing by the Integrated Genomics Operation (IGO) at MSKCC. Processing of RNAseq data is performed with the help of the bioinformatics core at the MSKCC. The raw count matrix generated by HTSeq are processed using the R/Bioconductor package DESeq, which is used to both normalize the full dataset and analyze differential expression between sample groups. Gene Ontology (GO) analysis is performed using the GO analysis function in GeneSpring GX 13.0 (Agilent), with the p-value calculated using a hypergeometric test with BenjaminiYekutieli correction. For example, genes with a fold change difference of ±2 between cells from BRAF$^{V600E}$ and controls animals are selected. Significantly regulated genes (t-test p<0.05; FDR<0.05) from this selection are grouped into GO terms. Heatmaps are generated using GeneSpring GX 13.0 (Agilent). All other analyses and plotting are performed in R.

This analysis identifies molecular pathways and candidates genes involved in BRAF$^{V600E}$ microglia activation. Following from these results, candidate genes and pathways involved for example in cytotoxicity, phagocytosis, or inflammation are selected for further study as they may represent mechanisms for tissue damage. RNASeq analysis in macrophages is performed in accordance with methods known in the art.

Determining the pathological consequences of targeting BRAF$^{V600E}$ outside the brain in vivo. The presence of BRAF$^{V600E}$ macrophages clones was not restricted to the nervous system of Csf1r$^{MeriCreMer}$; BRAF$^{V600E}$; Rosa26$^{LSL-YFP}$ mice, and was also documented particularly in the liver (FIGS. 5 and 11).

Figure 11A:
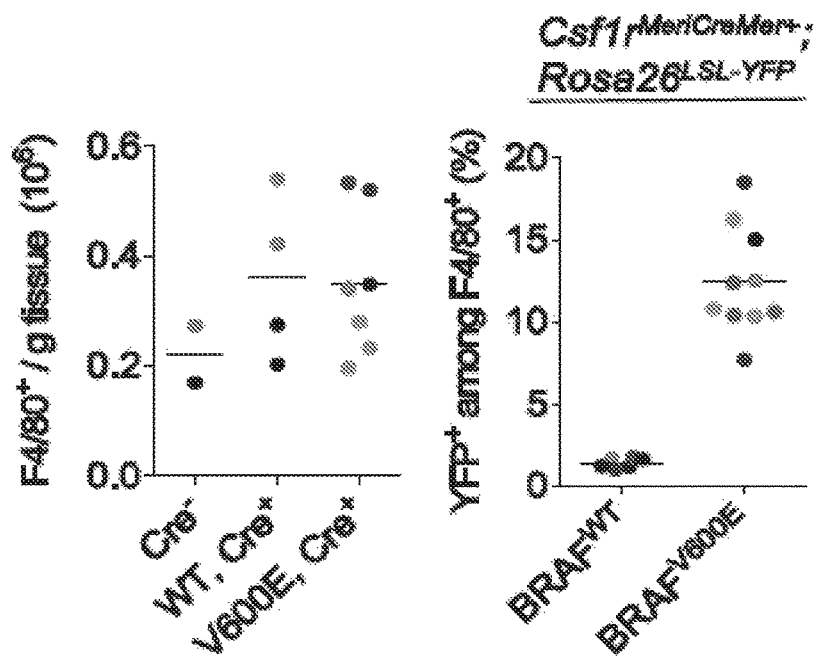
FIGS. 11A-11C show the analysis of the liver in 6-8 month old $Csf1r^{MeriCreMer}$; $BRAF^{V600E}$; $Rosa26^{LSL-YFP}$ and littermates.
Figure 11B:
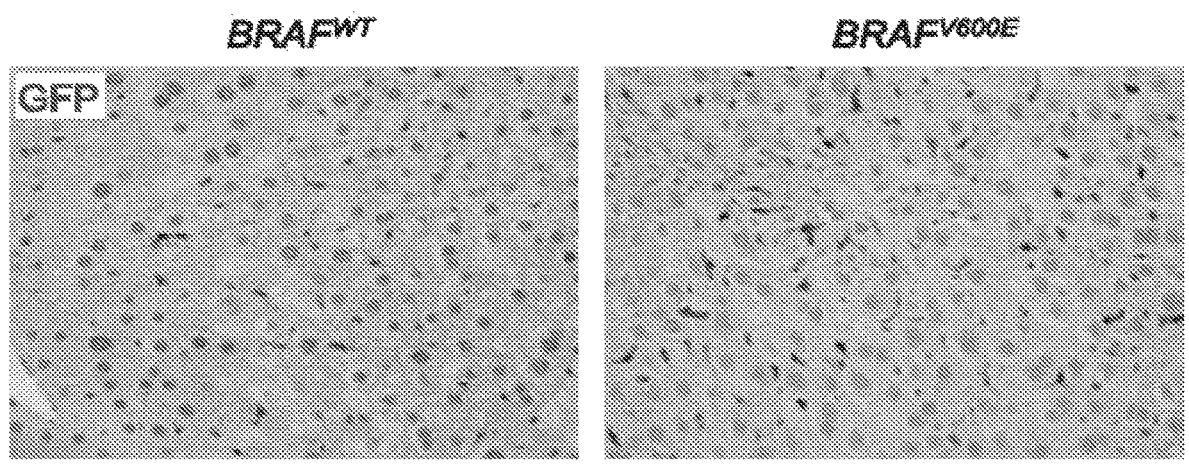
Figure 11C:
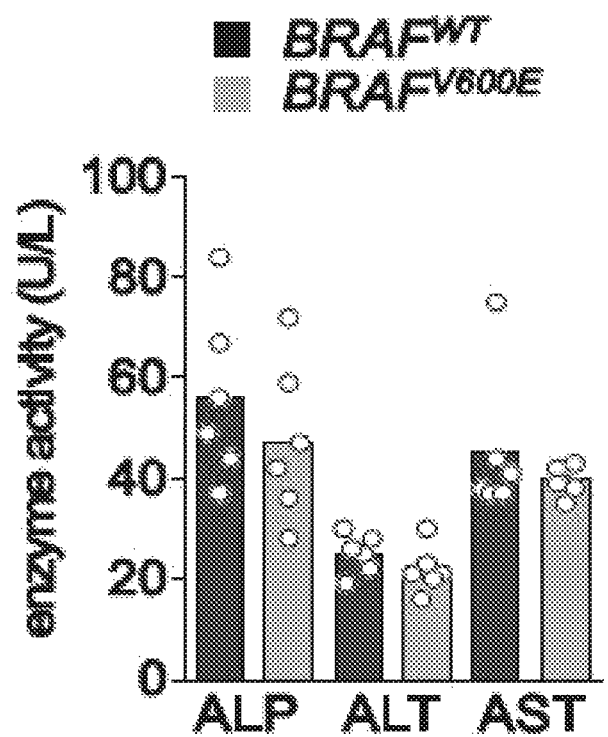

Example 9: Determining if Development of Liver Injury is Accelerated by the Presence of BRAF$^{V600E}$-Expressing Kupffer Cells Some degree of liver involvement is frequent in histiocytosis and severe sclerosing cholangitis with liver fibrosis occurs in ~5% of patients and has a high mortality. Our preliminary results showed that Csf1r$^{MeriCreMer}$; BRAF$^{V600E}$; Rosa26$^{LSL-YFP}$ mice develop focal accumulation of histiocytes in the liver (FIGS. 5C and 5D; FIG. 11). Flow cytometric analysis shows that YFP$^+$ and thus BRAF$^{V600E}$ expressing Kupffer cell clones were bigger (12-13% among F4/80$^+$) when compared to BRAF$^{WT}$ littermates (1-2%, FIG. 11A). In histological analysis, focal collections of histiocytes were noted in multiple sections of liver in BRAF$^{V600E}$ mice (FIG. 11B). However, liver enzyme function assessed by serum analysis of alkaline phosphatase (ALP), alanine aminotransferases (ALT) and aspartate aminotransferases (AST), were normal (FIG. 11C), and a limited histopathological analysis did not observe evidence of cholestasis, interstitial fibrosis in the portal area, or reactive hyperplasia of small bile ducts, which are features of the disease. Therefore it is believed that the clonal Kupffer cell expansion observed in BRAF$^{V600E}$ mice in specific-pathogen free (SPF) conditions does not trigger portal fibrosis or cholangitis on its own. However, this provides an opportunity to manipulate the mice to investigate the impact of environmental factors that could promote the escape from a "silent mode" and trigger liver disease. Csf1r$^{MeriCreMer}$; BRAF$^{V600E}$; Rosa26$^{LSL-YFP}$ mice housed under SPF conditions, and fed irradiated chow are protected from many harmful xenobiotics such as carcinogens, drugs, environmental pollutants, food additives, hydrocarbons, and pesticides. To phenocopy possible environmental factors that might accelerate or cause the liver pathophysiology seen in histiocytosis patients, xenobiotic-induced cholangiopathy will be effected. Csf1r$^{MeriCreMer}$; BRAF$^{V600E}$; Rosa26$^{LSL-YFP}$ mice and BRAF$^{WT}$ littermates (n=8 per genotype) will receive 0.1% 3,5-diethoxycarbonyl-1,4-dihydrocollidine (DDC)-chow over a period of 4 weeks, starting at 4 weeks of age. Wild-type mice exhibit sclerosing cholangitis and a biliary type of liver fibrosis in a highly reproducible manner at this time point. Morphological alterations of the liver are accompanied by a continuous increase in ALT levels as an indicator of hepatocyte injury followed by significant elevations of cholestasis parameters, such as AP and bilirubin. Thus, to follow onset and severity of disease, mice are bled from the facial vein, and serum is analyzed for ALT, AP, and bilirubin before the diet and weekly thereafter. Sclerosing cholangitis and fibrosis are analyzed histologically on paraffin sections as well as cryosections, thus livers of BRAF$^{WT}$ and BRAF$^{V600E}$ animals are pre-fixed with 4% PFA, or with a modified formalin/methanol/acetone fixation, depending on downstream procedure. H&E and Sirius red stain are the first readout for fibrosis severity. Morphometry of K19-positive cells indicates ductular reaction, and is compared in BRAF$^{V600E}$ mice and BRAF$^{WT}$ littermates by measuring bile duct mass and normalizing it to the size of portal veins. In addition, well-established markers for liver fibrosis such as osteopontin, a profibrogenic cytokine, and a-smooth muscle actin (SMA) staining, which indicates hepatic stellate cell activation, are used to quantify the excess of fibrosis. Resident Kupffer cells (F4/80 and YFP) in BRAF$^{V600E}$ mice and BRAF$^{WT}$ littermates are also stained to assess the anatomical proximity of YFP$^+$ Kupffer cell clones to the lesion site. The inflammatory phenotype characterised by an infiltration of neutrophils (CD11b$^+$Ly6G$^+$) and monocytes (CD11b$^+$Ly6C$^+$) is evaluated by flow cytometry. For statistical analyses Student's t-test is performed and all P-values of <0.05 will be considered significant.

The well-established carbon tetrachloride (CCl$_4$) model to induce liver fibrosis in BRAF$^{V600E}$ and BRAF$^{WT}$ littermate controls is used to confirm a possible acceleration of liver fibrosis with BRAF$^{V600E}$ expressing Kupffer cell clones. BRAF$^{WT}$ and BRAF$^{V600E}$ littermates (4 week old, n=8 per genotype) are injected with 1 µl/g body weight of a 1:7 ratio CCl$_4$:olive oil mix or just olive oil as control treatment every 5 days for 4 weeks to induce fibrosis. The grade of liver injury is assessed as described above.

Example 10: Assessing and Monitoring the Extent of Organ Involvement in Csf1r$^{MeriCreMer}$; BRAF$^{V600E}$; Rosa26$^{LSL-YFP}$ Using Whole Animal Imaging The following studies are used to characterize extra-neurological involvement and its pathological consequence more broadly. In patients, neurodegeneration as well as liver, lung, and bone disease are associated with MRI and PET/CT radiographic findings. To complete the analysis the presence of lung inflammatory or fibrotic lesions and of bone lytic lesions is investigated by whole animal imaging of a cohort (n=8 per genotype) of 6 month old Csf1r$^{MeriCreMer}$, BRAF$^{V600E}$; Rosa26$^{LSL-YFP}$ mice and BRAF$^{WT}$ littermates. Mice are imaged under anesthesia at the MSKCC small imaging core facility. To identify skeletal lesions, microCT (microCAT II Imtek Corp, Oak Ridge, Tenn.), which yields spatial resolution on the order of 100 microns, delivering a radiation dose on the order of 20 cGy, will be used. Soft tissue analysis (lung) will be carried out by whole body PET/CT using FDG. In addition, these experiments will provide an analysis of the liver, and will also image the brain of these mice using a 7 tesla MRI with gadolinium injection. Data analysis is performed in close collaboration with the MSKCC small imaging core facility. Histological and flow cytometry analysis of lung tissue and bone are performed on groups of BRAF$^{V600E}$ and BRAF$^{WT}$ littermates (n=5 per genotype). Histology of bone tissue are performed after fixation with 4% paraformaldehyde for 3 days, decalcification for 4 days in 14% EDTA pH 7.1. and dehydration. Histology of lung is performed on paraffin sections, H&E and Sirius red stain are the first readout to analyze the presence of fibrosis. For flow cytometry analysis of the lung tissue, cell suspensions are prepared and stained with antibodies for alveolar and interstitial macrophages (F4/80, CD11b, CD45, Siglec-F, CD11c), T cells (CD3, CD4, CD8), B cells (CD19), eosinophils, monocytes and neutrophils (Ly6C, Ly6G, Siglec-F, CD11b) to identify and quantify an inflammatory infiltrate. Live-dead discrimination is performed by Hoechst or 7-AAD staining.

Results from these imaging studies complete the characterization of the model, providing a strategy to follow disease activity that could be used in aim 3, and may reveal the presence of bone and/or lung lesions in the Csf1r$^{MeriCreMer}$ Rosa26$^{LSL-YFP}$; BRAF$^{V600E}$ mice. Soft tissue lesions that may correspond to inflammatory granuloma, demyelination, and bone defects are expected to be visible with MRI, FDG-PET/CT and microCT permitting observation of the progression of disease in live mice.

Example 11: Determining Whether Targeting of a Small Number of HSCs Also Results in the Differentiation of BRAF$^{V600E}$ Macrophages and Features of Histiocytoses (Particularly Neurodegenerative Disease)

The strategy of targeting the BRAF$^{V600E}$ mutation to a small number of EMPs appears to model some aspects of histiocytic disorders, while targeting of HSCs in contrast leads to a leukemic disorder. However, it is possible that targeting a small proportion of HSCs, as has been done for EMPs, may also lead to histiocytic phenotype. BRAF$^{V600E}$; Rosa26$^{LSL-YFP}$ crossed with Cxcr4$^{CreERT2}$ mice, which were recently characterized with the lab of Ralf Stumm (Jena University, Germany) are analyzed. Cxcr4 is expressed in HSCs but not in EMPs, fetal macrophages, or adult tissue-resident macrophages. A low-dose (20 mg/kg) pulse of OH-TAM at E9.5 allows transient and limited induction of Cre expression to pulse-label ~10% of HSCs in adults (FIG. 4). If expression of BRAF$^{V600E}$ in LSK in embryos is lethal and embryos results in a leukemic phenotype in utero, the dose of OH-TAM is titrated down and mice are treated postnatally. Blood and bone marrow, brain, liver, spleen, and lung of Cxcr4$^{CreERT2}$; BRAF$^{V600E}$; Rosa26$^{LSL-YFP}$ mice (n=5) and their littermates are then analyzed at 4 weeks by multiparameter flow cytometry analysis. Cell suspensions prepared from the indicated organs are stained using antibodies directed against hematopoietic progenitors (CD45, Kit, Sca1, CD48, CD150), myeloid cells (CD115, Ly6C, CD11b, CD11c, MHCII, F4/80, SiglecF) and lymphoid cells (CD3, CD4, CD8, CD19). Results are analyzed with FlowJo and with the PhenoGraph algorithm, which partitions high-dimensional single-cell data as obtained by multi-color flow cytometry into subpopulations without a priori gating. If flow cytometry suggests expansion of macrophages and/or the presence of an inflammatory infiltrate, histological analysis of bone marrow, brain, liver, spleen, and lung is performed to look for granulomas, inflammatory infiltrates, and fibrosis using H&E and Sirius red stains and immunostaining for YFP and macrophage antigens F4/80 and CD68. If Cxcr4$^{CreERT2}$; BRAF$^{V600E}$; Rosa26$^{LSL-YFP}$ mice are viable and do not present with an overt phenotype at 4 weeks, a cohort of Cxcr4$^{CreERT2}$; BRAF$^{V600E}$; Rosa26$^{LSL-YFP}$ and littermates are monitored for the development of an histiocytic phenotype for >6 months and are then autopsied for histopathological and FACS analysis to examine for infiltration in hematopoietic tissues, liver, lung, and brain. In case of positive results, to ensure that a phenotype is due to cell-autonomous expression of BRAF$^{V600E}$ in HSC-derived cells, BRAF$^{V600E}$ and BRAF$^{V600E}$-LSK from Cxcr4$^{CreERT2}$; BRAF$^{V600E}$; Rosa26$^{LSL-YFP}$ mice are co-transplanted into lethally irradiated (2×450 cGy) wild type recipients and these recipient mice are analyzed as described above.

Figure 12:
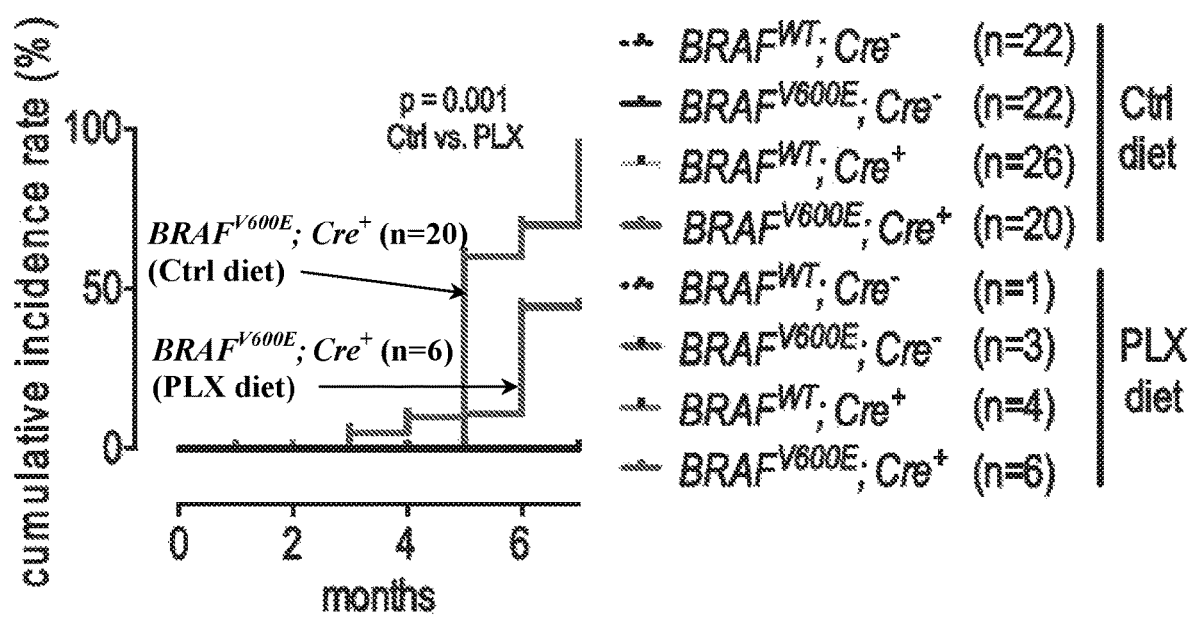
FIG. 12 shows cumulative incidence rate of behavioral abnormalities in Csf1r$^{MeriCreMer}$; BRAF$^{V600E}$; Rosa26$^{LSL-YFP}$ mice placed on long-term PLX4720 diet (PLX diet) at 3 months of age, and mice on normal control diet (Ctrl diet).

Example 12: Testing Whether the Pathological Changes Associated with BRAF$^{V600E}$ Expression in Macrophages are Reversible or can be Prevented by BRAF Inhibitors Whether PLX4720 can prevent the onset of neurological disease by continuous feeding of Csf1r$^{MeriCreMer}$; BRAF$^{V600E}$; Rosa26$^{LSL-YFP}$ mice with PLX4720-impregnated chow (417 mg/kg, Research Diets, Inc.) was investigated. A cohort of 3 month-old BRAF$^{V600E}$ and BRAF$^{WT}$ littermates were placed on PLX4720 or control diet. As a readout, hind limb clasping reflexes were examined every week and footprint assays were performed as described above before treatment and every 4 weeks during treatment. Preliminary results evaluating the cumulative incidence of the ataxic phenotype in this small group of mice suggested that the PLX4720-diet delays but does not totally prevent the onset of neurologic disease (FIG. 12).

Example 13: Assessing the Effects of BRAF Inhibitor Treatment In Vivo on the Incidence and Severity of Neurological Disease and Microglial Activation Cohorts of age matched Csf1r$^{MeriCreMer}$; BRAF$^{V600E}$; Rosa26$^{LSL-YEP}$ mice and BRAF littermate controls (n=10 for each genotype and treatment group) are placed on PLX4720-impregnated (417 mg/kg) or control chow from the age of 4 weeks and 3 months. Incidence and severity of the neurological phenotype are assessed by measurement of hind-limb clasping reflex every week and footprint assays every two weeks; rotarod analysis is performed monthly and the open field test and MRI (depending on results from Example 10) are performed on mice that do not exhibit neurological symptoms by 8 months. Surviving mice are sacrificed for pathological analysis (H&E, Luxol fast blue stainings, and IHC for GFP, Iba1, and pERK) and flow cytometry analysis as in Example 7 to assess the extent of microglial activation and the inflammatory infiltrate. On the same set of mice, RNAseq analysis is performed according to the protocol described in Example 8 to assess change of the BRAF$^{V600E}$ signature upon BRAF inhibitor treatment Briefly, mice are sacrificed by 8 months and microglial cells FACS sorted (200 cell into 96-well plates, to assess those gene expression changes affected by the BRAF$^{V600E}$ activation (comparison of BRAF$^{V600E}$ to BRAFWT control treated mice) and those altered by PLX4720-treatment in each BRAF genotype. In addition to longitudinal experiments to assess for prevention of development of neurodegenerative disease, mice with established neurodegenerative disease are treated. Cohorts of age matched Csf1r$^{MeriCreMer}$; BRAF$^{V600E}$; Rosa26$^{LSL-YFP}$ mice and BRAF$^{WT}$ littermate controls with established neurologic disease as assessed by the physiologic, behavioral, and radiographic assays described in Example 6 (n=10 for each genotype and treatment group) are placed on PLX4720-impregnated (417 mg/kg) or control chow. Mice are evaluated using hind-limb clasping reflex, footprint assays, rotarod analysis, open field test, and MRI using the methods and schedule above. The effect of treatment on survival of these mice are evaluated using Kaplan-Meier estimates of survival (with log-ranked (Mantel-Cox) used to determine statistical significance).

Example 14: Conserved Pathways and Genes Regulated by BRAF$^{V600E}$ Expression in Mouse and Human Histiocytosis Lesions Prior and ongoing RNAseq analysis of human histiocyte tissue biopsy samples are utilized to correlate with the isogenic tissue-specific RNAseq data obtained from murine BRAF$^{V600E}$ and BRAF$^{WT}$ macrophages as described above. Currently this includes RNAseq patient tissue biopsies from brain, skin, and bone (n=10 distinct patients from each site, approximately half of whom are BRAF$^{V600E}$ mutant). Results from the murine RNAseq studies are compared with our human RNAseq data from patients to identify i) genes differentially expressed in the presence of the BRAF$^{V600E}$ mutation in mouse and human macrophages that are mutant versus WT for BRAF regardless of tissue source, and ii) BRAF$^{V600E}$-dependent transcriptional changes that are tissue-specific. Also included in the analysis will be published microarray data from sorted CD207$^+$ cells (presumably pathologic macrophages) from biopsies of LCH patients. Gene Set Enrichment Analysis (GSEA) is performed on the various human samples and the murine macrophages using the C7 collection (immunologic signatures) offered by the Broad institute, as has been done previously. Expression of candidate genes common to mouse and human cells are validated at the protein level using flow cytometry, immunohistochemistry, and/or ELISA/Luminex technology (available in the laboratory) in murine and human tissues and cells.

Methods for the isolation of resident macrophages from the nervous system, and methods for determining the BRAF$^{V600E}$ status of those cells are well known. Cell suspensions prepared from brain or spinal cord of Csf1r$^{MeriCreMer}$; BRAF$^{V600E}$; Rosa26$^{LSL-YFP}$ mice are stained using antibodies directed against macrophages (CD45, CD11b, F4/80). YFP expression allows to sort BRAF$^{V600E+}$ cells. The mutation can be detected in the Braf locus after RNAseq or alternatively by digital PCR, if the sequenced reads do not cover the whole locus.

Figure 13A:
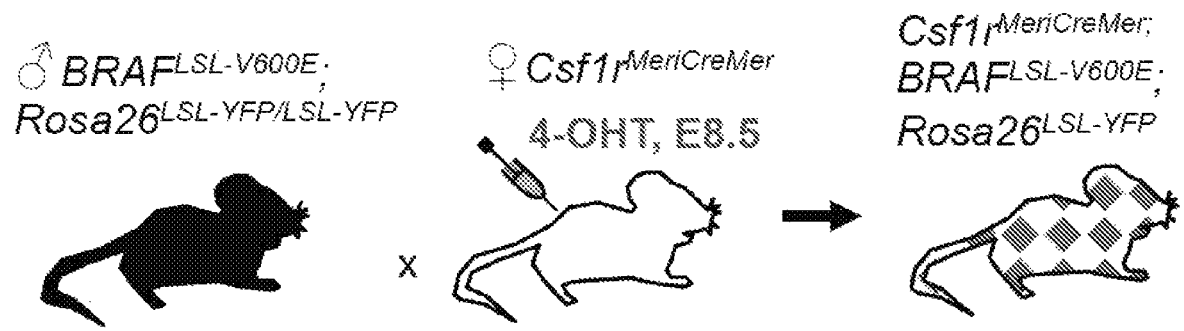
FIGS. 13A-13I. Targeting BRAF$^{V600E}$ in tissue-resident macrophages.
Figure 13B:
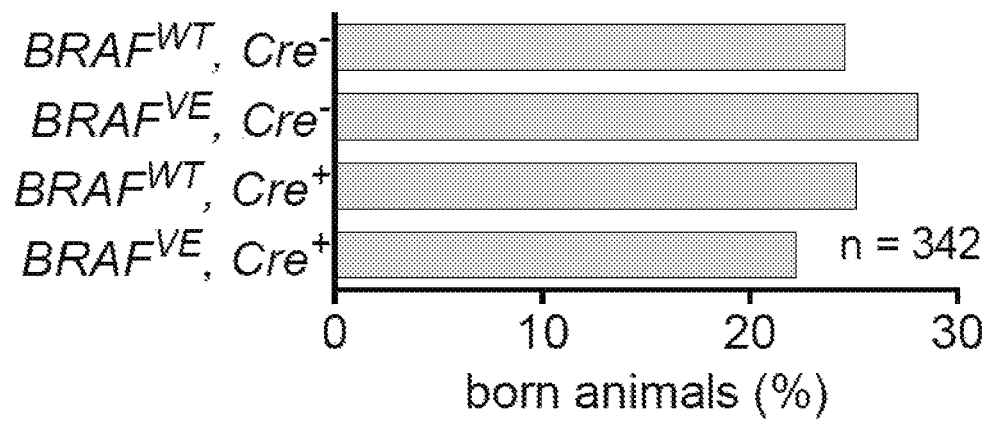
Figure 13C:
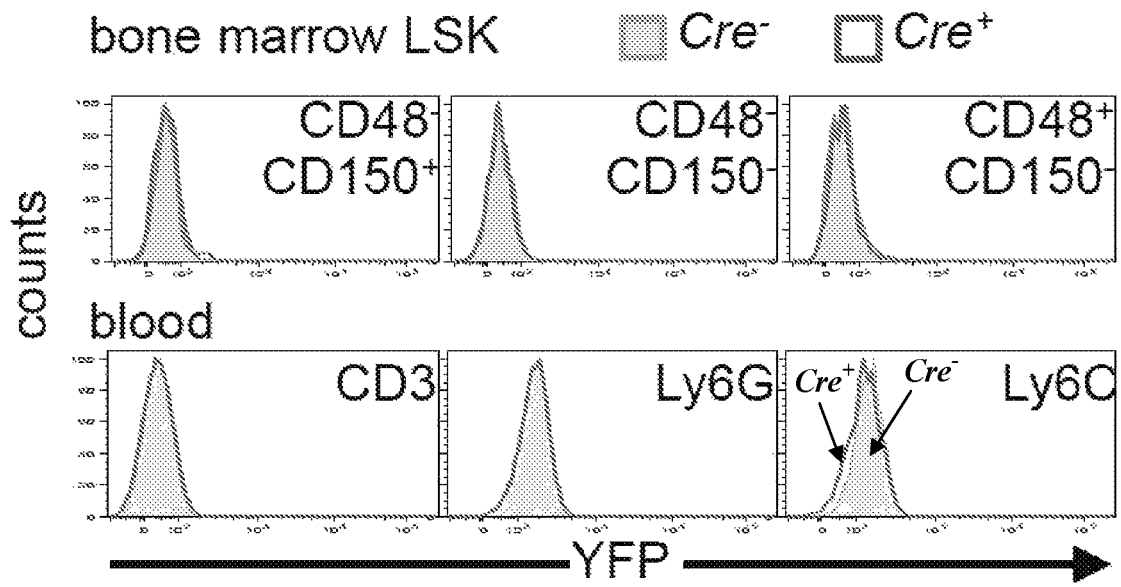
Figure 13D:
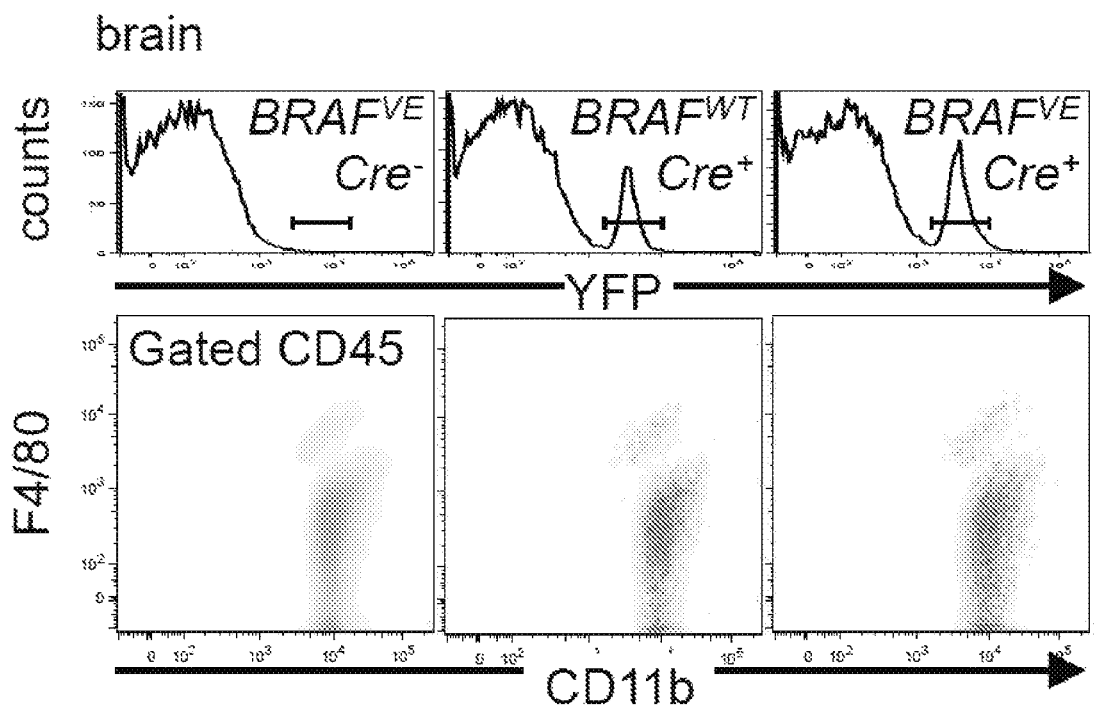
Figure 13E:
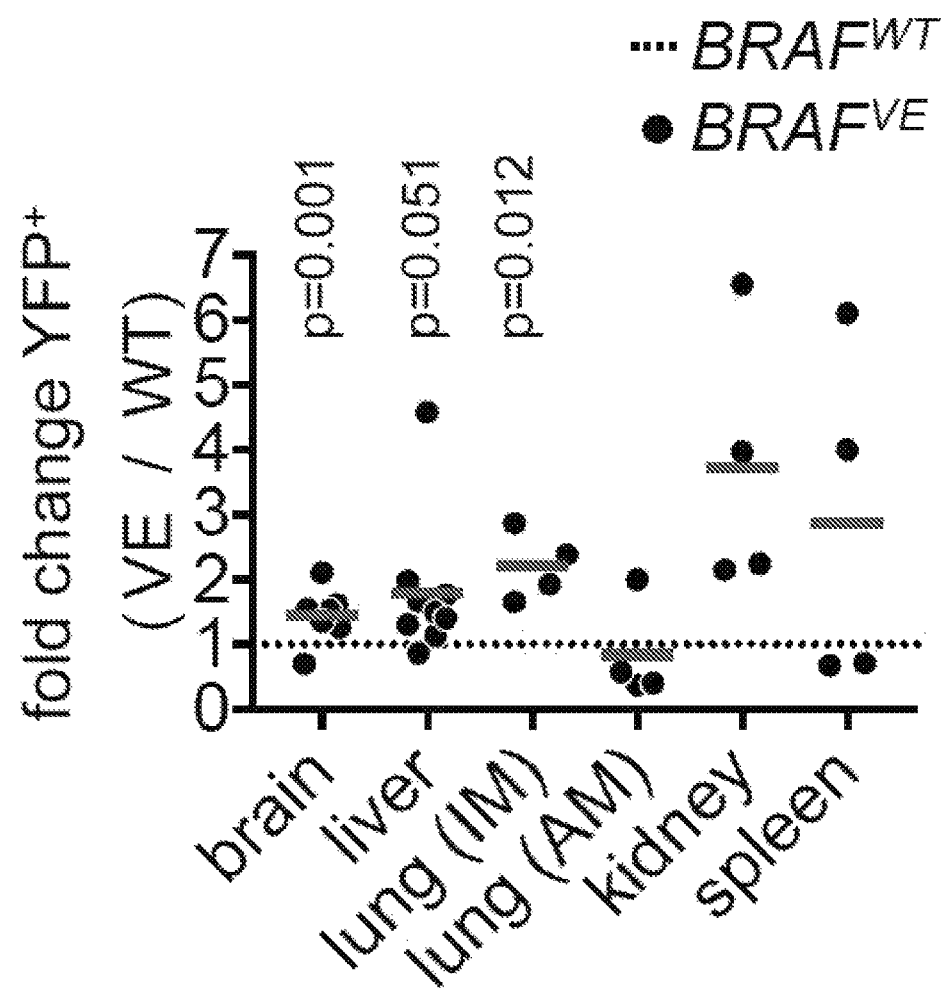
Figure 13F:
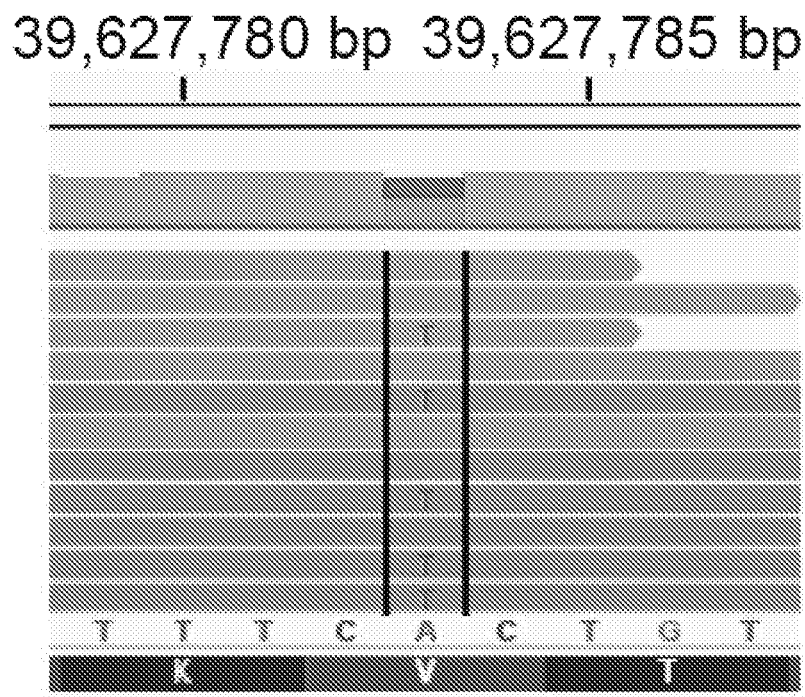
Figure 13G:
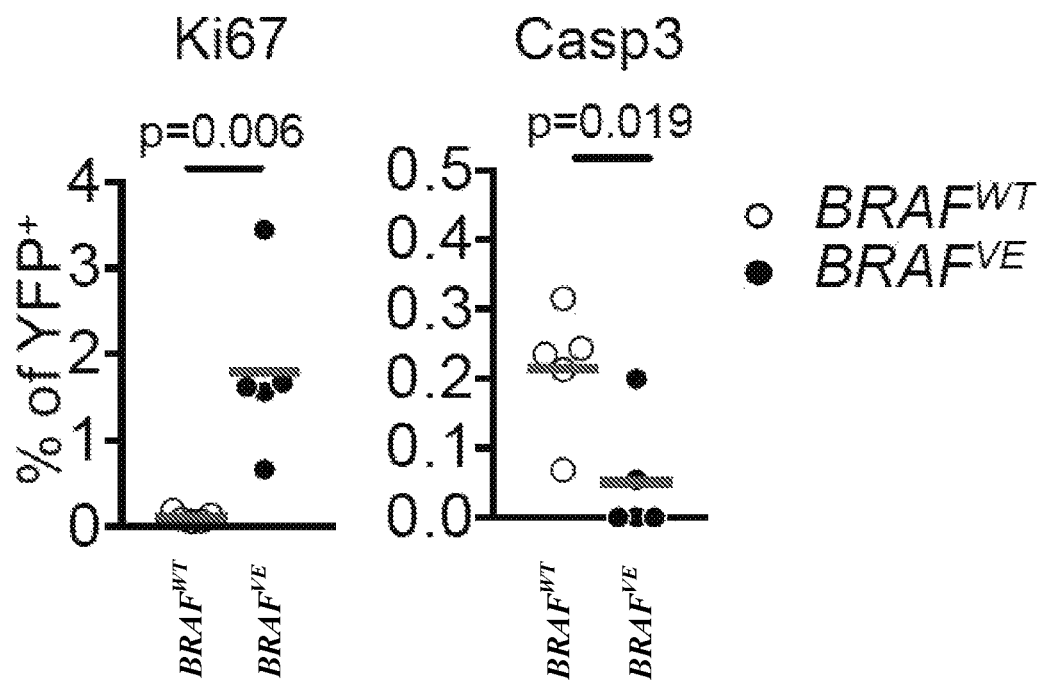
Figure 13H:
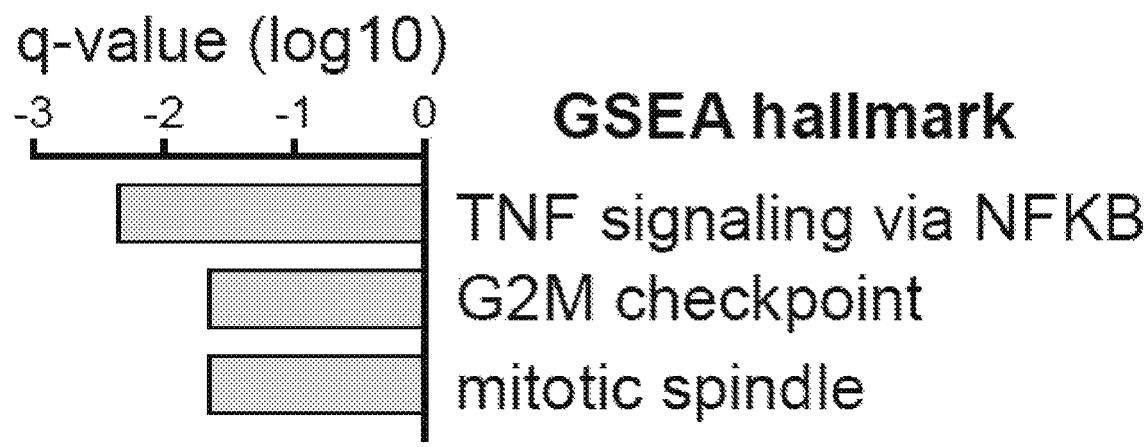
Figure 13I:
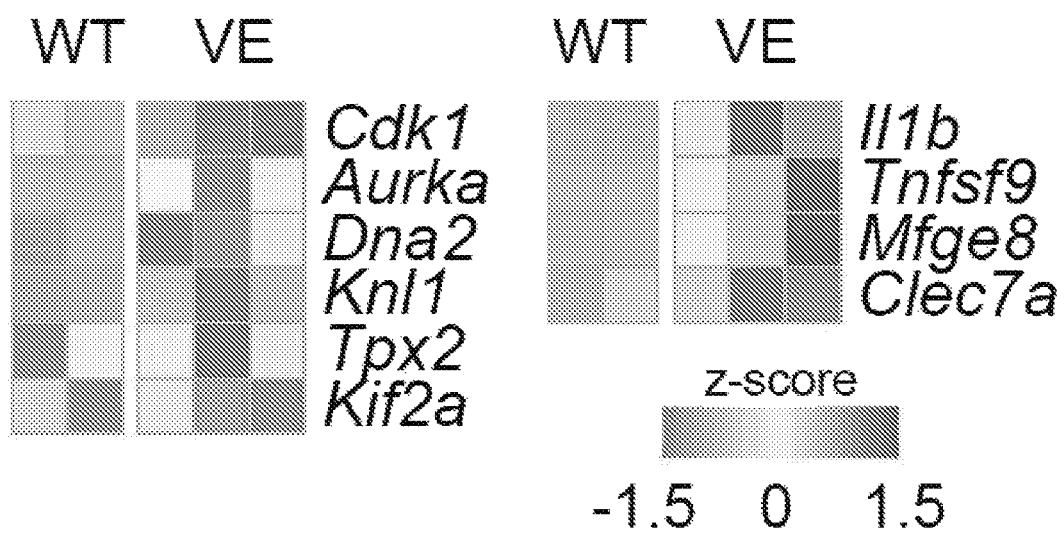
Figure 17A:
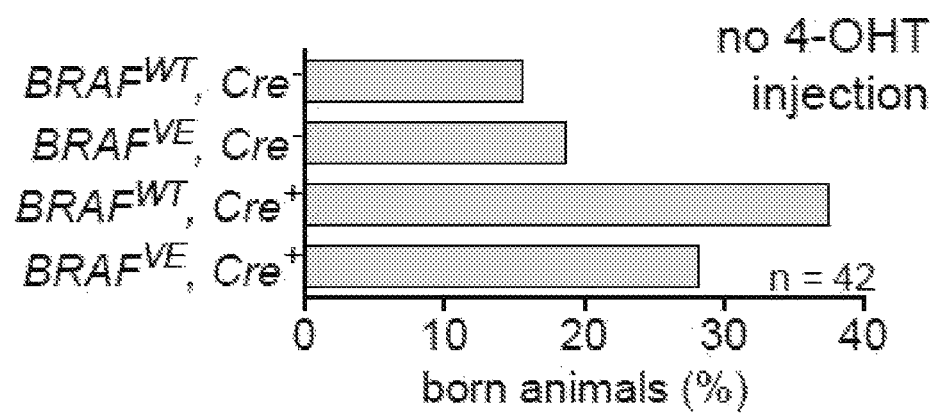
FIGS. 17A-17H. Analysis of one-month old Csf1r$^{MeriCreMer}$; BRAF$^{LSL-V600E}$ Rosa26$^{LSL-YFP}$ mice.
Figure 17B:
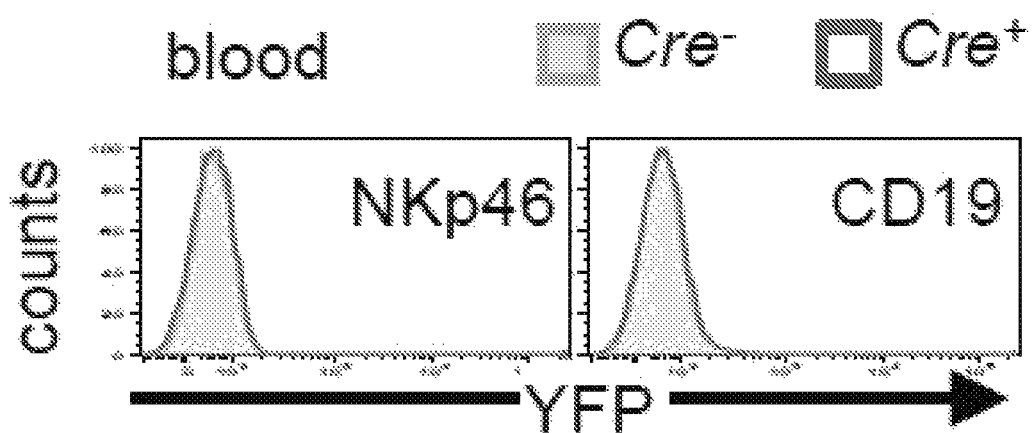
Figure 17C:
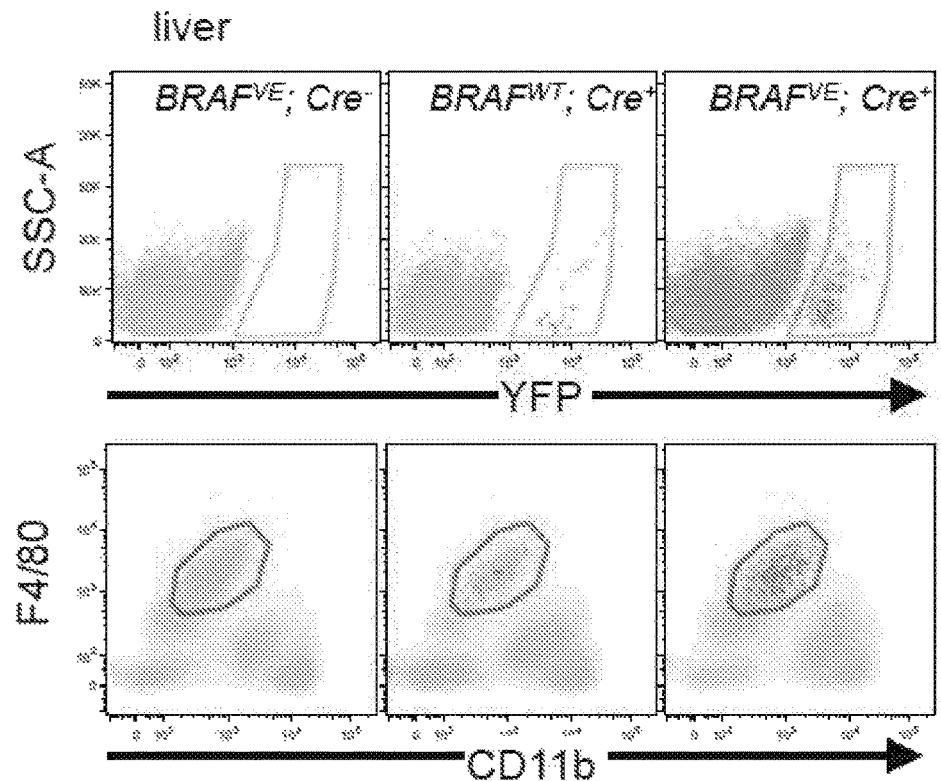
Figure 17D:
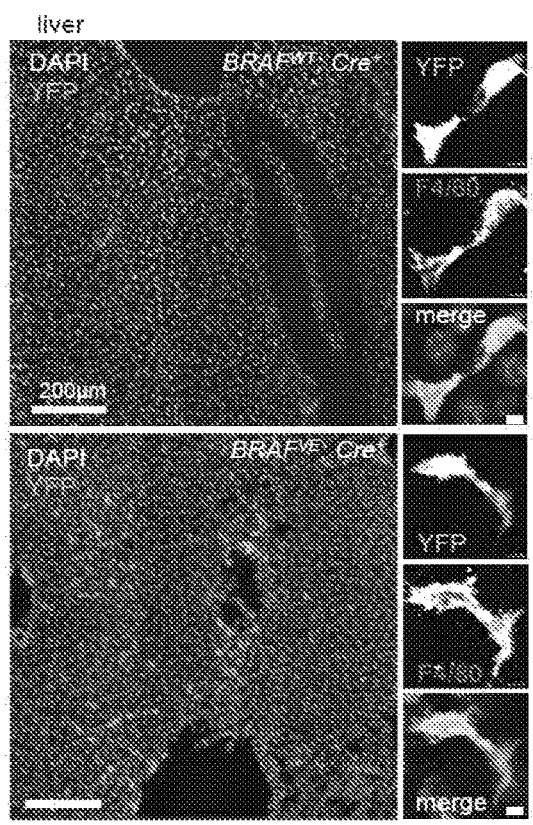
Figure 17E:
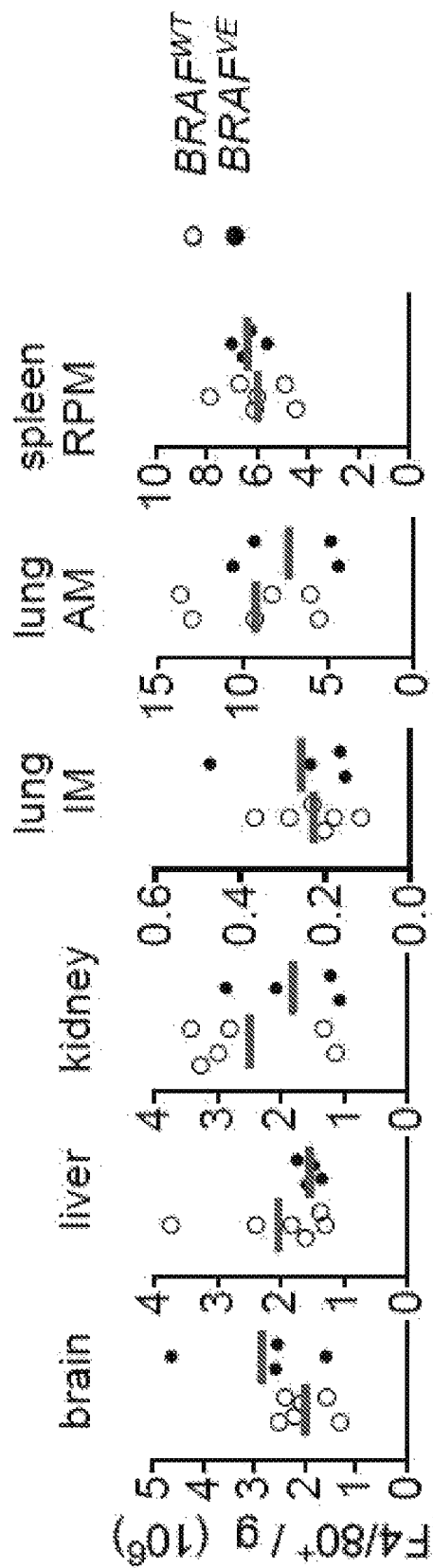
Figure 17F:
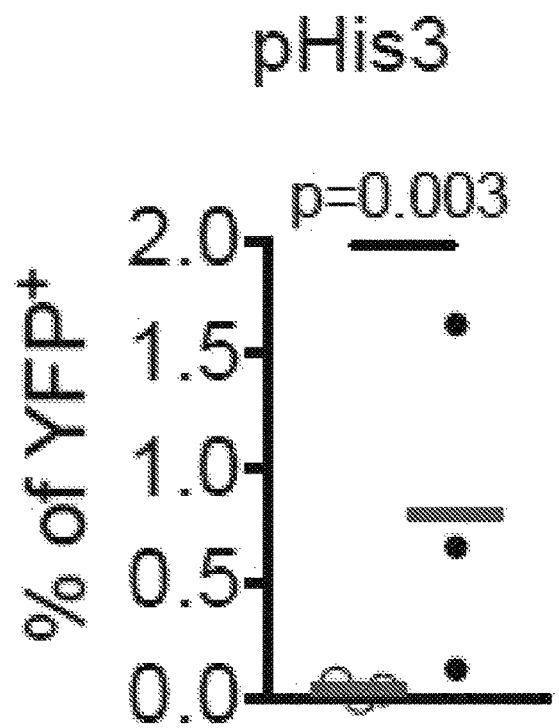
Figure 17G:
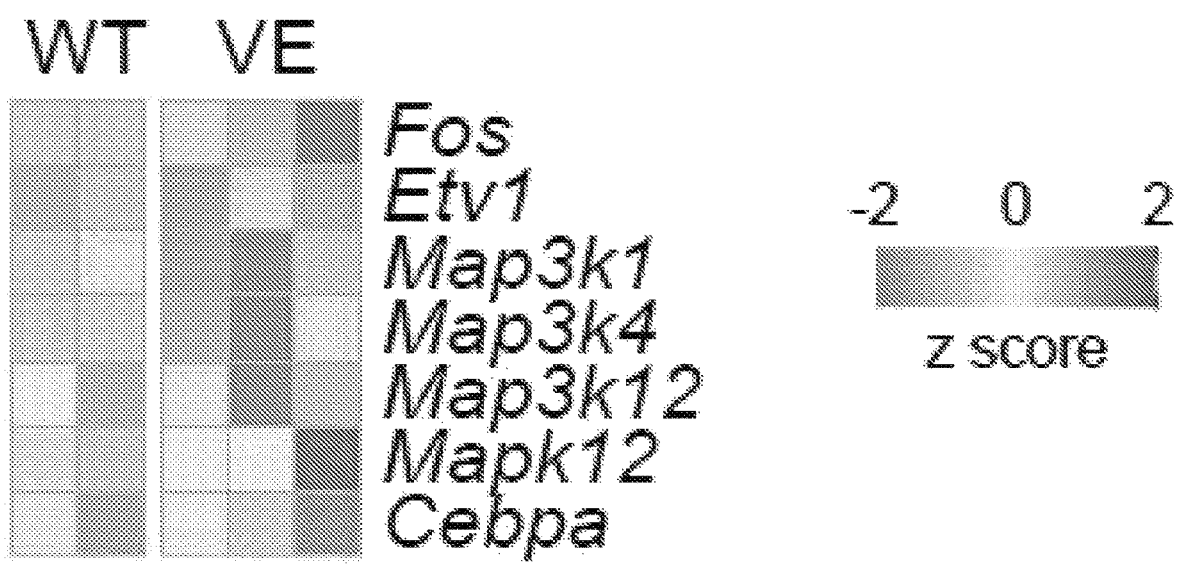
Figure 17H:
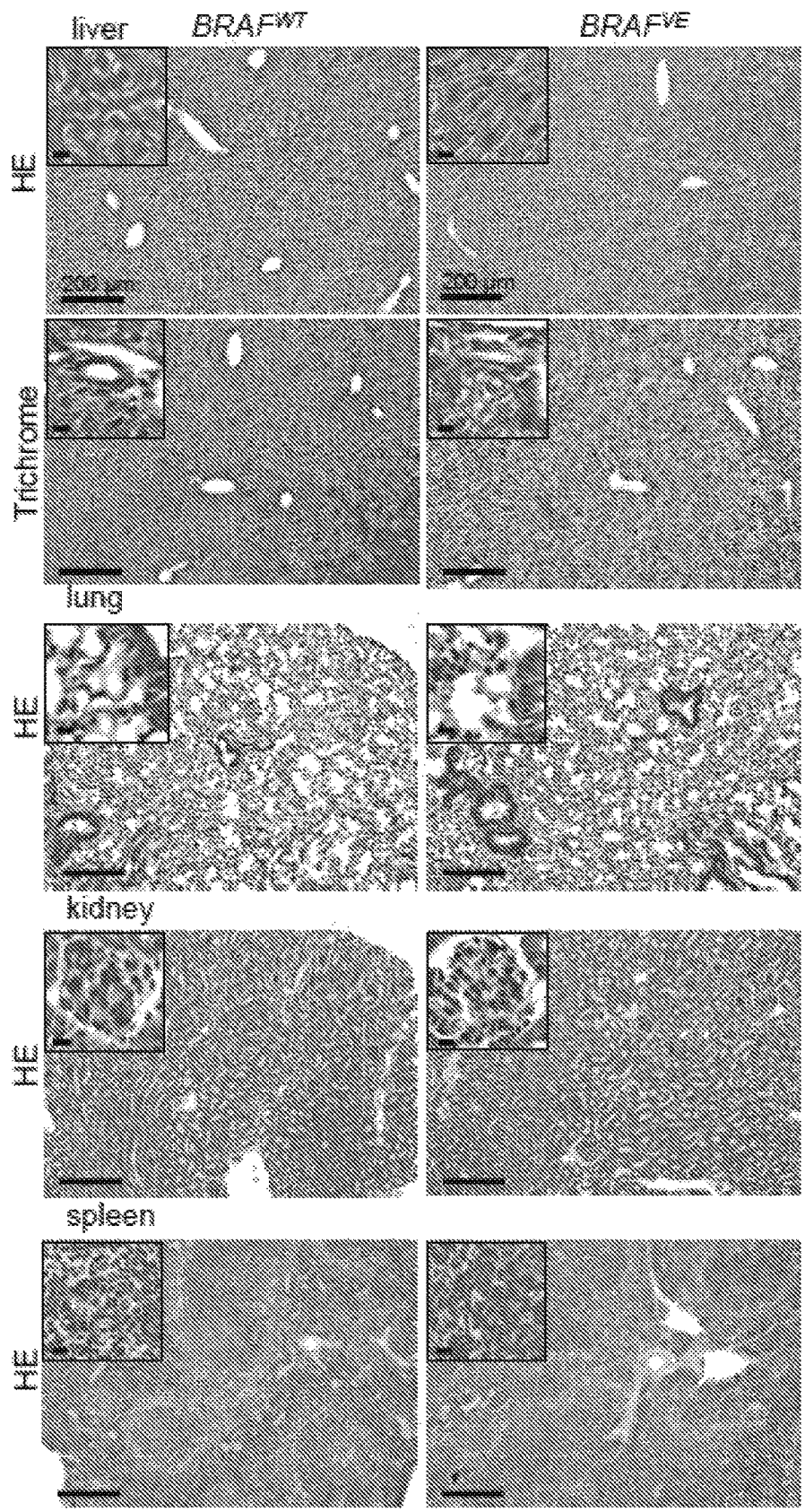
Figure 18A:
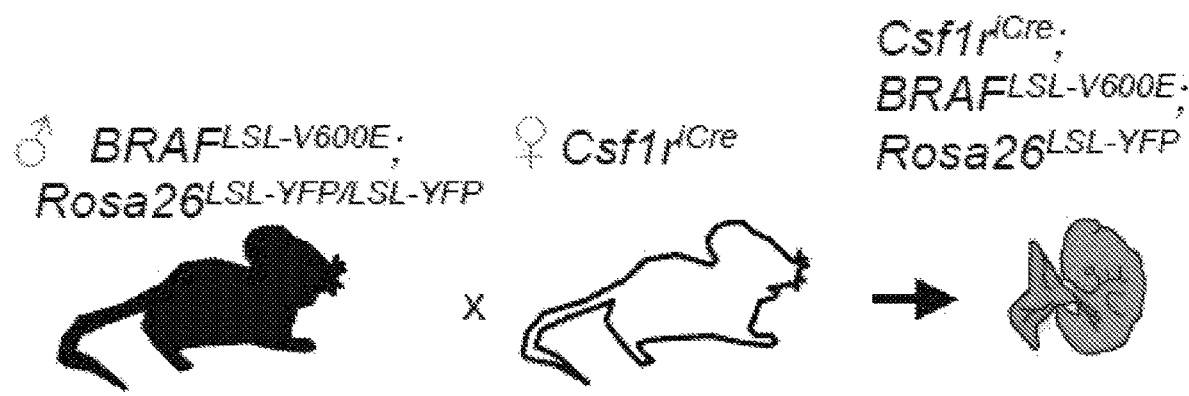
FIGS. 18A-18F. Effect of constitutive BRAF$^{V600E}$ expression in Csf1r-expressing cells.
Figure 18B:
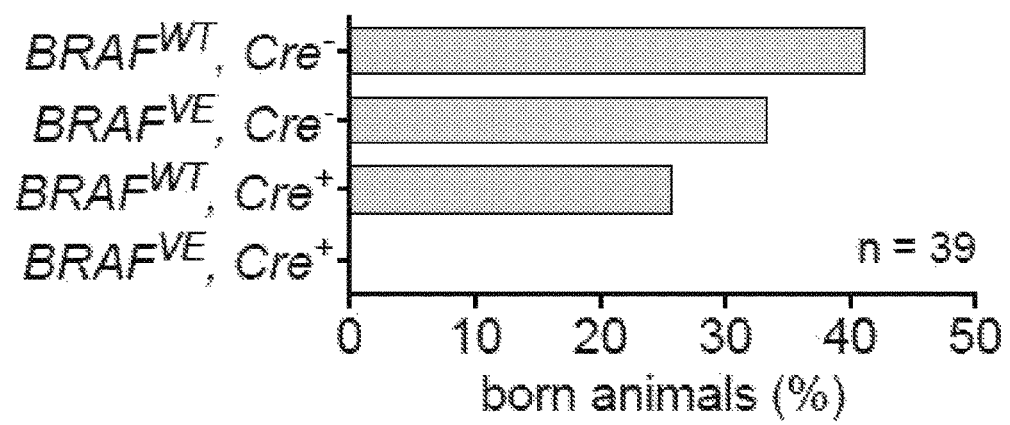
Figures 18C, 18D:
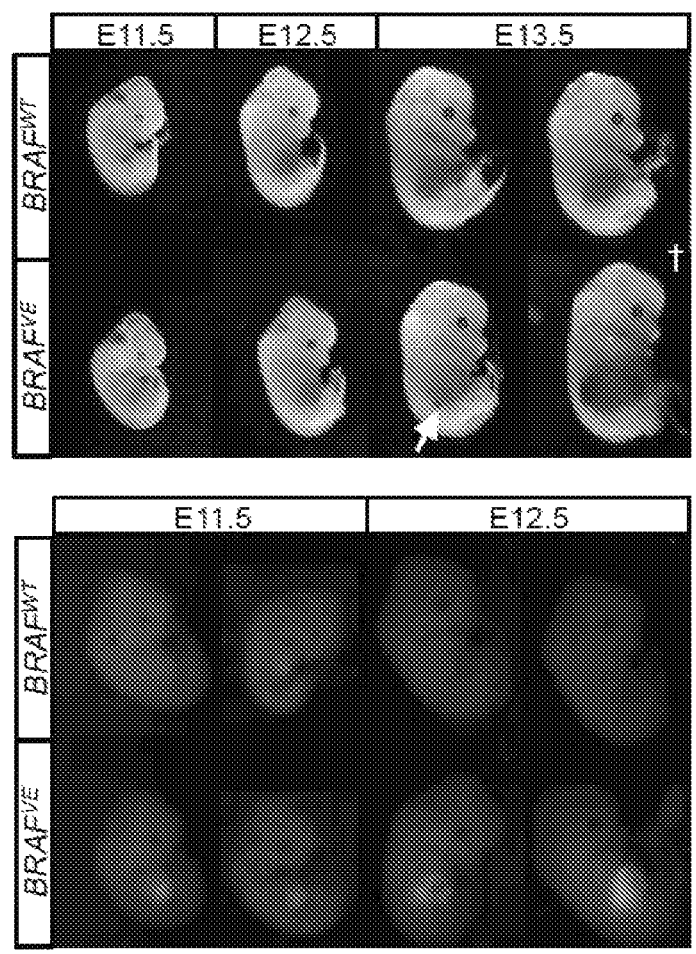
Figure 18E:
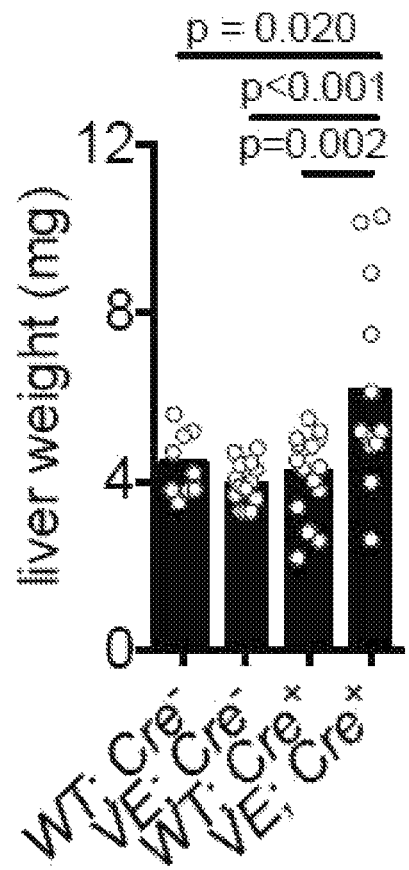
Figure 18F:
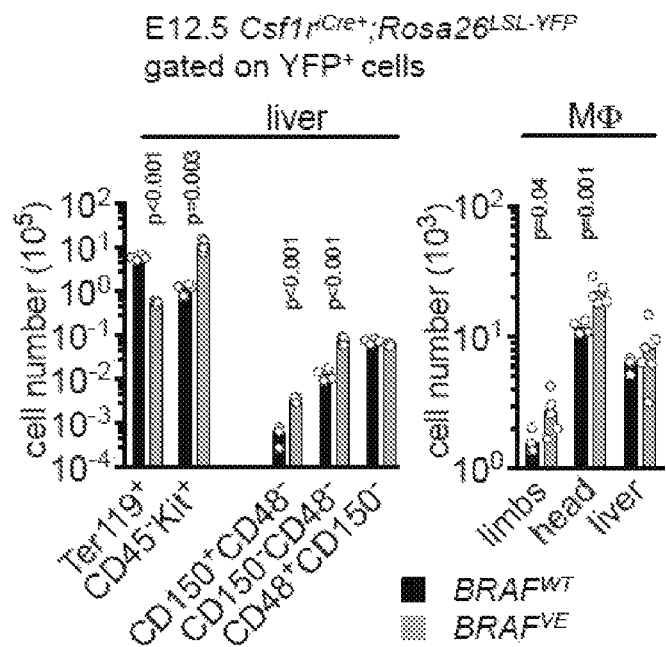
Figure 19A:
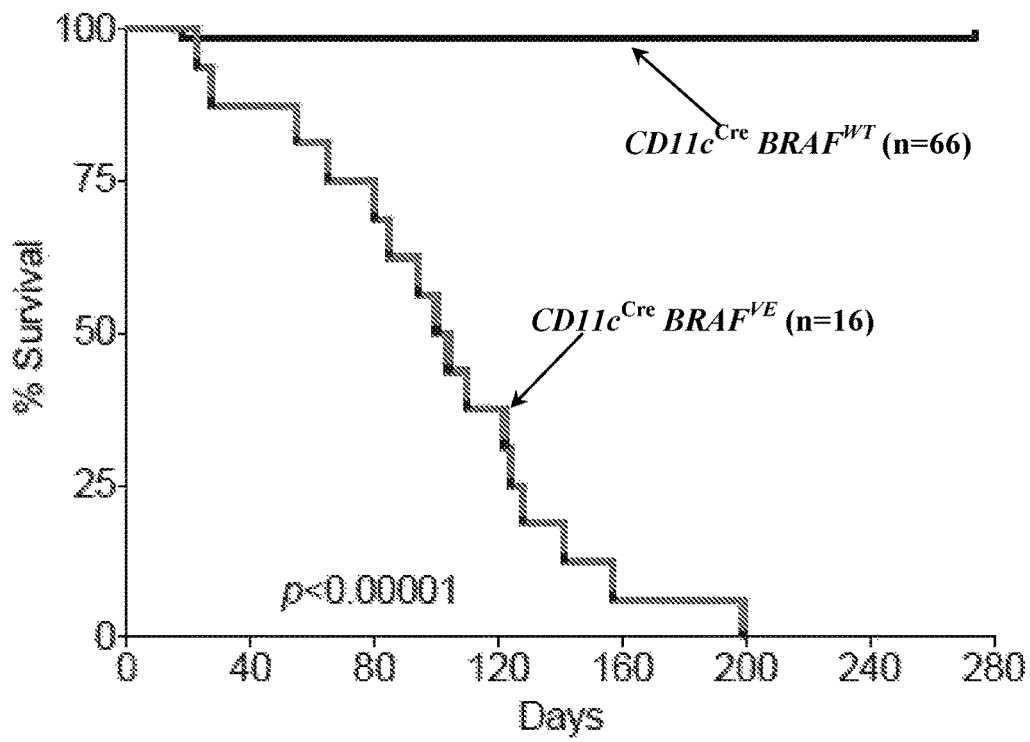
FIGS. 19A-19G. Analysis of CD11c$^{Cre}$; BRAF$^{V600E}$ mouse model.
Figure 19B:
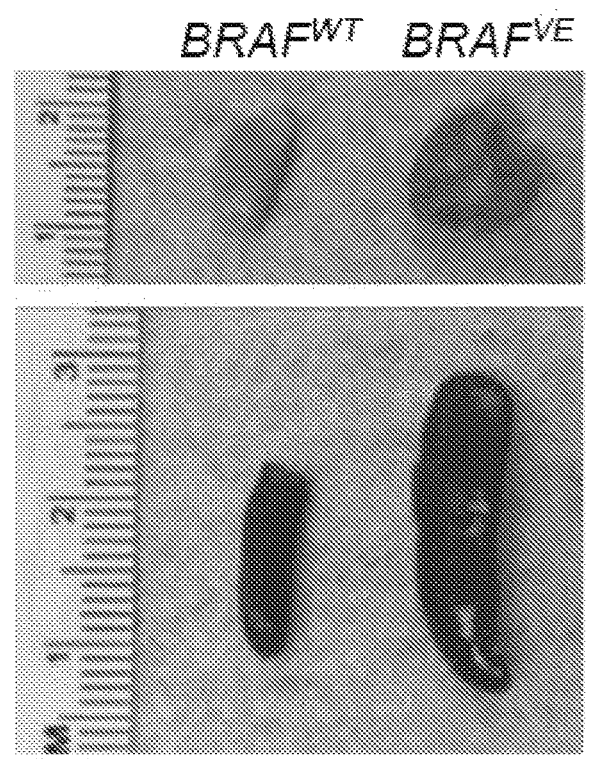
Figure 19C:
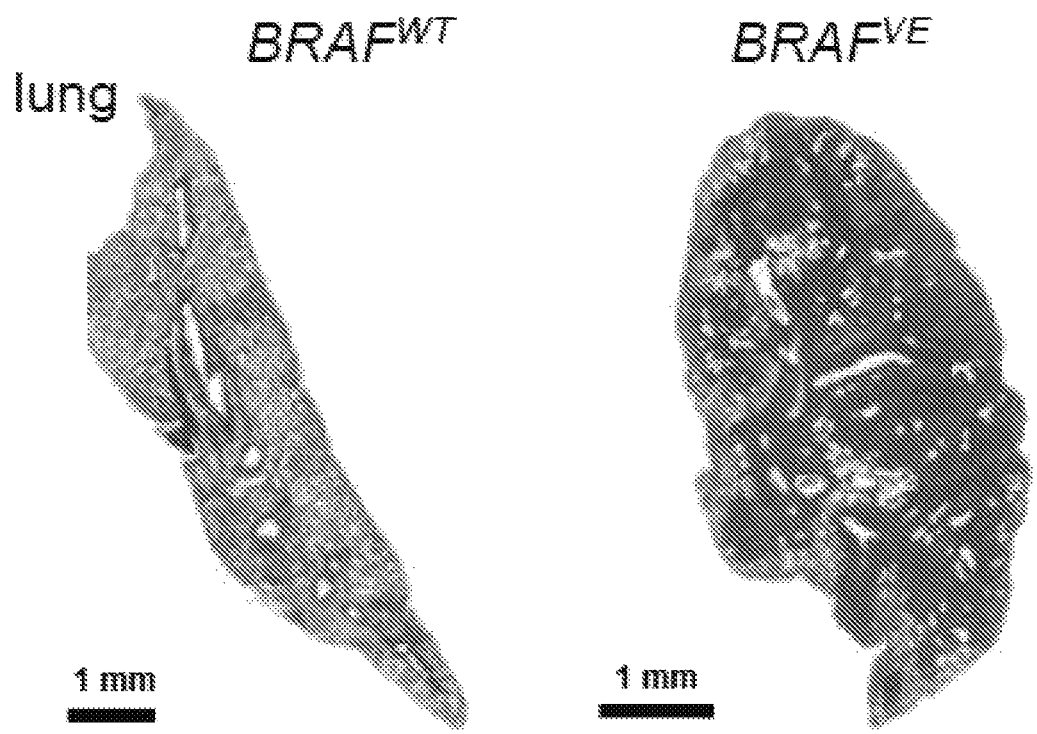
Figure 19D:
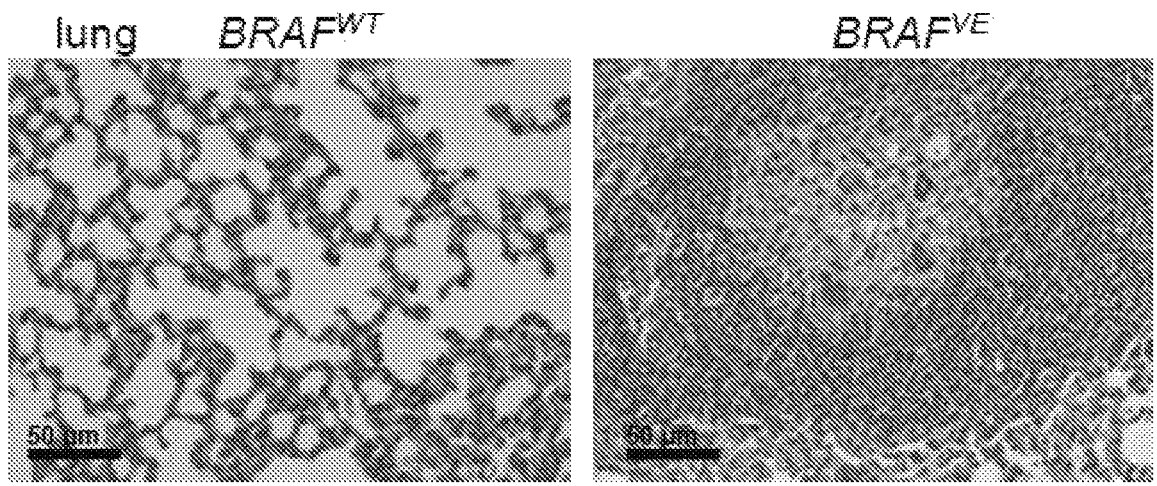
Figure 19E:
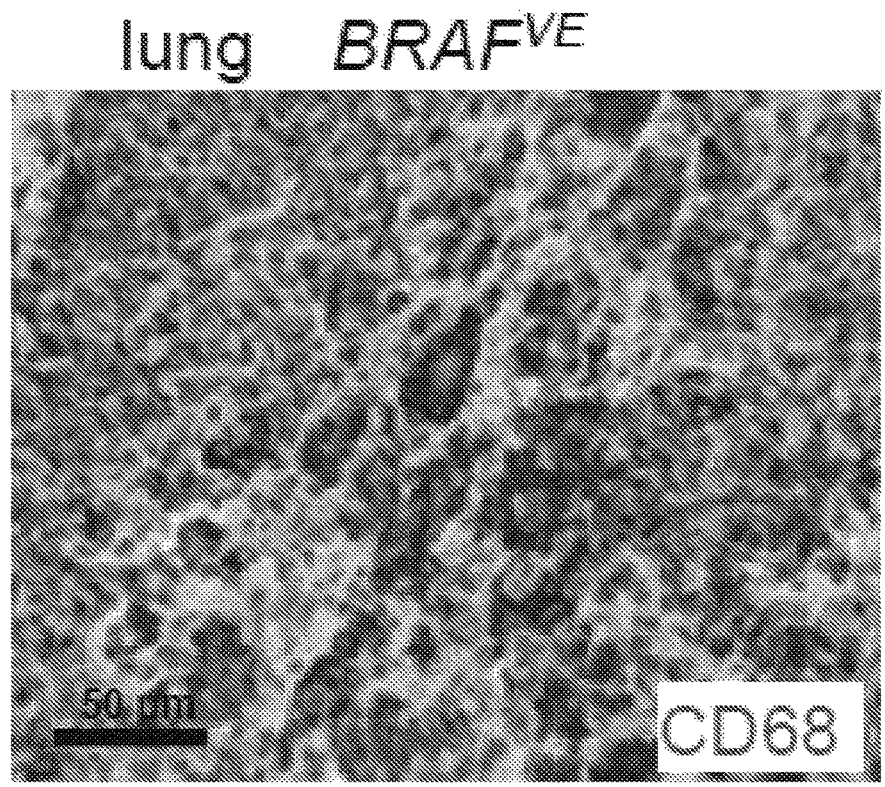
Figure 19F:
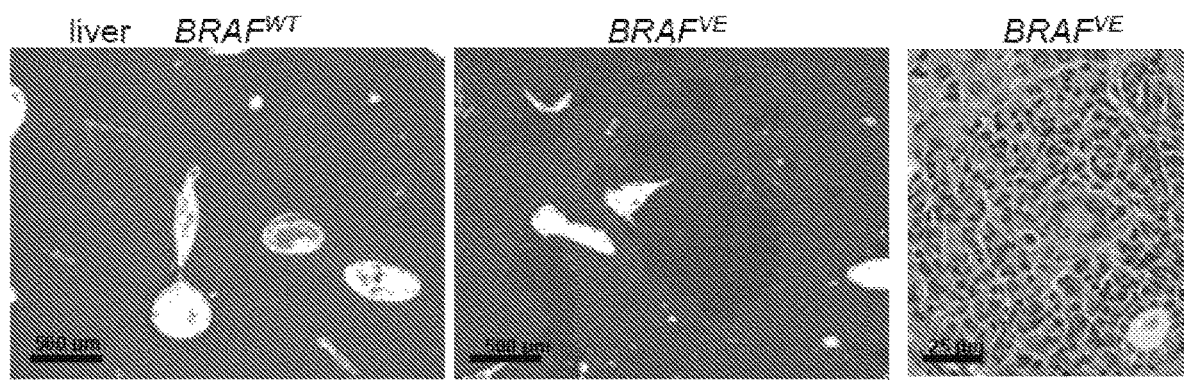
Figure 19G:
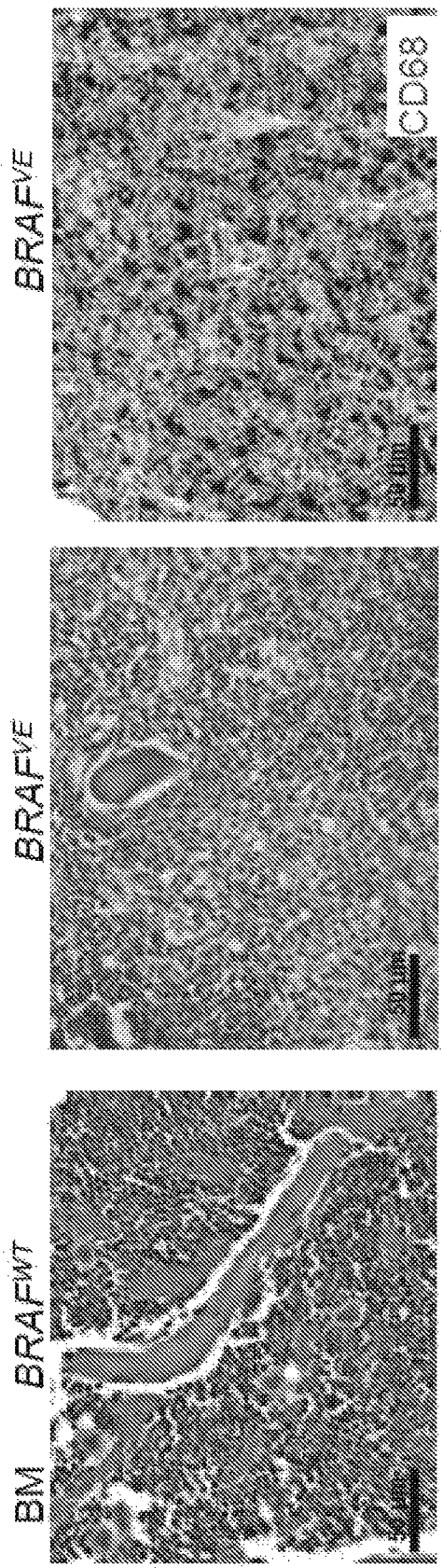
Figure 20A:
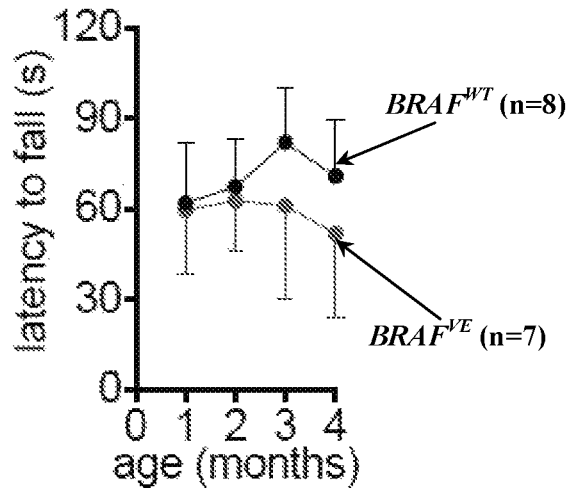
Figure 20B:
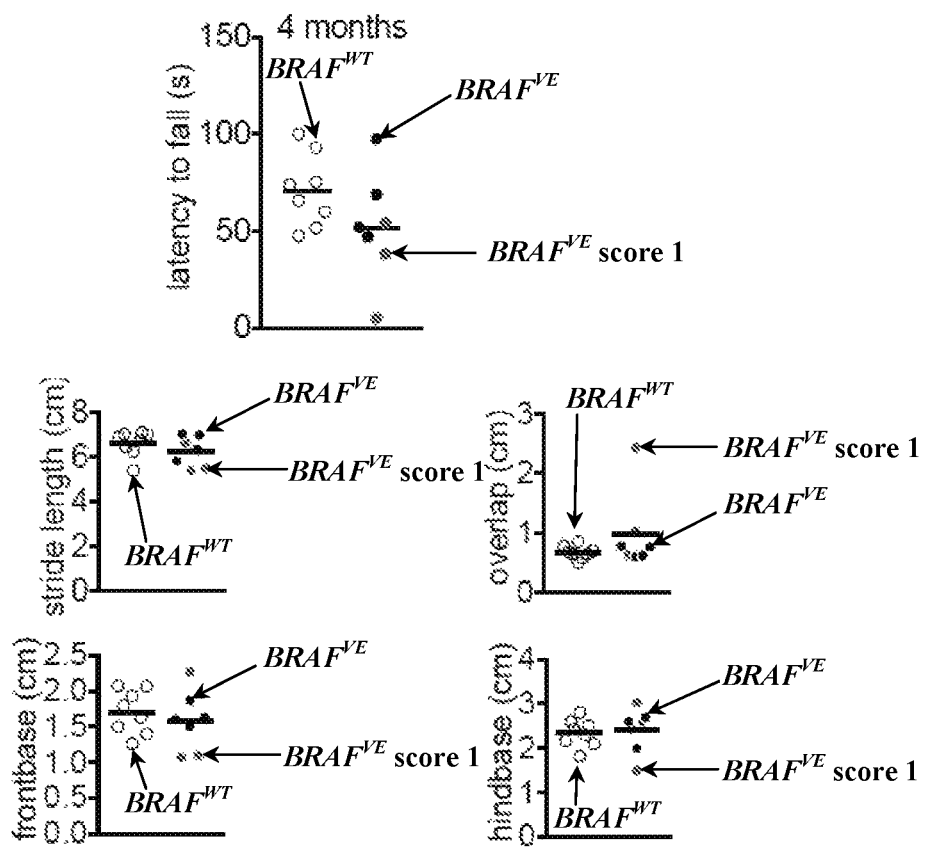
Figure 20C:
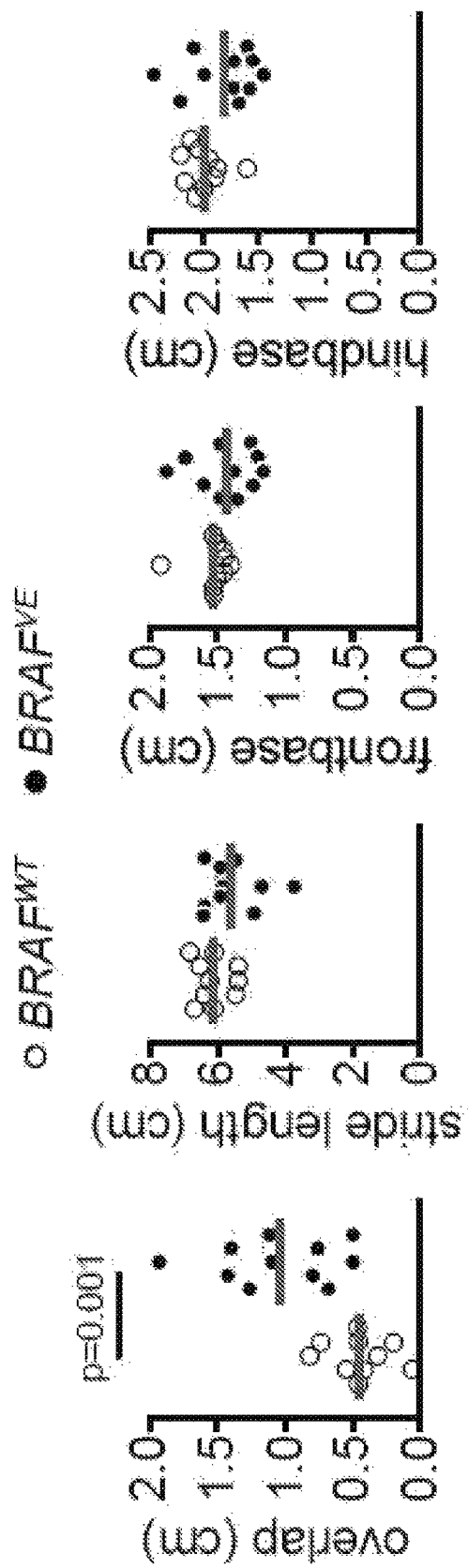
Figure 20D:
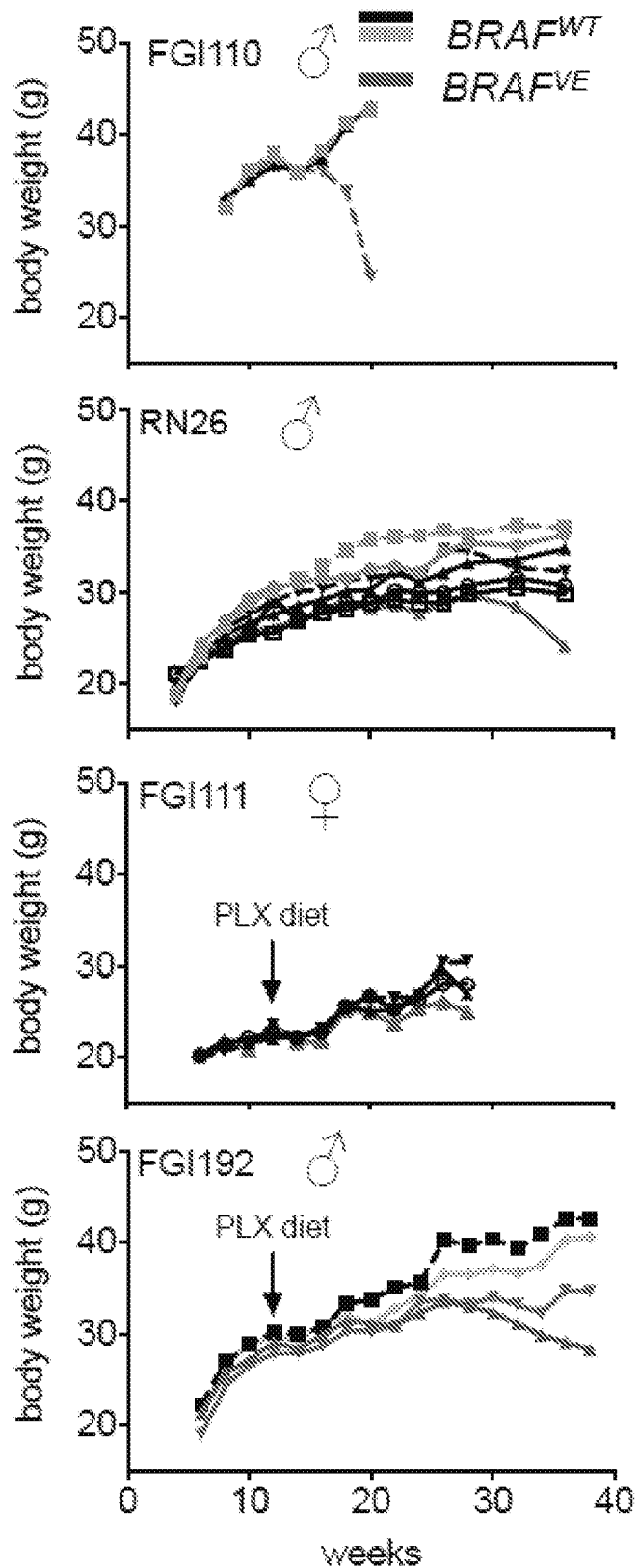
Figure 20E:
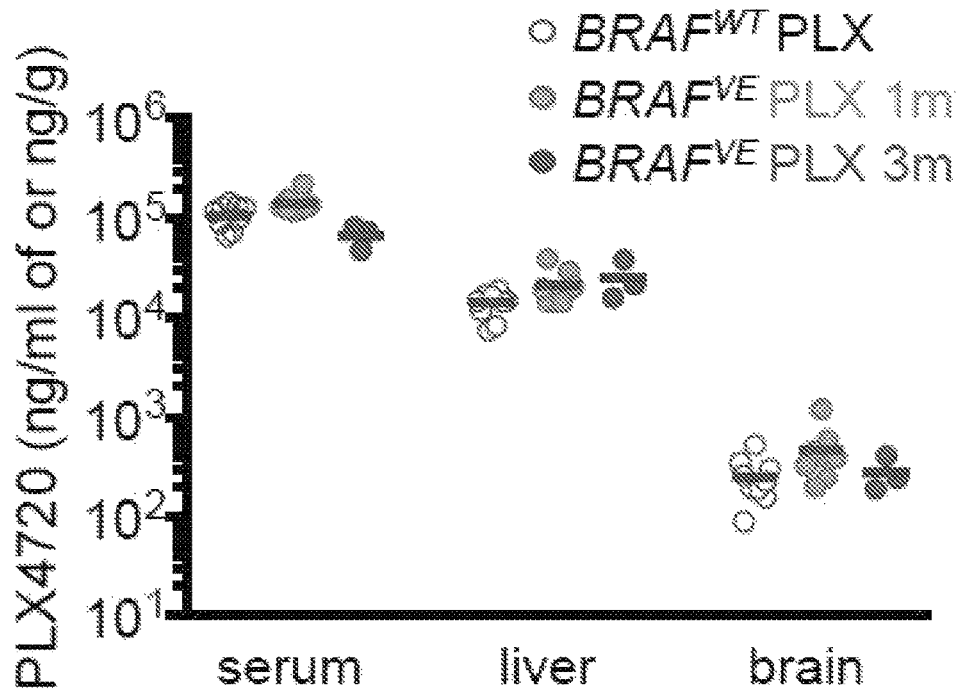
Figure 20F:
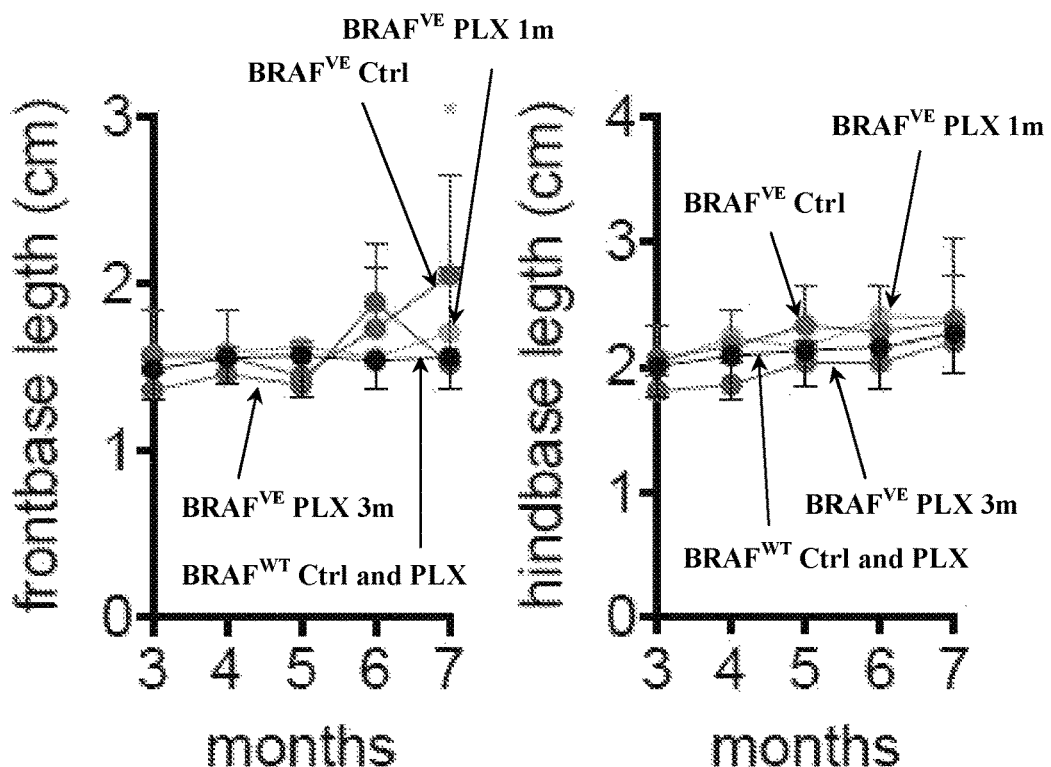

Example 15: Somatic Mosaicism for a BRAF$^{V600E}$ Allele and YFP in Resident Macrophage Lineage Using Inducible Genetic Targeting in Csf1r$^{MerCreMer}$ Mice Somatic mosaicism was achieved for a BRAF$^{V600E}$ allele and yellow fluorescent protein (YFP) in the resident macrophage lineage using inducible genetic targeting in Csf1r$^{MerCreMer}$ mice (FIG. 13A and FIG. 17). Mice reached weaning age in normal Mendelian ratio (n=342, FIG. 13B). YFP expression was absent from HSC-derived cells in the bone marrow and blood but was detected in tissue F4/80+ macrophages (FIGS. 13C-13E). RNA-seq analysis of sorted YFP+F4/80+ macrophages confirmed expression of BRAF$^{V600E}$ transcripts in BRAF$^{VE}$ mice (FIG. 13F). The proportion of F4/80+ YFP+ macrophages were increased in tissues from BRAF$^{VE}$ mice in comparison to littermates (FIG. 13E). In situ Ki67, phospho-Histone H3, and cleaved caspase 3 staining of brain microglia indicated an increased proliferative index and decreased apoptosis in BRAF$^{V600E}$ YFP+ microglia (FIG. 13G and FIG. 17F). RNA-seq analysis of Kupffer cells and microglia from BRAF$^{VE}$ mice and littermates identified a mitotic gene expression signature, as well as expression of ERK target genes, inflammatory cytokines and lectins (FIGS. 13H and 13I; FIG. 17G) Nevertheless, histological and flow cytometry analysis of liver, brain, lung, kidney, bone marrow, and spleen from young BRAF$^{VE}$ mice revealed no overt abnormalities, and in particular no tumoral or leukemic phenotypes (FIG. 17H). This is in contrast to results obtained when targeting BRAF$^{V600E}$ alleles in HSC using Vav$^{Cre}$, BRAF$^{LSL-V600E}$ mice and Csf1r$^{iCre}$; BRAF$^{LSL-V600E}$ mice or in more mature HSC-derived myeloid precursors as achieved in CD11c$^{Cre}$; BRAF$^{LSL-V600E}$ mice (FIGS. 18 and 19). In each of these models, expression of BRAF$^{V600E}$ in HSCs or HSC-derived cells resulted in a highly penetrant (100%) leukemic or tumoral histiocytic phenotype in the bone marrow, spleen and lung. Altogether, these data show that targeted expression of a BRAF$^{V600E}$ allele in EMP does not lead to leukemic/tumoral transformation, in contrast to the targeting of HSC-derived progenitors, and results in otherwise healthy mice carrying clones of BRAF$^{V600E}$ resident macrophages endowed with a small proliferative advantage.

Example 16: Effects of BRAF$^{V600E}$ Macrophage Clones in Adult Tissues

Figure 14A:
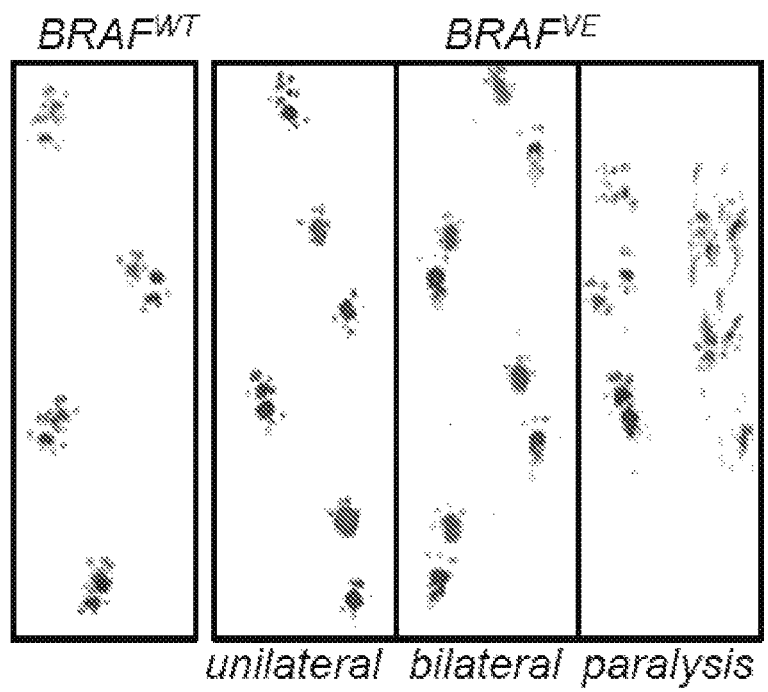
FIGS. 14A-14H. Neurodegenerative disease in BRAF$^{VE}$ mice.
Figure 14B:
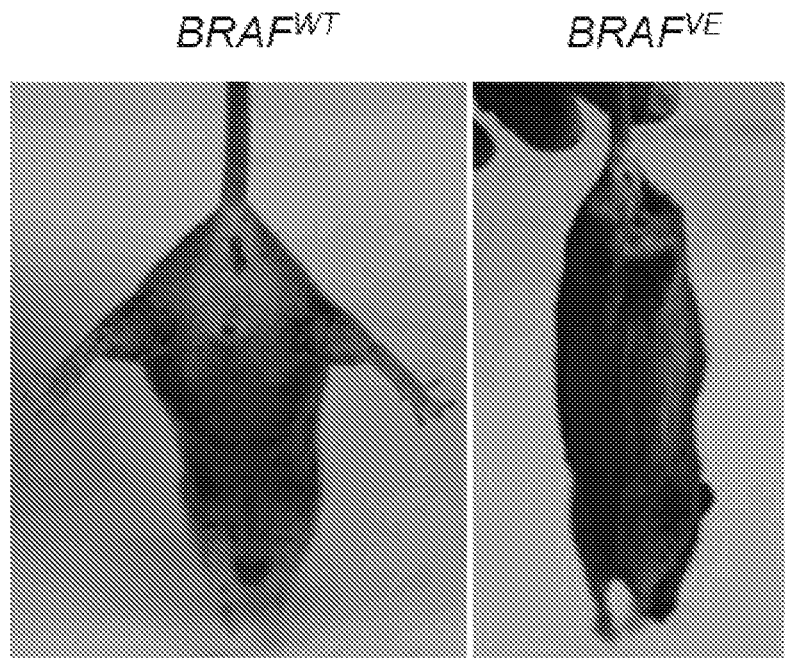
Figure 14C:
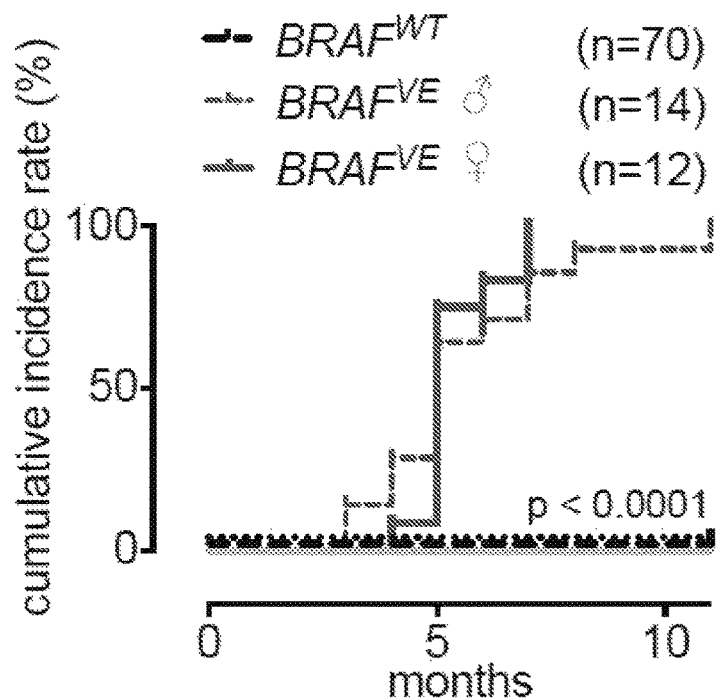
Figure 14D:
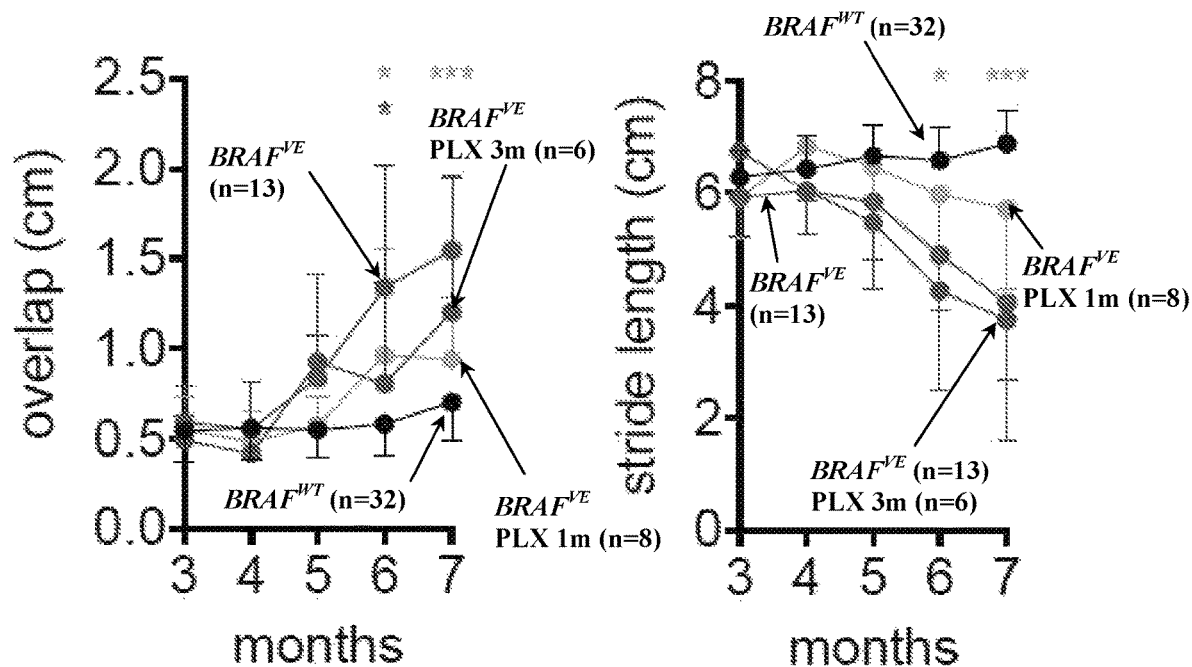
Figure 14E:
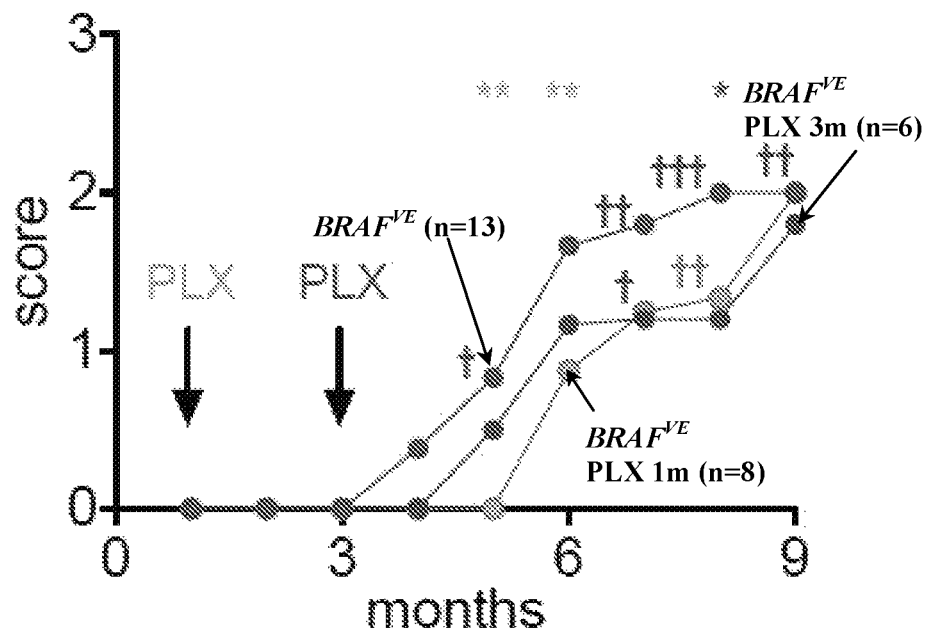
Figure 14F:
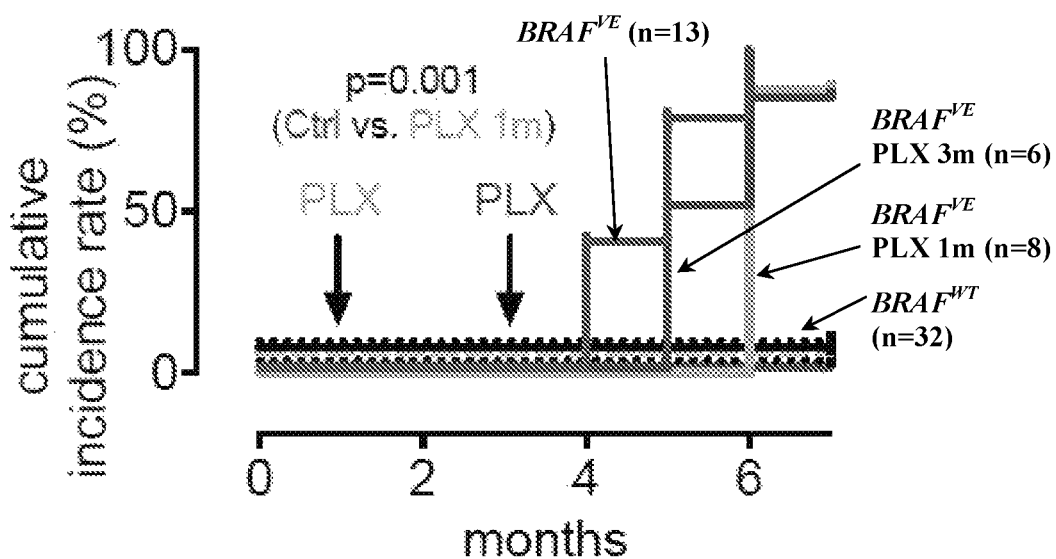

To determine the potential effects of BRAF$^{V600E}$ macrophage clones in adult tissues, a large cohort (n=155) of BRAF$^{VE}$ mice and littermate controls were analyzed. BRAF$^{VE}$ mice developed a slowly progressive neurologic impairment (FIGS. 14A-14C and FIG. 20). Young mice did not present with detectable neurological symptoms, as evaluated by the rotarod tes. However, from the age of 4-5 months, BRAF$^{VE}$ mice presented with axial rolling, a unilateral loss of hindlimb reflexes, and unilateral increase in overlap distance between hind and front paws followed by decreased stride length as measured by footprint assays (score 1) (FIGS. 14A and 14D). BRAF$^{VE}$ mice later developed hindlimb paresis or loss of hindlimb reflexes (score 2), associated with weight loss. At a more advanced stage, BRAF$^{VE}$ mice presented in rapid succession with paralysis of one and subsequently both hindlimbs (score 3 and 4) and full loss of hindlimb reflexes (FIGS. 14A and 14B), at which time mice were flagged as moribund by veterinary staff and were sacrificed. Cumulative evidence of score 1 criteria indicated that ~90% of male and female BRAF$^{VE}$ mice presented with a neurological disease by 7 months of age, and ~60% of BRAF$^{VE}$ mice had progressed to full paralysis by 9 months of age (FIGS. 14C-14F). To further investigate if the neurologic disease was dependent on constitutively active BRAF, BRAF$^{VE}$ and BRAF$^{WT}$ mice were placed on an ad libitum diet containing a BRAF inhibitor (PLX4720, FIG. 20) at one and three months of age. PLX4720 treatment delayed the onset of the neurological phenotype when initiated early (e.g., at one month of age) and mitigated disease progression in both cases. By 9 months of age, 80% of BRAF$^{VE}$ mice treated with PLX4720 were alive with an average clinical score of 2 (FIGS. 14D-14F). These results demonstrate that BRAF$^{V600E}$ mosaicism in tissue-resident macrophages causes a late-onset progressive neurological disorder with features of cerebellar ataxia, also found in patients with cerebral histiocytoses.

Figure 14G:
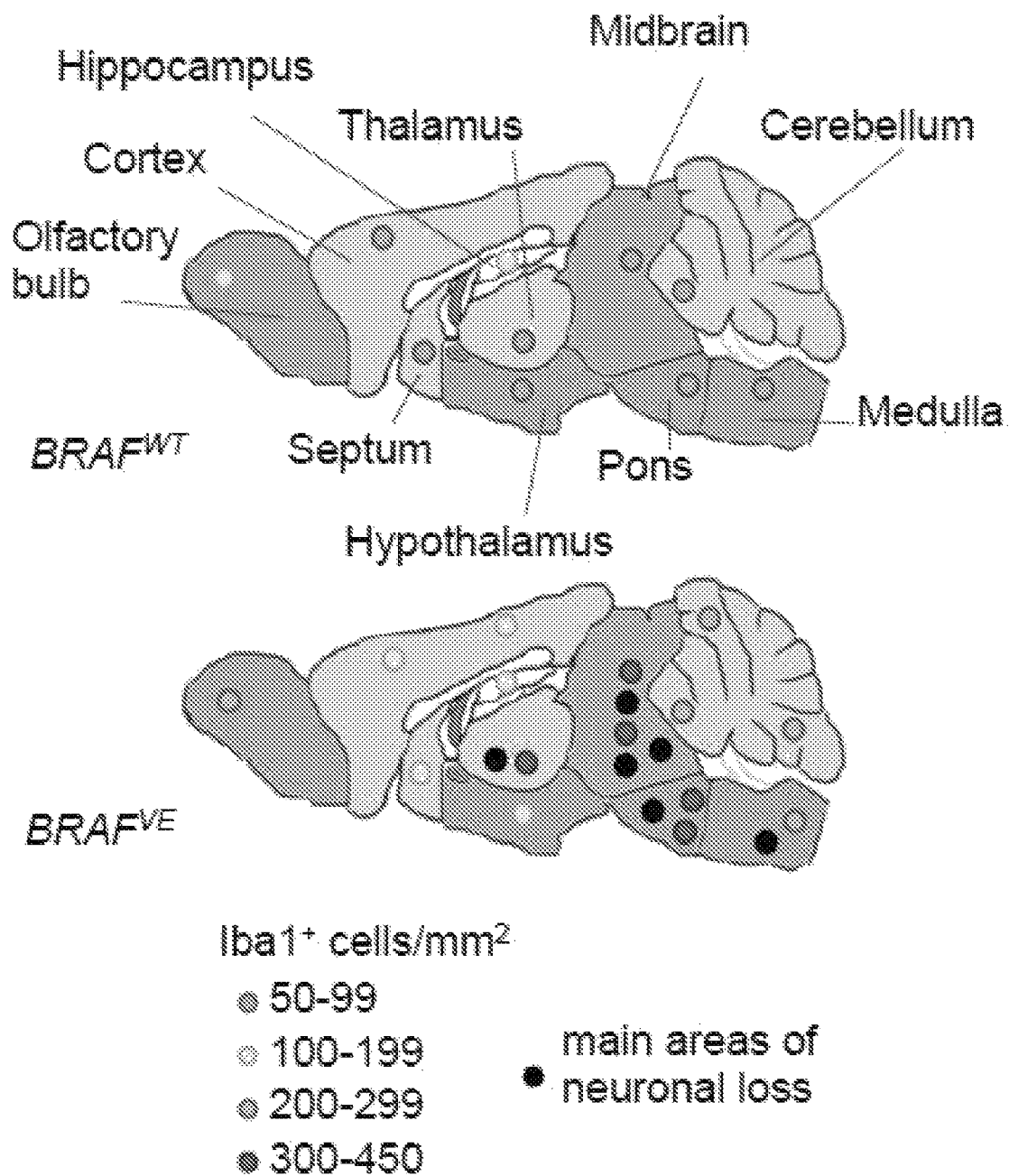
Figure 14H:
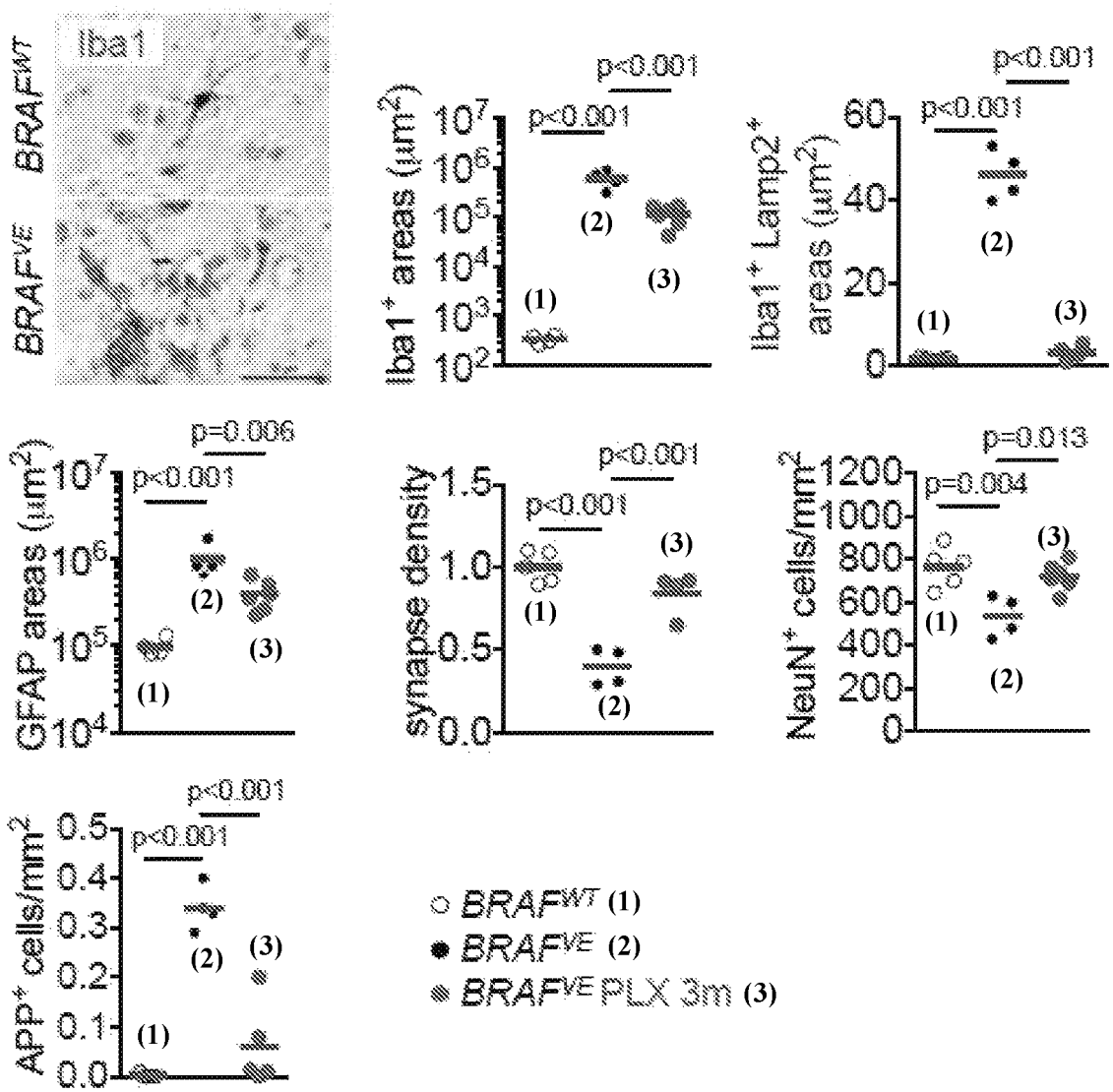
Figure 21A:
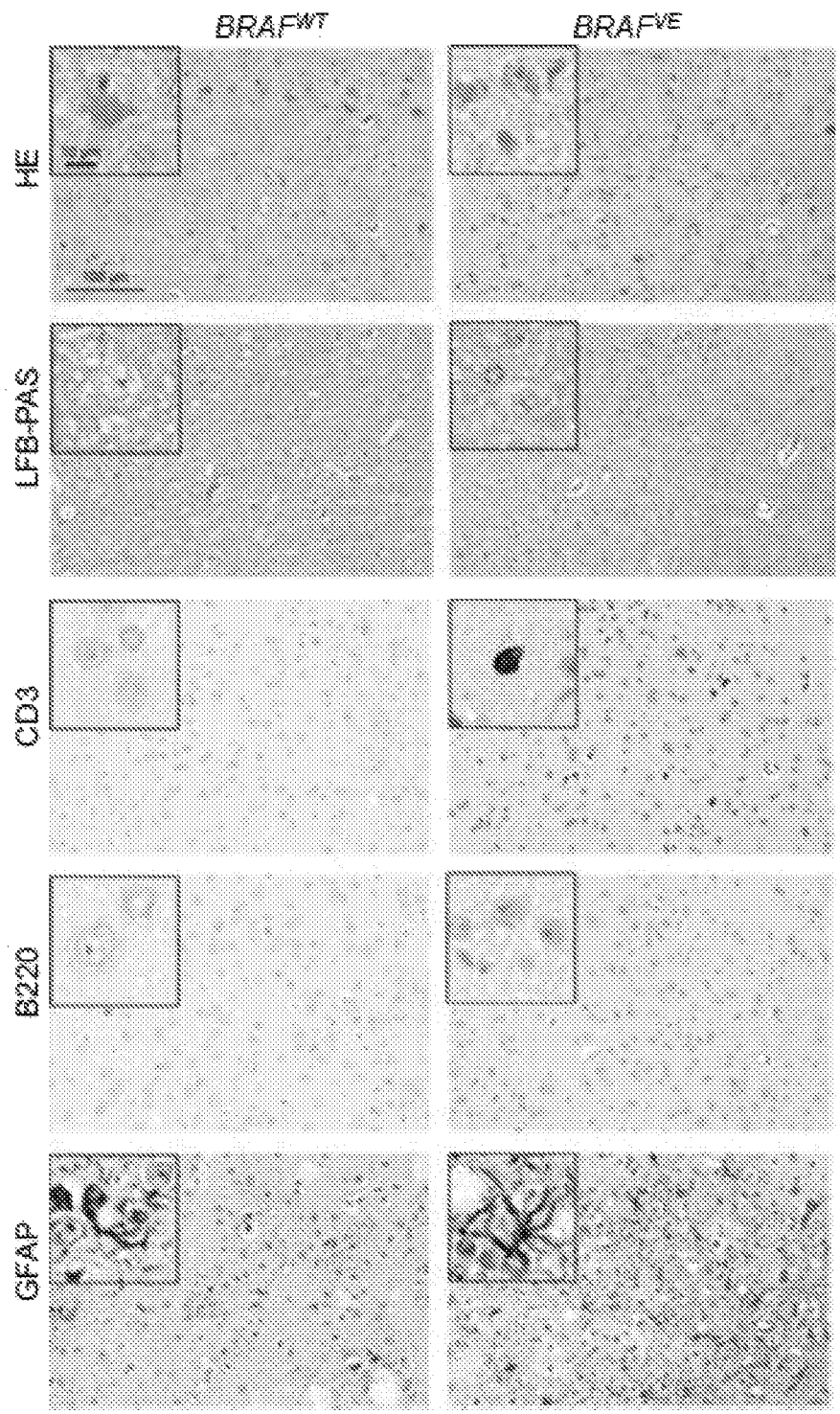
FIGS. 21A and 21B. Microglia activation in the brain starts at early, preclinical stages.
Figure 21B:
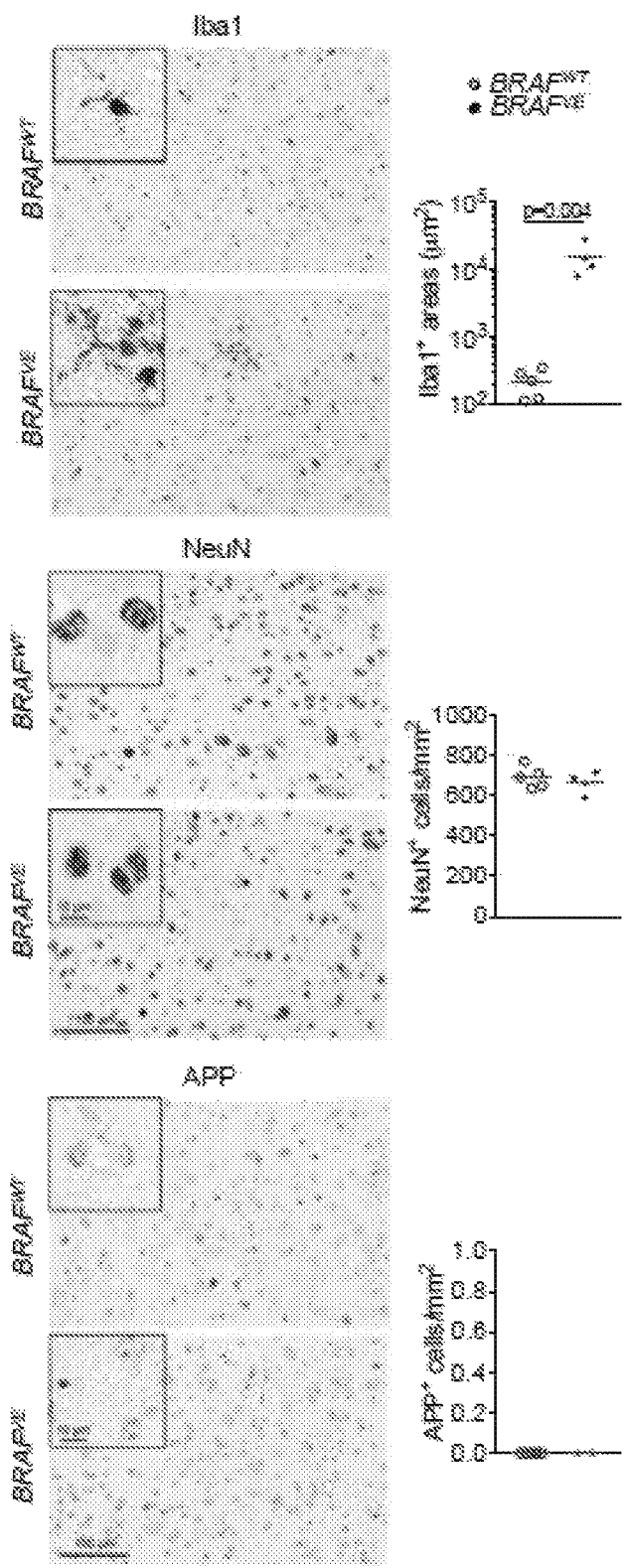
Figure 22A:
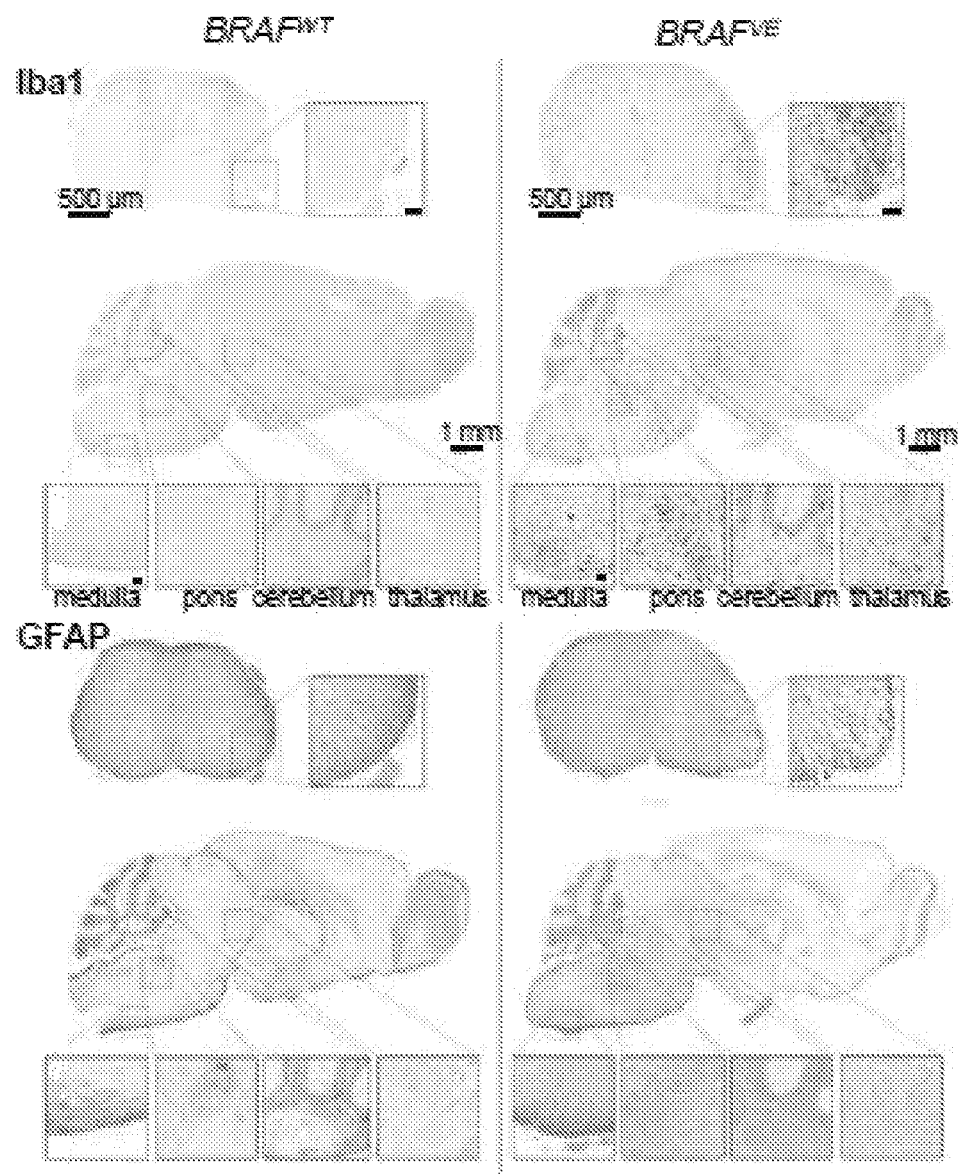
FIGS. 22A-22D. Neurodegenerative process in BRAF$^{VE}$ mice.
Figure 22B:
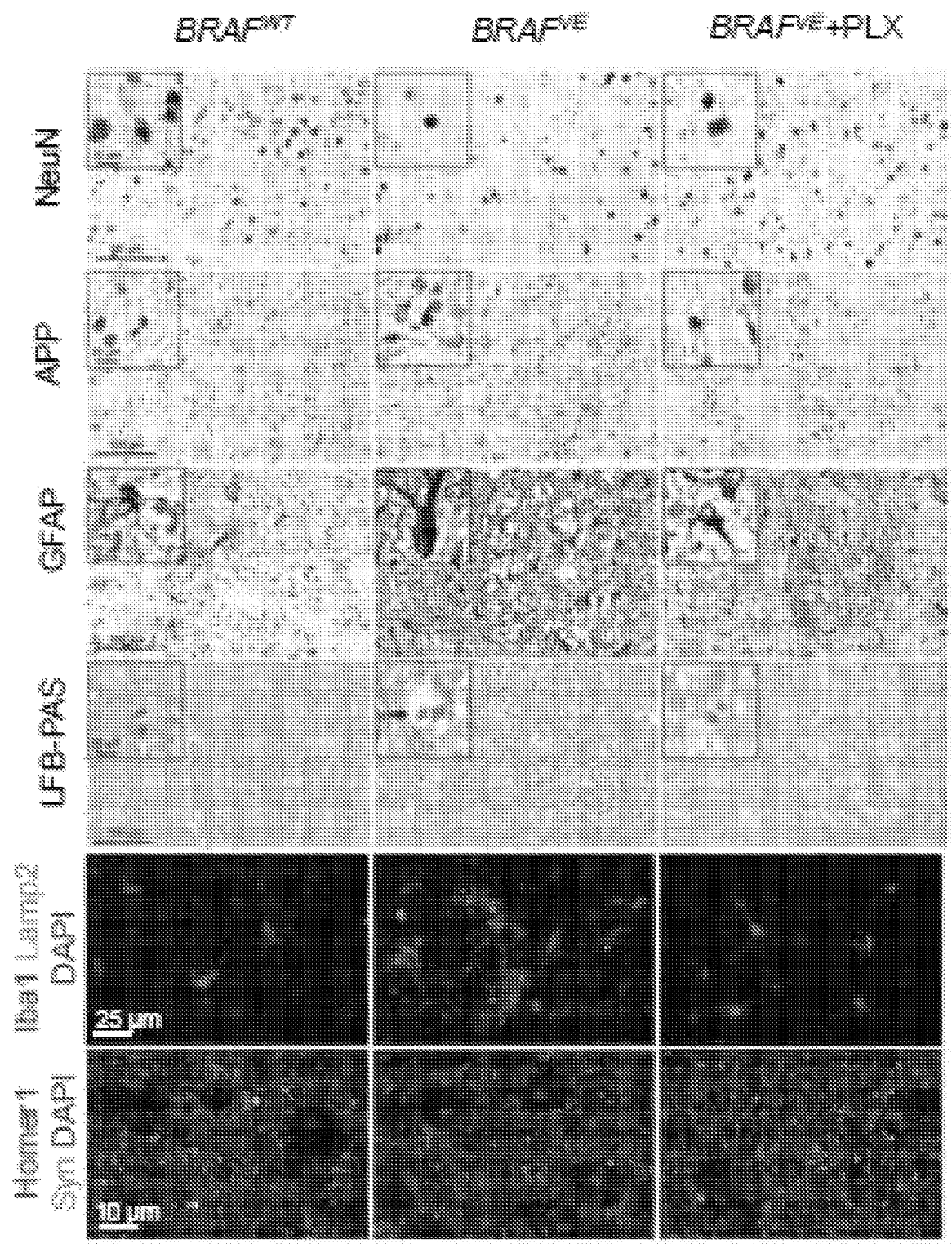
Figure 22C:
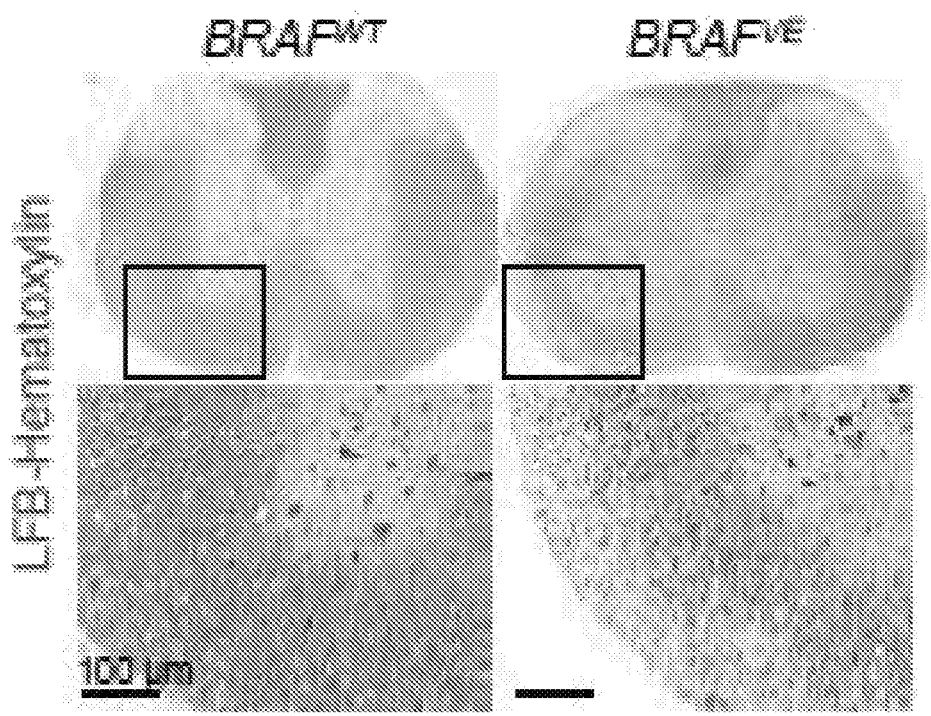
Figure 22D:
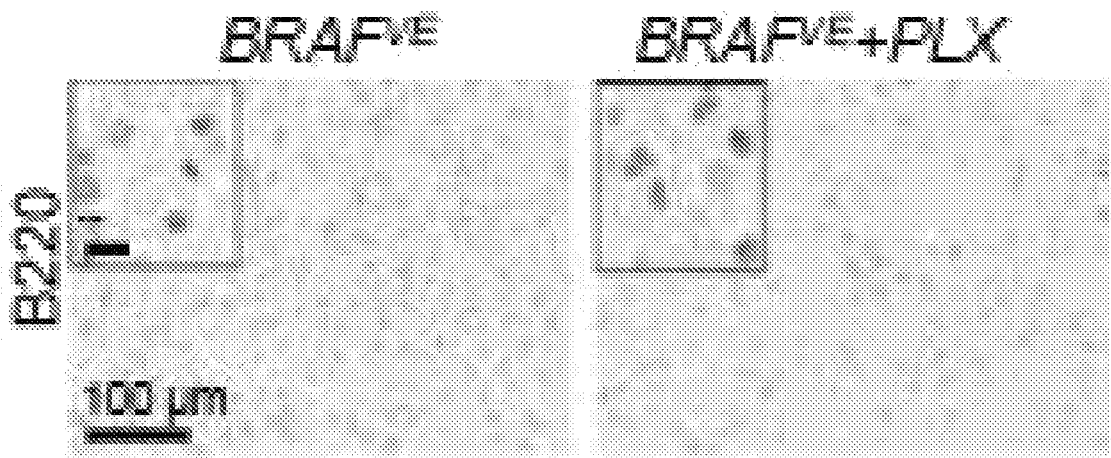
Figure 23A:
FIGS. 23A-23G. Microglia and T-cell phenotype in BRAF$^{VE}$ mice.
Figure 23B:
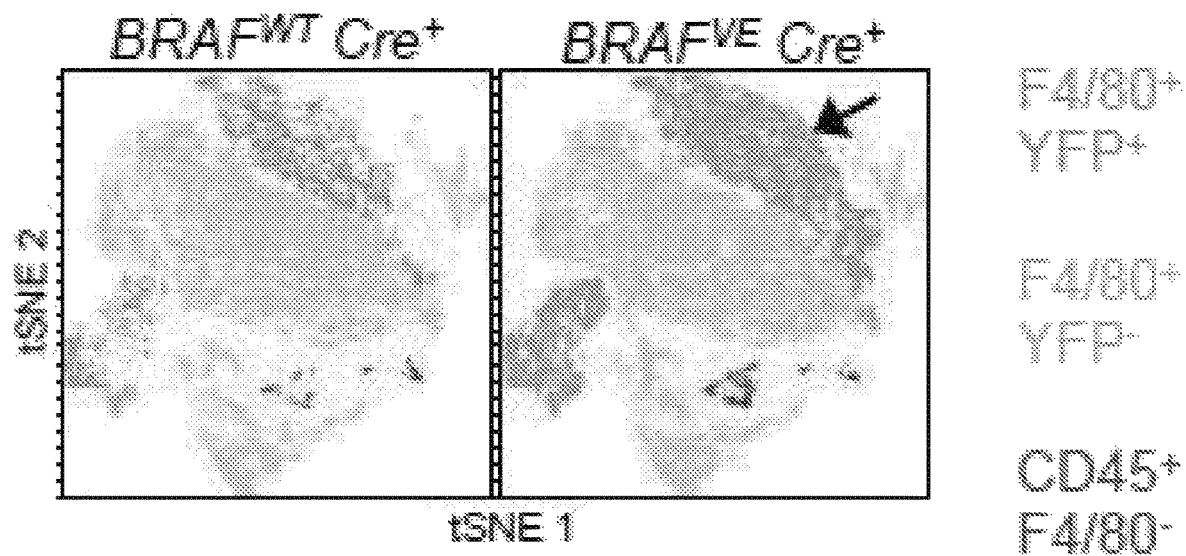
Figure 23C:
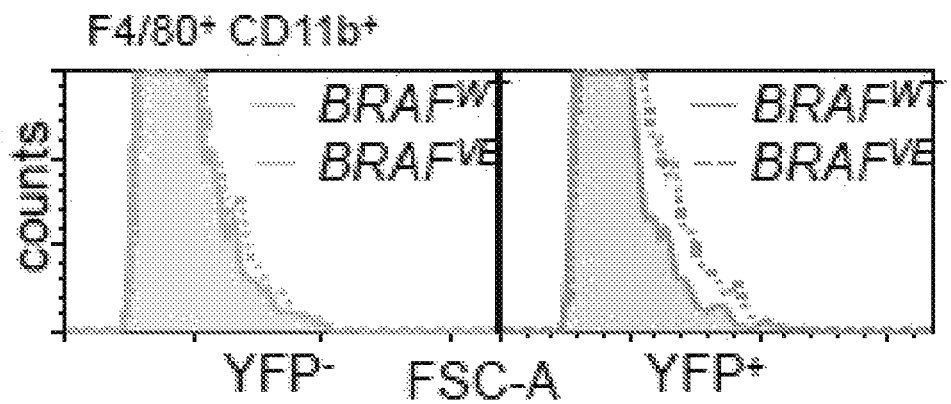
Figure 23D:
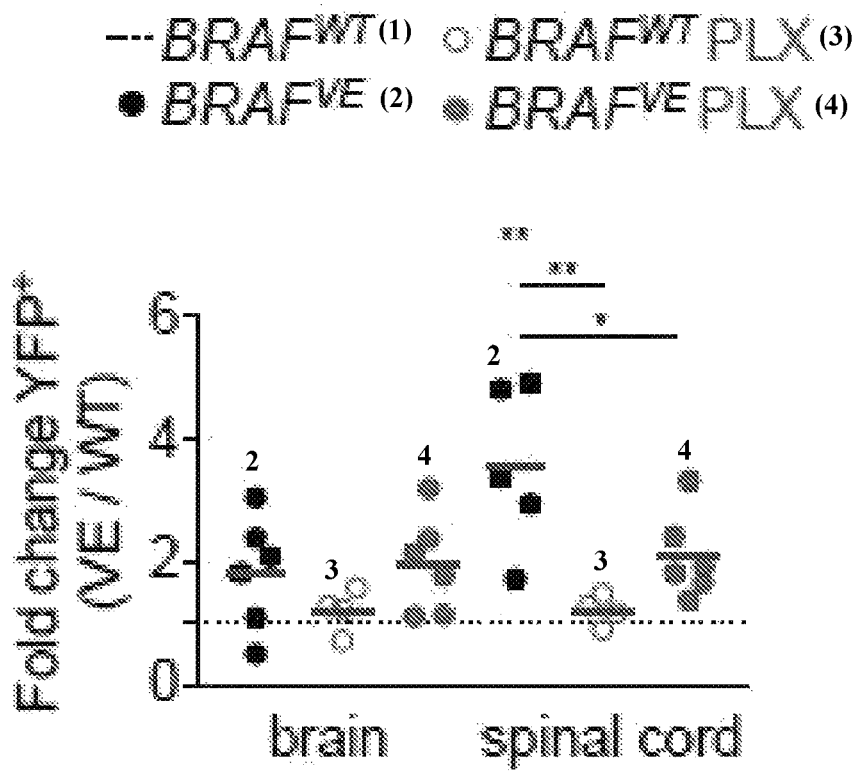
Figure 23E:
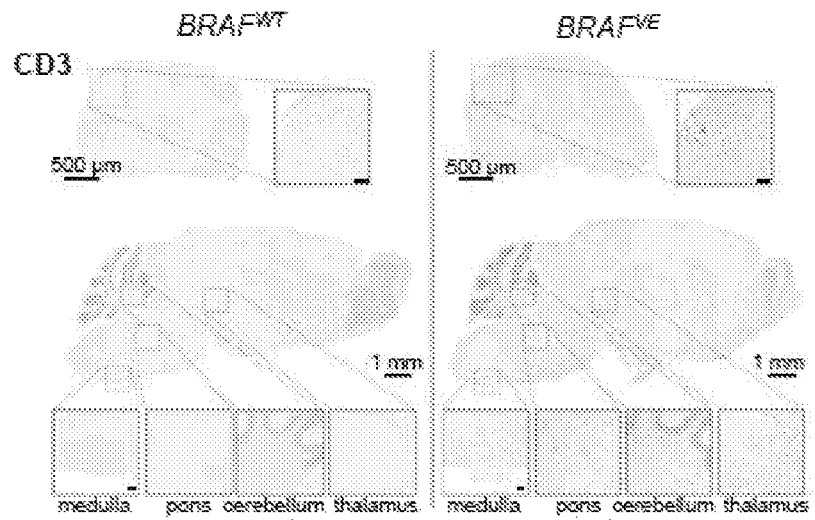
Figure 23F:
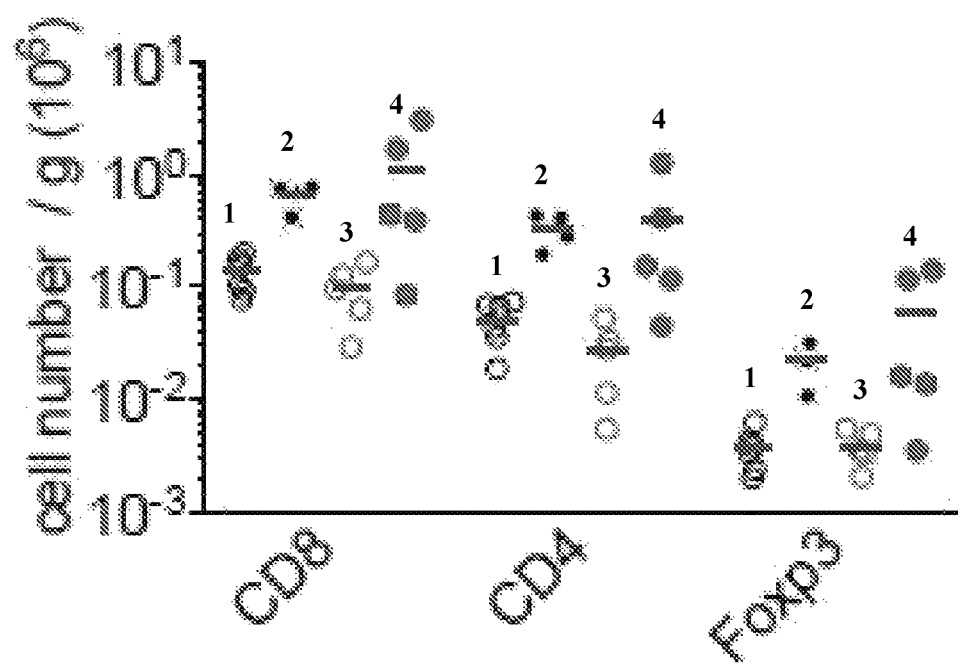
Figure 23G:
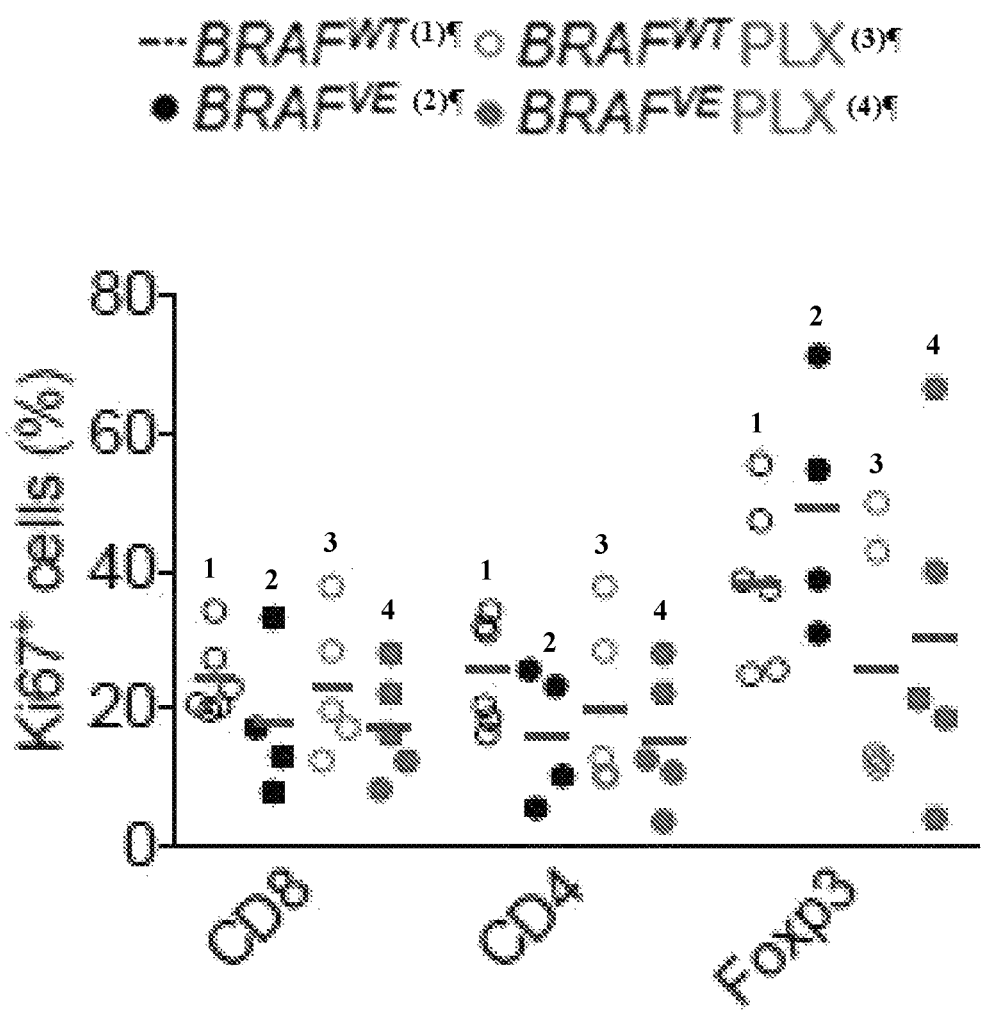

The pathological changes that may underlie neurologic impairment were investigated in asymptomatic one-month old BRAF$^{VE}$ mice, and early signs of microglial and astrocyte activation, without signs of neuronal damage, such as deposit of amyloid precursor protein (APP) in the brain or neuronal loss (FIG. 21) were found. However, in ~6 month-old BRAF$^{VE}$ mice, large clusters of amoeboid Iba1+ microglia were present in the cerebrum, preferentially located in the thalamus, brain stem, cerebellum, and spinal cord (FIGS. 14G and 14H; FIG. 22). In these areas, Lamp2+ phagocytic microglia, marked astrogliosis, synaptic and neuronal loss, and APP deposits (FIGS. 14G and 14H) were observed. Luxol Fast Blue/PAS staining also indicated demyelination, potentially secondary to axonal damage (FIG. 22). BRAF inhibition reduced microglia accumulation and astrogliosis, phagocytosis, demyelination, neuronal loss, and APP deposition (FIG. 14H and FIG. 22). Thus, mice presented with a neurodegenerative disease driven by constitutive active BRAF in microglia. Accordingly, this example demonstrates that BRAF inhibitors, such as those described herein, are useful in methods of treating the symptoms of neurodegenerative disease.

Example 17: BRAF Inhibition Mitigates Microglial Accumulation

Figure 15A:
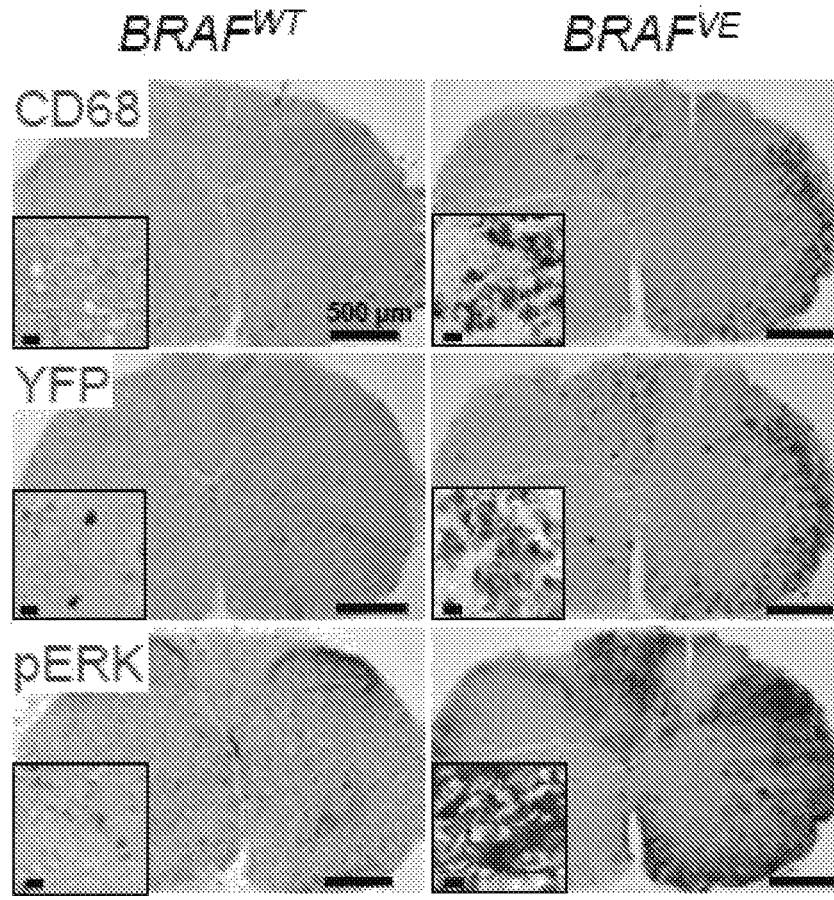
FIGS. 15A-15G. ERK activation in BRAF$^{V600E}$ microglia.
Figure 15B:
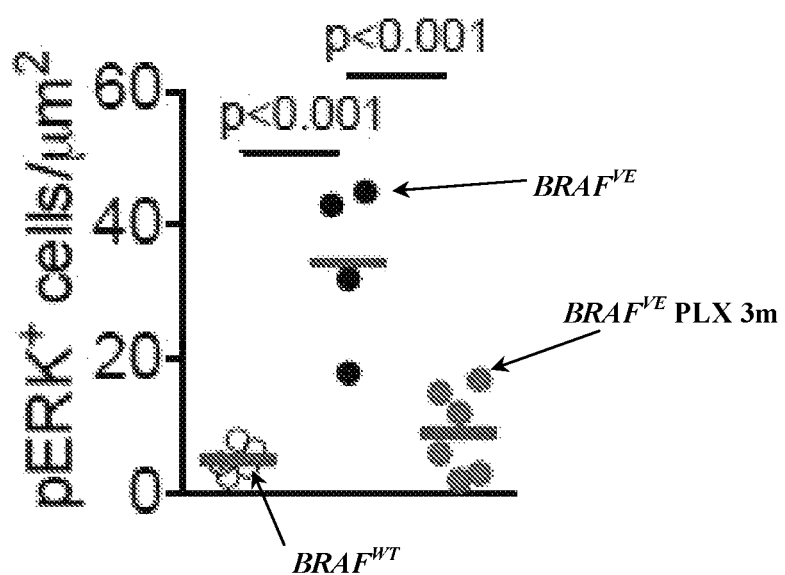
Figure 15C:
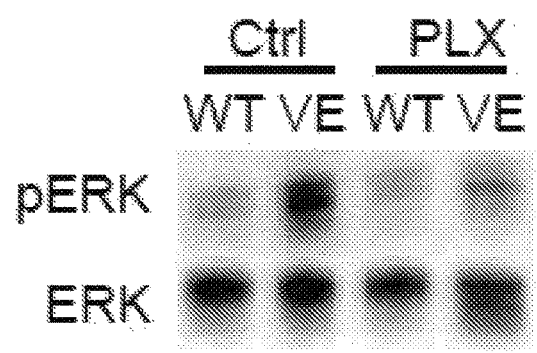
Figure 15C:
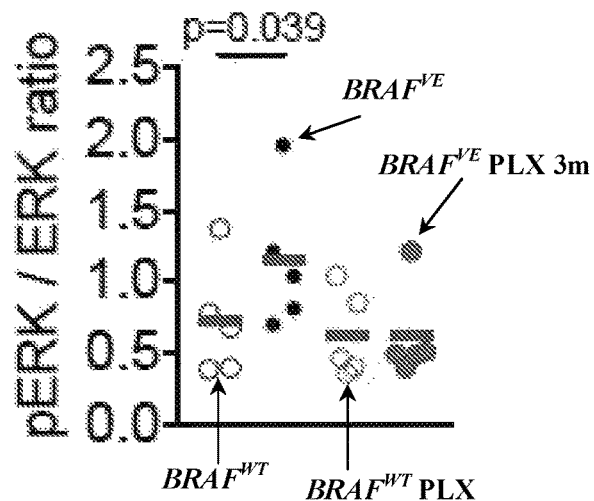
Figure 15D:
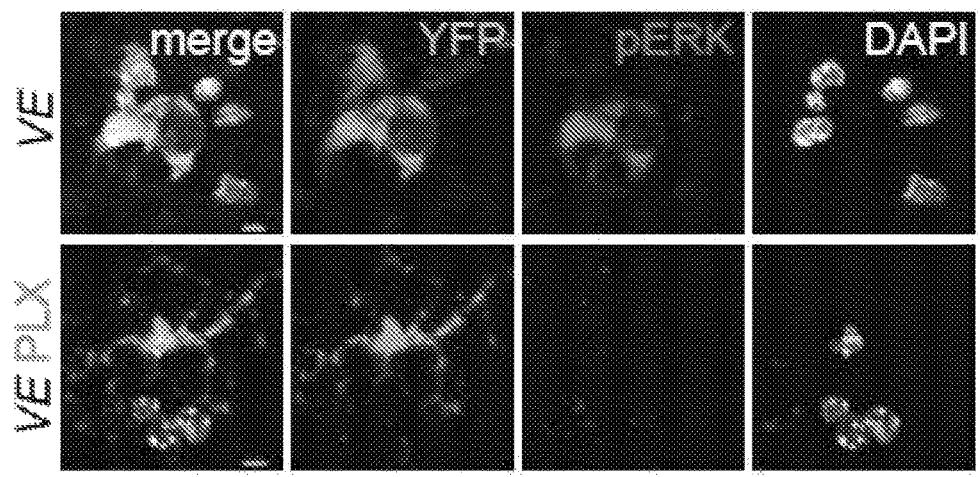
Figure 15E:
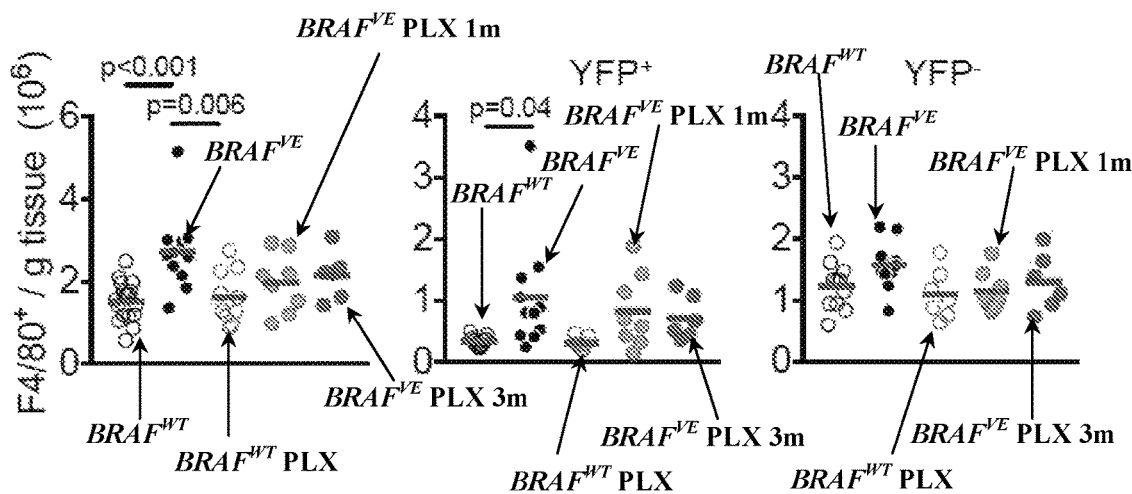
Figure 15F:
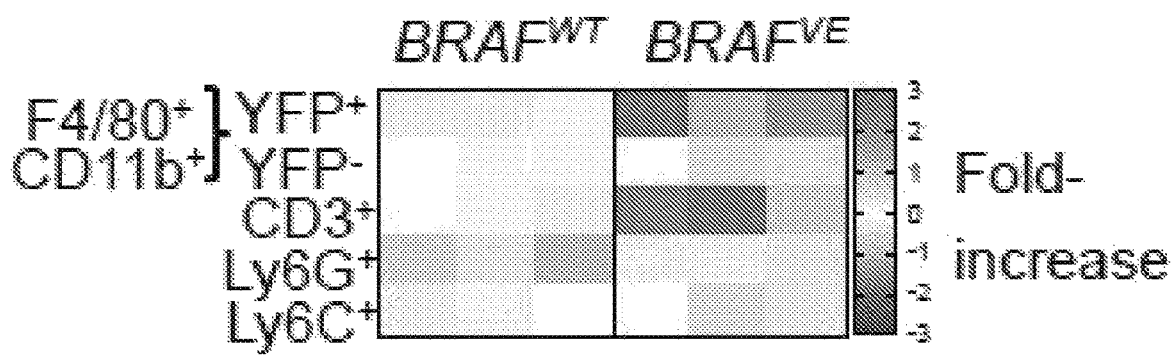
Figure 15G:
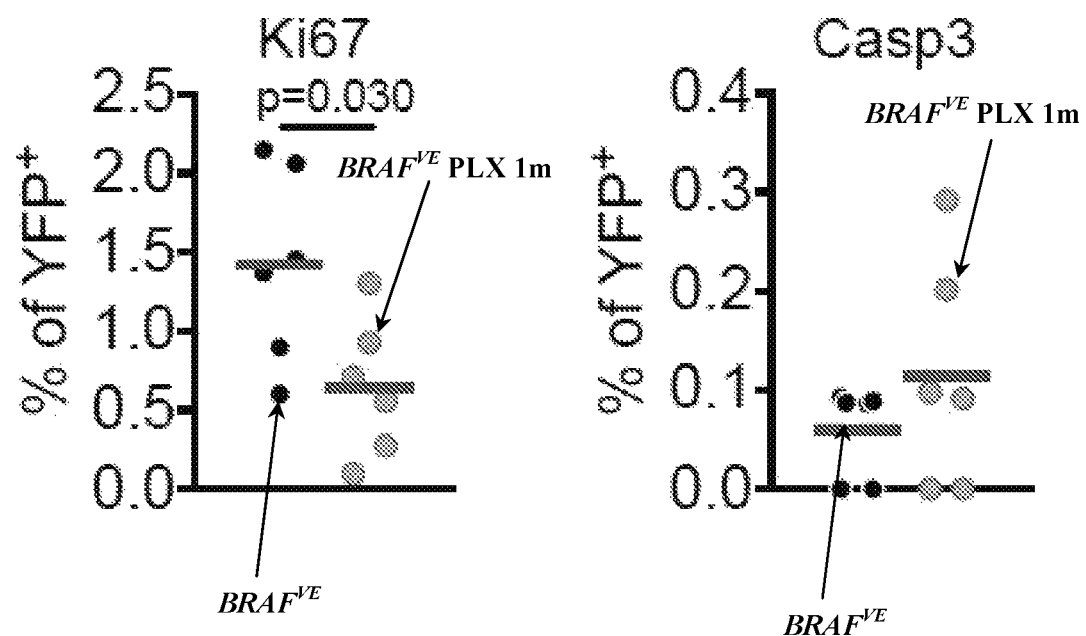

Immunostaining for CD68, Iba1, YFP, and pERK demonstrated that microglial clusters represented the accumulation of EMP-derived (YFP$^+$) pERK$^+$ microglia (FIGS. 15A and 15B; FIG. 23). Microglial ERK-activation in brain and spinal cord were confirmed by western blot on whole tissue and by confocal microscopy (FIGS. 15C and 15D). Immunofluorescence analyses also indicated that pERK$^+$YFP$^+$ amoeboid microglia had lost their ramifications (FIG. 15D). Flow cytometry analysis confirmed the preferential expansion of YFP$^+$ microglia (FIGS. 15E and 15F). Granulocytes, monocytes, and B-cells were absent or rare, but CD3$^+$CD8$^+$, CD4$^+$, and Foxp3$^+$ T-cells were increased (FIG. 15F and FIG. 23). Finally, BRAF inhibition mitigated the accumulation of YFP$^+$ microglia, likely by decreasing their proliferation (FIGS. 15E and 15G), and prevented ERK phosphorylation and the amoeboid phenotype of microglia (FIGS. 15B-3D). Altogether, the data suggest that BRAF$^{V600E}$ somatic mosaicism in microglia drives a neurodegenerative disease mediated by microglial activation. Accordingly, this example demonstrates that BRAF inhibitors, such as those described herein, are useful in methods of treating symptoms of neurodegenerative disease.

Figure 16A:
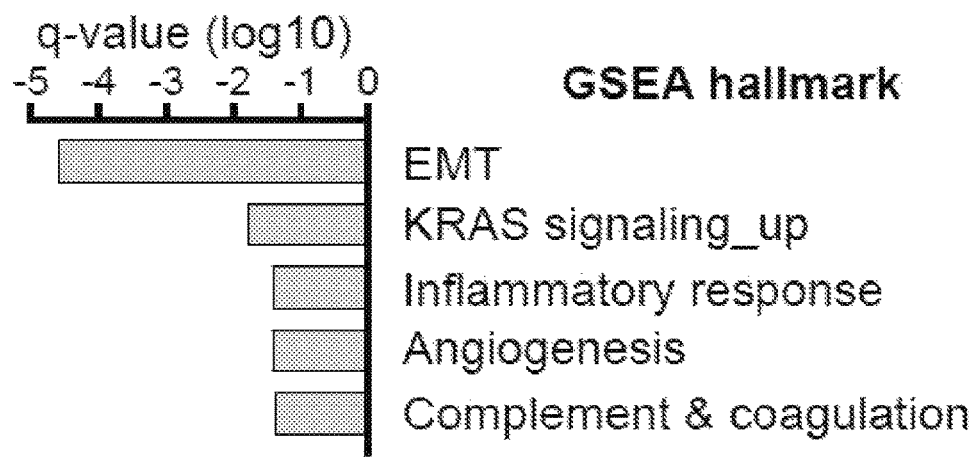
FIGS. 16A-16I. Molecular features of ERK-activated microglia, and their presence in histiocytoses patients.
Figure 16B:
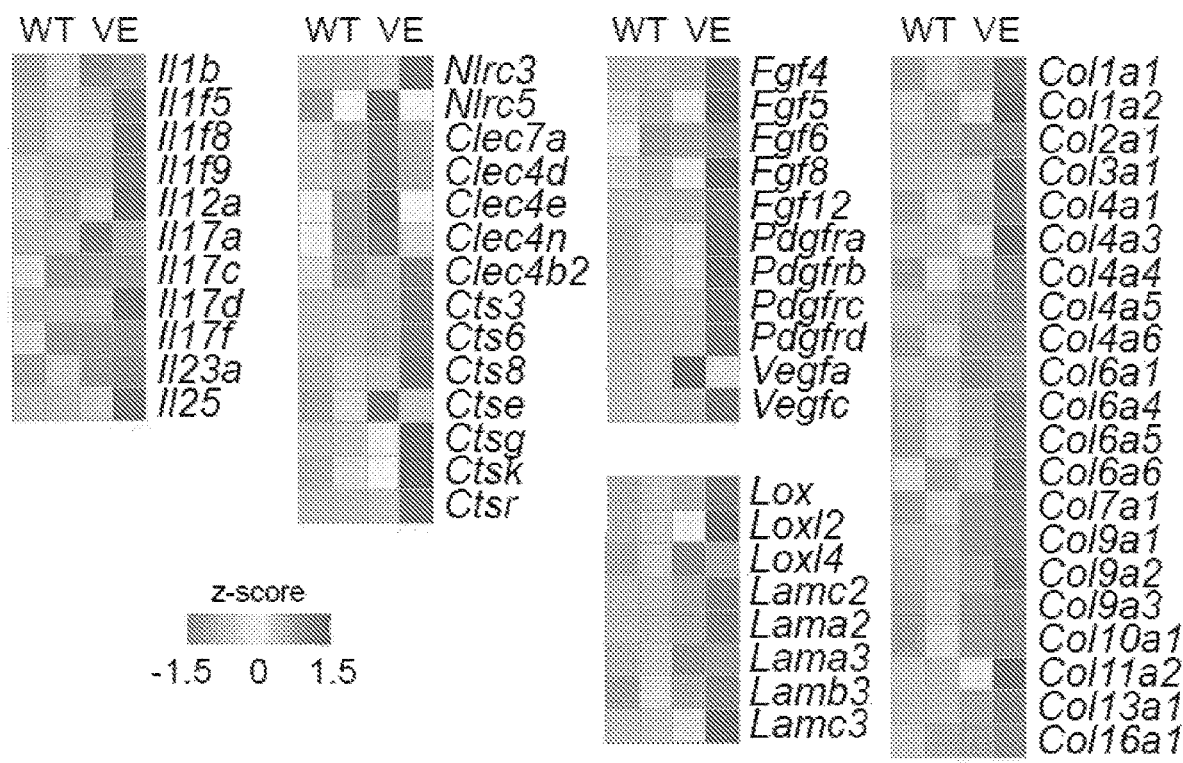
Figure 16C:
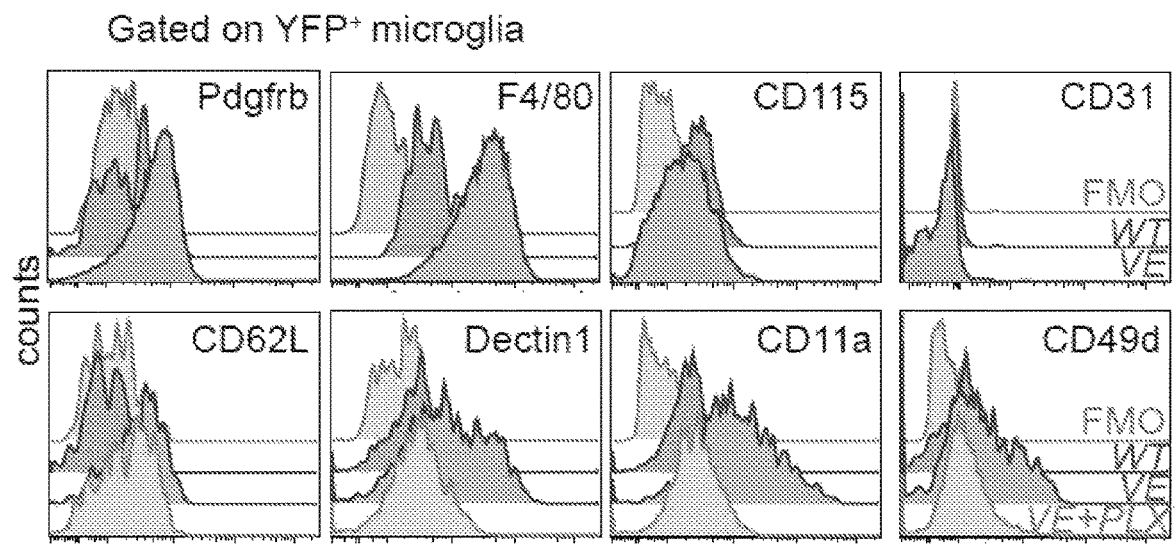
Figure 16D:
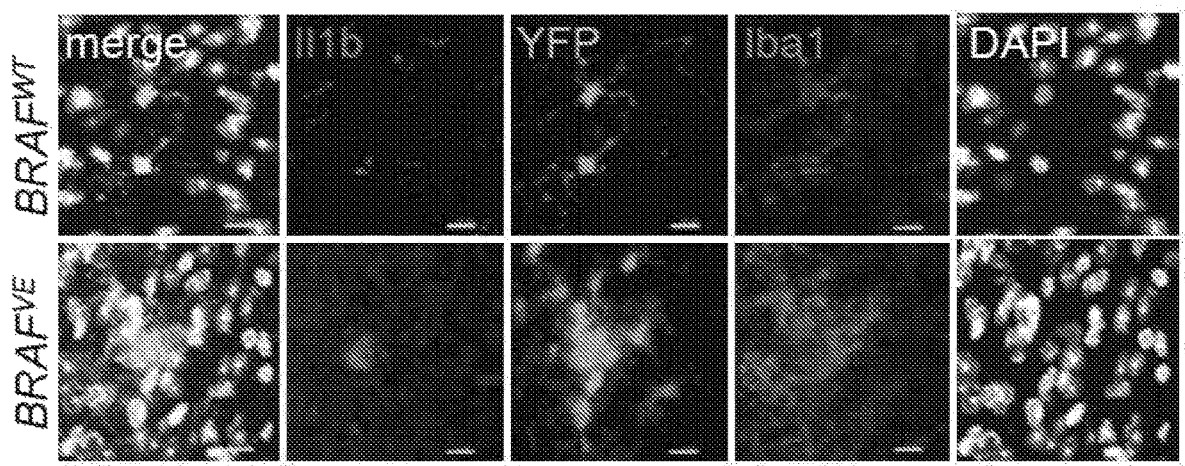
Figure 16E:
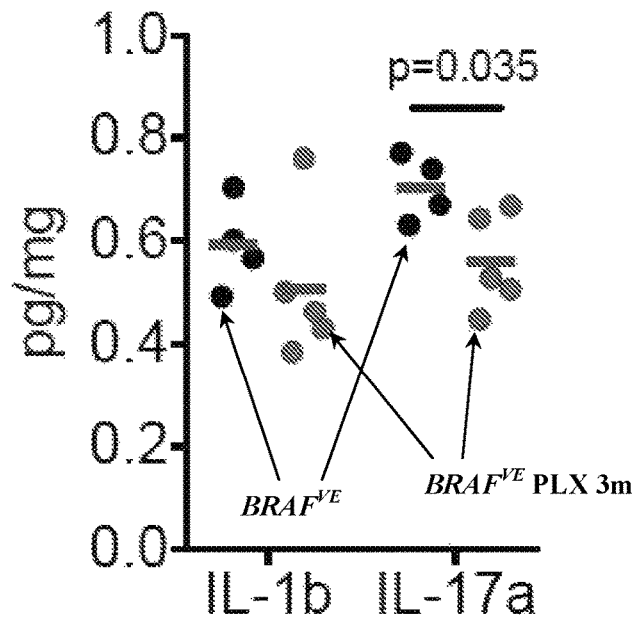
Figure 16F:
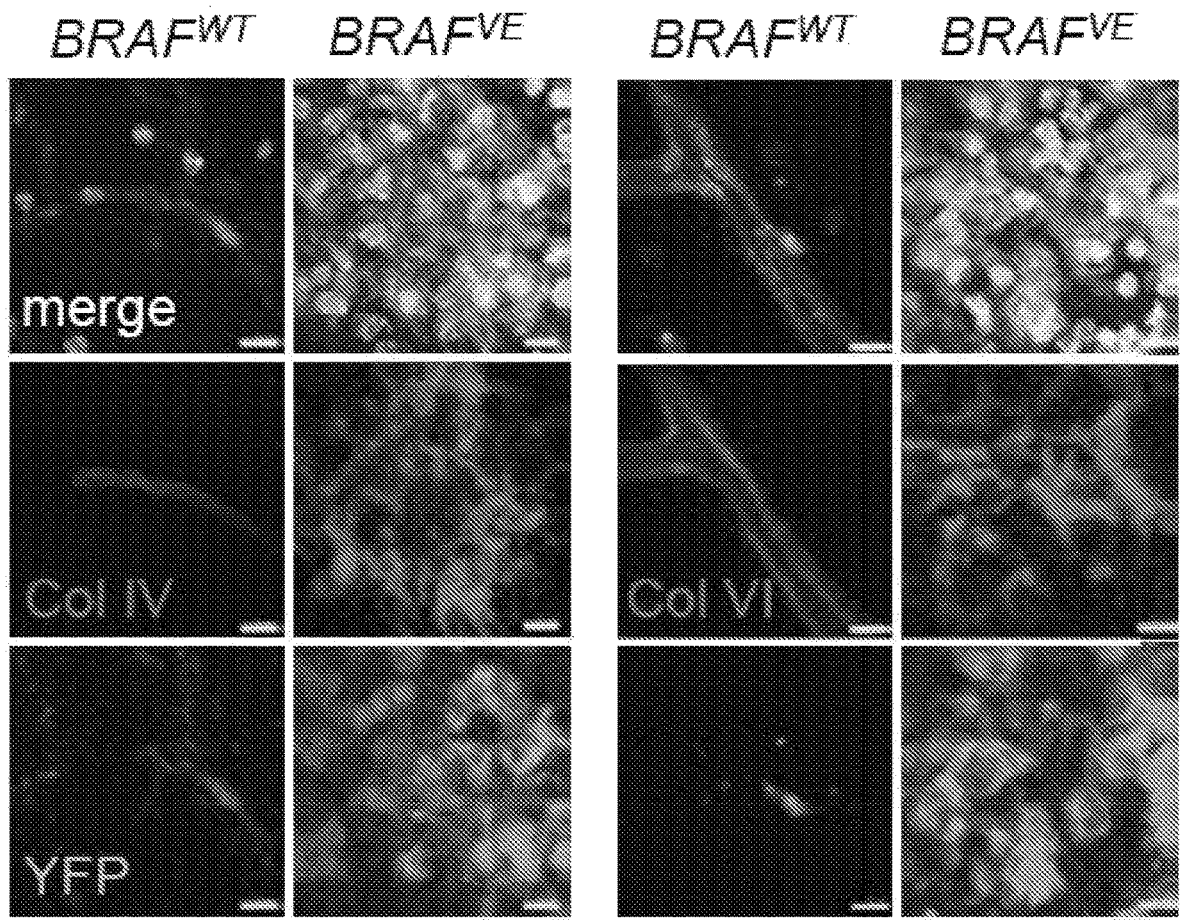

Example 18: Analysis of Cellular and Molecular Mechanisms Operating in Microglia to Drive Neurodegenerative Disease The cellular and molecular mechanisms that may operate in microglia to drive neurodegenerative disease were investigated. RNA-seq analysis of FACS-sorted YFP$^+$ microglia from paralyzed BRAF$^{VE}$ mice and control littermates identified ~8000 differentially expressed genes (DEG), 80% of them being upregulated (data not shown). GSEA analysis of DEG identified Ras signaling, complement activation, and inflammatory response signatures, including expression of Il1b, Il18, Il6 and Il17, genes associated with phagocytosis, such as cathepsins and pattern recognition receptors, growth factors, and growth factor receptors usually expressed by fibroblasts, and matrix-associated genes laminins and collagens (FIGS. 16A and 16B). Expression of Dectin-1 (Clec7a), LFA-1 (CD11a), VLA-4 (CD49d), the Pdgf receptor, Il1b, and Il17a, and their decrease following PLX4720 treatment was confirmed at the protein level and collagen IV and VI deposition was observed at sites of YFP$^+$ microglia accumulation (FIGS. 16C-16F). These results indicate that the pathological consequences of microglial ERK activation include the accumulation of amoeboid microglia producing inflammatory cytokines of the Il1/18 and Il6/17 families, which are mediators of neuronal loss and neurodegeneration and local matrix remodeling, including the production of collagen. Accordingly, these results demonstrate that BRAF inhibitors, such as those described herein, are useful in methods of treating neurodegenerative diseases.

Figure 24A:
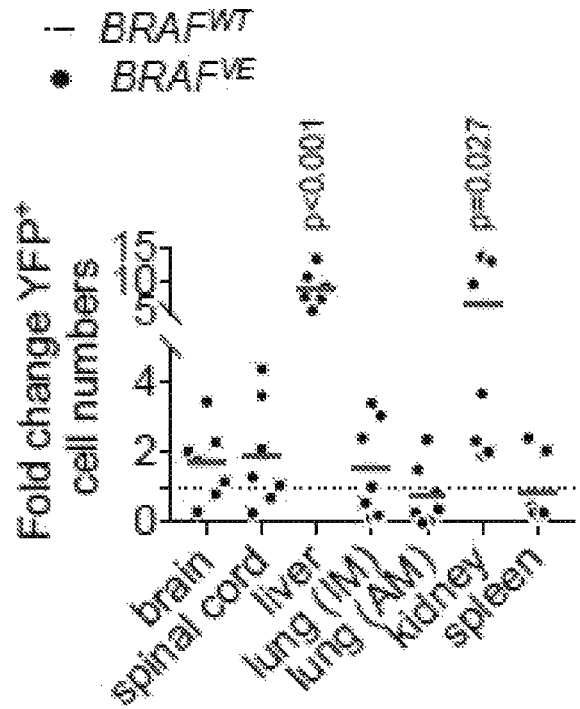
FIGS. 24A-24F. BRAF$^{VE}$ mice analysis outside the central nervous system.
Figure 24B:
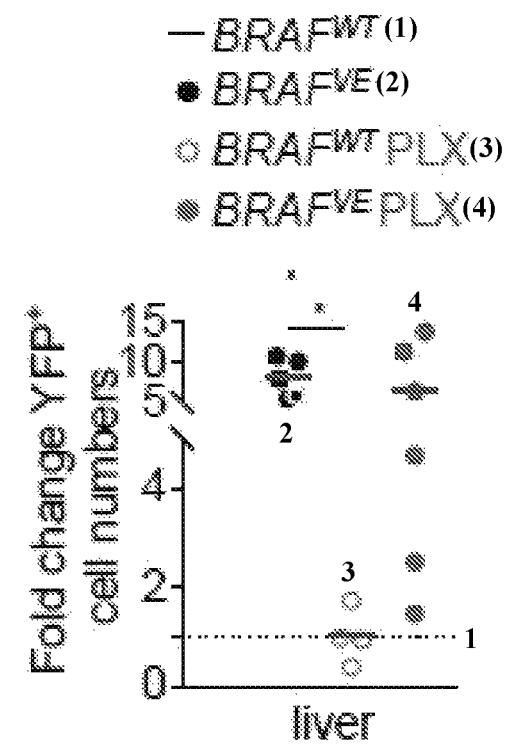
Figure 24C:
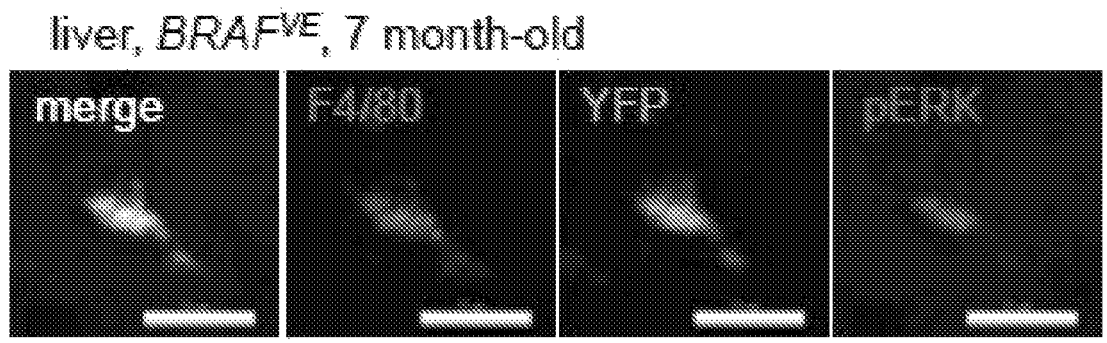
Figure 24D:
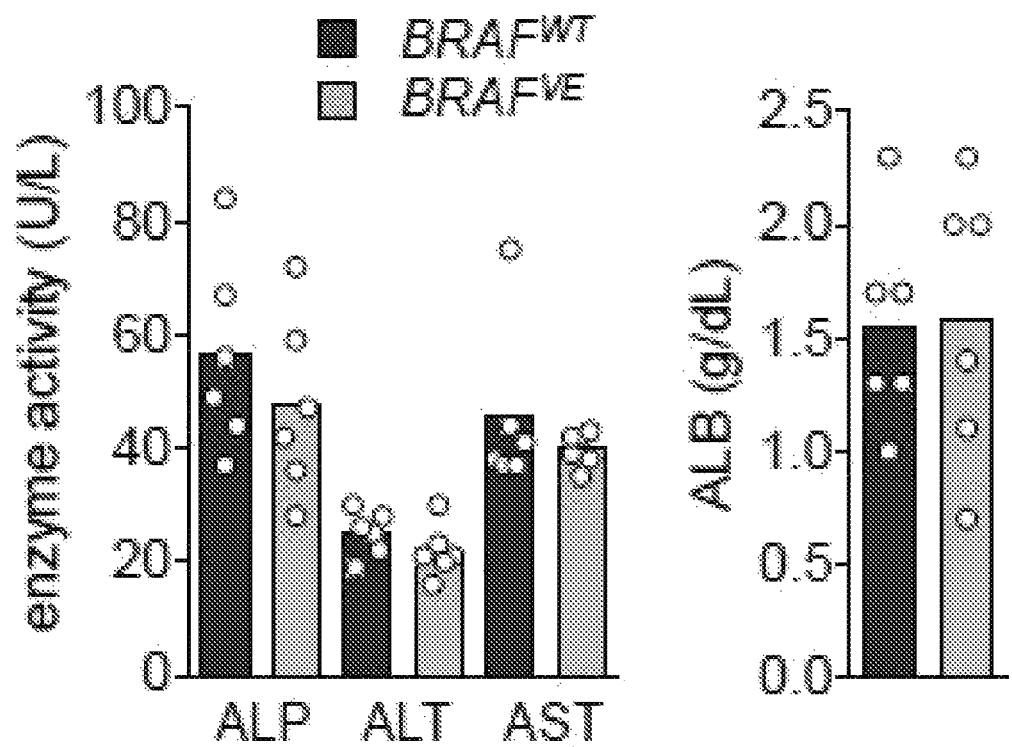
Figure 24E:
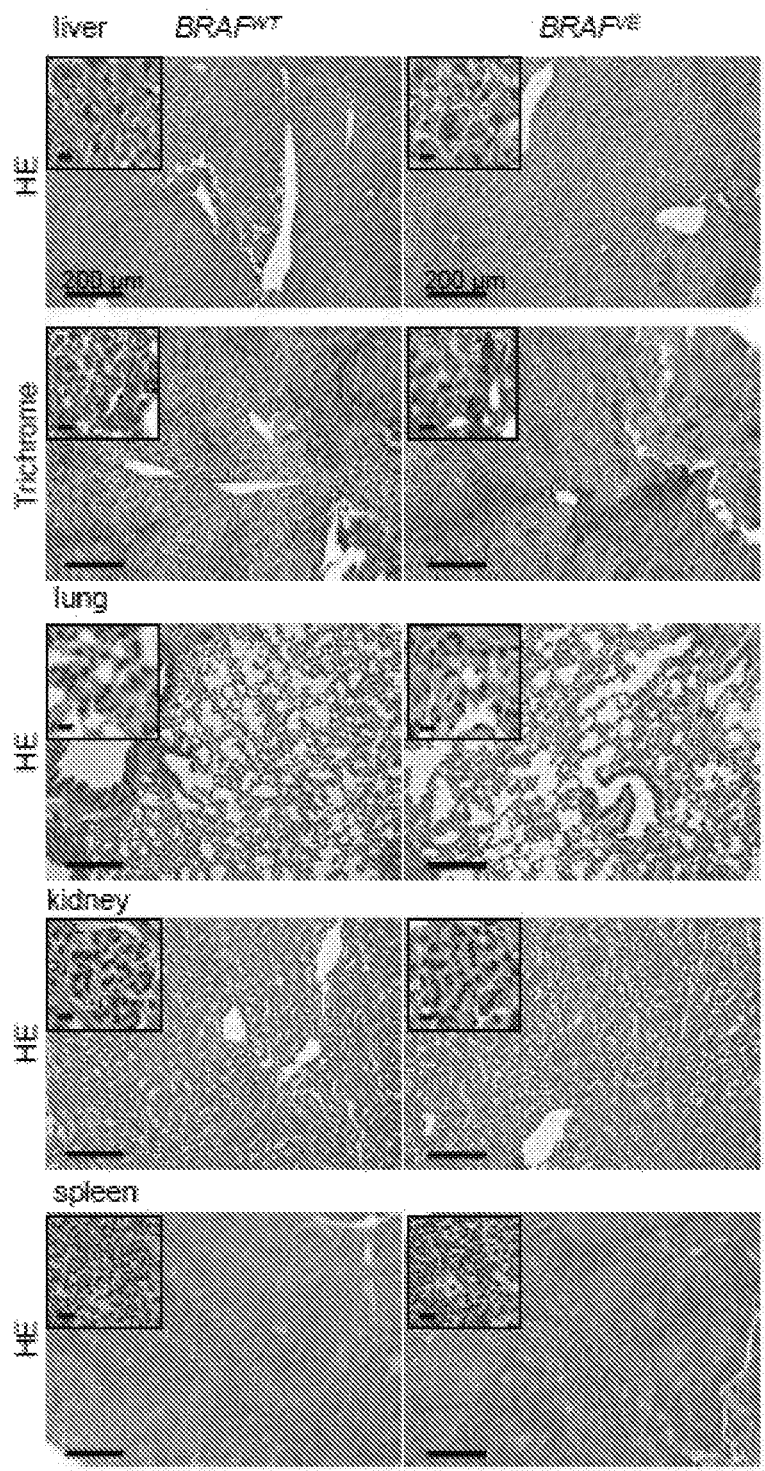
Figure 24F:
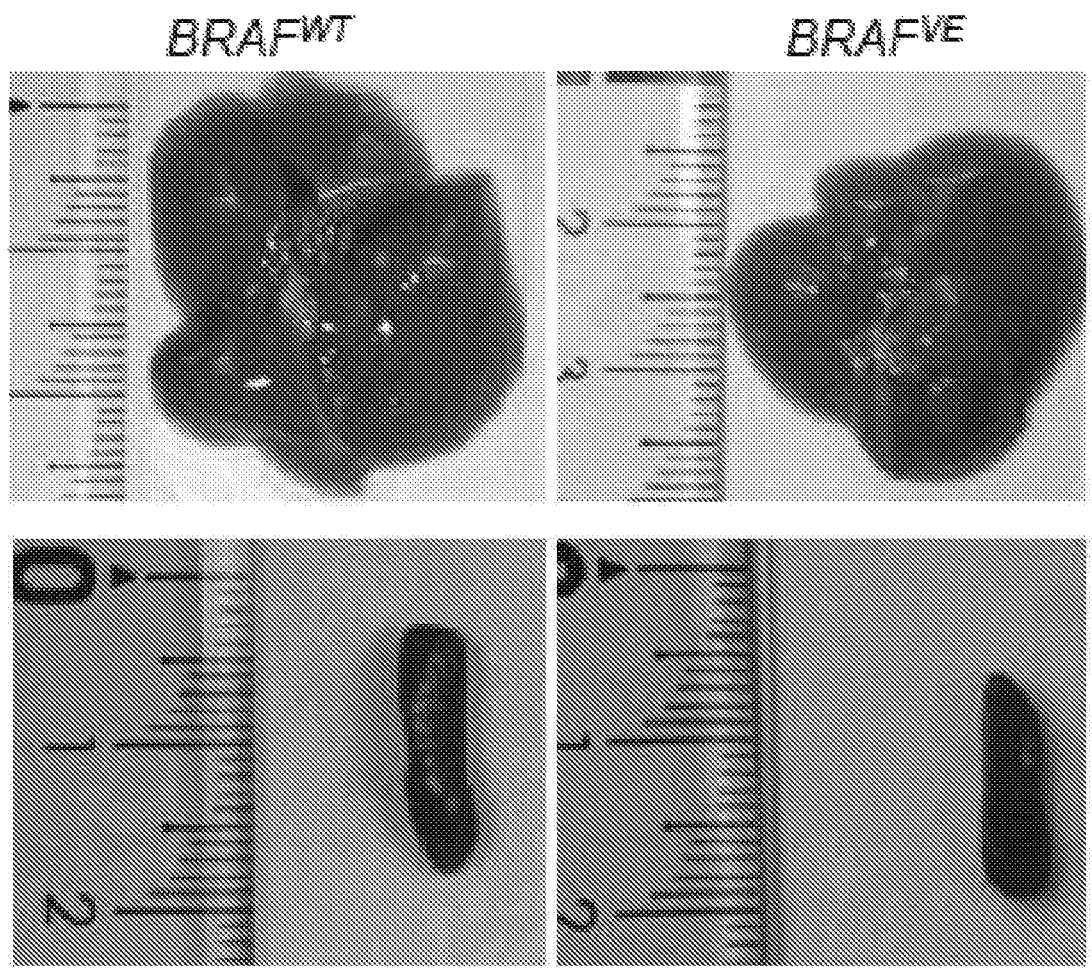

Of note, apart from the hindbrain, midbrain and thalamus, expansion of YFP$^+$F4/80$^+$pERK$^+$macrophages was also detected in the forebrain and in organs outside of the central nervous system, such as the liver (FIGS. 24A-24C). However, histological or biological signs of liver, spleen, lung, or kidney damage in mice housed in SPF conditions in the course of this study (FIGS. 24D-24F) was not observed. Possible explanations for the intriguing finding that ERK-activated macrophages are better tolerated outside the posterior part of the brain may relate to cell-autonomous or cell-extrinsic homeostatic mechanisms that operate in various anatomical locations and tissue niches, such as the greater exposure to microbial and environmental stimuli in the liver.

Figure 16G:
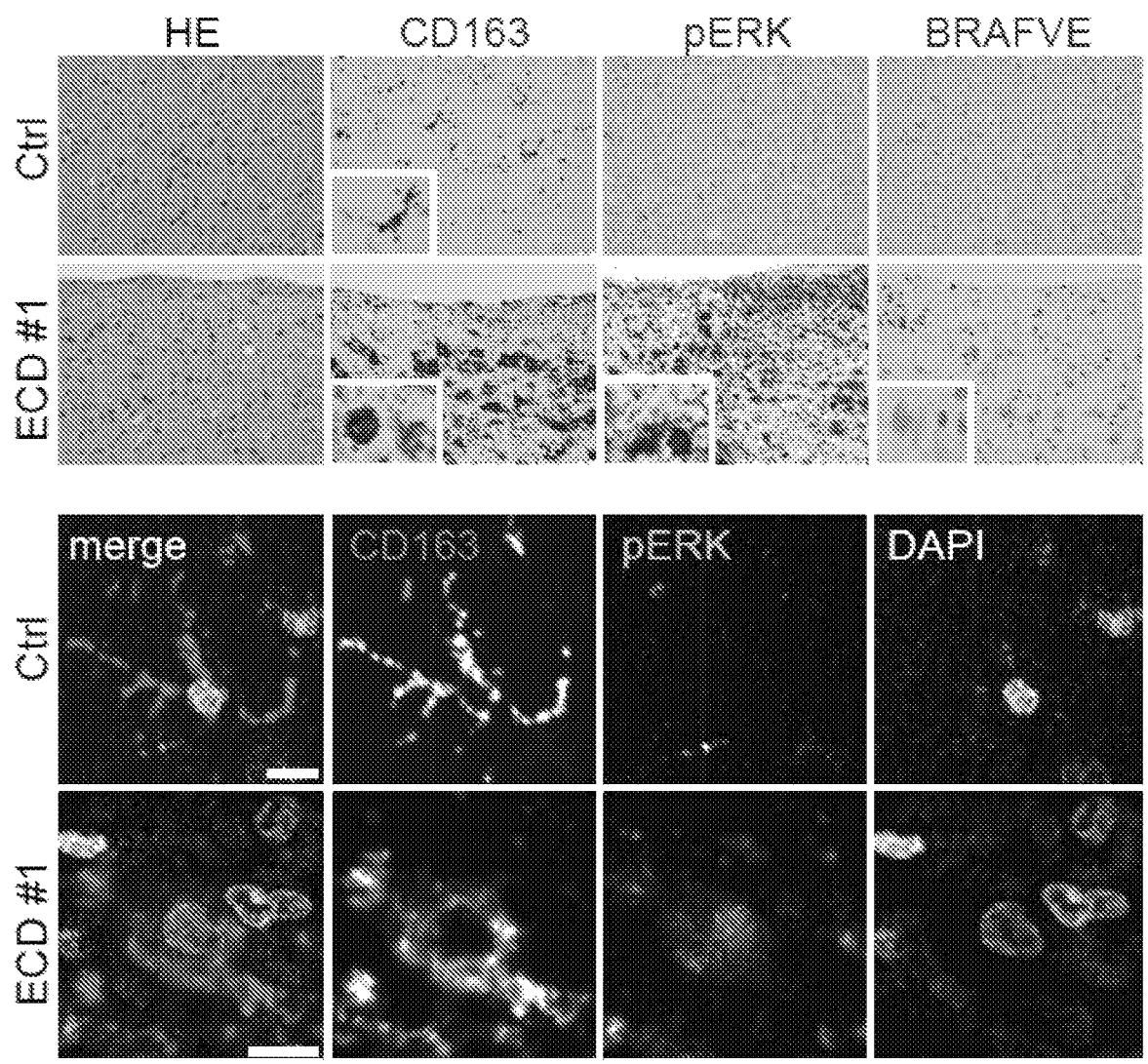
Figure 16H:
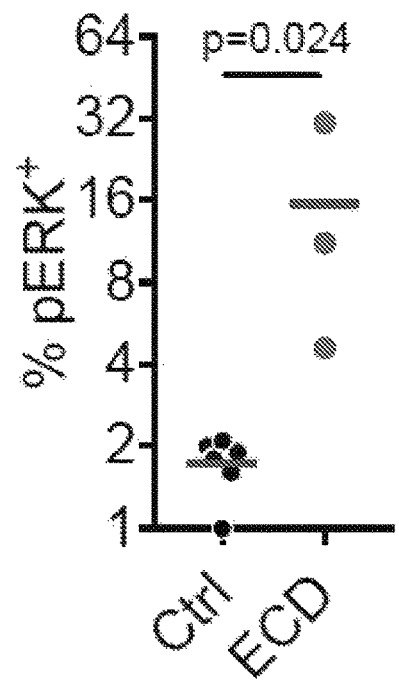
Figure 16I:
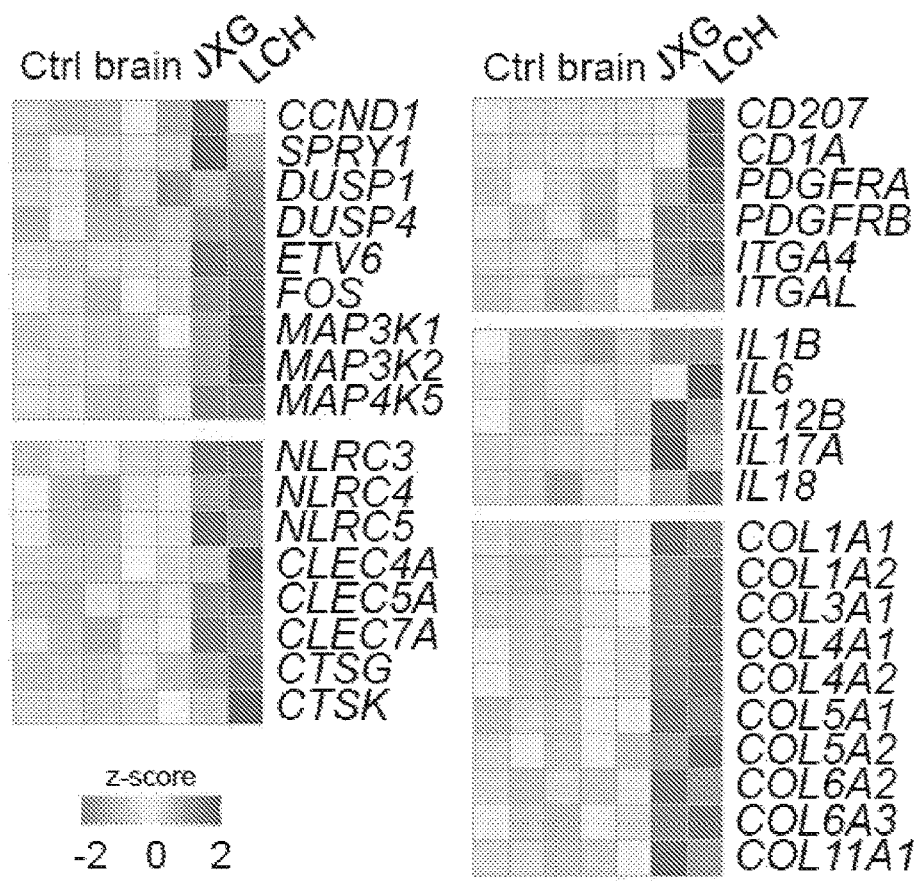
Figure 25B:
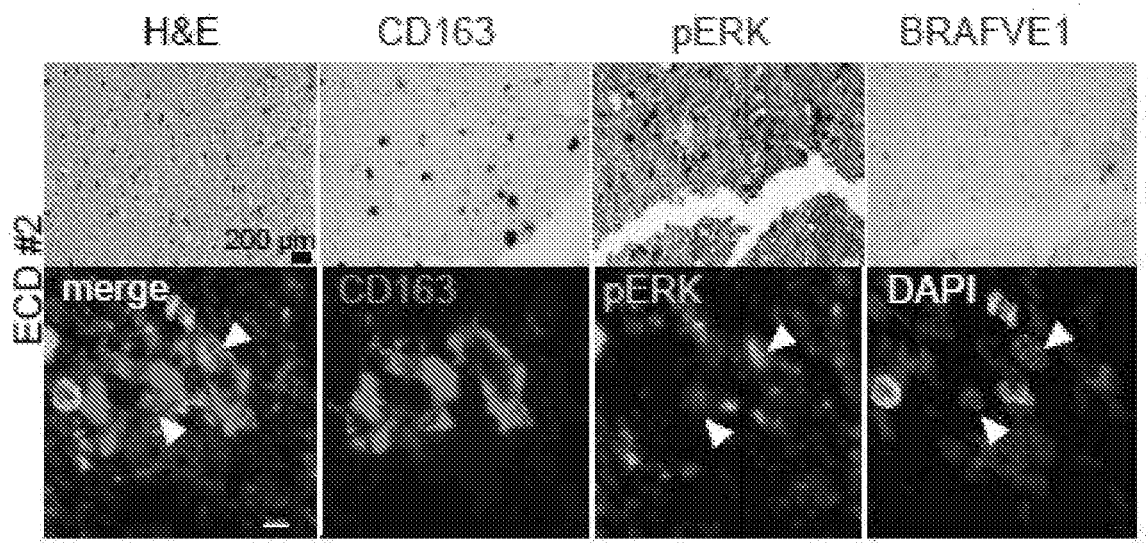
Figure 25C:
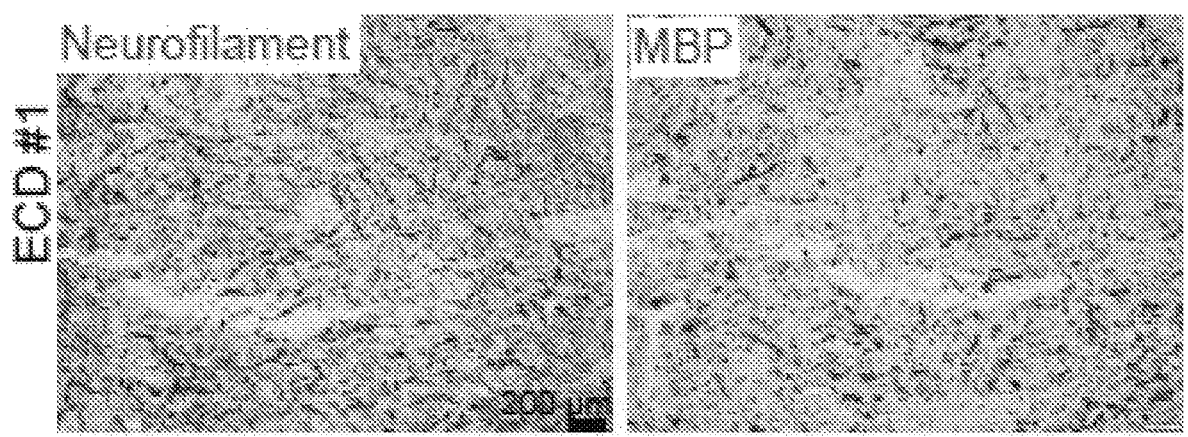

Results from model described herein show that neurodegenerative diseases in histiocytoses patients may involve the accumulation of ERK-activated microglia, producing inflammatory cytokines and collagen at sites of neurodegeneration. Brain tissue from 5 patients with ECD-, LCH-, and Juvenile Xanthogranuloma-(JXG) associated neurodegenerative disease, carrying a BRAF mutation (FIG. 25A) was analyzed. In ECD patients, microglial activation, in the form of numerous amoeboid BRAF$^{V600E+}$CD163$^+$ microglia with nuclear pERK$^+$ staining at sites of neuronal loss, astrogliosis, and demyelination (FIGS. 16G and 16H; FIGS. 25B and 25C) was observed. Comparison of the transcriptome from the JXG and LCH brain biopsies with control brain tissue also identified a MAPK-pathway activation signature, and indicated increased expression of IL 1b, IL18, IL6 and IL17A, pattern recognition receptors and cathepsins, as well as PDGF receptor and collagen genes (FIG. 16I). Therefore, brain tissues from human patients shared key histological, cellular and molecular features observed in the mouse.

Example 19: Analysis of Somatic Mutations in Brain Cells from Human Samples

Figure 26A:
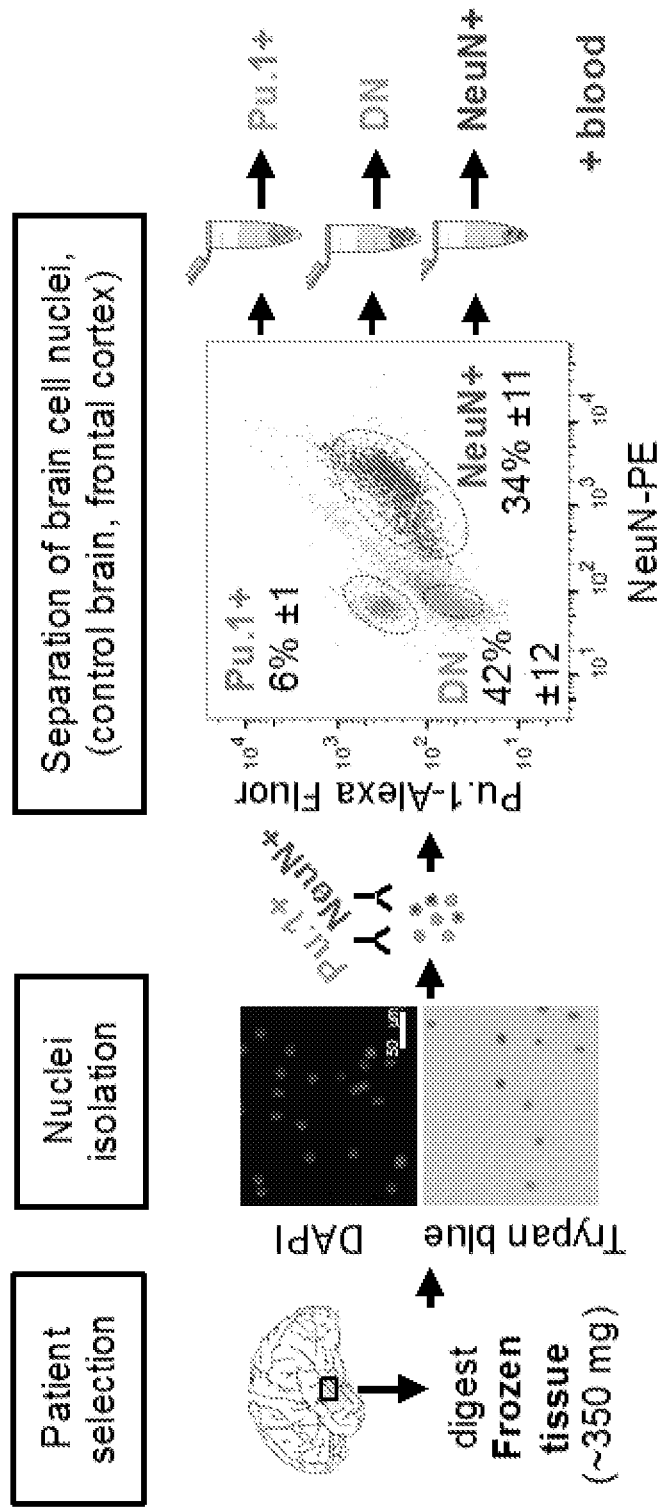
FIGS. 26A-26C. Isolation of microglia, neuron, and glia nuclei by cell sorting in a patient with neurodegeneration.
Figure 26B:
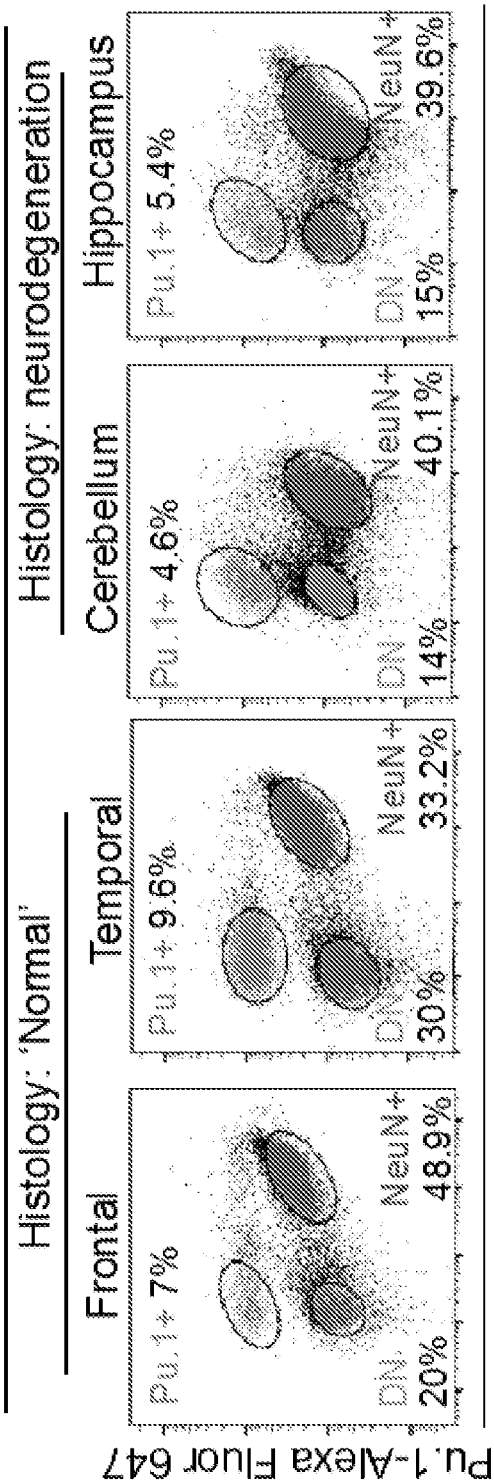
Figure 26B:
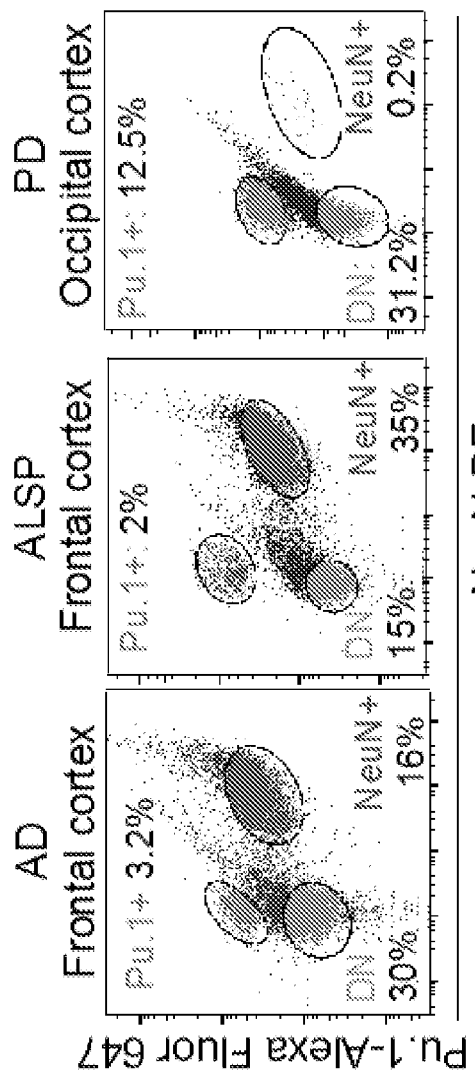
Figure 26C:
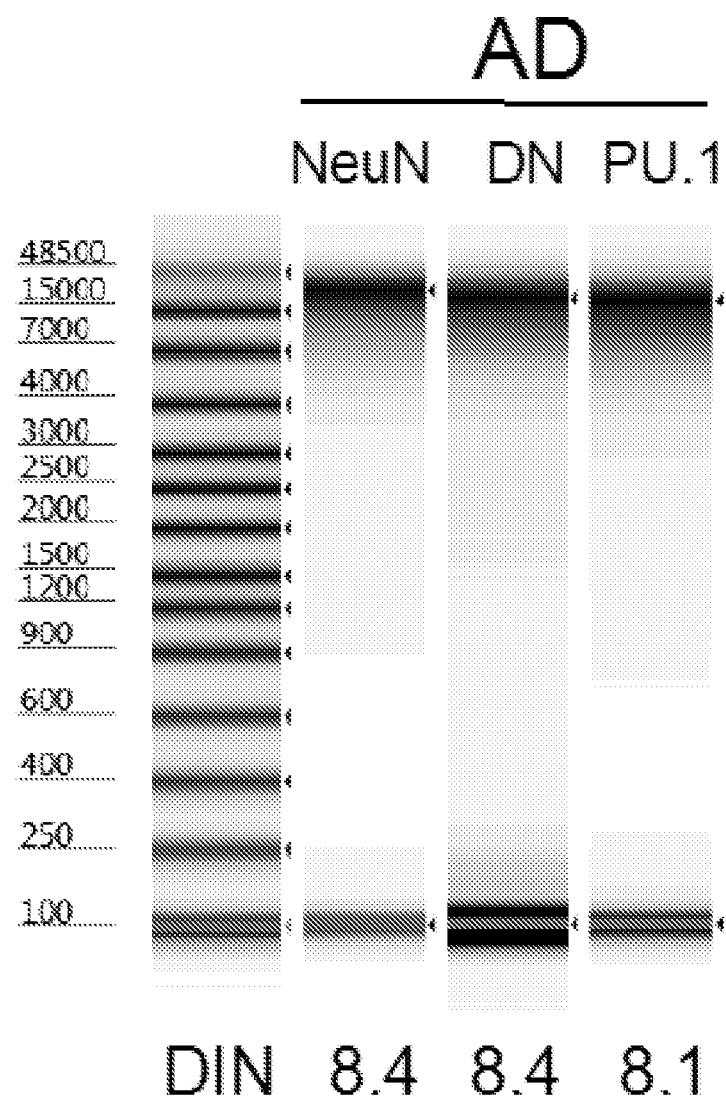

Microglia represent only ~5% (2-10%) of brain cells, thus sequencing of whole brain tissue at current sequencing depths is unlikely to reliably detect somatic mutations in microglial clones. In addition, fresh brain tissue is in general not available for genetic studies. This example describes a protocol to extract and purify nuclei from microglia (Pu.1+ NeuN−), neurons (Pu.1−NeuN+), and double negative cells (Pu.1−NeuN−) from frozen brain samples by immunotagging nuclei suspensions with antibodies (FIGS. 26A-26B).

Protocol for isolation of nuclei from individual brain cell nuclei in frozen samples. Different nuclei sorting protocols were adapted to extract and FACS-sort brain cell nuclei from frozen samples (FIGS. 26A-26B). In brief, ~350 mg of frozen tissue is homogenized in a sterile Dounce tissue grinder using a nonionic surfactant based buffer (250 mM sucrose, 25 mM KCl, 5 Mm MgCl2, 10 mM Tris buffer, pH 8.0, Triton X-100 0.1% (v/v), DAPI 3 µM and nuclease-free water) that lyses the cell membrane while releasing intact nuclei. To improve the efficiency and purity of the nuclei sorting, the homogenate preparation is followed with a sucrose-iodixanol gradient centrifugation to obtain clean nuclei suspensions. Samples are immunotagged first with anti-NeuN-PE (clone A60; Milli-Mark, 1:500, 45 min), followed by fixation (15 min) and permeabilization (eBioscience Transcription Factor Staining Buffer Set, eBioscience) and immunotagging with anti-Pu.1-Alexa Fluor 647 (clone 9G7, Cell Signaling, 1:50, 45 min). After fixation and permeabilization, centrifugations are carried out without breaks to reduce nuclei loss. Samples are FACS-sorted in a BD FACSAria with a 100-µm nozzle and a sheath pressure 20 psi, operating at 1000 events per second. Microglia (Pu.1+NeuN−), neuron (Pu.1−NeuN+) and double negative (DN) cells (Pu.1−NeuN−) are sorted in bulk into 1.5 ml tubes, pre-coated with 10% BSA (FIG. 26A). After sorting, nuclei are centrifuged for 20 minutes at 6000 g. Nuclei pellets are processed for DNA extraction immediately using QIAamp DNA Mini Kit (QIAGEN) following manufacture recommendations. Samples are processed at all times in an Air Clean PCR Workstation. Criteria for sequencing: resulting DNA is analyzed for quality and quantity with Agilent 4200 TapeStation, and Quant-it (ThermoScientific), respectively. Samples with a DNA integrity number (DIN)>6 and a total quantity >200 ng will proceed to library preparation. Based on extensive testing, it has been determined that isolation of brain nuclei from ~350 mg (>150.000 nuclei p/population) of tissue using this protocol reproducibly allows DNA extraction with yield and quality for deep sequencing (data not shown, FIGS. 26A-26B and 27A-27B).

Protocol for library preparation, targeted sequencing using the MSKCC Heme-PACT platform. To explore the presence of mutations in the microglia genome targeted deep DNA sequencing of microglia, neurons, double negative, and blood was performed using the Heme-PACT sequencing panel. Matched samples obtained in (g) are sequenced in the Integrated Genomics Operation (IGO) at Memorial Sloan Kettering (MSKCC). Before sequencing, DNA samples are normalized to a yield 200 ng of input (~150.000 cells) and diluted in 55 µl of TE buffer on the Biomek FXP Laboratory Automation Workstation (Beckman Coulter) before shearing on the Covaris instrument. Sequencing libraries are prepared on the Biomek FXP through a series of enzymatic steps including shearing, end-repair, A-base addition, ligation of barcoded sequence adaptors and low-cycle PCR amplification (Kapa Biosystems, Roche). Libraries are analyzed for quantity and are combined in pools of 24-36 libraries for multiplexed capture using custom-designed biotinylated probes (NimbleGen). Captured DNA fragments are sequenced on an Illumina HiSeq 2500 as paired-end 100-bp reads. All DNA samples are sequenced to the same coverage (>400×), which will allow multiple comparisons during the analysis.

Example 20: Identification of BRAF Somatic Mutations in Microglia from a Human Patient with LCH and Neurodegenerative Disease Brain, blood, and skin samples from a patient (patient A) from the French Histiocytosis Study Group database/biobank were analyzed. Prior written informed consent was obtained from the patient with histiocytosis for DNA sequencing and immunohistochemical studies according to the Helsinki convention. This study received approval from the Institutional Review Board at MSKCC (IRB Protocol X17-047). This patient presented with a $BRAF^{V600E}$ mutation in peripheral (skin) macrophages at 6 months of age (histiocytosis, an eczema type lesion that resolves by itself, with topical treatment, or in some case mild chemotherapy) and who later developed a lethal neurodegenerative disease over the following two decades.

Figure 28:
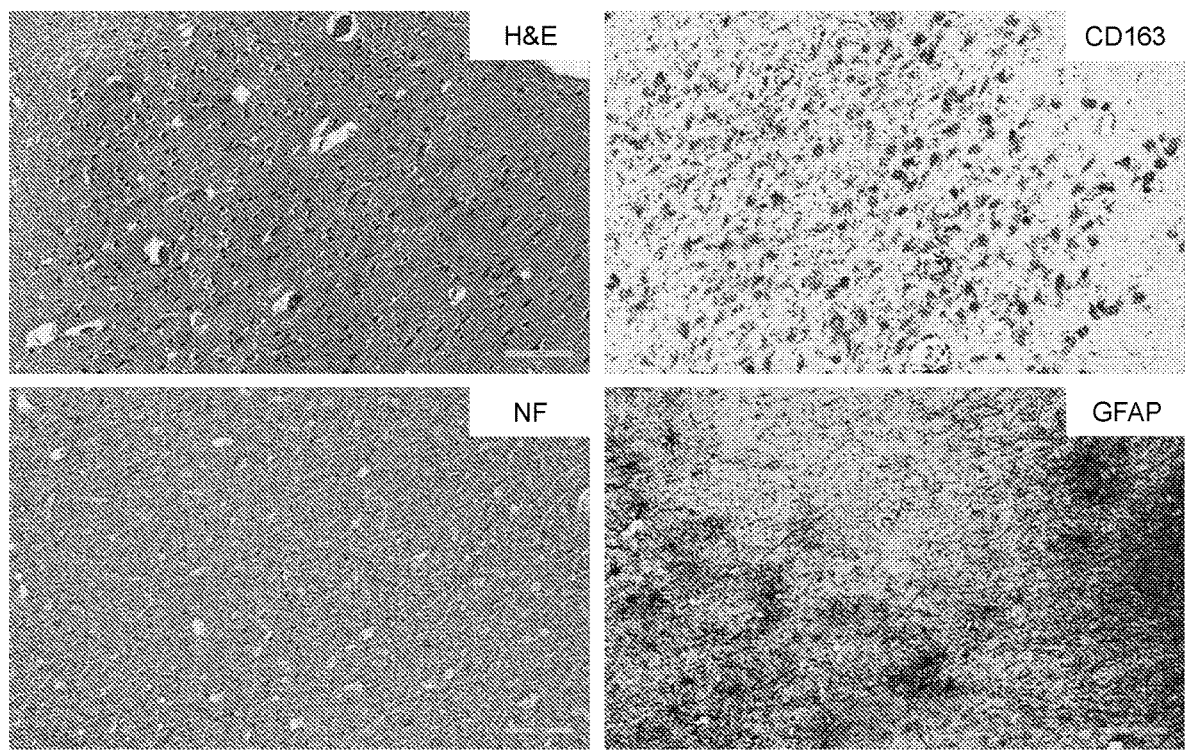
FIG. 28. Hippocampus of patient with neurodegenerative disease due to BRAF$^{V600E}$ microglia. Immunohistochemistry analysis for CD163, Neurofilament-1 (NF), and GFAP of post-mortem brain tissue from the hippocampal area.

The presence of $BRAF^{V600E}$ was analyzed using ddPCR and the MSKCC Heme-Pact sequencing panel in blood cells and post-mortem brain microglia, neurons, and glial cells from 8 different brain areas involved or not with neurodegenerative process after histlgical examination. $BRAF^{V600E}$ was detected at allelic frequencies of 9%, 12% and 20% in Pu.1+ cells (microglia) from pons, cerebellum, and hippocampus, respectively (FIGS. 26A-26B and 27A-27B), which correspond with brain regions that present with severe histological signs of microgliosis, astrogliosis, and neurodegeneration (FIG. 28). Allelic frequencies of 0.2% and 0.3% were detected in amygdala and midbrain where discrete lesions were also observed. In contrast the $BRAF^{V600E}$ clones were undetectable in neurons and blood cells, and in Pu.1+ cells from unaffected areas of the brain (F2, T1, and medulla) (see FIGS. 26A-26B and 27A-27B).

Figure 29:
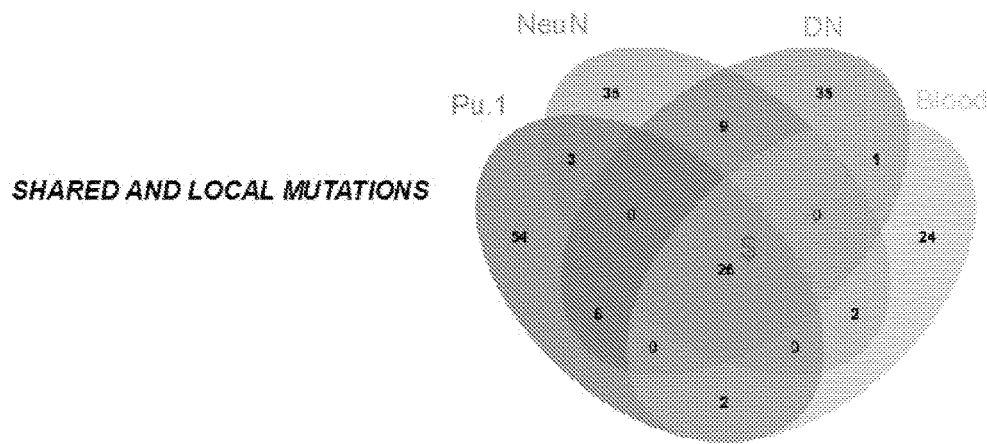
FIG. 29. Preliminary analysis of somatic mosaicism from Heme-PACT targeted sequencing. Venn diagrams represent the number and repartition among cell types and tissues (brain regions and blood) of somatic variants (SNV and indel) detected by Heme-PACT sequencing and analysis. Variants with an allele frequency >35% are considered germline and eliminated from analysis. SNVs are validated bioinformatically and by ddPCR and Ampli-seq. This analysis suggests that mutations are either common to all tissues ($, with high 15%-35% allelic frequency) and considered early somatic events, or local to a cell type and brain region (with lower allelic frequencies) for neurons, microglia, and DN (double negative) cells suggesting their local development independent of blood cells. The 2 mutations common to hippocampus and cerebellum (*) are at higher allelic frequencies and correspond to BRAF$^{V600E}$ (11% and 21%) and a non-coding mutation in MSH6 (16% and 26%).
Figure 29:
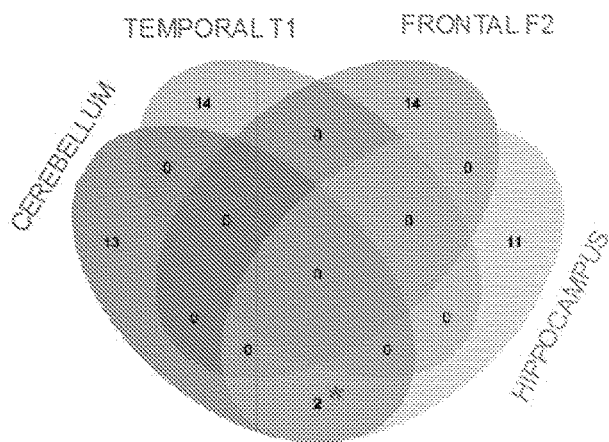
Figure 29:
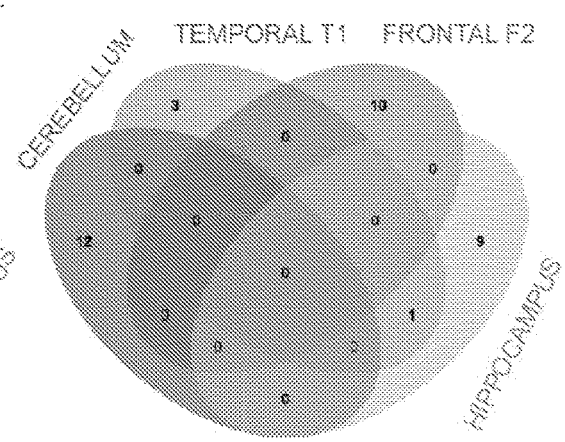

Additionally, analysis of mosaicism in blood cells, neurons, and microglia from this patient indicate that microglia mosaicism is private to each brain area and not shared with blood or neurons, which is compatible with an early developmental origin and local clonal evolution of microglia, similar to what has been observed in mice (FIG. 29).

These results on the presence of $BRAF^{V600E}$ positive macrophages in brain areas with severe neuronal loss and skin, and the absence of $BRAF^{V600E}$ positive cells in blood of a patient with neurodegeneration, recapitulates what has been reported in mice. These results demonstrate that microglia somatic mosaicism for a $BRAF^{V600E}$ mutations is associated and likely causative of neurodegenerative disease.

Example 21: Effect of Targeting $PIK3CA^{H1047R}$ to Macrophage Progenitors

Figure 30:
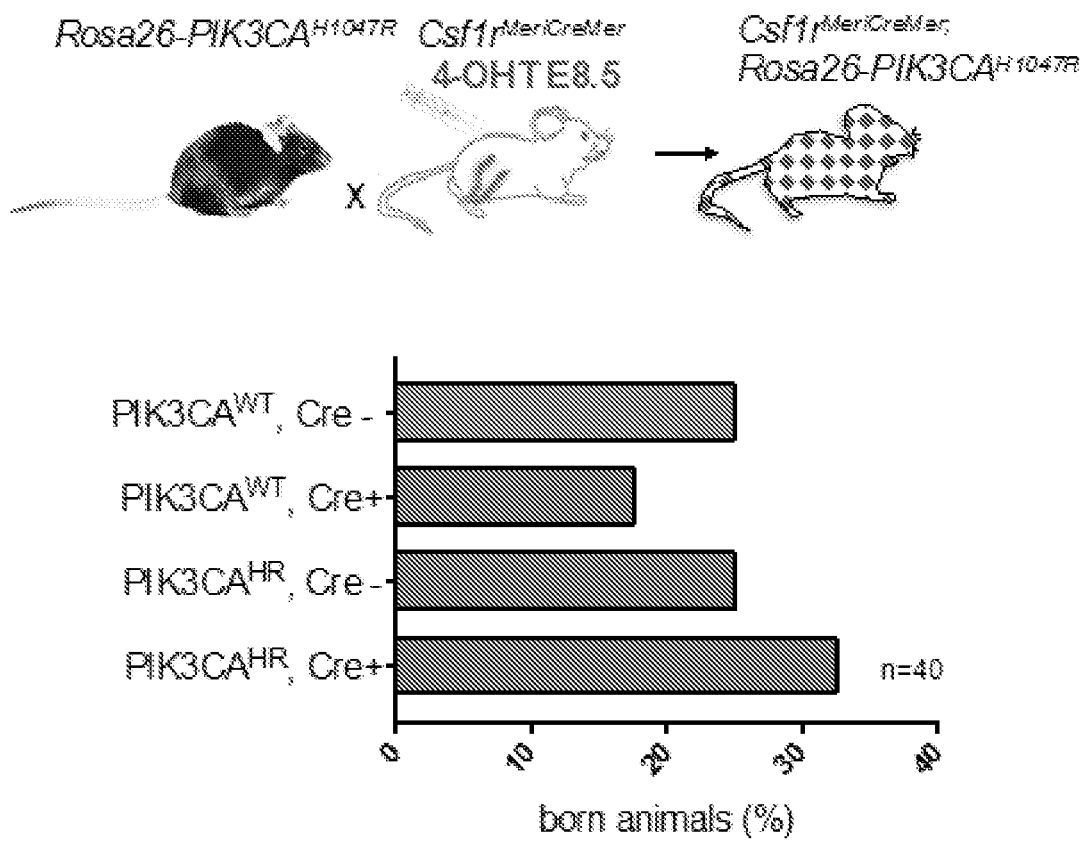
FIG. 30. Breeding strategy for experimental mice and genotype distribution (n=22). 4-OHT: 4-hydroxytamoxifen. E8.5, embryonic day 8.5.
Figure 31A:
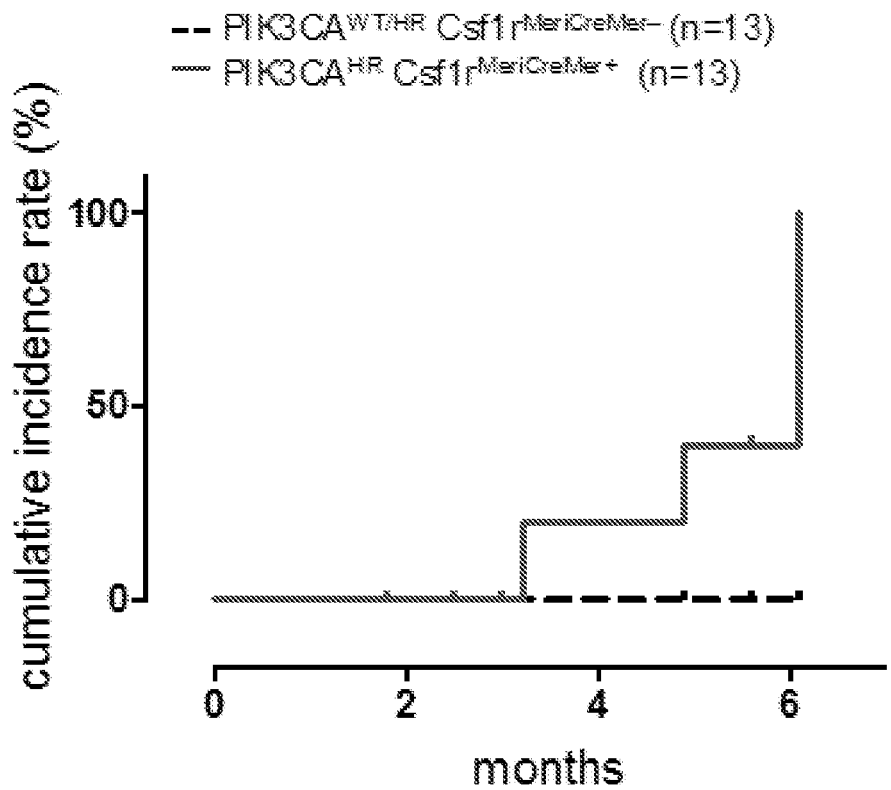
FIGS. 31A-31B. Neurodegenerative disease in PIK3CA$^{HR}$ mice.
Figure 31B:
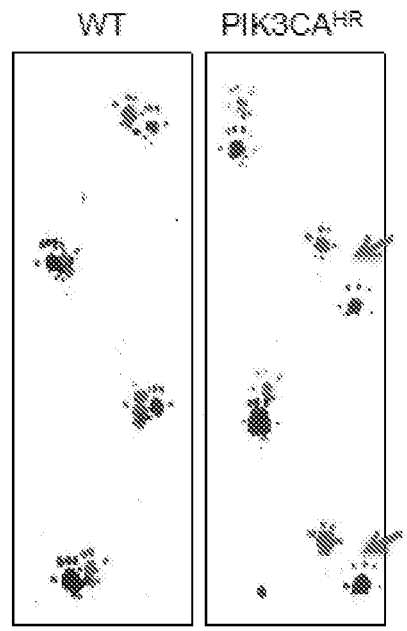

Mosaic expression of $BRAF^{V600E}$ mutation in microglia drives a neurodegenerative disease in mice and humans. Whether this phenotype is exclusive of BRAF mutations in the macrophage lineage or if mutations affecting other pathways may also drive a neurodeneraive disorder remains unexplored. Approximately 10% of histiocytoses patients (17% for Erdheim-Chester disease) present with gain of function somatic mutations in the phosphoinositide-3-kinase-(PI3K)-AKT pathway, $PIK3CA^{H1047R}$ being the most frequent. The $PIK3CA^{H1047R}$ mutation is located in the kinase domain of the protein and leads to elevated kinase activity. Targeting $PIK3CA^{H1074R}$ expression specifically to a small number of EMPs is accomplished by crossing FVB.12956-Gt(ROSA)26Sor$^{tm1(Pik3ca*H1047R)Egan}$/J(R26-Pik3ca$^{H1047R}$) males to tamoxifen-inducible Csf1r$^{MeriCreMer}$ females, thereby allowing selective targeting of EMPs when pulsed with OH-TAM at E8.5. Pregnant females receive low doses of OH-TAM via intraperitoneal injection so that only a small proportion of cells express $PIK3CA^{H1074R}$ (PIKRCA$^{HR}$) (FIG. 30). Mice are born in Mendelian ratios (FIG. 30). Similar to what has been reported on BRAF$^{V600}$ mice, $PIK3CA^{H1074R}$ and not their wild-type littermates, present with neurological symptoms by the age of ~5 months of age as measured by cumulative incidence of behavioral abnormalities (FIG. 31A). Footprint assays showed a unilateral increase in overlap distance between hind and front paws in PIK3CA$^{H1074R}$ mice (FIG. 31B). These results demonstrate that activation of PI3K-AKT pathway in the macrophage lineage, and therefore in microglia, also drives a neurological phenotype as previously observed in BRAF$^{V600E}$ mice. Accordingly, this example suggests that PI 3-kinase inhibitors, such as those described herein, are useful in methods of treating the symptoms of neurodegenerative disease.

REFERENCES

1. Berres M L, Lim K P, Peters T, Price J, Takizawa H, Salmon H, Idoyaga J, Ruzo A, Lupo P J, Hicks M J, Shih A, Simko S J, Abhyankar H, Chakraborty R, Leboeuf M, Beltrao M, Lira S A, Heym K M, Bigley V, Collin M, Manz M G, McClain K, Merad M, Allen C E. BRAF-V600E expression in precursor versus differentiated dendritic cells defines clinically distinct LCH risk groups. The Journal of experimental medicine. 2014; 211(4):669-83. doi: 10.1084/jem.20130977. PubMed PMID: 24638167; PMCID: PMC3978272.
2. Heritier S, Emile J F, Barkaoui M A, Thomas C, Fraitag S, Boudjemaa S, Renaud F, Moreau A, Peuchmaur M, Chassagne-Clement C, Dijoud F, Rigau V, Moshous D, Lambilliotte A, Mazingue F, Kebaili K, Miron J, Jeziorski E, Plat G, Aladjidi N, Ferster A, Pacquement H, Galambrun C, Brugieres L, Leverger G, Mansuy L, Paillard C, Deville A, Armari-Alla C, Lutun A, Gillibert-Yvert M, Stephan J L, Cohen-Aubart F, Haroche J, Pellier I, Millot F, Lescoeur B, Gandemer V, Bodemer C, Lacave R, Helias-Rodzewicz Z, Taly V, Geissmann F, Donadieu J. BRAF Mutation Correlates With High-Risk Langerhans Cell Histiocytosis and Increased Resistance to First-Line Therapy. Journal of clinical oncology: official journal of the American Society of Clinical Oncology. 2016; 34(25):3023-30. doi: 10.1200/JC0.2015.65.9508. PubMed PMID: 27382093.
3. Diamond E L, Durham B H, Haroche J, Yao Z, Ma J, Parikh S A, Wang Z, Choi J, Kim E, Cohen-Aubart F, Lee S C, Gao Y, Micol J B, Campbell P, Walsh M P, Sylvester B, Dolgalev I, Aminova O, Heguy A, Zappile P, Nakitandwe J, Ganzel C, Dalton J D, Ellison D W, Estrada-Veras J, Lacouture M, Gahl W A, Stephens P J, Miller V A, Ross J S, Ali S M, Briggs S R, Fasan O, Block J, Heritier S, Donadieu J, Solit D B, Hyman D M, Baselga J, Janku F, Taylor B S, Park C Y, Amoura Z, Dogan A, Emile J F, Rosen N, Gruber T A, Abdel-Wahab O. Diverse and Targetable Kinase Alterations Drive Histiocytic Neoplasms. Cancer discovery. 2015. doi: 10.1158/2159-8290.CD-15-0913. PubMed PMID: 26566875.
4. Diamond E L, Abdel-Wahab O, Pentsova E, Borsu L, Chiu A, Teruya-Feldstein J, Hyman D M, Rosenblum M. Detection of an NRAS mutation in Erdheim-Chester disease. Blood. 2013; 122(6):1089-91. doi: 10.1182/blood-2013-02-482984. PubMed PMID: 23929840.
5. Emile J F, Diamond E L, Helias-Rodzewicz Z, Cohen-Aubart F, Charlotte F, Hyman D M, Kim E, Rampal R, Patel M, Ganzel C, Aumann S, Faucher G, Le Gall C, Leroy K, Colombat M, Kahn J E, Trad S, Nizard P, Donadieu J, Taly V, Amoura Z, Abdel-Wahab O, Haroche J. Recurrent RAS and PIK3 A mutations in Erdheim-Chester disease. Blood. 2014; 124(19):3016-9. doi: 10.1182/blood-2014-04-570937. PubMed PMID: 25150293; PMCID: PMC4224196.
6. Badalian-Very G, Vergilio J A, Degar B A, MacConaill L E, Brandner B, Calicchio M L, Kuo F C, Ligon A H, Stevenson K E, Kehoe S M, Garraway L A, Hahn W C, Meyerson M, Fleming M D, Rollins B J. Recurrent BRAF mutations in Langerhans cell histiocytosis. Blood. 2010; 116(11):1919-23. Epub 2010/06/04. doi: 10.1182/blood-2010-04-279083. PubMed PMID: 20519626; PMCID: 3173987.
7. Satoh T, Smith A, Sarde A, Lu H C, Mian S, Trouillet C, Mufti G, Emile J F, Fraternali F, Donadieu J, Geissmann F. B-RAF Mutant Alleles Associated with Langerhans Cell Histiocytosis, a Granulomatous Pediatric Disease. PloS one. 2012; 7(4):e33891. Epub 2012/04/17. doi: 10.1371/journal.pone.0033891. PubMed PMID: 22506009; PMCID: 3323620.
8. Haroche J, Charlotte F, Arnaud L, von Deimling A, Helias-Rodzewicz Z, Hervier B, Cohen-Aubart F, Launay D, Lesot A, Mokhtari K, Canioni D, Galmiche L, Rose C, Schmalzing M, Croockewit S, Kambouchner M, Copin M C, Fraitag S, Sahm F, Brousse N, Amoura Z, Donadieu J, Emile J F. High prevalence of BRAF V600E mutations in Erdheim-Chester disease but not in other non-Langerhans cell histiocytoses. Blood. 2012; 120(13):2700-3. doi: 10.1182/blood-2012-05-430140. PubMed PMID: 22879539.
9. Hyman D M, Puzanov I, Subbiah V, Faris J E, Chau I, Blay J Y, Wolf J, Raje N S, Diamond E L, Hollebecque A, Gervais R, Elez-Fernandez M E, Italiano A, Hofheinz R D, Hidalgo M, Chan E, Schuler M, Lasserre S F, Makrutzki M, Sirzen F, Veronese M L, Tabernero J, Baselga J. Vemurafenib in Multiple Nonmelanoma Cancers with BRAF V600 Mutations. The New England journal of medicine. 2015; 373(8):726-36. doi: 10.1056/NEJMoa1502309. PubMed PMID: 26287849; PMCID: PMC4971773.
10. Hyman D M, Diamond E L, Vibat C R, Hassaine L, Poole J C, Patel M, Holley V R, Cabrilo G, Lu T T, Arcila M E, Chung Y R, Rampal R, Lacouture M E, Rosen N, Meric-Bernstam F, Baselga J, Kurzrock R, Erlander M G, Janku F, Abdel-Wahab O. Prospective blinded study of BRAFV600E mutation detection in cell-free DNA of patients with systemic histiocytic disorders. Cancer discovery. 2015; 5(1):64-71. doi: 10.1158/2159-8290.CD-14-0742. PubMed PMID: 25324352.
11. Charles J, Beani J C, Fiandrino G, Busser B. Major response to vemurafenib in patient with severe cutaneous Langerhans cell histiocytosis harboring BRAF V600E mutation. Journal of the American Academy of Dermatology. 2014; 71(3):e97-9. doi: 10.1016/j.jaad.2014.03.038. PubMed PMID: 25128147.
12. Haroche J, Cohen-Aubart F, Emile J F, Arnaud L, Maksud P, Charlotte F, Cluzel P, Drier A, Hervier B, Benameur N, Besnard S, Donadieu J, Amoura Z. Dramatic efficacy of vemurafenib in both multisystemic and refractory Erdheim-Chester disease and Langerhans cell histiocytosis harboring the BRAF V600E mutation. Blood. 2013; 121(9):1495-500. doi: 10.1182/blood-2012-07-446286. PubMed PMID: 23258922.
13. Pettirossi V, Santi A, Imperi E, Russo G, Pucciarini A, Bigerna B, Schiavoni G, Fortini E, Spanhol-Rosseto A, Sportoletti P, Mannucci R, Martelli M P, Klein-Hitpass L, Falini B, Tiacci E. BRAF inhibitors reverse the unique molecular signature and phenotype of hairy cell leukemia and exert potent antileukemic activity. Blood. 2015; 125 (8):1207-16. doi: 10.1182/blood-2014-10-603100. PubMed PMID: 25480661; PMCID: PMC4366655.

14. Perdiguero E G, Geissmann F. The development and maintenance of resident macrophages. Nature immunology. 2015; 17(1):2-8. doi: 10.1038/ni.3341. PubMed PMID: 26681456.
15. Schulz C, Gomez Perdiguero E, Chorro L, Szabo-Rogers H, Cagnard N, Kierdorf K, Prinz M, Wu B, Jacobsen S E, Pollard J W, Frampton J, Liu K J, Geissmann F. A lineage of myeloid cells independent of Myb and hematopoietic stem cells. Science. 2012; 336(6077):86-90. doi: 10.1126/science.1219179. PubMed PMID: 22442384.
16. Gomez Perdiguero E, Klapproth K, Schulz C, Busch K, Azzoni E, Crozet L, Garner H, Trouillet C, de Bruijn M F, Geissmann F, Rodewald H R. Tissue-resident macrophages originate from yolk-sac-derived erythro-myeloid progenitors. Nature. 2015; 518(7540):547-51. doi: 10.1038/nature13989. PubMed PMID: 25470051.
17. Mass E, Ballesteros I, Farlik M, Halbritter F, Gunther P, Crozet L, Jacome-Galarza C E, Handler K, Klughammer J, Kobayashi Y, Gomez-Perdiguero E, Schultze J L, Beyer M, Bock C, Geissmann F. Specification of tissue-resident macrophages during organogenesis. Science. 2016; 353 (6304). doi: 10.1126/science. aaf4238. PubMed PMID: 27492475.
18. Kierdorf K, Erny D, Goldmann T, Sander V, Schulz C, Perdiguero E G, Wieghofer P, Heinrich A, Riemke P, Holscher C, Muller D N, Luckow B, Brocker T, Debowski K, Fritz G, Opdenakker G, Diefenbach A, Biber K, Heikenwalder M, Geissmann F, Rosenbauer F, Prinz M. Microglia emerge from erythromyeloid precursors via Pu.1- and Irf8-dependent pathways. Nat Neurosci. 2013; 16(3):273-80. doi: 10.1038/nn.3318. PubMed PMID: 23334579.
19. Gomez Perdiguero E, Geissmann F. Myb-independent macrophages: a family of cells that develops with their tissue of residence and is involved in its homeostasis. Cold Spring Harbor symposia on quantitative biology. 2013; 78:91-100. doi: 10.1101/sqb.2013.78.020032. PubMed PMID: 24122769.
20. Yamasaki R, Lu H, Butovsky O, Ohno N, Rietsch A M, Cialic R, Wu P M, Doykan C E, Lin J, Cotleur A C, Kidd G, Zorlu M M, Sun N, Hu W, Liu L, Lee J C, Taylor S E, Uehlein L, Dixon D, Gu J, Floruta C M, Zhu M, Charo I F, Weiner H L, Ransohoff R M. Differential roles of microglia and monocytes in the inflamed central nervous system. The Journal of experimental medicine. 2014; 211(8):1533-49. doi: 10.1084/jem.20132477. PubMed PMID: 25002752; PMCID: PMC4113947.
21. Gosselin D, Link V M, Romanoski C E, Fonseca G J, Eichenfield D Z, Spann N J, Stender J D, Chun H B, Garner H, Geissmann F, Glass C K. Environment drives selection and function of enhancers controlling tissue-specific macrophage identities. Cell. 2014; 159(6):1327-40. doi: 10.1016/j.cell.2014.11.023. PubMed PMID: 25480297; PMCID: PMC4364385.
22. Lavin Y, Winter D, Blecher-Gonen R, David E, Keren-Shaul H, Merad M, Jung S, Amit I. Tissue-resident macrophage enhancer landscapes are shaped by the local microenvironment. Cell. 2014; 159(6):1312-26. doi: 10.1016/j.cell.2014.11.018. PubMed PMID: 25480296; PMCID: PMC4437213.
23. Bhatia S, Nesbit M E, Jr., Egeler R M, Buckley J D, Mertens A, Robison L L. Epidemiologic study of Langerhans cell histiocytosis in children. The Journal of pediatrics. 1997; 130(5):774-84. PubMed PMID: 9152288.
24. Wnorowski M, Prosch H, Prayer D, Janssen G, Gadner H, Grois N. Pattern and course of neurodegeneration in Langerhans cell histiocytosis. The Journal of pediatrics. 2008; 153(1):127-32. doi: 10.1016/j.jpeds.2007.12.042. PubMed PMID: 18571550.
25. Donadieu J, Chalard F, Jeziorski E. Medical management of langerhans cell histiocytosis from diagnosis to treatment. Expert opinion on pharmacotherapy. 2012; 13(9):1309-22. doi: 10.1517/14656566.2012.688028. PubMed PMID: 22578036.
26. Diamond E L, Durham B H, Haroche J, Yao Z, Ma J, Parikh S A, Wang Z, Choi J, Kim E, Cohen-Aubart F, Lee S C, Gao Y, Micol J B, Campbell P, Walsh M P, Sylvester B, Dolgalev I, Aminova O, Heguy A, Zappile P, Nakitandwe J, Ganzel C, Dalton J D, Ellison D W, Estrada-Veras J, Lacouture M, Gahl W A, Stephens P J, Miller V A, Ross J S, Ali S M, Briggs S R, Fasan O, Block J, Heritier S, Donadieu J, Solit D B, Hyman D M, Baselga J, Janku F, Taylor B S, Park C Y, Amoura Z, Dogan A, Emile J F, Rosen N, Gruber T A, Abdel-Wahab O. Diverse and Targetable Kinase Alterations Drive Histiocytic Neoplasms. Cancer Discov. 2016; 6(2):154-65. doi: 10.1158/2159-8290.CD-15-0913. PubMed PMID: 26566875; PMCID: PMC4744547.
27. Pritchard C, Carragher L, Aldridge V, Giblett S, Jin H, Foster C, Andreadi C, Kamata T. Mouse models for BRAF-induced cancers. Biochemical Society transactions. 2007; 35(Pt 5):1329-33. doi: 10.1042/BST0351329. PubMed PMID: 17956344; PMCID: PMC2637606.
28. Gibney G T, Messina J L, Fedorenko I V, Sondak V K, Smalley K S. Paradoxical oncogenesis—the long-term effects of BRAF inhibition in melanoma. Nature reviews Clinical oncology. 2013; 10(7):390-9. doi: 10.1038/nrclinonc.2013.83. PubMed PMID: 23712190; PMCID: PMC3983565.
29. Tiacci E, Trifonov V, Schiavoni G, Holmes A, Kern W, Martelli M P, Pucciarini A, Bigerna B, Pacini R, Wells V A, Sportoletti P, Pettirossi V, Mannucci R, Elliott O, Liso A, Ambrosetti A, Pulsoni A, Forconi F, Trentin L, Semenzato G, Inghirami G, Capponi M, Di Raimondo F, Patti C, Arcaini L, Musto P, Pileri S, Haferlach C, Schnittger S, Pizzolo G, Foa R, Farinelli L, Haferlach T, Pasqualucci L, Rabadan R, Falini B. BRAF mutations in hairy-cell leukemia. The New England journal of medicine. 2011; 364(24):2305-15. doi: 10.1056/NEJMoa1014209. PubMed PMID: 21663470; PMCID: PMC3689585.
30. Chung S S, Kim E, Park J H, Chung Y R, Lito P, Teruya-Feldstein J, Hu W, Beguelin W, Monette S, Duy C, Rampal R, Telis L, Patel M, Kim M K, Huberman K, Bouvier N, Berger M F, Melnick A M, Rosen N, Tallman M S, Park C Y, Abdel-Wahab O. Hematopoietic stem cell origin of BRAFV600E mutations in hairy cell leukemia. Science translational medicine. 2014; 6(238):238ra71. doi: 10.1126/scitranslmed.3008004. PubMed PMID: 24871132; PMCID: PMC4501573.
31. Chen M J, Yokomizo T, Zeigler B M, Dzierzak E, Speck N A. Runx1 is required for the endothelial to haematopoietic cell transition but not thereafter. Nature. 2009; 457 (7231):887-91. Epub 2009/01/09. doi: 10.1038/nature07619. PubMed PMID: 19129762; PMCID: 2744041.
32. Bertrand J Y, Jalil A, Klaine M, Jung S, Cumano A, Godin I. Three pathways to mature macrophages in the early mouse yolk sac. Blood. 2005; 106(9):3004-11. Epub 2005/07/16. doi: 10.1182/blood-2005-02-0461. PubMed PMID: 16020514.
33. Palis J, Robertson S, Kennedy M, Wall C, Keller G. Development of erythroid and myeloid progenitors in the 34. McGrath K E, Frame J M, Fegan K H, Bowen J R, Conway S J, Catherman S C, Kingsley P D, Koniski A D, Palis J. Distinct Sources of Hematopoietic Progenitors Emerge before HSCs and Provide Functional Blood Cells in the Mammalian Embryo. Cell reports. 2015; 11(12): 1892-904. Epub 2015/06/23. doi: 10.1016/j.celrep.2015.05.036. PubMed PMID: 26095363; PMCID: 4490098.
35. Bertrand J Y, Giroux S, Golub R, Klaine M, Jalil A, Boucontet L, Godin I, Cumano A. Characterization of purified intraembryonic hematopoietic stem cells as a tool to define their site of origin. Proc Natl Acad Sci USA. 2005; 102(1):134-9. Epub 2004/12/30. doi: 10.1073/pnas.0402270102. PubMed PMID: 15623562; PMCID: 544043.
36. Sumner R, Crawford A, Mucenski M, Frampton J. Initiation of adult myelopoiesis can occur in the absence of c-Myb whereas subsequent development is strictly dependent on the transcription factor. Oncogene. 2000; 19(30):3335-42. Epub 2000/08/05. doi: 10.1038/sj.onc.1203660. PubMed PMID: 10918590.
37. Bartunek P, Kralova J, Blendinger G, Dvorak M, Zenke M. GATA-1 and c-myb crosstalk during red blood cell differentiation through GATA-1 binding sites in the c-myb promoter. Oncogene. 2003; 22(13):1927-35. Epub 2003/04/04. doi: 10.1038/sj.onc.1206281. PubMed PMID: 12673198.
38. Kieusseian A, Brunet de la Grange P, Burlen-Defranoux O, Godin I, Cumano A. Immature hematopoietic stem cells undergo maturation in the fetal liver. Development. 2012; 139(19):3521-30. Epub 2012/08/18. doi: 10.1242/dev.079210. PubMed PMID: 22899849.
39. Bain C C, Bravo-Blas A, Scott C L, Gomez Perdiguero E, Geissmann F, Henri S, Malissen B, Osborne L C, Artis D, Mowat A M. Constant replenishment from circulating monocytes maintains the macrophage pool in the intestine of adult mice. Nature immunology. 2014; 15(10):929-37. doi: 10.1038/ni.2967. PubMed PMID: 25151491; PMCID: PMC4169290.
40. Hashimoto D, Chow A, Noizat C, Teo P, Beasley M B, Leboeuf M, Becker C D, See P, Price J, Lucas D, Greter M, Mortha A, Boyer S W, Forsberg E C, Tanaka M, van Rooijen N, Garcia-Sastre A, Stanley E R, Ginhoux F, Frenette P S, Merad M. Tissue-resident macrophages self-maintain locally throughout adult life with minimal contribution from circulating monocytes. Immunity. 2013; 38(4):792-804. Epub 2013/04/23. doi: 10.1016/j.immuni.2013.04.004. PubMed PMID: 23601688.
41. Yona S, Kim K W, Wolf Y, Mildner A, Varol D, Breker M, Strauss-Ayali D, Viukov S, Guilliams M, Misharin A, Hume D A, Perlman H, Malissen B, Zelzer E, Jung S. Fate mapping reveals origins and dynamics of monocytes and tissue macrophages under homeostasis. Immunity. 2013; 38(1):79-91. Epub 2013/01/01. doi: 10.1016/j.immuni.2012.12.001. PubMed PMID: 23273845.
42. Metzger D, Clifford J, Chiba H, Chambon P. Conditional site-specific recombination in mammalian cells using a ligand-dependent chimeric Cre recombinase. Proceedings of the National Academy of Sciences of the United States of America. 1995; 92(15):6991-5. Epub 1995/07/18. PubMed PMID: 7624356; PMCID: 41457.
43. Qian B Z, Li J, Zhang H, Kitamura T, Zhang J, Campion L R, Kaiser E A, Snyder L A, Pollard J W. CCL2 recruits inflammatory monocytes to facilitate breast-tumour metastasis. Nature. 2011; 475(7355):222-5. Epub 2011/06/10. doi: 10.1038/nature10138. PubMed PMID: 21654748; PMCID: 3208506.
44. Hoeffel G, Chen J, Lavin Y, Low D, Almeida F F, See P, Beaudin A E, Lum J, Low I, Forsberg E C, Poidinger M, Zolezzi F, Larbi A, Ng L G, Chan J K, Greter M, Becher B, Samokhvalov I M, Merad M, Ginhoux F. C-Myb(+) erythro-myeloid progenitor-derived fetal monocytes give rise to adult tissue-resident macrophages. Immunity. 2015; 42(4):665-78. Epub 2015/04/23. doi: 10.1016/j.immuni.2015.03.011. PubMed PMID: 25902481.
45. Del Rio-Hortega P. El "tercer elemento" de los centros nerviosus. I. La microglia en estado normal. I I. Intervencion de la microglia en los procesos patologicos (Celulas en bastoncito y cuerpos granuloadiposos). III. Naturaleza probable de la microglia. Bol Soc Espan Biol. 1919; 9:68-120.
46. Kupffer C. Ueber Sternzellen der Leber. Arch Fur Mikrosk Anat. 1876; 12:353-8.
47. Langerhans P. Ueber die Nerven der menschlichen Haut. Arch Fur Pathol Anat Physiol Fur Klin Med. 1868; 44(2-3):325-37.
48. Nimmerjahn A, Kirchhoff F, Helmchen F. Resting microglial cells are highly dynamic surveillants of brain parenchyma in vivo. Science. 2005; 308(5726):1314-8. Epub 2005/04/16. doi: 10.1126/science.1110647. PubMed PMID: 15831717.
49. Chorro L, Sarde A, Li M, Woollard K J, Chambon P, Malissen B, Kissenpfennig A, Barbaroux J B, Groves R, Geissmann F. Langerhans cell (L C) proliferation mediates neonatal development, homeostasis, and inflammation-associated expansion of the epidermal L C network. The Journal of experimental medicine. 2009; 206(13): 3089-100. Epub 2009/12/10. doi: 10.1084/jem.20091586. PubMed PMID: 19995948; PMCID: 2806478.
50. Stamatiades E G, Tremblay M E, Bohm M, Crozet L, Bisht K, Kao D, Coelho C, Fan X, Yewdell W T, Davidson A, Heeger P S, Diebold S, Nimmerjahn F, Geissmann F. Immune Monitoring of Trans-endothelial Transport by Kidney-Resident Macrophages. Cell. 2016; 166(4):991-1003. doi: 10.1016/j.cell.2016.06.058. PubMed PMID: 27477514; PMCID: PMC4983224.
51. Davalos D, Grutzendler J, Yang G, Kim J V, Zuo Y, Jung S, Littman D R, Dustin M L, Gan W B. ATP mediates rapid microglial response to local brain injury in vivo. Nature neuroscience. 2005; 8(6):752-8. Epub 2005/05/17. doi: 10.1038/nn1472. PubMed PMID: 15895084.
52. Nishibu A, Ward B R, Jester J V, Ploegh H L, Boes M, Takashima A. Behavioral responses of epidermal Langerhans cells in situ to local pathological stimuli. The Journal of investigative dermatology. 2006; 126(4):787-96. doi: 10.1038/sj.jid.5700107. PubMed PMID: 16439974.
53. Terpstra V, van Berkel T J. Scavenger receptors on liver Kupffer cells mediate the in vivo uptake of oxidatively damaged red blood cells in mice. Blood. 2000; 95(6): 2157-63. PubMed PMID: 10706889.
54. Paolicelli R C, Bolasco G, Pagani F, Maggi L, Scianni M, Panzanelli P, Giustetto M, Ferreira T A, Guiducci E, Dumas L, Ragozzino D, Gross C T. Synaptic pruning by microglia is necessary for normal brain development. Science. 2011; 333(6048):1456-8. Epub 2011/07/23. doi: 10.1126/science.1202529. PubMed PMID: 21778362.
55. Li M O, Sarkisian M R, Mehal W Z, Rakic P, Flavell R A. Phosphatidylserine receptor is required for clearance 56. Munoz-Espin D, Canamero M, Maraver A, Gomez-Lopez G, Contreras J, Murillo-Cuesta S, Rodriguez-Baeza A, Varela-Nieto I, Ruberte J, Collado M, Serrano M. Programmed cell senescence during mammalian embryonic development. Cell. 2013; 155(5):1104-18. doi: 10.1016/j.cell.2013.10.019. PubMed PMID: 24238962.

57. Fantin A, Vieira J M, Gestri G, Denti L, Schwarz Q, Prykhozhij S, Peri F, Wilson S W, Ruhrberg C. Tissue macrophages act as cellular chaperones for vascular anastomosis downstream of VEGF-mediated endothelial tip cell induction. Blood. 2010; 116(5):829-40. doi: Doi 10.1182/Blood-2009-12-257832. PubMed PMID: ISI: 000280596500025.

58. Ingman W V, Wyckoff J, Gouon-Evans V, Condeelis J, Pollard J W. Macrophages promote collagen fibrillogenesis around terminal end buds of the developing mammary gland. Developmental dynamics: an official publication of the American Association of Anatomists. 2006; 235(12):3222-9. Epub 2006/10/10. doi: 10.1002/dvdy.20972. PubMed PMID: 17029292.

59. DeFalco T, Bhattacharya I, Williams A V, Sams D M, Capel B. Yolk-sac-derived macrophages regulate fetal testis vascularization and morphogenesis. Proceedings of the National Academy of Sciences of the United States of America. 2014; 111(23):E2384-93. Epub 2014/06/10. doi: 10.1073/pnas.1400057111. PubMed PMID: 24912173; PMCID: 4060703.

60. Banaei-Bouchareb L, Gouon-Evans V, Samara-Boustani D, Castellotti M C, Czernichow P, Pollard J W, Polak M. Insulin cell mass is altered in Csflop/Csflop macrophage-deficient mice. Journal of leukocyte biology. 2004; 76(2): 359-67. Epub 2004/06/05. doi: 10.1189/jlb.1103591. PubMed PMID: 15178709.

61. Kubota Y, Takubo K, Shimizu T, Ohno H, Kishi K, Shibuya M, Saya H, Suda T. M-CSF inhibition selectively targets pathological angiogenesis and lymphangiogenesis. Journal of Experimental Medicine. 2009; 206(5):1089-102. doi: Doi 10.1084/Jem.20081605. PubMed PMID: ISI:000266010000015.

62. Gordon E J, Rao S, Pollard J W, Nutt S L, Lang R A, Harvey N L. Macrophages define dermal lymphatic vessel calibre during development by regulating lymphatic endothelial cell proliferation. Development. 2010; 137 (22):3899-910. doi: Doi 10.1242/Dev.050021. PubMed PMID: ISI:000283671100018.

63. Rymo S F, Gerhardt H, Sand F W, Lang R, Uv A, Betsholtz C. A Two-Way Communication between Microglial Cells and Angiogenic Sprouts Regulates Angiogenesis in Aortic Ring Cultures. PloS one. 2011; 6(1). doi: ARTN e15846 DOI 10.1371/j ournal.pone.0015846. PubMed PMID: ISI:000286513100013.

64. Yoshida H, Kawane K, Koike M, Mori Y, Uchiyama Y, Nagata S. Phosphatidylserine-dependent engulfment by macrophages of nuclei from erythroid precursor cells. Nature. 2005; 437(7059):754-8. Epub 2005/09/30. doi: 10.1038/nature03964. PubMed PMID: 16193055.

65. Wynn T A, Chawla A, Pollard J W. Macrophage biology in development, homeostasis and disease. Nature. 2013; 496(7446):445-55. Epub 2013/04/27. doi: 10.1038/nature12034. PubMed PMID: 23619691; PMCID: 3725458.

66. Kierdorf K, Prinz M, Geissmann F, Gomez Perdiguero E. Development and function of tissue resident macrophages in mice. Seminars in immunology. 2015; 27(6): 369-78. doi: 10.1016/j.smim.2016.03.017. PubMed PMID: 27036090.

67. Ajami B, Bennett J L, Krieger C, Tetzlaff W, Rossi F M. Local self-renewal can sustain CNS microglia maintenance and function throughout adult life. Nat Neurosci. 2007; 10(12):1538-43. Epub 2007/11/21. doi: 10.1038/nn2014. PubMed PMID: 18026097.

68. Ajami B, Bennett J L, Krieger C, McNagny K M, Rossi F M. Infiltrating monocytes trigger EAE progression, but do not contribute to the resident microglia pool. Nature neuroscience. 2011; 14(9):1142-9. Epub 2011/08/02. doi: 10.1038/nn.2887. PubMed PMID: 21804537.

69. Evans T A, Barkauskas D S, Myers J T, Hare E G, You J Q, Ransohoff R M, Huang A Y, Silver J. High-resolution intravital imaging reveals that blood-derived macrophages but not resident microglia facilitate secondary axonal dieback in traumatic spinal cord injury. Exp Neurol. 2014; 254:109-20. doi: 10.1016/j.expneurol.2014.01.013. PubMed PMID: 24468477; PMCID: PMC3954731.

70. Jenkins S J, Ruckerl D, Cook P C, Jones L H, Finkelman F D, van Rooijen N, MacDonald A S, Allen J E. Local macrophage proliferation, rather than recruitment from the blood, is a signature of TH2 inflammation. Science. 2011; 332(6035):1284-8. Epub 2011/05/14. doi: 10.1126/science.1204351. PubMed PMID: 21566158; PMCID: 3128495.

71. Gomez Perdiguero E, Geissmann F. Myb-Independent Macrophages: A Family of Cells That Develops with Their Tissue of Residence and Is Involved in Its Homeostasis. Cold Spring Harbor symposia on quantitative biology. 2013. Epub 2013/10/15. doi: 10.1101/sqb.2013.78.020032. PubMed PMID: 24122769.

72. Gomez-Nicola D, Fransen N L, Suzzi S, Perry V H. Regulation of microglial proliferation during chronic neurodegeneration. The Journal of neuroscience: the official journal of the Society for Neuroscience. 2013; 33(6): 2481-93. Epub 2013/02/09. doi: 10.1523/JNEUROSCI.4440-12.2013. PubMed PMID: 23392676.

73. Croker B A, Metcalf D, Robb L, Wei W, Mifsud S, DiRago L, Cluse L A, Sutherland K D, Hartley L, Williams E, Zhang J G, Hilton D J, Nicola N A, Alexander W S, Roberts A W. SOCS3 is a critical physiological negative regulator of G-CSF signaling and emergency granulopoiesis. Immunity. 2004; 20(2):153-65. PubMed PMID: 14975238.

74. de Boer J, Williams A, Skavdis G, Harker N, Coles M, Tolaini M, Norton T, Williams K, Roderick K, Potocnik A J, Kioussis D. Transgenic mice with hematopoietic and lymphoid specific expression of Cre. European journal of immunology. 2003; 33(2):314-25. doi: 10.1002/immu.200310005. PubMed PMID: 12548562.

75. Carter R J, Lione L A, Humby T, Mangiarini L, Mahal A, Bates G P, Dunnett S B, Morton A J. Characterization of progressive motor deficits in mice transgenic for the human Huntington's disease mutation. J Neurosci. 1999; 19(8):3248-57. PubMed PMID: 10191337.

76. Donadieu J, Rolon M A, Thomas C, Brugieres L, Plantaz D, Emile J F, Frappaz D, David M, Brauner R, Genereau T, Debray D, Cabrol S, Barthez M A, Hoang-Xuan K, Polak M, French LCHSG. Endocrine involvement in pediatric-onset Langerhans' cell histiocytosis: a population-based study. The Journal of pediatrics. 2004; 144(3): 344-50. doi: 10.1016/j.jpeds.2003.12.030. PubMed PMID: 15001940.

77. Brooks S P, Dunnett S B. Tests to assess motor phenotype in mice: a user's guide. Nat Rev Neurosci. 2009; 10(7):519-29. doi: 10.1038/nrn2652. PubMed PMID: 19513088.

78. Schaefer A, Sampath S C, Intrator A, Min A, Gertler T S, Surmeier D J, Tarakhovsky A, Greengard P. Control of cognition and adaptive behavior by the GLP/G9a epigenetic suppressor complex. Neuron. 2009; 64(5):678-91. doi: 10.1016/j.neuron.2009.11.019. PubMed PMID: 20005824; PMCID: PMC2814156.

79. Menalled L B, Sison J D, Wu Y, Olivieri M, Li X J, Li H, Zeitlin S, Chesselet M F. Early motor dysfunction and striosomal distribution of huntingtin microaggregates in Huntington's disease knock-in mice. J Neurosci. 2002; 22(18):8266-76. PubMed PMID: 12223581.

80. Ransohoff R M. A polarizing question: do M1 and M2 microglia exist? Nat Neurosci. 2016; 19(8):987-91. doi: 10.1038/nn.4338. PubMed PMID: 27459405.

81. Schmued L C, Albertson C, Slikker W, Jr. Fluoro-Jade: a novel fluorochrome for the sensitive and reliable histochemical localization of neuronal degeneration. Brain research. 1997; 751(1):37-46. PubMed PMID: 9098566.

82. Erny D, Hrabe de Angelis A L, Jaitin D, Wieghofer P, Staszewski O, David E, Keren-Shaul H, Mahlakoiv T, Jakobshagen K, Buch T, Schwierzeck V, Utermohlen O, Chun E, Garrett W S, McCoy K D, Diefenbach A, Staeheli P, Stecher B, Amit I, Prinz M. Host microbiota constantly control maturation and function of microglia in the CNS. Nat Neurosci. 2015; 18(7):965-77. doi: 10.1038/nn.4030. PubMed PMID: 26030851.

83. Mittheisz E, Seidl R, Prayer D, Waldenmair M, Neophytou B, Potschger U, Minkov M, Steiner M, Prosch H, Wnorowski M, Gadner H, Grois N. Central nervous system-related permanent consequences in patients with Langerhans cell histiocytosis. Pediatric blood & cancer. 2007; 48(1):50-6. doi: 10.1002/pbc.20760. PubMed PMID: 16470521.

84. Grois N, Barkovich A J, Rosenau W, Ablin A R. Central nervous system disease associated with Langerhans' cell histiocytosis. Am J Pediatr Hematol Oncol. 1993; 15(2): 245-54. PubMed PMID: 8498649.

85. Grois N, Tsunematsu Y, Barkovich A J, Favara B E. Central nervous system disease in Langerhans cell histiocytosis. Br J Cancer Suppl. 1994; 23:S24-8. PubMed PMID: 8075002; PMCID: PMC2149701.

86. Rouco I, Arostegui J, Canovas A, Gonzalez Del Tanago J, Fernandez I, Zarranz J J. Neurological manifestations in Erdheim-Chester disease: Two case reports. Neurologia. 2016; 31(6):426-8. doi: 10.1016/j.nrl.2014.01.010. PubMed PMID: 24735941.

87. Lachenal F, Cotton F, Desmurs-Clavel H, Haroche J, Taillia H, Magy N, Hamidou M, Salvatierra J, Piette J C, Vital-Durand D, Rousset H. Neurological manifestations and neuroradiological presentation of Erdheim-Chester disease: report of 6 cases and systematic review of the literature. J Neurol. 2006; 253(10):1267-77. doi: 10.1007/s00415-006-0160-9. PubMed PMID: 17063320.

88. Wright R A, Hermann R C, Parisi J E. Neurological manifestations of Erdheim-Chester disease. J Neurol Neurosurg Psychiatry. 1999; 66(1):72-5. PubMed PMID: 9886456; PMCID: PMC1736172.

89. Lai C F, Chaudhary L, Fausto A, Halstead L R, Ory D S, Avioli L V, Cheng S L. Erk is essential for growth, differentiation, integrin expression, and cell function in human osteoblastic cells. The Journal of biological chemistry. 2001; 276(17):14443-50. doi: 10.1074/jbc.M010021200. PubMed PMID: 11278600.

90. Goke J, Chan Y S, Yan J, Vingron M, Ng H H. Genome-wide kinase-chromatin interactions reveal the regulatory network of ERK signaling in human embryonic stem cells. Molecular cell. 2013; 50(6):844-55. doi: 10.1016/j.molcel.2013.04.030. PubMed PMID: 23727019.

91. Zhang W, Liu H T. MAPK signal pathways in the regulation of cell proliferation in mammalian cells. Cell research. 2002; 12(1):9-18. doi: 10.1038/sj.cr.7290105. PubMed PMID: 11942415.

92. Yamamoto T, Ebisuya M, Ashida F, Okamoto K, Yonehara S, Nishida E. Continuous ERK activation downregulates antiproliferative genes throughout G1 phase to allow cell-cycle progression. Current biology: C B. 2006; 16(12):1171-82. doi: 10.1016/j.cub.2006.04.044. PubMed PMID: 16782007.

93. Hatemi I, Baysal B, Senturk H, Behzatoglu K, Bozkurt E R, Ozbay G. Adult Langerhans cell histiocytosis and sclerosing cholangitis: a case report and review of the literature. Hepatology international. 2010; 4(3):653-8. doi: 10.1007/s12072-010-9205-3. PubMed PMID: 21063491; PMCID: PMC2940001.

94. Fickert P, Stoger U, Fuchsbichler A, Moustafa T, Marschall H U, Weiglein A H, Tsybrovskyy O, Jaeschke H, Zatloukal K, Denk H, Trauner M. A new xenobiotic-induced mouse model of sclerosing cholangitis and biliary fibrosis. Am J Pathol. 2007; 171(2):525-36. doi: 10.2353/ajpath.2007.061133. PubMed PMID: 17600122; PMCID: PMC1934539.

95. Fickert P, Fuchsbichler A, Marschall H U, Wagner M, Zollner G, Krause R, Zatloukal K, Jaeschke H, Denk H, Trauner M. Lithocholic acid feeding induces segmental bile duct obstruction and destructive cholangitis in mice. Am J Pathol. 2006; 168(2):410-22. doi: 10.2353/ajpath.2006.050404. PubMed PMID: 16436656; PMCID: PMC1606500.

96. Constandinou C, Henderson N, Iredale J P. Modeling liver fibrosis in rodents. Methods Mol Med. 2005; 117: 237-50. doi: 10.1385/1-59259-940-0:237. PubMed PMID: 16118456.

97. Levine J H, Simonds E F, Bendall S C, Davis K L, Amir el A D, Tadmor M D, Litvin O, Fienberg H G, Jager A, Zunder E R, Finck R, Gedman A L, Radtke I, Downing J R, Pe'er D, Nolan G P. Data-Driven Phenotypic Dissection of AML Reveals Progenitor-like Cells that Correlate with Prognosis. Cell. 2015; 162(1):184-97. doi: 10.1016/j.cell.2015.05.047. PubMed PMID: 26095251; PMC4508757.

98. Tsai J, Lee J T, Wang W, Zhang J, Cho H, Mamo S, Bremer R, Gillette S, Kong J, Haass N K, Sproesser K, Li L, Smalley K S, Fong D, Zhu Y L, Marimuthu A, Nguyen H, Lam B, Liu J, Cheung I, Rice J, Suzuki Y, Luu C, Settachatgul C, Shellooe R, Cantwell J, Kim S H, Schlessinger J, Zhang K Y, West B L, Powell B, Habets G, Zhang C, Ibrahim P N, Hirth P, Artis D R, Herlyn M, Bollag G. Discovery of a selective inhibitor of oncogenic B-Raf kinase with potent antimelanoma activity. Proceedings of the National Academy of Sciences of the United States of America. 2008; 105(8):3041-6. doi: 10.1073/pnas.0711741105. PubMed PMID: 18287029; PMCID: PMC2268581.

99. Lito P, Pratilas C A, Joseph E W, Tadi M, Halilovic E, Zubrowski M, Huang A, Wong W L, Callahan M K, Merghoub T, Wolchok J D, de Stanchina E, Chandarlapaty S, Poulikakos P I, Fagin J A, Rosen N. Relief of profound feedback inhibition of mitogenic signaling by RAF inhibitors attenuates their activity in BRAFV600E melanomas. Cancer Cell. 2012; 22(5):668-82. doi: 10.1016/j.ccr.2012.10.009. PubMed PMID: 23153539; PMCID: PMC3713778.
100. Poulikakos P I, Zhang C, Bollag G, Shokat K M, Rosen N. RAF inhibitors transactivate RAF dimers and ERK signalling in cells with wild-type BRAF. Nature. 2010; 464(7287):427-30. doi: 10.1038/nature08902. PubMed PMID: 20179705; PMCID: PMC3178447.
101. Haroche J, Cohen-Aubart F, Emile J F, Donadieu J, Amoura Z. Vemurafenib as first line therapy in BRAF-mutated Langerhans cell histiocytosis. Journal of the American Academy of Dermatology. 2015; 73(1):e29-30. doi: 10.1016/j jaad.2014.10.045. PubMed PMID: 26089069.
102. Haroche J, Cohen-Aubart F, Emile J F, Maksud P, Drier A, Toledano D, Barete S, Charlotte F, Cluzel P, Donadieu J, Benameur N, Grenier P A, Besnard S, Ory J P, Lifermann F, Idbaih A, Granel B, Graffin B, Hervier B, Arnaud L, Amoura Z. Reproducible and sustained efficacy of targeted therapy with vemurafenib in patients with BRAF (V600E)-mutated Erdheim-Chester disease. Journal of clinical oncology: official journal of the American Society of Clinical Oncology. 2015; 33(5):411-8. doi: 10.1200/JCO.2014.57.1950. PubMed PMID: 25422482.
103. Tzoulis C, Schwarzlmuller T, Gjerde T O, Softeland E, Neckelmann G, Biermann M, Haroche J, Straume O, Vintermyr O K. Excellent response of intramedullary Erdheim-Chester disease to vemurafenib: a case report. BMC Res Notes. 2015; 8:171. doi: 10.1186/s13104-015-1135-7. PubMed PMID: 25926131; PMCID: PMC4450489.
104. Vanden Bone P, Gunda V, McFadden D G, Sadow P M, Varmeh S, Bernasconi M, Parangi S. Combined BRAF (V600E)- and SRC-inhibition induces apoptosis, evokes an immune response and reduces tumor growth in an immunocompetent orthotopic mouse model of anaplastic thyroid cancer. Oncotarget. 2014; 5(12):3996-4010. doi: 10.18632/oncotarget.2130. PubMed PMID: 24994118; PMCID: PMC4147301.
105. Chakravarty D, Santos E, Ryder M, Knauf J A, Liao X H, West B L, Bollag G, Kolesnick R, Thin T H, Rosen N, Zanzonico P, Larson S M, Refetoff S, Ghossein R, Fagin J A. Small-molecule MAPK inhibitors restore radioiodine incorporation in mouse thyroid cancers with conditional BRAF activation. The Journal of clinical investigation. 2011; 121(12):4700-11. doi: 10.1172/JCI46382. PubMed PMID: 22105174; PMCID: PMC3225989.
106. Rochet N M, Kottschade L A, Markovic S N. Vemurafenib for melanoma metastases to the brain. The New England journal of medicine. 2011; 365(25):2439-41. doi: 10.1056/NEJMc1111672. PubMed PMID: 22188003.
107. Larkin J, Ascierto P A, Dreno B, Atkinson V, Liszkay G, Maio M, Mandala M, Demidov L, Stroyakovskiy D, Thomas L, de la Cruz-Merino L, Dutriaux C, Garbe C, Sovak M A, Chang I, Choong N, Hack S P, McArthur G A, Ribas A. Combined vemurafenib and cobimetinib in BRAF-mutated melanoma. The New England journal of medicine. 2014; 371(20):1867-76. doi: 10.1056/NEJMoa1408868. PubMed PMID: 25265494.
108. Allen C E, Li L, Peters T L, Leung H C, Yu A, Man T K, Gurusiddappa S, Phillips M T, Hicks M J, Gaikwad A, Merad M, McClain K L. Cell-specific gene expression in Langerhans cell histiocytosis lesions reveals a distinct profile compared with epidermal Langerhans cells. Journal of immunology. 2010; 184(8):4557-67. doi: 10.4049/jimmunol.0902336. PubMed PMID: 20220088; PMCID: PMC3142675.
109. Egeler R M, Favara B E, van Meurs M, Laman J D, Claassen E. Differential In situ cytokine profiles of Langerhans-like cells and T cells in Langerhans cell histiocytosis: abundant expression of cytokines relevant to disease and treatment. Blood. 1999; 94(12):4195-201. PubMed PMID: 10590064.
110. Arnaud L, Gorochov G, Charlotte F, Lvovschi V, Parizot C, Larsen M, Ghillani-Dalbin P, Hervier B, Kahn J E, Deback C, Musset L, Amoura Z, Haroche J. Systemic perturbation of cytokine and chemokine networks in Erdheim-Chester disease: a single-center series of 37 patients. Blood. 2011; 117(10):2783-90. doi: 10.1182/blood-2010-10-313510. PubMed PMID: 21205927.
111. Sevcikova S, Kubiczkova L, Sedlarikova L, Rihova L, Kryukov F, Szturz P, Hajek R, Pour L, Adam Z. Impact of anakinra treatment on cytokine and lymphocytes/monocytes profile of an Erdheim-Chester patient. Klin Onkol. 2014; 27(4):276-82. PubMed PMID: 25115717.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A method for treating $BRAF^{V600E}$-associated neurodegenerative disease in a subject in need thereof, comprising administering to the subject a therapeutically effective amount of a BRAF, MEK, and/or CSF-1R inhibitor, or a pharmaceutically acceptable salt thereof,
wherein the BRAF inhibitor is selected from the group consisting of vemurafenib, PLX7904, PLX8394, and PLX4720, the MEK inhibitor is selected from the group consisting of AZD8330, refametinib, E6201, MEK162 (binimetinib), PD0325901, pimasertib, RO4987655, selumetinib, TAK-733, GDC-0623, WX-544, cobimetinib, and trametinib, and the CSF-1R inhibitor is selected from the group consisting of GW2580, BLZ945, pexidartinib (PLX3397), ARRY-382, PLX7486, and JNJ-40346527.

2. The method of claim 1, wherein at least a portion of the resident macrophages in the central nervous system of the subject are $BRAF^{V600E+}$.

3. A method for treating $BRAF^{V600E}$-associated neurodegenerative disease comprising:
(a) isolating resident macrophages from a neuronal environment of the subject;

(b) determining whether the resident macrophages express BRAF$^{V600E+}$; and (c) administering to the subject a therapeutically effective amount of a BRAF, MEK, and/or CSF-1R inhibitor, or a pharmaceutically acceptable salt thereof, when the isolated resident macrophages express BRAF$^{V600E+}$, wherein the BRAF inhibitor is selected from the group consisting of vemurafenib, PLX7904, PLX8394, and PLX4720, the MEK inhibitor is selected from the group consisting of AZD8330, refametinib, E6201, MEK162 (binimetinib), PD0325901, pimasertib, R04987655, selumetinib, TAK-733, GDC-0623, WX-544, cobimetinib, and trametinib, and the CSF-1R inhibitor is selected from the group consisting of GW2580, BLZ945, pexidartinib (PLX3397), ARRY-382, PLX7486, and JNJ-40346527.

4. The method of claim 1, wherein the neurodegenerative disease is characterized by one or more of impaired cognitive functions, dementia, ataxia, dysarthria, reduced motor coordination and synchrony as compared to a normal control subject, paralysis, microglia accumulation, astrogliosis, microglia phagocytosis, demyelination, neuronal loss in the central nervous system, synaptic loss in the central nervous system, and amyloid precursor protein (APP) deposits in the brain.

5. The method of claim 1, wherein the route of administration of the BRAF, MEK, or CSF-1R inhibitor is parenteral, intradermal, intramuscular, intraperitoneal, intravenous, subcutaneous, intranasal, epidural, oral, sublingual, intranasal, intracerebral, intrathecal, intravaginal, transdermal, rectal, by inhalation, or topical.

6. The method of claim 1, wherein treatment of the neurodegenerative disease comprises one or more of improving cognitive functions, reducing dementia, reducing ataxia, reducing dysarthria, increasing motor coordination and synchrony, relieving paralysis, reducing microglia accumulation, reducing astrogliosis, reducing microglia phagocytosis, reducing demyelination, reducing neuronal loss, reducing synaptic loss, or reducing amyloid precursor protein (APP) expression in the brain as compared to an untreated control.

7. The method of claim 1, wherein the BRAF inhibitor is vemurafenib.

8. The method of claim 1, wherein the BRAF inhibitor is PLX4720.

9. A method for treating neurodegenerative disease in a subject in need thereof, comprising administering to the subject a therapeutically effective amount of a PI 3-kinase inhibitor, or a pharmaceutically acceptable salt thereof, wherein at least a portion of the resident macrophages in the central nervous system of the subject comprise one or more PI 3-kinase mutations, wherein the PI 3-kinase inhibitor is selected from the group consisting of idelalisib, BKM120, GDC-0980, PF-04691502, XL147, IPI-145, BYL719, SF1126, BAY80-6946, GSK2126458, NVP-BEZ235, GDC-0941, PX-866, XL765, and ZSTK474.

10. The method of claim 9, wherein at least a portion of the resident macrophages in the central nervous system of the subject are PIK3CA$^{H104R+}$.

11. The method of claim 9, wherein the neurodegenerative disease is characterized by one or more of impaired cognitive functions, dementia, ataxia, dysarthria, reduced motor coordination and synchrony as compared to a normal control subject, paralysis, microglia accumulation, astrogliosis, microglia phagocytosis, demyelination, neuronal loss in the central nervous system, synaptic loss in the central nervous system, and amyloid precursor protein (APP) deposits in the brain.

12. The method of claim 9, wherein the route of administration of the PI 3-kinase inhibitor is parenteral, intradermal, intramuscular, intraperitoneal, intravenous, subcutaneous, intranasal, epidural, oral, sublingual, intranasal, intracerebral, intrathecal, intravaginal, transdermal, rectal, by inhalation, or topical.

* * * * *